United States Patent
Poitout et al.

(10) Patent No.: US 7,501,525 B2
(45) Date of Patent: Mar. 10, 2009

(54) DERIVATIVES OF BENZIMIDAZOLE AND THEIR USE AS MEDICAMENTS

(75) Inventors: Lydie Poitout, Le Kremlin Bicetre (FR); Valerie Brault, Saint-Arnoult-En-Yvelines (FR); Carole Sackur, Paris (FR); Pierre Roubert, Paris (FR); Pascale Plas, Chatillon (FR)

(73) Assignee: Societe de Conseils de Recherches et d'Applications Scientifiques (S.C.R.A.S.), Paris (FR)

( * ) Notice: Subject to any disclaimer, the term of this patent is extended or adjusted under 35 U.S.C. 154(b) by 0 days.

(21) Appl. No.: 12/012,184

(22) Filed: Jan. 31, 2008

(65) Prior Publication Data

US 2008/0139619 A1   Jun. 12, 2008

Related U.S. Application Data

(62) Division of application No. 10/504,033, filed as application No. PCT/FR2004/000418 on Feb. 25, 2004, now Pat. No. 7,355,052.

(30) Foreign Application Priority Data

Feb. 26, 2003   (FR) .................................. 03 02320

(51) Int. Cl.
C07D 235/00   (2006.01)
A61K 31/44   (2006.01)

(52) U.S. Cl. ..................................... 548/307.4; 514/323
(58) Field of Classification Search .............. 548/307.4; 514/323

See application file for complete search history.

(56) References Cited

U.S. PATENT DOCUMENTS 4,882,342 A * 11/1989 von der Saal et al. ....... 514/338

OTHER PUBLICATIONS

Poitout et al. Bioorganic & Medicinal Chemistry Letters (2007),17(16), 4464-4470.*

* cited by examiner

*Primary Examiner*—D. Margaret Seaman
*Assistant Examiner*—Nizal S Chandrakumar
(74) *Attorney, Agent, or Firm*—Charles A. Muserlian

(57) ABSTRACT

A subject of the present Application is novel derivatives of benzimidazole and imidazo-pyridine which have a good affinity for certain sub-types of melanocortin receptors, in particular the MC4 receptors. They are particularly useful for treating pathological conditions and diseases in which one or more melanocortin receptors are involved. The invention also relates to pharmaceutical compositions containing said products.

4 Claims, No Drawings

DERIVATIVES OF BENZIMIDAZOLE AND THEIR USE AS MEDICAMENTS

PRIOR APPLICATION

This application is a division of U.S. patent Ser. No. 10/504,033 filed Sep. 28, 2004 now U.S. patent application Ser. No. 7,355,052 which is a 371 of PCT/FR04/00418 filed Feb. 25, 2004.

A subject of the present Application is novel derivatives of benzimidazole and imidazo-pyridine. These products have a good affinity for certain sub-types of melanocortin receptors, in particular the MC4 receptors. They are particularly useful for treating pathological conditions and diseases in which one or more melanocortin receptors are involved. The invention also relates to pharmaceutical compositions containing said products and their use for preparing a medicament.

The melanocortins represent a group of peptides which derive from the same precursor, proopiomelanocortin (POMC), and which are structurally close: the adrenocorticotropic hormone (ACTH), the α-melanocyte stimulating hormone (α-MSH), β-MSH and γ-MSH (Eipper B. A. and Mains R. E., *Endocr. Rev.* 1980, 1, 1-27). The melanocortins carry out numerous physiological functions. They stimulate the synthesis of the steroids by the adrenal cortex and the synthesis of eumelanine by the melanocytes. They regulate the intake of food, energetic metabolism, sexual function, neuronal regeneration, blood pressure and heart rate, as well as the perception of pain, learning, attention and memory. The melanocortins also possess anti-inflammatory and anti-pyretic properties and control the secretion of several endocrine or exocrine glands such as the sebaceous, lacrimal and mammary glands, the prostate and the pancreas (Wikberg J. E. et al. *Pharmacol. Res.* 2000, 42, 393-420; Abdel-Malek Z. A., *Cell. Mol. Life. Sci.* 2001, 58, 434-441).

The effects of the melanocortins are mediated by a family of membrane receptors specific to seven transmembrane domains and coupled to G proteins. Five sub-types of receptors, named MC1 to MC5, have been cloned and characterized to date. These receptors differ in their tissue distribution and in the affinity of different melanocortins, the MC2 receptors only recognizing the ACTH. The stimulation of the melanocortin receptors activates adenylate cyclase with production of cyclic AMP. If the specific functional roles of each of the receptors are not totally elucidated, the treatment of pathological disorders or diseases can be associated with an affinity for certain sub-types of receptors. Thus activation of the MC1 receptors has been associated with the treatment of inflammations, while blocking them has been associated with the treatment of cutaneous cancers. The treatment of nutritional disorders has been associated with the MC3 and MC4 receptors, the treatment of obesity with agonists and the treatment of cachexia and anorexia with antagonists. Other indications linked to the activation of the MC3 and MC4 receptors are problems with sexual activity, neuropathic pain, anxiety, depression and drug addiction. The activation of the MC5 receptors has been associated with the treatment of acne and dermatoses.

The Applicants have discovered that the novel compounds of general formula (I) described hereafter possess a good affinity for the melanocortin receptors. They preferably act on the MC4 receptors. Said compounds, agonists or antagonists of the melanocortin receptors, can be used for treating the pathological conditions or diseases of the metabolism, of the nervous system or dermatological diseases in which one or more melanocortin receptors are involved such as the following examples: inflammatory conditions, energetic homeostasis disorders, intake of food disorders, weight disorders (obesity, cachexia, anorexia), sexual activity disorders (erective disorders), pain and more particularly neuropathic pain. Mental health problems (anxiety, depression), drug addiction, skin diseases (acne, dermatoses, skin cancer, melanomas) can also be mentioned. These compounds can also be used to stimulate nerve regeneration.

A subject of the invention is therefore a compound of general formula (I)

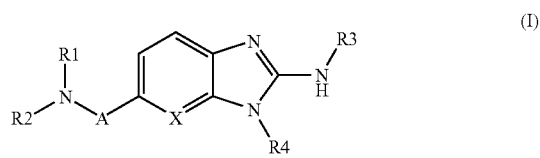

in racemic or enantiomeric form or any combinations of these forms and in which:

A represents $-CH_2-$, $-C(O)-$, $-C(O)-C(R_a)(R_b)-$;
X represents $-CH-$ or $-N-$;
$R_a$ and $R_b$ represent, independently, the hydrogen atom or a ($C_1$-$C_6$)alkyl radical;
$R_1$ represents the hydrogen atom; a ($C_1$-$C_8$)alkyl radical optionally substituted by hydroxy or one or more identical or different halo radicals; ($C_2$-$C_6$)alkenyl; or a radical of formula $-(CH_2)_n-X_1$;
$R_2$ represents a ($C_1$-$C_8$)alkyl radical optionally substituted by hydroxy or one or more identical or different halo radicals; ($C_2$-$C_6$)alkenyl; or a radical of formula $-(CH_2)_n-X_1$;
each $X_1$ independently represents ($C_1$-$C_6$)alkoxy, ($C_3$-$C_7$)cycloalkyl, adamantyl, heterocycloalkyl, aryl or heteroaryl, the ($C_3$-$C_7$)cycloalkyl, heterocycloalkyl, aryl and heteroaryl radicals being optionally substituted by one or more identical or different substituents chosen from: $-(CH_2)_{n'}-V_1-Y_1$, halo, nitro, cyano and aryl;
$V_1$ represents $-O-$, $-S-$ or a covalent bond;
$Y_1$ represents a ($C_1$-$C_6$)alkyl radical optionally substituted by one or more identical or different halo radicals;
n represents an integer from 0 to 6 and n' an integer from 0 to 2 (it being understood that when n is equal to 0, then $X_1$ does not represent the alkoxy radical);

or $R_1$ and $R_2$ form together with the nitrogen atom to which they are attached, a heterobicycloalkyl or a heterocycloalkyl optionally substituted by one or more identical or different substituents chosen from: hydroxy, ($C_1$-$C_6$)alkyl optionally substituted by hydroxy, ($C_1$-$C_6$)alkoxy-carbonyl, heterocycloalkyl and $-C(O)NV_1'Y_1'$ with $V_1'$ and $Y_1'$ independently representing the hydrogen atom or a ($C_1$-$C_6$)alkyl; or $R_1$ and $R_2$ together form a radical of formula:

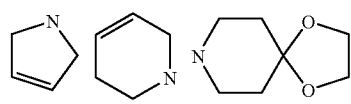

$R_3$ represents $-Z_3$, $-C(R_{Z3})(R'_{Z3})-Z_3$, $-C(R_{Z3})(R'_{Z3})-(CH_2)_p-Z_3$ or $-C(O)-Z'_3$
$R_{Z3}$ and $R'_{Z3}$ represent, independently, the hydrogen atom or a ($C_1$-$C_6$)alkyl radical;
$Z_3$ represents $Z_{3a}$, $Z_{3b}$, $Z_{3c}$, $Z_{3d}$, or $Z_{3e}$;
$Z_{3a}$ represents a ($C_1$-$C_6$)alkyl radical;
$Z_{3b}$ represents a ($C_1$-$C_6$)alkoxy, ($C_1$-$C_6$)alkylthio, ($C_1$-$C_6$) alkylamino or di(($C_1$-$C_6$)alkyl)amino radical;

$Z_{3c}$ represents an aryl or heteroaryl radical;

$Z_{3d}$ represents a $(C_1-C_6)$ alkoxy-carbonyl, amino-carbonyl, $(C_1-C_6)$alkylamino-carbonyl, $di((C_1-C_6)alkyl)$ amino-carbonyl, $(C_1-C_6)$alkyl-C(O)—NH—, $(C_3-C_7)$ cycloalkyl, heterocycloalkyl radical;

the $(C_3-C_7)$cycloalkyl and heterocycloalkyl radicals being optionally substituted by one or more identical or different substituents chosen from: halo, nitro, $(C_1-C_6)$alkoxy optionally substituted by one or more identical or different halo radicals, $(C_1-C_6)$alkyl optionally substituted by one or mere identical or different halo radicals, $(C_1-C_6)$ alkyl-carbonyl, $(C_1-C_6)$alkoxy-carbonyl, amino-carbonyl, $(C_1-C_6)$alkylamino-carbonyl, $di((C_1-C_6)alkyl)$ amino-carbonyl and oxy, the aryl and heteroaryl radicals being optionally substituted by one or more identical or different substituents chosen from: halo, cyano, nitro, azido, oxy, $(C_1-C_6)$ alkoxy-carbonyl-$(C_1-C_6)$alkenyl, $(C_1-C_6)$alkylamino-carbonyl-$(C_1-C_6)$alkenyl, —$SO_2$—$NR_{31}R_{32}$, heterocycloalkyl, heteroaryl or —$(CH_2)_{p'}$—$V_3$—$Y_3$;

$R_{31}$ and $R_{32}$ form together with the nitrogen atom to which they are attached, a heterocycloalkyl;

$V_3$ represents —O—, —S—, —C(O)—, —C(O)—O—, —O—C(O)—, —$SO_2$—, —$SO_2NH$—, —$NR'_3$—$SO_2$—, —$NR'_3$—, —$NR'_3$—C(O)—, —C(O)—$NR'_3$—, —NH—C(O)—$NR'_3$— or a covalent bond;

$Y_3$ represents the hydrogen atom; a $(C_1-C_6)$alkyl radical optionally substituted by one or more identical or different halo radicals or different substituents chosen from: halo nitro, $(C_1-C_6)$alkyl and $(C_1-C_6)$alkoxy; or an aryl-$(C_1-C_6)$alkyl radical optionally substituted by one or more identical or different substitutents chosen from: halo, nitro, $(C_1-C_6)$alkyl and $(C_1-C_6)$alkoxy;

$Z_{3e}$ represents a radical of formula

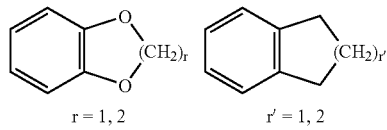

r = 1, 2    r' = 1, 2

$Z'_3$ represents an aryl radical optionally substituted by one or more identical or different substituents chosen from: halo, nitro and —$(CH_2)_{p''}$—$V'_3$—$Y'_3$;

$V'_3$ represents —O—, —C(O)—, —C(O)—O—, —C(O)—$NR'_3$—, —NH—C(O)—$NR'_3$— or a covalent bond;

$Y'_3$ represents the hydrogen atom or a $(C_1-C_6)$alkyl radical optionally substituted by one or more identical or different halo radicals;

$R'_3$ represents the hydrogen atom, a $(C_1-C_6)$alkyl or $(C_1-C_6)$alkoxy radical;

p represents an integer from 1 to 4; p' and p" represent, independently, an integer from 0 to 4;

$R_4$ represents a radical of formula —$(CH_2)_s$—$R'_4$ $R'_4$ represents the guanidine radical; a herterocycloalkyl containing at least one nitrogen atom and optionally substituted by $(C_1-C_6)$alkyl or aralkyl; a heteroaryl containing at least one nitrogen atom and optionally substituted by $(C_1-C_6)$alkyl; or a radical of formula —$NW_4W'_4$ $W_4$ represents the hydrogen atom or $(C_1-C_8)$alkyl;

$W'_4$ represents a radical of formula —$(CH_2)_{s'}$-$Z_4$;

$Z_4$ represents the hydrogen atom, $(C_1-C_8)$alkyl optionally substituted by one or more identical or different substituents chosen from: $(C_1-C_6)$alkoxy, $(C_1-C_6)$alkylthio and hydroxy; $(C_2-C_6)$alkenyl; $(C_3-C_7)$cycloalkyl optionally substituted by one or more identical or different $(C_1-C_6)$alkyl substituents; cyclohexene; heteroaryl and aryl;

the aryl and heteroaryl radicals being optionally substituted by one or more identical or different radicals chosen of formula: —$(CH_2)_{s''}$—$V_4$—$Y_4$, hydroxy, halo, nitro and cyano;

$V_4$ represents —O—, —S—, —NH—C(O)—, —$NV_4'$— or a covalent bond;

$Y_4$ represents a hydrogen atom or a $(C_1-C_6)$alkyl radical optionally substituted by one or more identical or different halo radicals;

$V_4'$ represents a hydrogen atom or a $(C_1-C_6)$alkyl;

s" represents an integer from 0 to 4;

or $Z_4$ represents a radical of formula

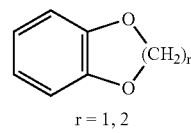

r = 1, 2 s and s' represent, independently, an integer from 0 to 6;

and i) when $R_3$ represents —C(O)-$Z'_3$ and $R_4$ represents a radical of formula —$(CH_2)_s$—$NW_4W'_4$ and $W_4$ and $W'_4$ represent, independently, the hydrogen atom or the $(C_1-C_6)$alkyl radical, then —$(CH_2)_s$ represents neither the ethylene radical nor the —$(CH_2)$—$CH((C_1-C_4)alkyl)$- radical and ii) when $R_3$ represents -$Z_{3c}$ and $Z_{3c}$ represents a phenyl or naphthyl radical, then phenyl and naphthyl are not substituted by cyano; and it being understood that when $R_3$ represents -$Z_{3d}$ then $Z_{3d}$ only represents one $(C_3-C_7)$ cycloalkyl or heterocycloalkyl radical; or a pharmaceutically acceptable salt thereof.

In the definitions given above, the expression halo represents the fluoro, chloro, bromo or iodo radical, preferably chloro, fluoro or bromo. The expression alkyl (unless otherwise specified), preferably represents a linear or branched alkyl radical having from 1 to 6 carbon atoms, such as the methyl, ethyl, propyl, isopropyl, butyl, isobutyl, sec-butyl and tert-butyl, pentyl or amyl, isopentyl, neopentyl, 2,2-dimethyl-propyl, hexyl, isohexyl or 1,2,2-trimethyl-propyl radicals. The term $(C_1-C_8)$alkyl designates a linear or branched alkyl radical having from 1 to 8 carbon atoms, such as the radicals containing from 1 to 6 carbon atoms as defined above but also heptyl, octyl, 1,1,2,2-tetramethyl-propyl, 1,1,3,3-tetramethyl-butyl. The term hydroxyalkyl designates the radicals in which the alkyl radical is as defined above such as for example hydroxymethyl, hydroxyethyl. By the expression alkyl substituted by hydroxy is meant any linear or branched alkyl chain, containing a hydroxy radical positioned along the chain; thus for a chain containing 3 carbon atoms and one hydroxy radical, HO—$(CH_2)_3$—, $CH_3$—CH(OH)—$CH_2$— and $CH_3$—$CH_2$—CH(OH)— can be cited as examples.

By alkenyl, unless otherwise specified, is meant a linear or branched alkyl radical containing from 1 to 6 carbon atoms and having at least one unsaturation (double bond), such as for example vinyl, allyl, propenyl, butenyl or pentenyl.

The term alkoxy designates the radicals in which the alkyl radical is as defined above such as for example the methoxy, ethoxy, propyloxy or isopropyloxy radicals but also linear, secondary or tertiary butoxy, pentyloxy. The term alkoxy-carbonyl preferably designates the radicals in which the alkoxy radical is as defined above such as for example methoxycarbonyl, ethoxycarbonyl. The term alkylthio designates the radicals in which the alkyl radical is as defined above such as for example methylthio, ethylthio. The term guanidine represents the —NHC(=NH)NH$_2$ radical.

The term (C$_3$-C$_7$)cycloalkyl designates a saturated carbon monocyclic system comprising from 3 to 7 carbon atoms, and preferably the cyclopropyl, cyclobutyl, cyclopentyl, cyclohexyl or cycloheptyl rings. The expression heterocycloalkyl designates a condensed monocyclic or bicyclic saturated system containing from 2 to 9 carbon atoms and at least one heteroatom. This radical can contain several identical or different heteroatoms. Preferably, the heteroatoms are chosen from oxygen, sulphur or nitrogen. As an example of a heterocycloalkyl, there may be mentioned the rings containing at least one nitrogen atom such as pyrrolidine, imidazolidine, pyrrazolidine, isothiazolidine, thiazolidine, isoxazolidine, oxazolidine, piperidine, piperazine, aspire (azacycloheptane), azacyclooctane, diazepane, morpholine, decahydroisoquinoline (or decahydroquinoline) but also the rings not containing any nitrogen atom such as tetrahydrofuran or tetrahydrothiophene. As an example of cycloalkyl or heterocycloalkyl substituted by oxy, for example pyrrolidinone and imidazolidinone can be mentioned.

The term heterobicycloalkyl designates a non-condensed saturated hydrocarbon bicyclic system containing from 5 to 8 carbon atoms and at least one heteroatom chosen from nitrogen, oxygen and sulphur. As an example of heterobicycloalkyl, aza-bicycloheptane and aza-bicyclooctane such as 7-aza-bicyclo[2,2,1]heptane, 2-aza-bicyclo[2,2,2]octane or 6-aza-bicyclo[3,2,1]octane can be mentioned.

The expression aryl represents an aromatic radical, constituted by a ring or condensed rings, such as for example the phenyl, naphthyl, fluorenyl or anthryl radical. The expression heteroaryl designates an aromatic radical, constituted by a ring or condensed rings, with at least one ring containing one or more identical or different heteroatoms chosen from sulphur, nitrogen or oxygen. As an example of a heteroaryl radical, there can be mentioned the radicals containing at least one nitrogen atom such as pyrrolyl, imidazolyl, pyrazolyl, isothiazolyl, thiazolyl, isoxazolyl, oxazolyl, triazolyl, thiadiazolyl, pyridyl, pyrazinryl, pyrimidyl, quinolyl, isoquinolyl, quinioxalirnyl, indolyl, dihydroindolyl, benzoxadiazoyl, carbazolyl, phenoxazinyl but also the radicals not containing a nitrogen atom such as thienyl, benzothienyl, furyl, benzofuryl dibenzofuryl, dihydrobenzofuryl, dibenzothienyl, thioxanthenyl, or pyranyl. The term aralkyl (arylalkyl) preferably designates the radicals in which the aryl and alkyl radicals are as defined above such as for example benzyl or phenethyl. As an example of an aryl or heteroaryl radical substituted by oxy, for example fluorenone, acridone, xanthenone, benzothienyl-dione, anthraquinone, thioxanthene, benzocoumarine can be mentioned.

In the present application also, the (CH$_2$)$_i$ radical (i integer being able to represent n, n', p, p', p", s, s' and s" as defined above), represents a linear or branched hydrocarbon chain, with i carbon atoms. Thus the —(CH$_2$)$_3$ radical can represent —CH$_2$—CH$_2$—CH$_2$— but also —CH(CH$_3$)—CH$_2$—, —CH$_2$—CH(CH$_3$)— or —C(CH$_3$)$_2$—.

According to the present Application also, when a radical has the formula —B-D-E with D representing for example —C(O)—NH—, this means that the carbon atom of —C(O)—NH—is bound to B and the nitrogen atom to E.

Preferably, the invention relates to compounds of formula I as defined above and characterized in that X represents —CH—; or a pharmaceutically acceptable salt thereof.

Preferably, the invention relates to compounds of formula I as defined above, characterized in that X represents —CH— and A represents —CH$_2$—, and more particularly
R$_1$ and R$_2$ represent, independently, a (C$_1$-C$_8$)alkyl radical;
R$_3$ represents -Z$_{3c}$, —C(R$_{Z3}$)(R'$_{Z3}$)-Z$_{3c}$, —C(R$_{Z3}$)(R'$_{Z3}$)-Z$_{3d}$, —C(R$_{Z3}$)(R'$_{Z3}$)—(CH$_2$)$_p$-Z$_{3d}$;
R$_4$ represents a radical of formula —(CH$_2$), —R'$_4$;
R'$_4$ represents a heterocycloalkyl containing at least one nitrogen atom and optionally substituted by (C$_1$-C$_6$) alkyl; or a radical of formula —NW$_4$W'$_4$;
W$_4$ represents the hydrogen atom or (C$_1$-C$_8$)alkyl;
W'$_4$ represents a radical of formula —(CH$_2$)$_{s'}$-Z$_4$;
Z$_4$ represents the hydrogen atom;
s represents an integer from 2 to 4; s' represents an integer from 0 to 4;

and preferably
the heterocycloalkyl represented by R'$_4$ is the piperidine ring;
R$_{Z3}$ and R'$_{Z3}$ represent the hydrogen atom;
Z$_{3c}$ represents the thienyl, furyl or phenyl radical,
the phenyl radical being substituted by one or more identical or different substituents chosen from: halo and —(CH$_2$)$_{p'}$—V$_3$—Y$_3$;
V$_3$ represents —O—, —C(O)—, —C(O)—O—, —C(O)—NR'$_3$— or a covalent bond;
R'$_3$ represents the hydrogen atom or a (C$_1$-C$_6$)alkyl radical;
Y$_3$ represents the hydrogen atom; a (C$_1$-C$_6$)alkyl radical optionally substituted by one or more identical or different halo radicals;
Z$_{3d}$ represents the (C$_1$-C$_6$)alkoxy-carbonyl or heterocycloalkyl radical, and preferably the heterocycloalkyl is imidazolidine; or a pharmaceutically acceptable salt thereof.

Preferably, the invention also relates to compounds of formula I as defined above, characterized in that X represents —CH— and A represents —C(O)—C(R$_a$)(R$_b$)— with R$_a$ and R$_b$ representing the methyl radical; and more particularly
R$_1$ and R$_2$ represent, independently, a (C$_1$-C$_8$)alkyl radical;
R$_3$ represents -Z$_{3c}$, —C(R$_{Z3}$)(R'$_{Z3}$)-Z$_{3c}$, —C(R$_{Z3}$)(R'$_{Z3}$)-Z$_{3d}$ or —C(R$_{Z3}$)(R'$_{Z3}$)—(CH$_2$)$_p$-Z$_{3d}$;
R$_4$ represents a radical of formula —(CH$_2$)$_s$—R'$_4$;
R'$_4$ represents a heterocycloalkyl containing at least one nitrogen atom and optionally substituted by (C$_1$-C$_6$) alkyl; or a radical of formula —NW$_4$W'$_4$;
W$_4$ represents the hydrogen atom or (C$_1$-C$_8$)alkyl;
W'$_4$ represents a radical of formula —(CH$_2$)$_{s'}$-$_{Z4}$;
Z$_4$ represents the hydrogen atom, the phenyl radical or a heteroaryl;
s represents an integer from 2 to 4; s' represents an integer from 0 to 4;

and preferably
R$_{Z3}$ and R'$_{Z3}$ represent, independently, the hydrogen atom;
Z$_{3c}$ represents a thienyl radical optionally substituted by (C$_1$-C$_6$)alkoxy-carbonyl; or phenyl substituted by one or more identical or different substituents chosen from: halo, nitro or —(CH$_2$)$_{p'}$—V$_3$—Y$_3$;
V$_3$ represents —O—, —C(O)—, —C(O)—O—, —C(O)—NR'$_3$— or a covalent bond;
Y$_3$ represents the hydrogen atom; a (C$_1$-C$_6$)alkyl radical optionally substituted by one or more identical or different halo radicals;
R'$_3$ represents the hydrogen atom;
Z$_{3d}$ represents a (C$_1$-C$_6$)alkoxy-carbonyl radical;
the heterocycloalkyl represented by R'$_4$ is piperidine;

the heteroaryl represented by $Z_4$ is pyridine; or a pharmaceutically acceptable salt thereof.

Preferably, the invention also relates to compounds of formula I as defined above, characterized in that X represents —CH— and A represents —C(O)—, and more particularly $R_3$ represents —C(O)-$Z'_3$;

$R_1$ and $R_2$ represent, independently, a ($C_1$-$C_8$)alkyl radical;

$Z'_3$ represents a phenyl radical optionally substituted by one or more identical or different substituents chosen from: halo, nitro and —(CH$_2$)$_{p''}$—V'$_3$—Y'$_3$ V'$_3$ represents —O—, —C(O)—O— or a covalent bond;

Y'$_3$ represents the hydrogen atom or a ($C_1$-$C_6$)alkyl radical;

p" represents the integer 0;

$R_4$ represents a radical of formula —(CH$_2$)$_s$—R'$_4$ and R'$_4$ represents a radical of formula —NW$_4$W'$_4$ W$_4$ represents the hydrogen atom or ($C_1$-$C_8$)alkyl;

W'$_4$ represents a radical of formula —(CH$_2$)$_{s'}$-$Z_4$ and $Z_4$ represents the hydrogen atom;

s represents an integer from 2 to 4; s' represents an integer from 0 to 4;

or a pharmaceutically acceptable salt thereof.

Preferably, the invention also relates to compounds of formula I as defined above, characterized in that X represents —CH— and A represents —C(O)—, and $R_1$ represents a hydrogen atom, a ($C_1$-$C_8$)alkyl radical optionally substituted by hydroxy, ($C_2$-$C_6$)alkenyl or a radical of formula —(CH$_2$)$_n$—$X_1$;

$R_2$ represents a ($C_1$-$C_8$)alkyl radical optionally substituted by hydroxy, ($C_2$-$C_6$)alkenyl or a radical of formula —(CH$_2$)$_n$—$X_1$;

each $X_1$ represents, independently, ($C_1$-$C_6$)alkoxy, ($C_3$-$C_7$) cycloalkyl, aryl or heteroaryl, the aryl radical being optionally substituted by one or more identical or different substituents chosen from: —(CH$_2$)$_{n'}$V$_1$—Y$_1$, halo;

V$_1$ represents —O— or a covalent bond;

Y$_1$ represents a ($C_1$-$C_6$)alkyl radical optionally substituted by one or more identical or different halo radicals; or aryl;

or $R_1$ and $R_2$ form together with the nitrogen atom to which they are attached, a heterocycloalkyl optionally substituted by one or more identical or different substituents chosen from: hydroxy, ($C_1$-$C_6$)alkyl optionally substituted by hydroxy, ($C_1$-$C_6$)alkoxy-carbonyl, heterocycloalkyl and —C(O)NV$_1$'Y$_1$' with V$_1$' and Y$_1$' independently representing the hydrogen atom or a ($C_1$-$C_6$) alkyl, or $R_1$ and $R_2$ together form a radical of formula:

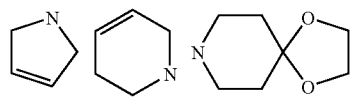

$R_3$ represents -$Z_3$, —C($R_{Z3}$)(R'$_{Z3}$)-$Z_3$ or —C($R_{Z3}$)(R'$_{Z3}$)— (CH$_2$)$_p$-$Z_3$;

$R_4$ represents a radical of formula —(CH$_2$)$_s$—R'$_4$

R'$_4$ represents a heterocycloalkyl containing at least one nitrogen atom and optionally substituted by ($C_1$-$C_6$) alkyl or aralkyl; a heteroaryl containing at least one nitrogen atom and optionally substituted by ($C_1$-$C_6$) alkyl; or a radical of formula —NW$_4$W'$_4$ W$_4$ represents the hydrogen atom or ($C_1$-$C_8$)alkyl;

W'$_4$ represents a radical of formula —(CH$_2$)$_{s'}$-$Z_4$;

$Z_4$ represents the hydrogen atom, ($C_3$-$C_7$)cycloalkyl or aryl;

s represents an integer from 0 to 5; s' represents an integer from 0 to 4;

and more particularly characterized in that they have at least one of the following characteristics:

the ($C_3$-$C_7$)cycloalkyl radical represented by $X_1$ is cyclopropyl;

the aryl radical represented by $X_1$ the phenyl radical;

the heteroaryl radical represented by $X_1$ is pyridine;

the heterocycloalkyl that $R_1$ and $R_2$ form together with the nitrogen atom to which they are attached is chosen from: pyrrolidine, piperidine, azepane, azacyclooctane, morpholine, piperazine and decahydroisoquinoline;

the heterocycloalkyl radical represented by R'$_4$, optionally substituted by $C_1$-$C_6$)alkyl or benzyl, is chosen from: pyrrolidinyl, piperidinyl, morpholinyl or piperazinyl;

the heteroaryl radical represented by R'$_4$ is the imidazolyl radical;

the cycloalkyl represented by $Z_4$ is chosen from: cyclopropyl, cyclobutyl, cyclopentyl, cyclohexyl or cycloheptyl;

the aryl represented by $Z_4$ is phenyl; or a pharmaceutically acceptable salt thereof.

Very preferably, the invention relates to compounds of formula I as defined above, characterized in that $R_4$ represents a radical of formula —(CH$_2$)$_s$—R'$_4$ with R'$_4$ representing the pyrrolidinyl or piperidinyl radical; or a radical of formula —NW$_4$W'$_4$ W$_4$ represents the hydrogen atom or ($C_1$-$C_8$)alkyl;

W'$_4$ represents a radical of formula —(CH$_2$)$_{s'}$-$Z_4$ with $Z_4$ representing the hydrogen atom;

s represents an integer from 2 to 4; s' represents an integer from 0 to 4; or a pharmaceutically acceptable salt thereof.

Very preferably also, the invention relates to compounds of formula I as defined above, characterized in that $R_1$ and $R_2$ represent, independently, a ($C_1$-$C_8$)alkyl radical; or a pharmaceutically acceptable salt thereof.

Preferably, the invention also relates to compounds of formula I as defined above, characterized in that X represents —CH—, A represents —C(O)—, and $R_3$ represents -$Z_3$ and $Z_3$ represents $Z_{3c}$, $Z_{3d}$ or $Z_{3e}$;

$Z_{3d}$ represents a ($C_3$-$C_7$)cycloalkyl or heterocycloalkyl radical;

and more particularly $Z_{3c}$ represents a heteroaryl radical chosen from thienyl, furyl, indolyl, dihydroindolyl, pyridyl, benzothienyl and benzofuryl; or an aryl radical chosen from phenyl, naphthyl and fluorenyl;

the heteroaryl radical being optionally substituted by one or more identical or different substituents chosen from: ($C_1$-$C_6$)alkyl-carbonyl and ($C_1$-$C_6$)alkoxy-carbonyl;

the aryl radical being optionally substituted by one or more identical or different substituents chosen from: halo, cyano, nitro, azido, ($C_1$-$C_6$)alkoxy-carbonyl-($C_1$-$C_6$) alkenyl, oxy, —SO$_2$—NR$_{31}$R$_{32}$, heterocycloalkyl, heteroaryl, or —(CH$_2$)$_{p'}$—V$_3$—Y$_3$;

$R_{31}$ and $R_{32}$ form together with the nitrogen atom to which they are attached, the piperidine ring;

V$_3$ represents —O—, —S—, —C(O)—, —C(O)—O—, —SO$_2$—, —SO$_2$NH—, —NR'$_3$—, —NR'$_3$—C(O)—, —C(O)—NR'$_3$—, —NH—C(O)—NR'$_3$— or a covalent bond;

$Y_3$ represents the hydrogen atom; a $(C_1-C_6)$alkyl radical optionally substituted by one or more identical or different halo radicals; phenyl; or benzyl;

$R'_3$ represents the hydrogen atom, a $(C_1-C_6)$alkyl or $(C_1-C_6)$alkoxy radical;

$Z_{3d}$ represents the cyclopropyl, cyclohexyl or piperidinyl radical, each being able to be substituted by a $(C_1-C_6)$ alkoxy-carbonyl radical; or a pharmaceutically acceptable salt thereof.

Preferably, the invention also relates to compounds of formula I as defined above, characterized in that X represents —CH—, A represents —C(O)—, and $R_3$ represents $-Z_3$ and $Z_3$ represents $Z_{3c}$, $Z_{3d}$ or $Z_{3e}$;

$Z_{3d}$ represents a $(C_3-C_7)$cycloalkyl or heterocycloalkyl radical;

and more particularly $Z_{3c}$ represents a heteroaryl radical chosen from thienyl, indolyl and benzothienyl; or an aryl radical chosen from phenyl and naphthyl;

the heteroaryl radical being optionally substituted by one or more oxy radicals;

the aryl radical being optionally substituted by one or more identical or different substituents chosen from: halo, nitro, heteroaryl or —$(CH_2)_{p'}$—$V_3$—$Y_3$;

$V_3$ represents —O—, —S—, —C(O)—, —C(O)—O—, —$SO_2$—, —$SO_2NH$—, —$NR'_3$—C(O)—, —C(O)—$NR'_3$—, —NH—C(O)—$NR'_3$— or a covalent bond;

$Y_3$ represents the hydrogen atom; a $(C_1-C_6)$alkyl radical optionally substituted by one or more identical or different halo radicals; a phenyl radical; or a benzyl radical;

$R'_3$ represents the hydrogen atom, a $(C_1-C_6)$alkyl or $(C_1-C_6)$alkoxy radical;

$Z_{3d}$ represents the cyclopropyl or piperidinyl radical, each optionally substituted by $(C_1-C_6)$alkoxy-carbonyl;

and preferably $Z_3$ represents $Z_{3c}$ or $Z_{3e}$;

$Z_{3c}$ represents a phenyl being optionally substituted by one or more identical or different substituents chosen from nitro and —$(CH_2)_{p'}$—$V_3$—$Y_3$;

$V_3$ represents —O—, —S—, —C(O)—, —C(O)—O—, —$SO_2$—, —$SO_2NH$—, —$NR'_3$—C(O)—, —C(O)—$NR'_3$— or a covalent bond;

$Y_3$ represents the hydrogen atom; a $(C_1-C_6)$alkyl radical; a phenyl radical; or a benzyl radical;

$R'_3$ represents the hydrogen atom;

$Z_{3e}$ represents

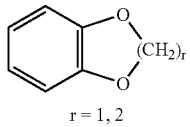

r = 1, 2 or a pharmaceutically acceptable salt thereof.

Preferably, the invention also relates to compounds of formula I as defined above, characterized in that X represents —CH—, A represents —C(O)—, $R_3$ represents —C($R_{Z3}$)($R'_{Z3}$)-$Z_3$ and $Z_3$ represents $Z_{3b}$, $Z_{3c}$, $Z_{3d}$ or $Z_{3e}$; or a pharmaceutically acceptable salt thereof.

Very preferably, the invention also relates to compounds of formula I as defined above, characterized in that X represents —CH—, A represents —C(O)—, and $R_3$ represents —C($R_{Z3}$)($R'_{Z3}$)-$Z_3$ and $Z_3$ represents $Z_{3b}$ or $Z_{3c}$;

$R_{Z3}$ and $R'_{Z3}$ represent the hydrogen atom;

and more particularly $Z_{3b}$ represents a $(C_1-C_6)$alkoxy radical;

$Z_{3c}$ represents a heteroaryl radical chosen from thienyl, furyl, pyridyl, benzothienyl and dihydrobenzofuryl; or an aryl radical chosen from phenyl and naphthyl, the aryl radical being optionally substituted by one or more identical or different substituents chosen from: halo or —$(CH_2)_{p'}$—$V_3$—$Y_3$;

$V_3$ represents —O—, —S—, —C(O)—, —C(O)—O—, —$SO_2$—, —$SO_2NH$—, —$NR'_3$—C(O)—, —C(O)—$NR'_3$—, $Y_3$ represents the hydrogen atom; a $(C_1-C_6)$alkyl radical optionally substituted by one or more identical or different halo radicals;

$R'_3$ represents the hydrogen atom;

or a pharmaceutically acceptable salt thereof.

Very preferably, the invention relates to compounds of formula I as defined above, characterized in that X represents —CH—, A represents —C(O)—, and $R_3$ represents —C($R_{Z3}$)($R'_{Z3}$)-$Z_3$ and $Z_3$ represents $Z_{3b}$ or $Z_{3c}$;

$R_{Z3}$ and $R'_{Z3}$ represent the hydrogen atom;

and more particularly $Z_{3b}$ represents a $(C_1-C_6)$alkoxy radical;

$Z_{3c}$ represents a heteroaryl radical chosen from thienyl, furyl, dihydrobenzofuryl; or a phenyl radical;

the phenyl radical being optionally substituted by one or more identical or different substituents chosen from: nitro or —$(CH_2)_p V_3$—$Y_3$;

$V_3$ represents —O—, —S—, —C(O)—, —C(O)—O—, —$SO_2$—, —$SO_2NH$—, —C(O)—$NR'_3$—, $Y_3$ represents the hydrogen atom; or a $(C_1-C_6)$alkyl radical optionally substituted by one or more identical or different halo radicals;

$R'_3$ represents the hydrogen atom;

and preferably $Z_3$ represents $Z_{3c}$;

$Z_{3c}$ represents a furyl or phenyl radical, the phenyl radical being optionally substituted by one or more identical or different substituents of formula —$(CH_2)_p V_3$—$Y_3$;

$V_3$ represents —O—, —S—, —C(O)—, —C(O)—O—, —$SO_2$—, —$SO_2NH$—, —C(O)—$NR'_3$—, $Y_3$ represents the hydrogen atom; or a $(C_1-C_6)$alkyl radical optionally substituted by one or more identical or different halo radicals;

$R'_3$ represents the hydrogen atom;

or a pharmaceutically acceptable salt thereof.

Very preferably, the invention also relates to compounds of formula I as defined above, characterized in that X represents —CH—, A represents —C(O)—, and $R_3$ represents —C($R_{Z3}$)($R'_{Z3}$)-$Z_3$ and $Z_3$ represents $Z_{3d}$ or $Z_{3e}$;

$R_{Z3}$ and $R'_{Z3}$ represent the hydrogen atom or $(C_1-C_6)$alkyl;

$Z_{3d}$ represents a $(C_1-C_6)$alkoxy-carbonyl, $(C_3-C_7)$cycloalkyl or heterocycloalkyl radical;

$Z_{3e}$ represents

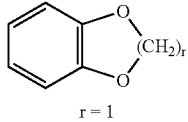

r = 1 and more particularly
$Z_{3d}$ represents a $(C_1-C_6)$alkoxy-carbonyl, cyclohexyl or a tetrahydrofuranyl radical; or a pharmaceutically acceptable salt thereof.

Very preferably, the invention also relates to compounds of formula. I as defined above, characterized in that X represents —CH—, A represents —C(O)—, and
$R_3$ represents —C($R_{Z3}$)($R'_{Z3}$)-$Z_3$ and $Z_3$ represents $Z_{3d}$ or $Z_{3e}$;
$Z_{3d}$ represents a $(C_1-C_6)$alkoxy-carbonyl radical;
$Z_{3e}$ represents

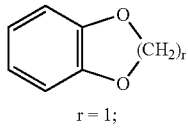

r = 1;

and preferably $Z_3$ represents $Z_{3e}$

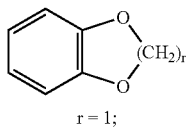

r = 1;

or a pharmaceutically acceptable salt thereof.

Preferably, the invention also relates to compounds of formula I as defined above, characterized in that X represents —CH—, A represents —C(O)—, $R_3$ represents —C($R_{Z3}$)($R'_{Z3}$)—(CH$_2$)$_p$-$Z_3$ and $Z_3$ represents $Z_{3b}$, $Z_{3c}$ or $Z_{3d}$; or a pharmaceutically acceptable salt thereof.

Very preferably, the invention relates to compounds of formula I as defined above, characterized in that X represents —CH—, A represents —C(O)—, and
$R_3$ represents —C($R_{Z3}$)($R'_{Z3}$)—(CH$_2$)$_p$-$Z_3$ and $Z_3$ represents $Z_{3b}$;

and more particularly
$R_{Z3}$ and $R'_{Z3}$ represent, independently, the hydrogen atom or a $(C_1-C_6)$alkyl radical;
$Z_{3b}$ represents a $(C_1-C_6)$alkoxy, $(C_1-C_6)$alkylthio or di(($C_1-C_6$)alkyl)amino radical; or a pharmaceutically acceptable salt thereof.

Very preferably, the invention also relates to compounds of formula I as defined above, characterized in that X represents —CH—, A represents —C(O)—, and $R_3$ represents —C($R_{Z3}$)($R'_{Z3}$)—(CH$_2$)$_p$-$Z_3$ and $Z_3$ represents $Z_{3b}$;

and more particularly
$R_{Z3}$ and $R'_{Z3}$ represent, independently, the hydrogen atom or a $(C_1-C_6)$alkyl radical;
$Z_{3b}$ represents a $(C_1-C_6)$alkoxy or $(C_1-C_6)$alkylthio radical; or a pharmaceutically acceptable salt thereof.

Very preferably, the invention also relates to compounds of formula I as defined above, characterized in that X represents —CH—, A represents —C(O)—, and
$R_3$ represents —C($R_{Z3}$)($R'_{Z3}$)—(CH$_2$)$_p$-$Z_3$ and $Z_3$ represents $Z_{3c}$ or $Z_{3d}$;

and more particularly
$R_{Z3}$ and $R'_{Z3}$ represent, independently, the hydrogen atom or a $(C_1-C_6)$alkyl radical;
$Z_{3c}$ represents an indolyl or phenyl radical;
the phenyl radical being optionally substituted by one or more identical or different substituents chosen from: halo and —(CH$_2$)$_{p'}$—V$_3$—Y$_3$;
$V_3$ represents —SO$_2$NH—,
$Y_3$ represents the hydrogen atom; or a $(C_1-C_6)$alkyl radical;
$Z_{3d}$ represents a $(C_1-C_6)$alkoxy-carbonyl, amino-carbonyl, $(C_1-C_6)$alkyl-amino-carbonyl, $(C_1-C_6)$alkyl-C(O)—NH—, or heterocycloalkyl radical optionally substituted by oxy, and preferably piperidinyl, morpholinyl, pyrrolidine or imidazolidinyl; or a pharmaceutically acceptable salt thereof.

Very preferably, the invention also relates to compounds of formula I as defined above, characterized in that X represents —CH—, A represents —C(O)—, and
$R_3$ represents —C($R_{Z3}$)($R'_{Z3}$)—(CH$_2$)$_p$-$Z_3$ and $Z_3$ represents $Z_{3c}$ or $Z_{3d}$;

and more particularly
$Z_3$ represents $Z_{3d}$;
$R_{Z3}$ and $R'_{Z3}$ represent, independently, the hydrogen atom or a $(C_1-C_6)$alkyl radical;
$Z_{3d}$ represents a $(C_1-C_6)$alkoxy-carbonyl, amino-carbonyl, $(C_1-C_6)$alkylamino-carbonyl, $(C_1-C_6)$alkyl-C(O)—NH— or heterocycloalkyl radical, and preferably pyrrolidine or imidazolidine, optionally substituted by oxy; or a pharmaceutically acceptable salt thereof.

In the present application, the symbol ->* corresponds to the attachment point of the radical. When the attachment site is not specified on the radical, this means that the attachment is carried out on one of the sites available on this radical for such an attachment.

Following the definitions of the variable groups A, X, $R_1$, $R_2$, $R_3$ and $R_4$, the compounds according to the invention can be prepared in liquid phase according to the different procedures A to G described below.

A. Preparation According to Reaction Diagram A:

The compounds of formula (I) according to the invention in which A represents —C(O)—, can be prepared according to the following diagram A:

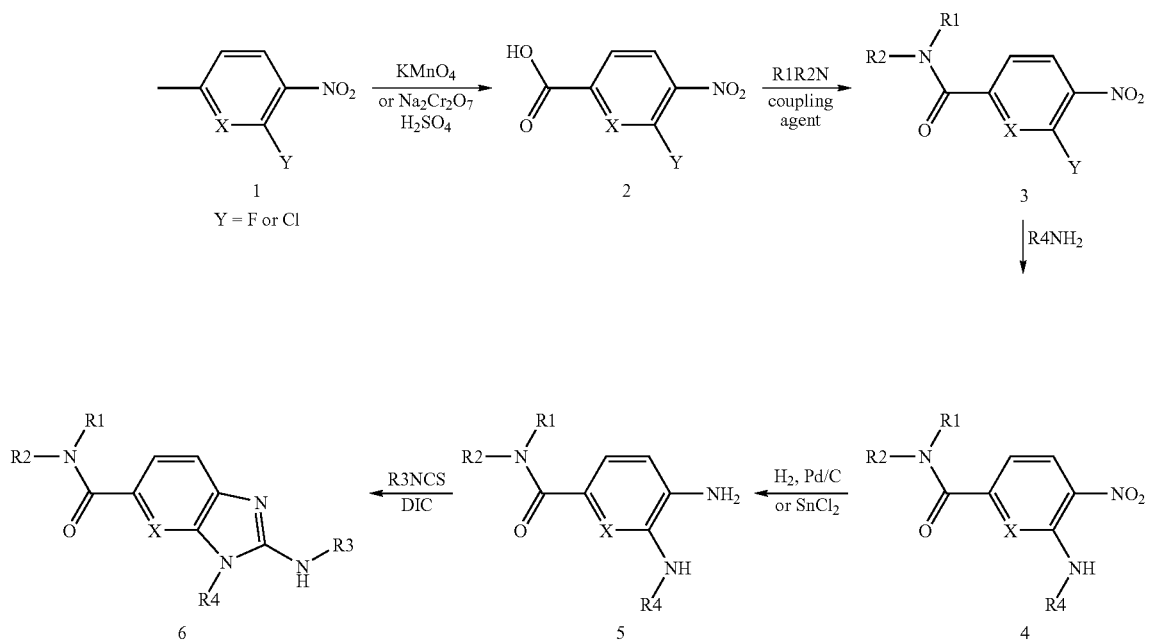

As described in diagram A, the methylated derivative (1) (for X=C commercial compound; for X=N compound prepared according to the procedure of Baumgarten et al, *J. Am. Chem. Soc,* 1952, 74, 3828-3831, from 6-methyl-3-nitro-pyridin2-amine) can be oxidized to carboxylic acid (2) by an aqueous solution of potassium permanganate at a temperature of 100° C. for 3 to 6 hours (according to procedure of Schmelkes et al., *J. Am. Chem. Soc,* 1944, 1631), or by an aqueous solution of sodium dichromate in the presence of sulphuric acid at a temperature of 20-90° C. for 1 to 3 hours (according to procedure of Howes et al., *European J. Med. Chem.,* 1999, 34, 225-234). The carboxylic acid (2) can be coupled with a primary or secondary amine in the presence of a coupling agent such as diisopropylcarbodiimide (DIC), dicyclohexylcarbodiimide (DCC), 1,3-dimethylaminopropyl)-3-ethylcarbodiimide hydrochloride (EDC) or carbonyldiimidazole (CDI) with or without 1-hydroxybenzotriazole (HOBt) in an inert organic solvent such as methylene chloride, tetrahydrofuran or dimethylformamide at ambient temperature for 3 to 24 hours in order to produce the corresponding amide (3). Treatment of the fluorinated or chlorinated derivative (3) by a primary amine in the presence of an inorganic base such as caesium or potassium carbonate in an inert organic solvent such as dimethylformamide or acetonitrile at a temperature of 20-100° C. for 2 to 48 hours leads to derivative (4). The nitro function of compound (4) is reduced by treatment with dihydrate tin chloride in an inert solvent such as ethyl acetate or dimethylformamide at a temperature of 60-80° C. for 3 to 15 hours, or by catalytic hydrogenation in the presence of 10% palladium on carbon in an inert solvent such as methanol, ethanol, ethyl acetate or a mixture of these solvents, at a temperature of 18-25° C., for 2 to 8 hours in order to produce the dianiline (5). The derivative (5) is then treated with an isothiocyanate in the presence of a coupling agent supported or not supported on a resin such as diisopropylcarbodiimide or dicyclohexylcarbodiimide or N-methylcyclohexylcarbodiimide N-methyl polystyrene resin in an inert solvent such as tetrahydrofuran, methylene chloride, or chloroform at a temperature of 20-70° C. for 2 to 72 hours in order to produce derivative (6). Alternatively, the derivative (5) can be treated with an isothiocyanate in an inert solvent such as tetrahydrofuran, methylene chloride, chloroform or ethanol at a temperature of 20-80° C. for 1-16 hours then the resultant thiourea can be treated by methyl iodide or yellow mercury (II) oxide in the presence of a catalytic quantity of sulphur in a polar solvent such as methanol or ethanol for 2 to 24 hours at a temperature of 20-80° C. in order to produce (6). Compound (6) can be isolated either by flash chromatography on silica gel, or by addition to the reaction mixture of a nucleophilic reagent supported on a polymer such as for example an aminomethylpolystyrene resin and/or an electrophilic reagent supported on a polymer such as for example methylisothiocyanate-polystyrene resin, followed by filtration and evaporation of the filtrate.

EXAMPLE A1 methyl 4-[(1-(3-aminopropyl)-6-{[bis(3-methylbutyl)amino]carbonyl}-1H-benzimidazol-2-yl)amino] benzoate dihydrochloride

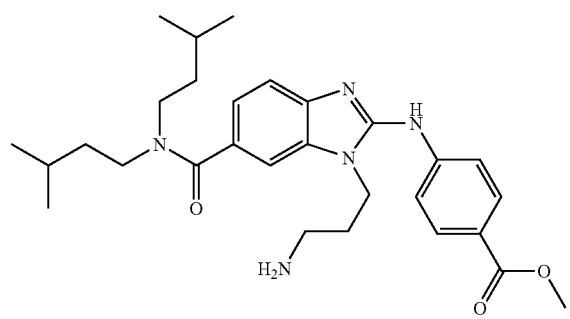

Stage 1: 3-fluoro-4-nitrobenzoic acid

A mixture of 3-fluoro-4-nitrotoluene (10 g, 1 eq) and potassium permanganate (25.5 g, 2.5 eq) in water (1 L) is heated under reflux for 6 hours then cooled down to ambient temperature. The mixture is filtered on celite and the aqueous phase is washed twice with diethyl ether (2×300 ml). The aqueous phase is acidified, at 0° C., with a solution of concentrated hydrochloric acid then concentrated under reduced pressure at 40° C. to a volume of approximately 300 ml. The precipitate formed is filtered then washed with petroleum ether and dried in order to produce the expected compound in the form of a white solid (6.9 g; 58% yield).

NMR ($^1$H, 400 MHz, DMSO-$d_6$): δ 7.93 (m, 2H), 8.25 (m, 1H), 13.95 (m, 1H).

Stage 2: 3-fluoro-N,N-bis(3-methylbutyl)-4-nitrobenzamide 1-(3-dimethylaminopropyl)-3-ethylcarbodiimide hydrochloride (EDC) (4.4 g, 1.1 eq) in solution in chloroform (25 ml) and 1-hydroxybenzotriazole (HOBt) (3.05 g, 1.1 eq) in solution in THF (40 ml) are added successively to 3-fluoro-4-nitrobenzoic acid (3.8 g, 1 eq) in solution in anhydrous THF (30 ml). The mixture is stirred for 1 hour at a temperature of approximately 20° C. then diisoamylamine (3.6 g, 1.1 eq) in solution in THF (30 ml) is added. After stirring for 16 hours at a temperature of approximately 20° C., the reaction mixture is concentrated under reduced pressure at 40° C. The residue is taken up in dichloromethane (200 ml) and water (70 ml). After decantation and extractions, the combined organic phases are washed with salt water, dried over $Na_2SO_4$ then concentrated under reduced pressure at 40° C. Purification of the compound by flash chromatography on silica gel (eluent: heptane/ethyl acetate 9:1) produces the expected compound in the form of a yellow oil (4.3 g; 65% yield).

MS/LC: calculated MM=324.4; m/z=325.2 (MH+)

NMR ($^1$H, 400 MHz, DMSO-$d_6$): δ 0.69 (m, 6H), 0.93 (m, 6H), 1.35-1.60 (m, 6H), 3.09 (m, 2H), 3.41 (m, 2H), 7.38 (d, 1H), 7.63 (d, 1H), 8.21 (t, 1H).

Stage 3: tert-butyl 3-[(5-{[bis(3-methylbutyl)amino]carbonyl}-2-nitrophenyl)amino]propylcarbamate A mixture of 3-fluoro-N,N-bis(3-methylbutyl)-4-nitrobenzamide (1.6 g, 1 eq), N-Boc-1,3-diaminopropane (0.9 g, 1.2 eq) and potassium carbonate (1.35 g, 2 eq) in acetonitrile (80 ml) is heated under reflux for 5 hours then concentrated under reduced pressure at 40° C. The residue is taken up in dichloromethane (100 ml) and water (40 ml). After decantation and extractions, the combined organic phases are washed with salt water, dried over $Na_2SO_4$ then concentrated under reduced pressure at 40° C. Purification of the residue by flash chromatography on silica gel (eluent:heptane/ethyl acetate 8:2 to 6:4) produces the expected compound in the form of a yellow oil (2.2 g; 96% yield).

MS/LC: calculated MM=478.6; m/z =479.2 (MH+)

NMR ($^1$H, 400 MHz, DMSO-$d_6$): δ 0.68 (m, 6H), 0.92 (m, 6H), 1.36 (s, 9H), 1.31-1.69 (m, 8H), 3.0 (m, 2H), 3.09 (m, 2H), 3.38 (m, 4H), 6.53 (d, 1H), 6.88 (m, 2H), 8.10 (d, 1H), 8.26 (m, 1H).

Stage 4: tert-butyl 3-[(2-amino-5-{[bis(3-methylbutyl)amino]carbonyl}phenyl)amino]propylcarbamate Tert-butyl 3-[(5-{[bis(3-methylbutyl)amino]carbonyl}-2-nitrophenyl)amino]propylcarbamate (1.65 g) in solution in a mixture of ethyl acetate/ethanol 2:1 (130 ml), and 10% palladium on carbon (165 mg) are introduced into an autoclave. After stirring for 3 hours under a hydrogen atmosphere (3 bar) at a temperature of approximately 20° C., the catalyst is eliminated by filtration on celite and the filtrate is concentrated under reduced pressure at 40° C. in order to produce the expected compound in the form of an oil (1.35 g; 89% yield).

MS/LC: calculated MM=448.6; m/z=449.2 (MH+)

NMR ($^1$H, 400 MHz, DMSO-$d_6$): δ0.81 (m, 12H), 1.37 (s, 9H), 1.32-1.53 (m, 6H), 1.70 (m, 2H), 3.0 (m, 4H), 3.26 (m, 4H), 4.47 (m, 1H), 4.79 (s, 2H), 6.35-6.51 (m, 3H), 6.85 (m, 1H).

Stage 5: methyl 4-[(6-{[bis(3-methylbutyl)amino]carbonyl}-1-{3-[(tert-butoxycarbonyl)amino]propyl}-1H-benzimidazol-2-yl)amino]benzoate 4-methoxycarbonylphenyl isothiocyanate (327 mg, 1.5 eq) and N-methylcyclohexylcarbodiimide-N-methyl-polystyrene resin (acquired from Novabiochem; charge 1.9 mmol/g; 1.75 g, 3 eq) are added successively to a solution of tert-butyl-3-[(2-amino-5-{[bis(3-methylbutyl)amino]carbonyl}phenyl)amino]propylcarbamate (500 mg, 1 eq) in tetrahydrofuran (30 ml). The mixture is heated under reflux for 17 hours then cooled down to ambient temperature and aminomethylpolystyrene resin (acquired from Novabiochem, 2 eq) is added. After stirring for 4 hours at ambient temperature, the mixture is filtered on frit and the filtrate is concentrated under reduced pressure at 40° C. Purification of the residue by flash chromatography on silica gel (eluent: heptane/ethyl acetate 1:1) produces the expected compound in the form of a white solid (409 mg; 60% yield).

MS/LC: calculated MM=607.8; m/z=608.1 (MH+)

NMR ($^1$H, 400 MHz, DMSO-$d_6$): δ0.65-0.90 (m, 12H), 1.36 (s, 9H), 1.31-1.44 (m, 6H), 1.81 (m, 2H), 3.0 (m, 2H), 3.26-3.39 (m, 4H), 3.82 (s, 3H), 4.29 (m, 2H), 6.95 (m, 1H), 7.04 (d, 1H), 7.36 (s, 1H), 7.44 (d, 1H), 7.94 (AB, 2H), 8.02 (AB, 2H), 9.34 (s, 1H).

Stage 6: methyl 4-[(1-(3-aminopropyl)-6-{[bis(3-methylbutyl)amino]carbonyl}-1H-benzimidazol-2-yl)amino]benzoate dihydrochloride A solution of hydrochloric acid in dioxane (4N, 2 ml) is added to a solution of methyl 4-[(6-{[bis(3-methylbutyl)amino]carbonyl}-1-{3-[(tert-butoxycarbonyl)amino]propyl}-1H-benzimidazol-2-yl)amino]benzoate (180 mg) in ethyl acetate (2 ml). After stirring for 1 hour at a temperature of approximately 20° C., the mixture is concentrated under reduced pressure at 40° C. The solid obtained is washed with ethyl ether and dried (165 mg; 96% yield).

MS/LC: calculated MM=507.7; m/z=508.3 (MH+)

NMR ($^1$H, 400 MHz, DMSO-$d_6$): δ0.63-0.98 (m, 12H), 1.45 (m, 6H), 2.08 (m, 2H), 2.98 (m, 2H), 3.12-3.45 (m, 4H), 3.85 (s, 3H), 4.59 (m, 2H), 7.20 (d, 1H), 7.46 (d, 1H), 7.67 (s, 1H), 7.90 (m, 2H), 8.01-8.07 (m, 5H), 11.08 (m, 1H).

EXAMPLE A2

2-[(4-acetylphenyl)amino]-N,N-bis(3-methylbutyl)-1-(3-piperidin-1-ylpropyl)-1H-benzimidazole-6-carboxamide dihydrochloride

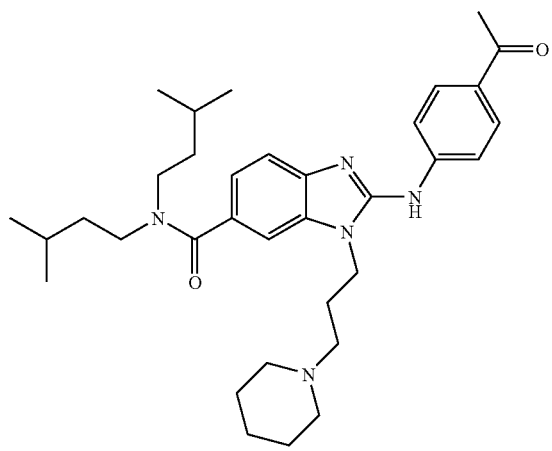

Stage 1: N,N-bis(3-methylbutyl)-4-nitro-3-[(3-piperidin-1-ylpropyl)amino]benzamide A mixture of 3-fluoro-N,N-bis(3-methylbutyl)-4-nitrobenzamide (430 mg, 1 eq, prepared according to Example A1), 3-piperidino-propylamine (212 mg, 1.1 eq) and potassium carbonate (365 mg, 2 eq) in acetonitrile (10 ml) is heated under reflux for 3 hours then concentrated under reduced pressure at 40° C. The residue is taken up in dichloromethane (50 ml) and water (20 ml). After decantation and extractions, the combined organic phases are washed with salt water, dried over $Na_2SO_4$ then concentrated under reduced pressure at 40° C. Purification of the residue by flash chromatography on silica gel (eluent: ethyl acetate 100%) produces the expected compound in the form of a yellow oil (460 mg; 78% yield).

MS/LC: calculated MM=446.6; m/z=447.3 (MH+)

NMR ($^1$H, 400 MHz, DMSO-$d_6$): δ0.68 (d, 6H), 0.92 (d, 6H), 1.31-1.69 (m, 12H), 1.74 (m, 2H), 2.32 (m, 6H), 3.10 (m, 2H), 3.38 (m, 4H), 6.53 (d, 1H), 6.91 (m, 1H), 8.09 (d, 1H), 8.44 (t, 1H).

Stage 2: 2-[(4-acetylphenyl)amino]-N,N-bis(3-methylbutyl)-1-(3-piperidine-1-ylpropyl)-1H-benzimidazole-6-carboxamide dihydrochloride N,N-bis(3-methylbutyl)-4-nitro-3-[(3-piperidin-1-yl-propyl)amino]benzamide (44 mg) in solution in a mixture of ethyl acetate/ethanol 2:1 (1.5 ml), and 10% palladium on carbon (5 mg) are introduced into a haemolysis tube placed in an autoclave. After stirring for 3 hours under a hydrogen atmosphere (3 bar) at a temperature of approximately 20° C., the catalyst is eliminated by filtration on celite and the filtrate is concentrated under reduced pressure at 40° C. 4-acetylphenyl isothiocyanate (27 mg, 1.5 eq) and N-methylcyclohexylcarbodiimide-N-methyl-polystyrene resin (acquired from Novabiochem; charge 1.9 mmol/g; 158 mg, 3 eq) are added successively to the aniline thus obtained, in solution in tetrahydrofuran (2 ml). The mixture is heated under reflux for 18 hours then cooled down to ambient temperature and aminomethylpolystyrene resin (acquired from Novabiochem, 2 eq) is added. After stirring for 4 hours at ambient temperature, the mixture is filtered on frit and the filtrate is concentrated under reduced pressure at 40° C. Purification of the residue by flash chromatography on silica gel (eluent: 100% dichloromethane to dichloromethane/methanol 9:1) produces the expected compound in the form of a base. The corresponding hydrochloride salt is formed by adding a 1N solution of hydrochloric acid in ether. The precipitate obtained is filtered and dried in order to produce the expected dihydrochloride compound.

MS/LC: calculated MM=559.8; m/z=560.3 (MH+)

NMR ($^1$H, 400 MHz, DMSO-$d_6$): δ0.68 (m, 6H), 0.94 (m, 6H), 1.31-1.56 (m, 6H), 1.57-1.90 (m, 6H), 2.28 (m, 2H), 2.60 (s, 3H), 2.86 (m, 2H), 3.21 (m, 4H), 3.40 (m, 4H), 4.62 (t, 2H), 7.24 (AB, 1H), 7.47 (AB, 1H), 7.76 (s, 1H), 7.81 (m, 2H), 8.07 (m, 2H), 10.40 (s, 1H), 11.64 (m, 1H).

EXAMPLE A3

2-(cyclohexylamino)-1-[3-(dimethylamino)propyl]-N,N-bis(3-methylbutyl)-1H-benzimidazole-6-carboxamide dihydrochloride

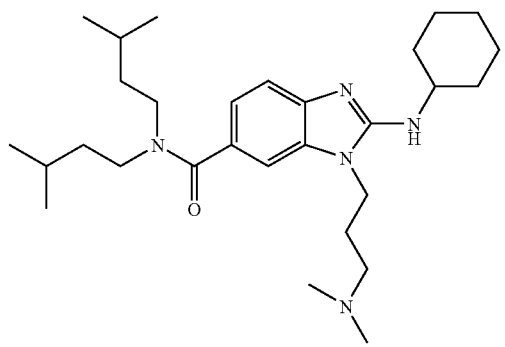

Stage 1: 3-{[3-(dimethylamino)propyl]amino}-N,N-bis(3-methylbutyl)-4-nitrobenzamide A mixture of 3-fluoro-N,N-bis(3-methylbutyl)-4-nitrobenzamide (2.5 g, 1 eq, prepared according to Example A1), 3-diethylamino-propylamine (877 mg, 1.1 eq) and potassium carbonate (2.13 g, 2 eq) in acetonitrile (80 ml) is heated under reflux for 5 hours then concentrated under reduced pressure at 40° C. The residue is taken up in dichloromethane (130 ml) and water (50 ml). After decantation and extractions, the combined organic phases are washed with salt water, dried over $Na_2SO_4$ then concentrated under reduced pressure at 40° C. Purification of the residue by flash chromatography on silica gel (eluent:dichloromethane/methanol 9:1) produces the expected compound in the form of a yellow oil (2.1 g mg; 68% yield).

MS/LC: calculated MM=406.6; m/z=407.3 (MH+)

NMR ($^1$H, 400 MHz, DMSO-$d_6$): δ0.68 (d, 6H), 0.92 (d, 6H), 1.31-1.51 (m, 5H), 1.59 (m, 1H), 1.74 (m, 2H), 2.14 (s, 6H), 2.31 (t, 2H), 3.11 (m, 2H), 3.39 (m, 4H), 6.53 (d, 1H), 6.90 (s, 1H), 8.09 (d, 1H), 8.57 (t, 1H).

Stage 2: 2-(cyclohexylamino)-1-[3-(dimethylamino) propyl]-N,N-bis(3-methylbutyl)-1H-benzimidazole-6-carboxamide dihydrochloride 3-{[3-(dimethylamino)propyl]amino}-N,N-bis(3-methylbutyl)-4-nitrobenzamide (81 mg) in solution in a mixture of ethyl acetate/ethanol 2:1 (4 ml), and 10% palladium on carbon (8 mg) are introduced into a haemolysis tube placed in an autoclave. After stirring for 3 hours under a hydrogen atmosphere (3 bar) at a temperature of approximately 20° C., the catalyst is eliminated by filtration on celite and the filtrate is concentrated under reduced pressure at 40° C. Cyclohexyl isothiocyanate (58 mg, 2 eq) is successively added to the aniline thus obtained, in solution in tetrahydrofuran (2 ml). The mixture is heated under reflux for 3 hours then cooled down to ambient temperature and concentrated under reduced pressure. Yellow mercury (II) oxide (87 mg, 2 eq) and sulphur (1.4 mg) are successively added to the thiourea thus formed in solution in ethanol (3 ml). The mixture is heated for 17 hours under reflux then cooled down to ambient temperature and filtered on microfibre paper. The filtrate is concentrated under reduced pressure. Purification of the residue by flash chromatography on silica gel (eluent:100% dichloromethane to dichloromethane/methanol 9:1) produces the expected compound in the form of a base. The corresponding hydrochloride salt is formed by adding a 1N solution of hydrochloric acid in ether. The precipitate obtained is filtered and dried in order to produce the expected dihydrochloride compound (87 mg, 78% yield).

MS/LC: calculated MM=483.7; m/z=484.4 (MH+)

NMR ($^1$H, 400 MHz, DMSO-d$_6$): δ0.58-1.03 (m, 12H), 1.18 (m, 1H), 1.30-1.71 (m, 11H), 1.80 (m, 2H), 2.01 (m, 4H), 2.73 (s, 6H), 3.14 (m, 4H), 3.25 (m, 2H), 3.71 (m, 1H), 4.32 (m, 2H), 7.16 (m, 1H), 7.39 (m, 1H), 7.54 (m, 1H), 8.42 (m, 1H), 10.40 (m, 1H), 13.41 (m, 1H).

Preparation of Non-Commercial isothiocyanates

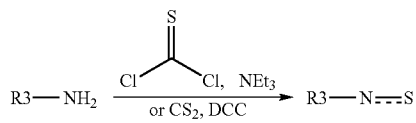

A primary amine can be converted to isothiocyanate, by treatment with thiophosgene in the presence of a tertiary base such as triethylamine, in an aprotic solvent such as dichloromethane or tetrahydrofuran, at a temperature of 0-20° C. for 0.3 to 2 hours, or alternatively by treatment with carbon disulphide and cyclohexylcarbodiimide supported or not supported on a resin in an aprotic solvent such as dichloromethane or tetrahydrofuran, at a temperature of 0-70° C. for 0.3 to 15 hours.

N-(4-isothiocyanatophenyl)acetamide

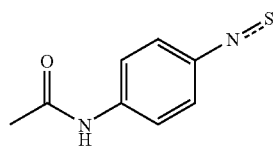

Thiophosgene (0.56 ml, 1.1 eq) is added dropwise to a solution cooled down to 0° C., of N-(4-aminophenyl)acetamide (1 g, 1 eq) and triethylamine (2.8 ml, 3 eq) in tetrahydrofuran (130 ml). The mixture is stirred for 30 minutes at 0° C. then the cold bath is removed and the stirring is continued for another 30 minutes. Water (70 ml) and diethyl ether (150 ml) are added to the mixture. After decantation and extractions, the organic phases are combined, washed with salt water, dried over Na$_2$SO$_4$ then concentrated under reduced pressure at 40° C. The solid obtained is recrystallized from a dichloromethane/petroleum ether mixture (0.95 g; 75% yield).

NMR ($^1$H, 400 MHz, DMSO-d$_6$): δ 2.04 (s, 3H), 7.35 (AB, 2H), 7.63 (AB, 2H), 10.14 (s, 1H).

The following isothiocyanates were prepared according to the same procedure as that described for N-(4-isothiocyanatophenyl)acetamide:

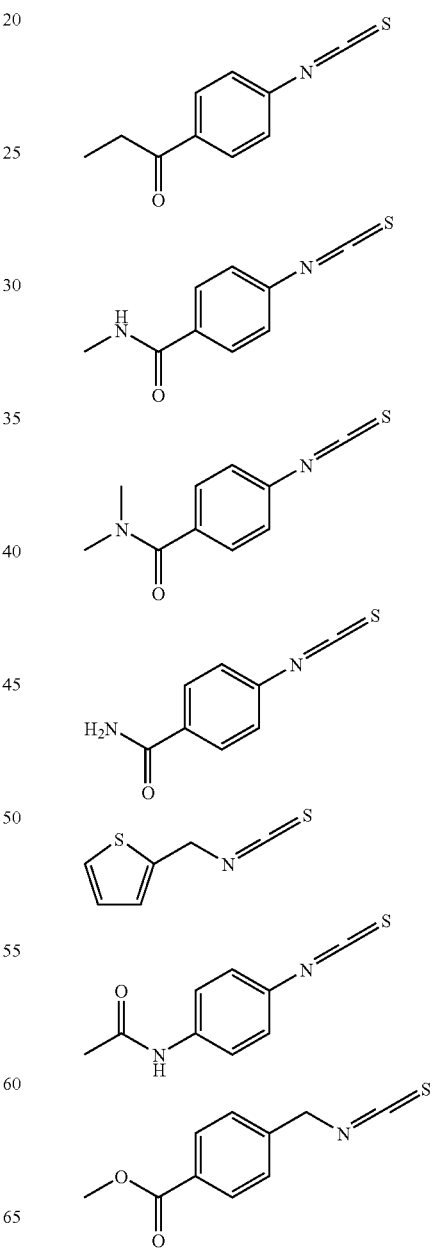

-continued
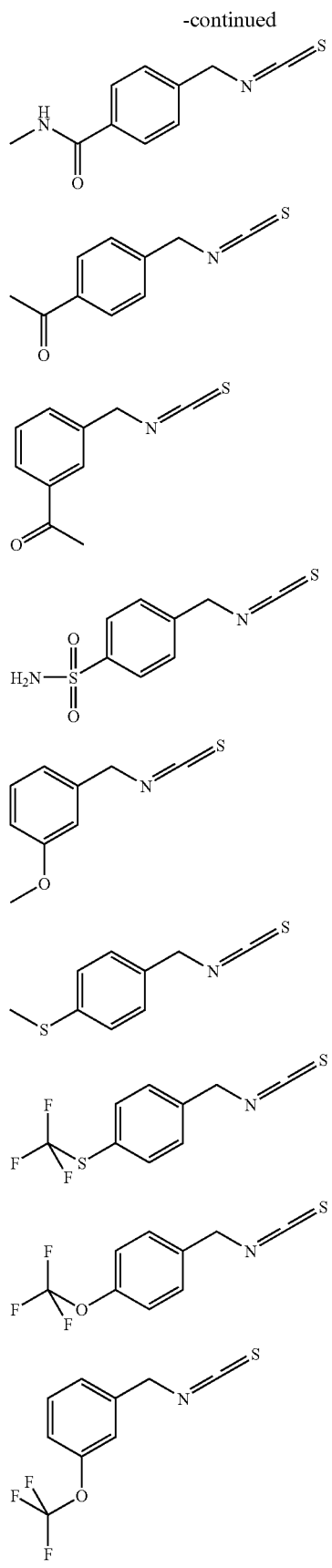
-continued
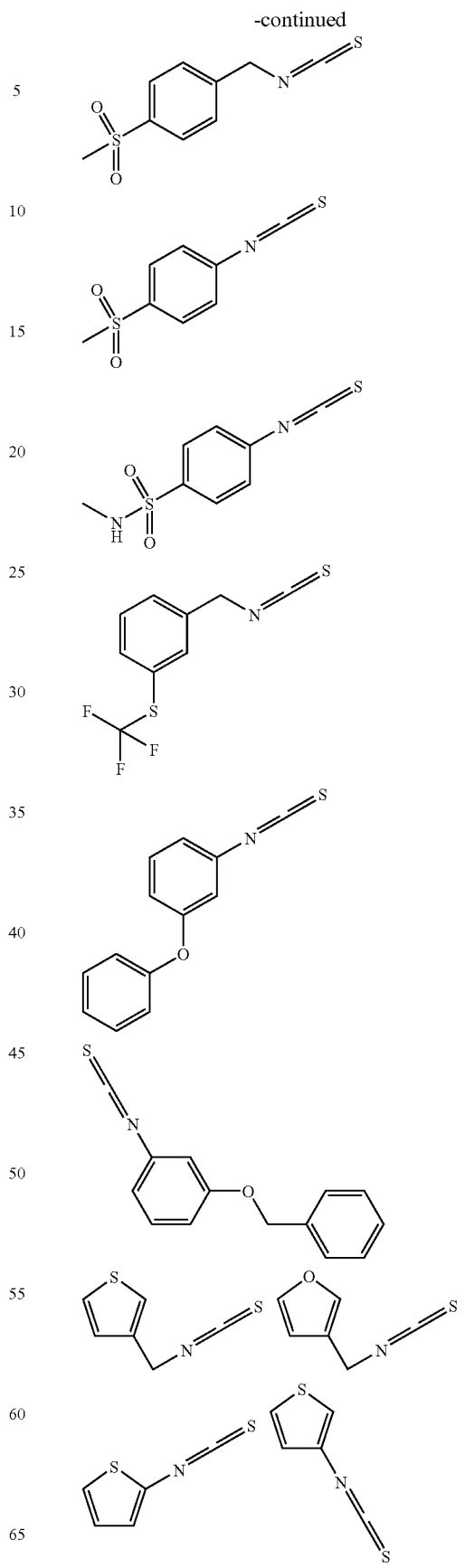

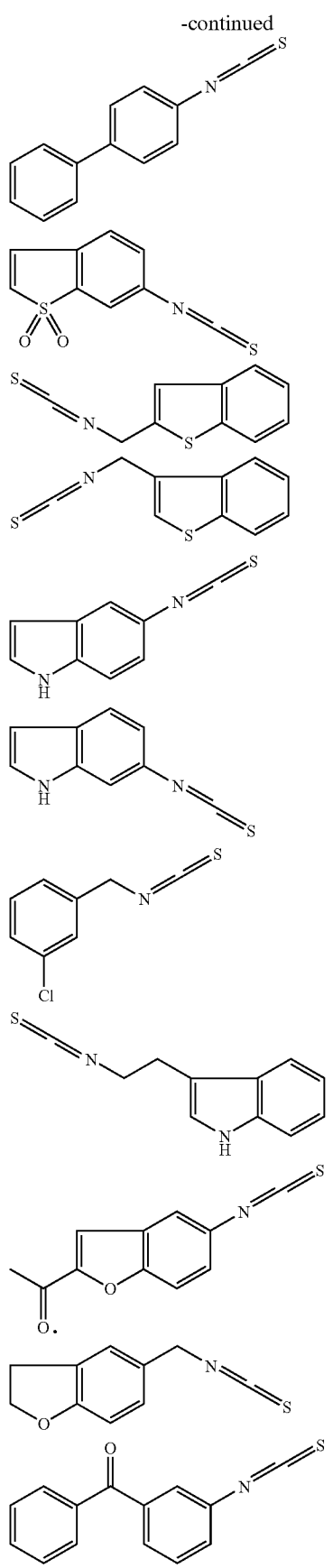
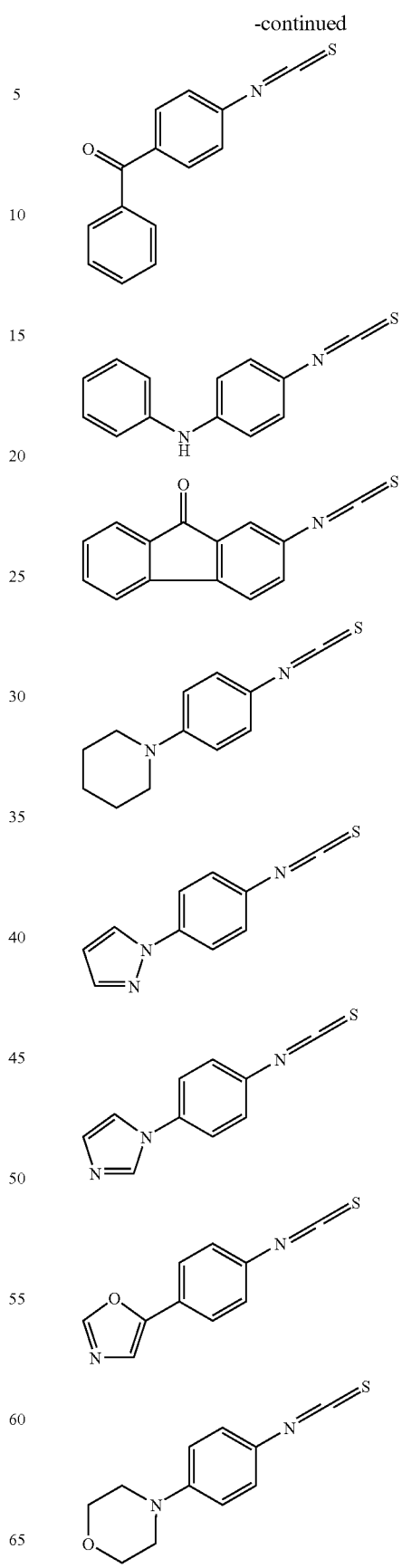

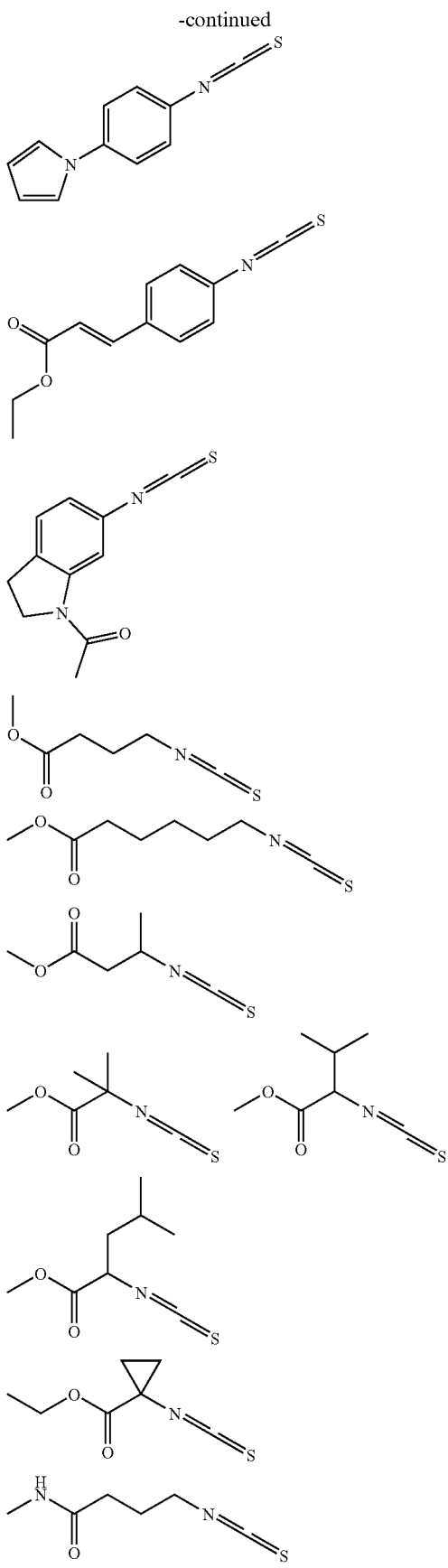
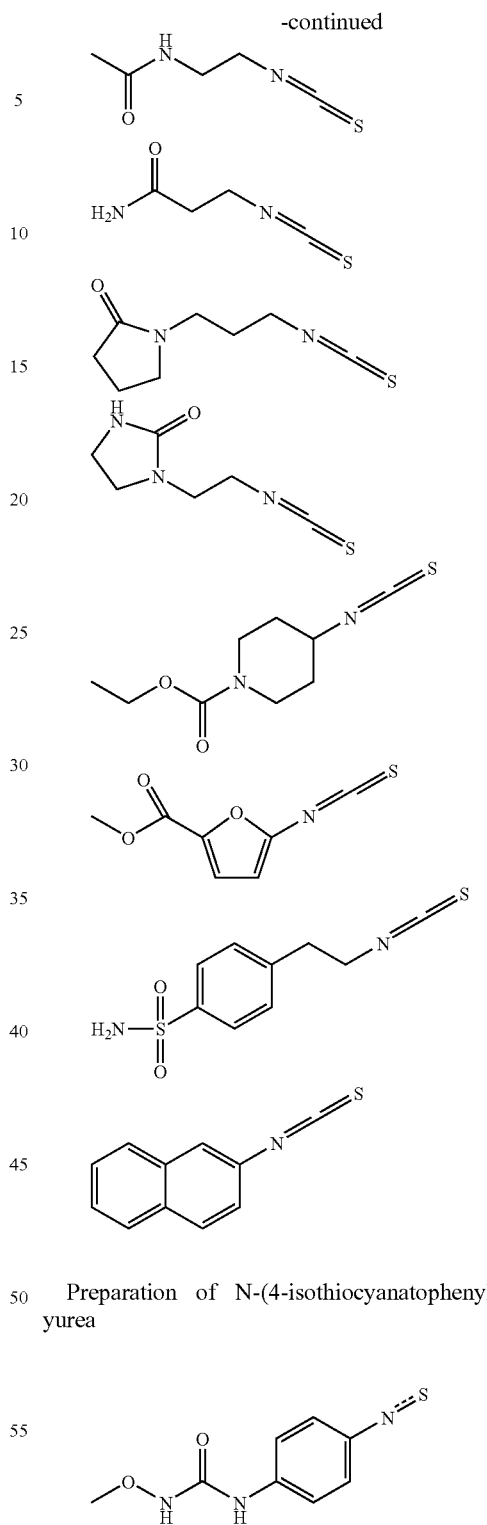

Preparation of N-(4-isothiocyanatophenyl)-N'-methoxyurea

Carbonyl-di-imidazole (1.62 g, 2 eq) is added to a solution cooled down to 0° C., of tert-butyl 4-aminophenylcarbamate (1.04 g) in anhydrous dichloromethane (100 ml). The mixture is taken to a temperature of 20° C. and is stirred at this temperature for 15 hours. Triethylamine (7 ml, 10 eq) followed by O-methylhydroxylamine hydrochloride (4.2 g, 10 eq) are successively added to the reaction medium cooled down to 0° C. After stirring for 3 hours at a temperature of approximately 20° C., water saturated with sodium hydrogen carbonate and chloroform is added to the mixture. After decantation and extractions, the combined organic phases are washed with salt water, dried over $Na_2SO_4$ then concentrated under reduced pressure at 40° C. in order to produce tert-butyl 4-{[(methoxyamino)carbonyl]amino}phenylcarbamate (1.33 g). A current of gaseous hydrochloric acid is passed through a suspension of this derivative in ethyl acetate until the reaction is complete. The precipitate obtained is filtered then washed with diethyl ether and dried in order to produce N-(4-aminophenyl)-N'-methoxyurea hydrochloride (1 g).

Thiophosgene (0.38 ml, 1.1 eq) is added dropwise to a solution cooled down to 0° C., of N-(4-aminophenyl)-N'-methoxyurea hydrochloride (1 g) and triethylamine (3.2 ml, 5 eq) in tetrahydrofuran (90 ml). The mixture is stirred for 15 min at 0° C. then water and diethyl ether are added. After decantation and extractions, the phases organic are combined, washed with salt water, dried over $Na_2SO_4$ then concentrated under reduced pressure at 40° C. Purification by flash chromatography on silica gel (eluent:heptane/ethyl acetate 7:3 to 3:7) produces the expected compound (630 mg; 62% yield).

NMR ($^1$H, 400 MHz, DMSO-$d_6$): δ 3.61 (s, 3H), 7.34 (AB, 2H), 7.67 (AB, 2H), 9.11 (s, 1H), 9.65 (s, 1H).

Preparation of Non-Commercial acyl-isothiocyanates

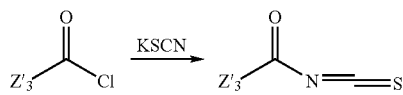

Acyl-isothiocyanates can be prepared starting from the corresponding acid chlorides by treatment with potassium thiocyanate in an aprotic solvent such as acetonitrile at a temperature of 0-60° C. for 0.2-5 hours.

Methyl 4-isothiocyanatocarbonylbenzoate

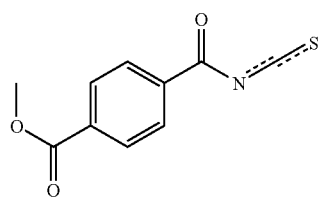

Potassium thiocyanate (1.08 g) is added to a solution of methyl 4-chlorocarbonylbenzoate (2 g) in acetonitrile (30 ml). After stirring for 1 hour at approximately 20° C., the mixture is filtered and the filtrate is concentrated under reduced pressure at 40° C. The solid obtained is purified by flash chromatography on silica gel (eluent:heptane/ethyl acetate 1:1) in order to produce the expected compound (2.1 g; 95% yield).

NMR ($^1$H, 400 MHz, DMSO-$d_6$): δ3.88 (s, 3H), 8.0 (m, 4H).

The following isothiocyanates were prepared according to the same procedure as that described for the methyl 4-isothiocyanatocarbonylbenzoate:

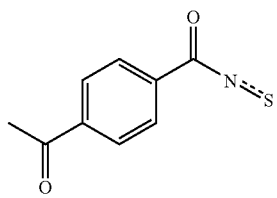

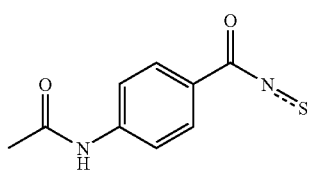

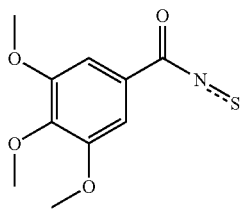

According to reaction diagram A and in a fashion analogous to the procedure described for the synthesis of methyl 4-[(1-(3-aminopropyl)-6-{[bis(3-methylbutyl) amino]carbonyl}-1H-benzimidazol-2-yl)amino]benzoate dihydrochloride, 2-[(4-acetylphenyl)amino]-N,N-bis(3-methylbutyl)-1-(3-piperidin-1-ylpropyl)-1H-benzimidazole-6-carboxamide dihydrochloride or 2-(cyclohexylamino)-1-[3-(dimethylamino)propyl]-N,N-bis(3-methylbutyl)-1H-benzimidazole-6-carboxamide dihydrochloride, the following compounds were prepared:

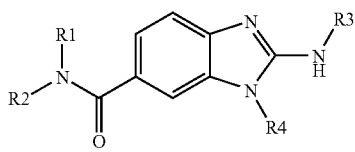

in which $R_1R_2N$ represents one of the radicals below:

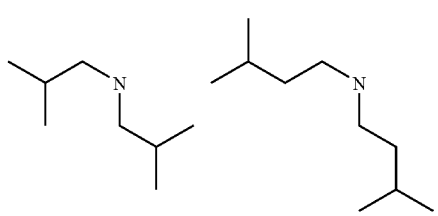

and $R_3$ represents one of the radicals below:

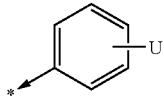

1 or more substitutions chosen from:
U = H, F, Cl, Br, I, NO$_2$, N$_3$, OMe, OEt, SMe, Me, Et, iPr, tBu, CF$_3$, OCF$_3$, SCF$_3$, C(O)OMe, C(O)OEt, C(O)Me, C(O)Et, C(O)Ph, NHC(O)Me, C(O)NHMe, C(O)N(Me)$_2$, C(O)NH$_2$, NHC(O)NHMe, NHC(O)NHOMe, S(O)$_2$Me, S(O)$_2$NH$_2$, S(O)$_2$NHMe, S(O)$_2$piperidine, NHphenyl, phenyl, phenoxy, benzyloxy

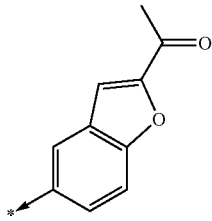
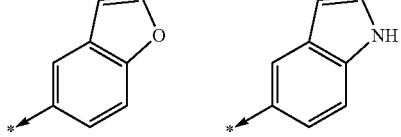
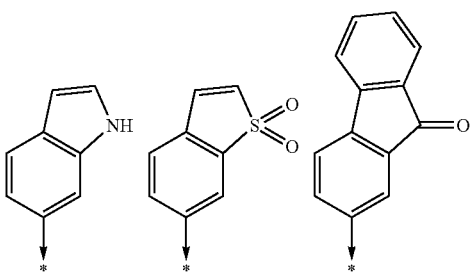
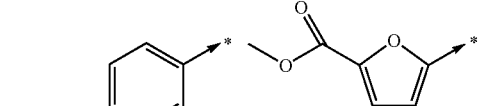
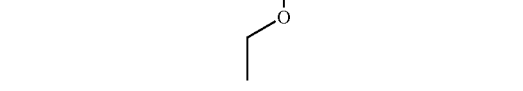

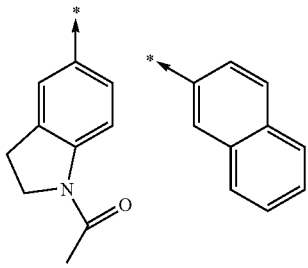
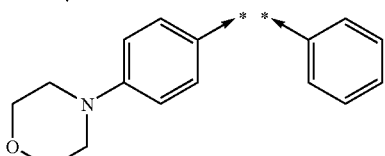
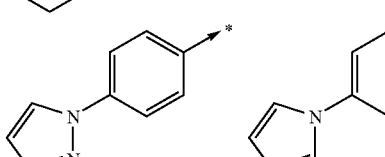
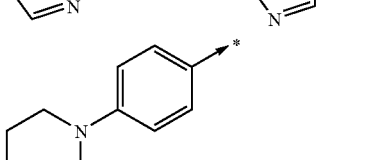

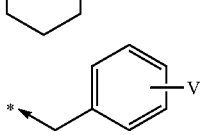

1 or more substitutions chosen from:
V = H, F, Cl, Br, I, NO$_2$, OMe, SMe, Me, Et, iPr, CF$_3$, OCF$_3$, SCF$_3$, C(O)OMe, C(O)OEt, C(O)Me, C(O)Et, C(O)NHMe, S(O)$_2$Me, S(O)$_2$NH$_2$

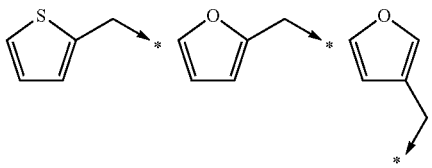
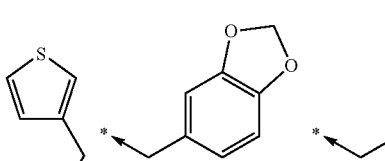
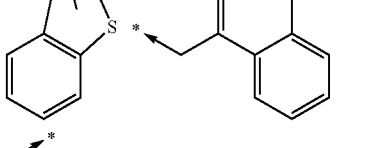
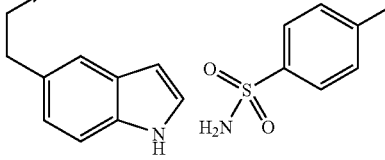

-continued
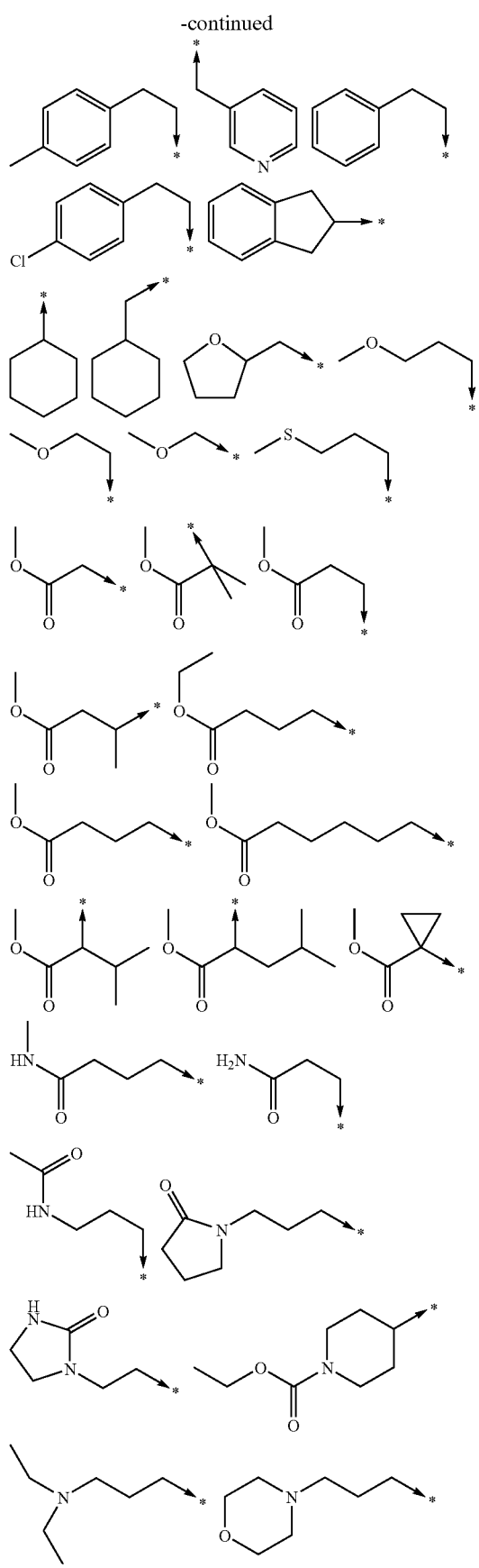
-continued
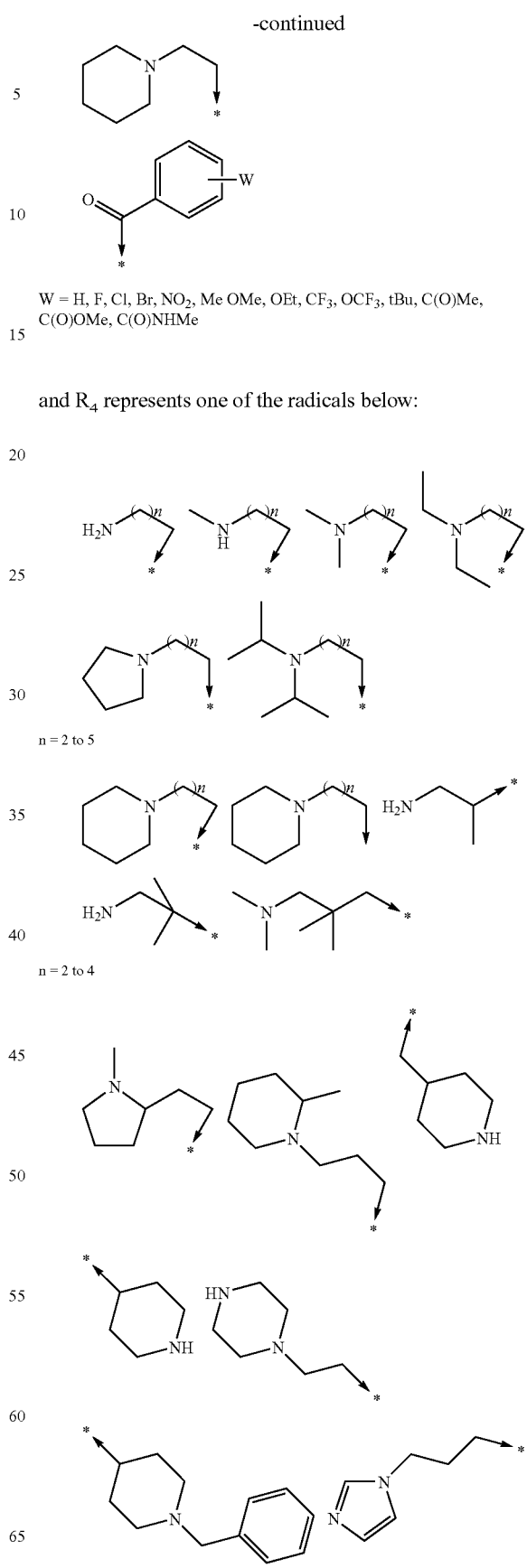
W = H, F, Cl, Br, NO$_2$, Me OMe, OEt, CF$_3$, OCF$_3$, tBu, C(O)Me, C(O)OMe, C(O)NHMe
and R$_4$ represents one of the radicals below:
n = 2 to 5
n = 2 to 4

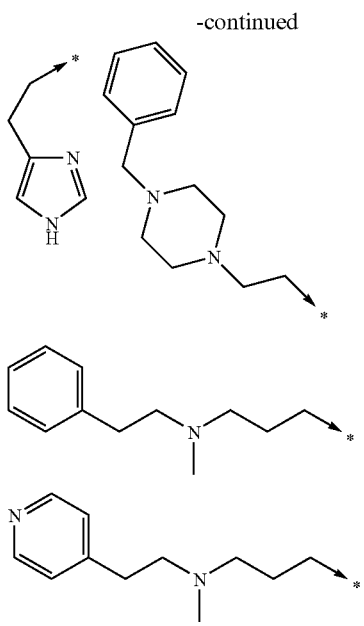

B. Preparation According to Reaction Diagram B:

The compounds of formula (I) according to the invention in which A represents —C(O)—, can also be prepared according to the following diagram B:

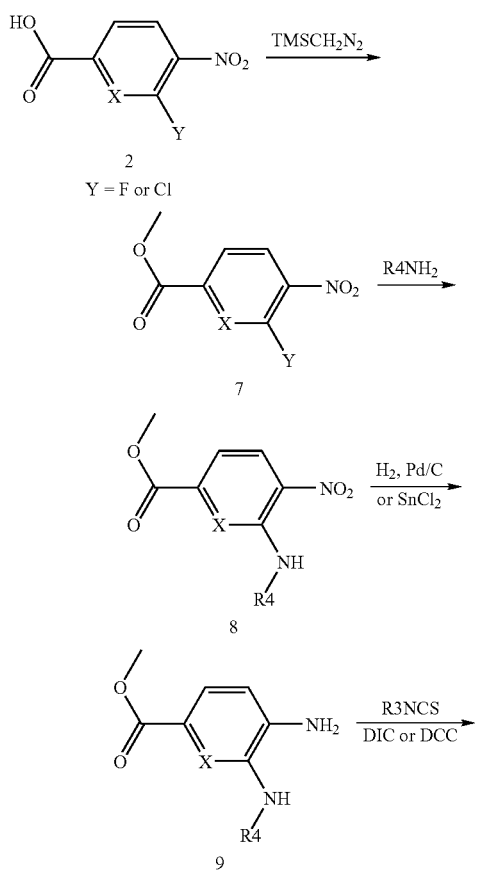

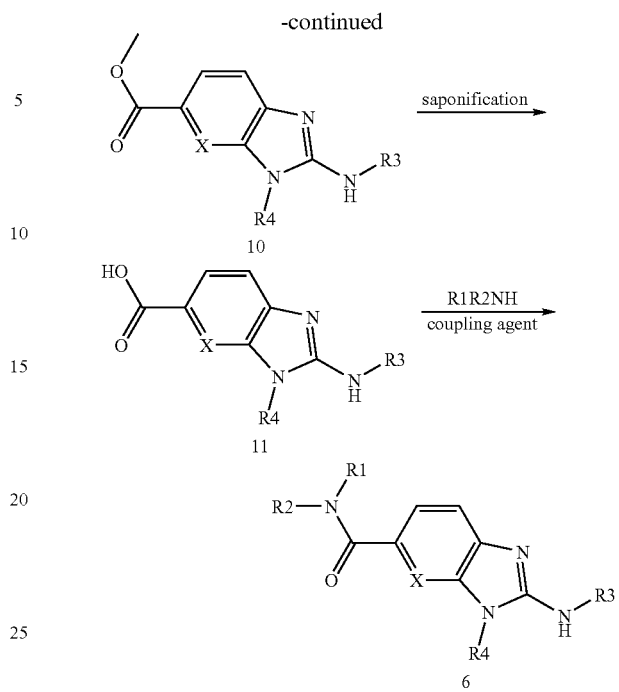

As described in diagram B, the carboxylic acid (2) can be converted to methyl ester (7) either by treatment with a solution of trimethylsilyl-diazomethane at a temperature of 0-20° C., or by formation of a carboxylate salt using an inorganic base such as lithium hydroxide dihydrate or caesium carbonate, at ambient temperature for 30 minutes to 2 hours, in an inert organic solvent such as tetrahydrofuran, followed by the addition of dimethylsulphate at ambient temperature and stirring under reflux for 5 to 15 hours. The fluorinated or chlorinated derivative (7) can be treated with a primary amine in the presence of an inorganic base such as caesium or potassium carbonate in an inert organic solvent such as dimethylformamide or acetonitrile at a temperature of 20-100° C. for 2 to 48 hours in order to produce derivative (8). The nitro function of compound (8) can be reduced by treatment with tin chloride dihydrate in an inert solvent such as ethyl acetate or dimethylformamide, at a temperature of 60-80° C. for 3 to 15 hours, or by catalytic hydrogenation in the presence of 10% palladium on carbon in an inert solvent such as methanol, ethanol, ethyl acetate or a mixture of these solvents, at a temperature of 18-25° C., for 2 to 8 hours, in order to produce the dianiline (9). The derivative (9) is then treated with an isothiocyanate in the presence of a coupling agent such as diisopropylcarbodiimide or dicyclohexylcarbodiimide in an inert solvent such as tetrahydrofuran, methylene chloride or chloroform at a temperature of 20-70° C. for 2 to 72 hours in order to produce derivative (10). Alternatively, derivative (9) can be treated with an isothiocyanate in an inert solvent such as tetrahydrofuran, methylene chloride, chloroform or ethanol at a temperature of 20-80° C. for 1-16 hours, then the resultant thiourea can be treated with methyl iodide or yellow mercury (II) oxide in the presence of a catalytic quantity of sulphur in a polar solvent such as methanol or ethanol for 2 to 24 hours at a temperature of 20-80° C. in order to produce (10). The methyl ester (10) can then be saponified in the presence of an inorganic base such as lithium hydroxide dihydrate in a mixture of polar solvents such as water and tetrahydrofuran at a temperature of 20 to 70° C. for 3 to 17 hours. The resultant carboxylic acid (11) can be coupled with a primary or secondary amine in the presence of a coupling agent such as diisopropylcarbodiimide (DIC), dicyclohexylcarbodiimide (DCC), 1-(3-dimethylaminopropyl)-3-ethylcarbodiimide hydrochloride (EDC) or carbonyldiimidazole (CDI), with or without 1-hydroxybenzotriazole (HOBt) in an inert organic solvent such as methylene chloride, tetrahydrofuran or dimethylformamide at ambient temperature for 3 to 24 hours in order to produce the corresponding amide (6) which can be isolated, either by flash chromatography on silica gel, or by the addition to the reaction mixture of a nucleophilic reagent supported on a polymer such as for example an aminomethylpolystyrene resin and an electrophilic reagent supported on a polymer such as for example methylisothiocyanate-polystyrene resin, followed by filtration and evaporation of the filtrate.

EXAMPLE B1

1-(3-aminopropyl)-6-(piperidin-1-ylcarbonyl)-N-(3, 4,5-trimethoxyphenyl)-1H-benzimidazol-2-amine dihydrochloride

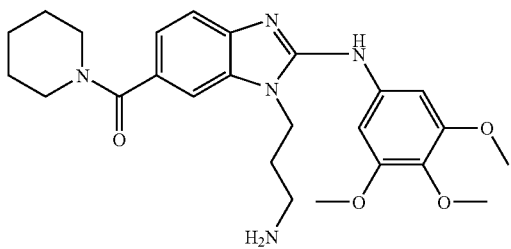

Stage 1: methyl 3-fluoro-4-nitrobenzoate

A solution of trimethylsilyldiazomethane (2M in hexane, 50 ml, 4 eq) is slowly added to a solution of 3-fluoro-4-nitrobenzoic acid (4.7 g, 1 eq) in methanol (70 ml) until the gas evolution ceases. The excess trimethylsilyldiazomethane is consumed by the dropwise addition of acetic acid until the solution becomes discoloured. The mixture is then concentrated under reduced pressure at a temperature of approximately 40° C. Water (200 ml) and dichloromethane (300 ml) are added to the residue. After decantation and extractions, the combined organic phases are washed with salt water, dried over $Na_2SO_4$ then concentrated under reduced pressure at 40° C. The solid obtained is washed with petroleum ether and dried (4.4 g; 87% yield).

NMR ($^1$H, 400 MHz, $CDCl_3$): δ4.0 (s, 3H), 7.97 (m, 2H), 8.11 (d, 1H).

Stage 2: methyl 3-({3-[(tert-butoxycarbonyl)amino] propyl}amino)-4-nitrobenzoate A mixture of methyl 3-fluoro-4-nitrobenzoate (5.8 g, 1 eq), N-Boc-1,3-diaminopropane (5.75 g, 1.1 eq) and potassium carbonate (8.04 g, 2 eq) in acetonitrile (200 ml) is heated under reflux for 2 hours then concentrated under reduced pressure at 40° C. The residue is taken up in dichloromethane (200 ml) and water (100 ml). After decantation and extractions, the combined organic phases are washed with salt water, dried over $Na_2SO_4$ then concentrated under reduced pressure at 40° C. The solid obtained is washed with petroleum ether and dried (10.2 g; 99% yield).

NMR ($^1$H, 400 MHz, $CDCl_3$): δ1.45 (s, 9H), 1.95 (m, 2H), 3.30 (m, 2H), 3.44 (m, 2H), 3.95 (s, 3H), 4.67 (m, 1H), 7.25 (m, 1H), 7.55 (s, 1H), 8.04 (m, 1H), 8.22 (m, 1H).

Stage 3: methyl 4-amino-3-({3-[(tert-butoxycarbonyl)amino]propyl}amino)benzoate

Methyl 3-({3-[(tert-butoxycarbonyl)amino] propyl}amino)-4-nitrobenzoate (10.2 g) in solution in a mixture of ethyl acetate/methanol 3:1 (300 ml), and 10% palladium on carbon (1.02 g) are introduced into an autoclave. After stirring for 4 hours under a hydrogen atmosphere (3 bar) at a temperature of approximately 20° C., the catalyst is eliminated by filtration on celite and the filtrate is concentrated under reduced pressure at 40° C. in order to produce the expected compound in the form of an oil (7.75 g; 83% yield).

MS/LC: calculated MM=323.4; m/z=324.2 (MH+)
NMR ($^1$H, 400 MHz, $CDCl_3$): 1.45 (s, 9H), 1.85 (m, 2H), 3.24 (m, 2H), 3.30 (m, 2H), 3.86 (m, 5H), 4.68 (m, 1H), 6.68 (d, 1H), 7.34 (s, 1H), 7.45 (d, 1H).

Stage 4: methyl 1-{3-[(tert-butoxycarbonyl)amino] propyl}-2-[(3,4,5-trimethoxyphenyl)amino]-1H-benzimidazole-6-carboxylate 3,4,5-trimethoxyphenyl isothiocyanate (6.6 g, 1.2 eq) and diisopropylcarbodiimide (9.1 g, 3 eq) are successively added to a solution of methyl 4-amino-3-({3-[(tert-butoxycarbonyl) amino]propyl}amino)benzoate (7.75 g, 1 eq) in tetrahydrofuran (130 ml). The mixture is heated under reflux for 16 hours then cooled down to ambient temperature and concentrated under reduced pressure at 40° C. Water (100 ml) and dichloromethane (200 ml) are added to the residue obtained. After decantation and extractions, the combined organic phases are washed with salt water, dried over $Na_2SO_4$ then concentrated under reduced pressure at 40° C. Purification of the residue by flash chromatography on silica gel (eluent: heptane/ethyl acetate 8:2 to 3:7) produces the expected compound in the form of a solid which is washed with ether. (4.4 g; 36% yield).

MS/LC: calculated MM=514.5; m/z=515.3 (MH+)
NMR ($^1$H, 400 MHz, $CDCl_3$): 1.54 (s, 9H), 2.11 (m, 2H), 3.26 (m, 2H), 3.83 (m, 3H), 3.90 (s, 3H), 3.93 (s, 6H), 4.22 (m, 2H), 5.03 (m, 1H), 7.23 (s, 2H), 7.53 (d, 1H), 7.90 (s, 1H), 7.92 (d, 1H), 9.12 (m, 1H).

Stage 5: 1-{3-[(tert-butoxycarbonyl)amino]propyl}-2-[(3,4,5-trimethoxyphenyl)amino]-1H-benzimidazole-6-carboxylic acid Lithium hydroxide (2.18 g, 6 eq) is added to a solution of methyl 1-{3-[(tert-butoxycarbonyl)amino]propyl}-2-[(3,4, 5-trimethoxyphenyl)amino]-1H-benzimidazole-6-carboxylate (4.4 g, 1 eq) in a mixture of tetrahydrofuran (40 ml) and water (30 ml). The mixture is heated under reflux for 18 hours then cooled down to ambient temperature and concentrated under reduced pressure at 40° C. Dichloromethane (150 ml) and water (100 ml) are added to the residue. The mixture is acidified by the addition of acetic acid to pH 5. After decantation and extractions, the combined organic phases are dried over sodium sulphate and concentrated under reduced pressure. The solid obtained is washed with ethyl ether (3.95 g; 93%).

MS/LC: calculated MM=500.5; m/z=501.3 (MH+)
NMR ($^1$H, 400 MHz, DMSO-$d_6$): 1.37 (s, 9H), 1.83 (m, 2H), 3.03 (m, 2H), 3.61 (s, 3H), 3.80 (s, 6H), 4.27 (m, 2H), 7.0 (m, 1H), 7.31 (s, 2H), 7.35 (d, 1H), 7.71 (d, 1H), 7.87 (s, 1H), 8.97 (s, 1H).

Stage 6: 1-(3-aminopropyl)-6-(piperidin-1-ylcarbonyl)-N-(3,4,5-trimethoxyphenyl)-1H-benzimidazol-2-amine dihydrochloride A solution of carbonyldiimidazole (CDI) (18 mg, 1.1 eq) in chloroform (0.2 ml) is added to a solution of 1-{3-[(tert-butoxycarbonyl)amino]propyl}-2-[(3,4,5-trimethoxyphenyl)amino]-1H-benzimidazole-6-carboxylic acid (50 mg, 1 eq) in tetrahydrofuran (0.45 ml) and dimethylformamide (0.05 ml). The mixture is stirred for 16 hours at a temperature of approximately 20° C., then a solution of piperidine (17 mg, 2 eq) in tetrahydrofuran (0.2 ml) is added. After stirring for 18 hours at a temperature of approximately 20° C., the mixture is diluted with dichloromethane (3 ml), and aminomethylpolystyrene resin (2 eq), TBD-methyl-polystyrene resin (2 eq) and methylisothiocyanate-polystyrene resin (4 eq) are added. After stirring for 6 hours at approximately 20° C., the mixture is filtered and the filtrate is concentrated under reduced pressure at 40° C. The residue obtained is dissolved in ethyl acetate (0.5 ml) and a solution of hydrochloric acid (1N in diethyl ether, 3 ml) is added. After stirring for 1 hour at a temperature of approximately 20° C., the precipitate obtained is filtered and dried in order to produce the expected compound (35 mg, 65%).

MS/LC: calculated MM=467.56; m/z=467.9 (MH+)

NMR ($^1$H, 400 MHz, DMSO-$d_6$): 1.48-1.63 (m, 6H), 2.05 (m, 2H), 2.90 (m, 2H), 3.50 (m, 4H), 3.65 (s, 3H), 3.79 (s, 6H), 4.45 (m, 2H), 7.10-7.60 (m, 5H), 7.54 (m, 1H), 7.94 (m, 3H), 8.41 (m, 1H), 14.3 (m, 1H).

According to reaction diagram B and in a fashion analogous to the procedure described for the synthesis of 1-(3-aminopropyl)-6-(piperidin-1-ylcarbonyl)-N-(3,4,5-trimethoxyphenyl)-1H-benzimidazol-2-amine dihydrochloride, the following compounds were prepared:

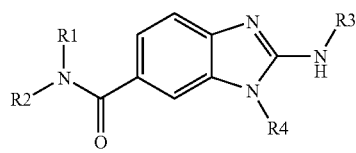

in which $R_1R_2N$ represents one of the radicals below:

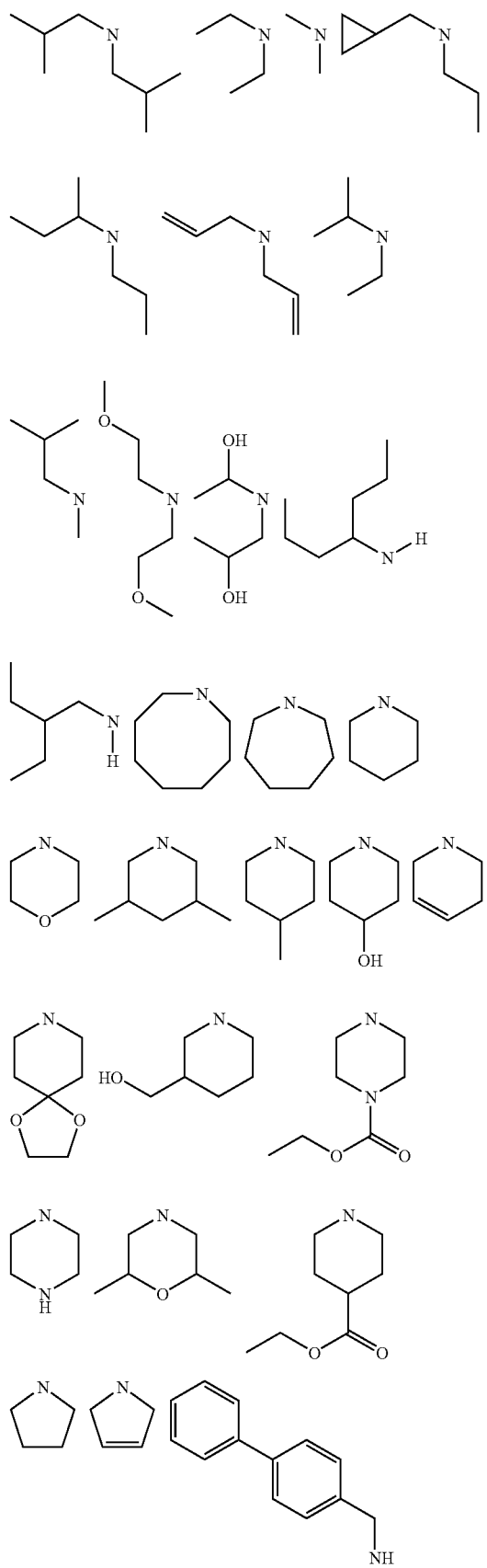

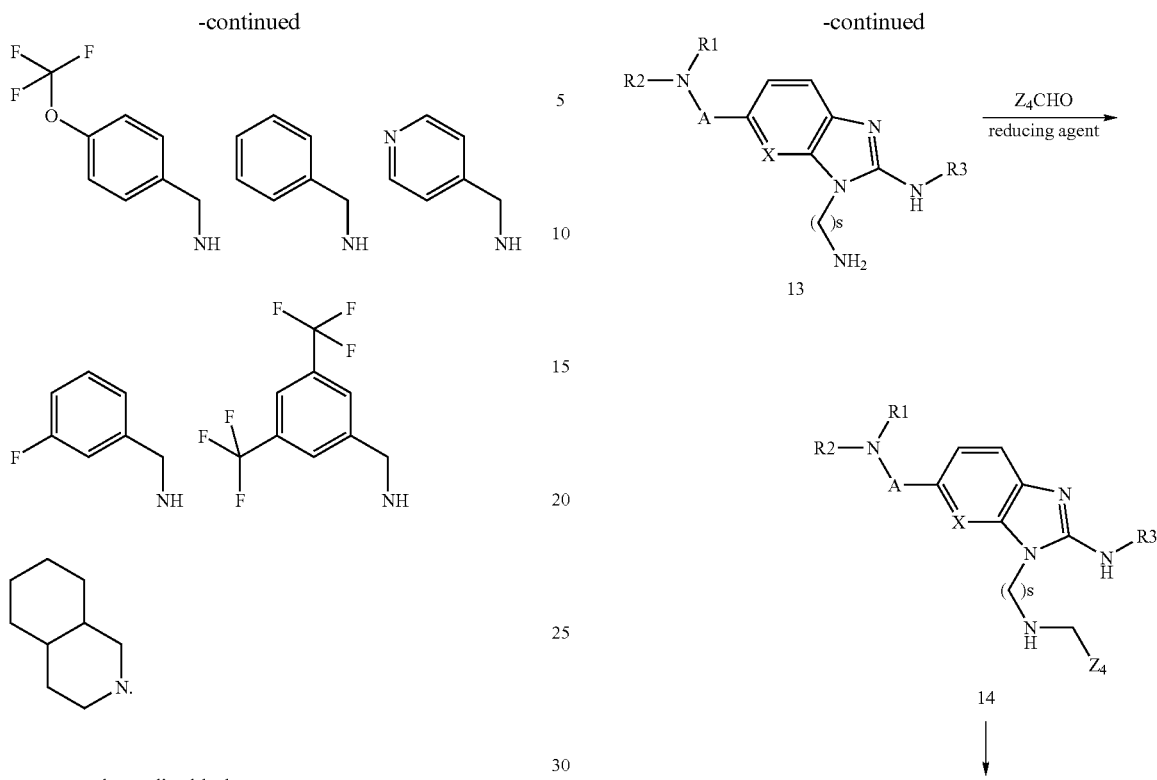

$R_3$ represents the radical below:

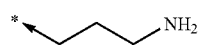

and $R_4$ represents one of the radicals below:

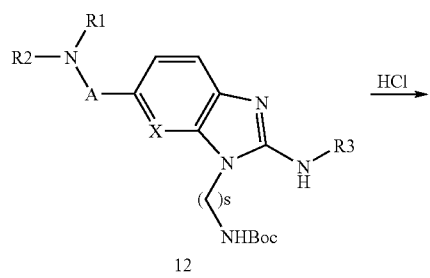

C. Preparation According to Reaction Diagram C:

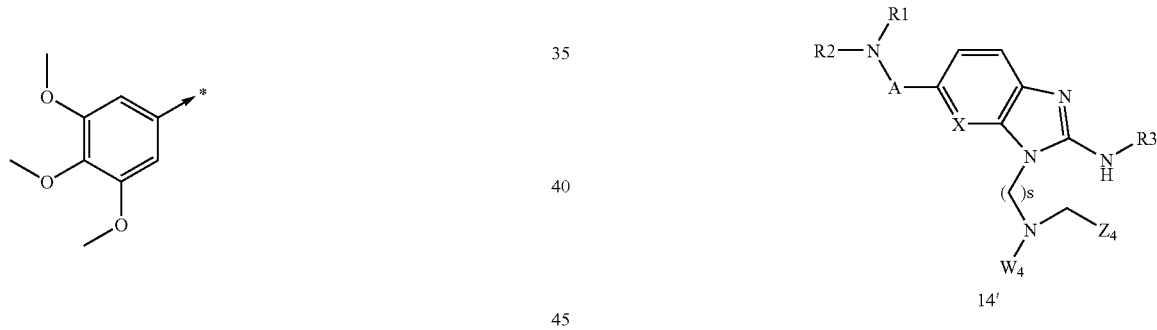

As described in diagram C, the derivative (12), prepared according to reaction diagrams A or B can be treated with an organic or inorganic acid such as trifluoroacetic acid or hydrochloric acid (aqueous or in gaseous form) in an aprotic solvent such as dichloromethane, diethyl ether or ethyl acetate at a temperature of 0-20° C. for 0.5 to 5 hours, in order to produce the amine (13). The amine (13) can react with an aldehyde in a protic or aprotic solvent; such as dichloromethane, tetrahydrofuran or methanol, for 1 to 15 hours at a temperature of 0-50° C. The resultant imine is then reduced in situ by a reducing agent supported or not supported on a resin, preferably sodium triacetoxyborohydride, sodium cyanoborohydride or borohydride supported on a resin, with or without the presence of an acid such as acetic acid, at a temperature of 20 to 50° C. for a duration of 0.2 to 5 hours, in order to produce compound (14). The secondary amine (14) can optionally undergo a second reducing amination under the same operating conditions as those described previously in order to produce the tertiary amine (14').

EXAMPLE C1

N,N-diisobutyl-1-[3-(neopentylamino)propyl]-2-[(3,4,5-trimethoxyphenyl)amino]-1H-benzimidazole-6-carboxamide dihydrochloride

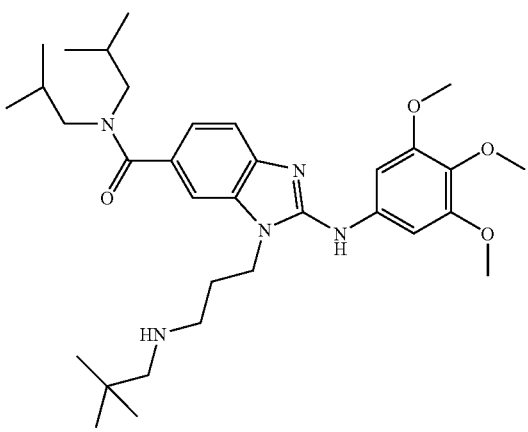

Stage 1: 1-(3-aminopropyl)-N,N-diisobutyl-2-[(3,4,5-trimethoxyphenyl)amino]-1H-benzimidazole-6-carboxamide A current of dry HCl is passed through a solution of tert-butyl 3-{6-[(diisobutylamino)carbonyl]-2-[(3,4,5-trimethoxyphenyl)amino]-1H-benzimidazol-1-yl}propylcarbamate (350 mg; prepared according to diagram A) in ethyl acetate (30 ml), cooled down to 0° C., until TLC (eluent:100% ethyl acetate) shows the total disappearance of the starting product. The mixture is then concentrated under reduced pressure at 40° C. The solid obtained is triturated in ethyl ether then filtered, washed with dichloromethane and dried. The dihydrochloride obtained is taken up in dichloromethane and water saturated with sodium hydrogen carbonate. After decantation and extractions, the combined organic phases are washed with salt water, dried over $Na_2SO_4$ then concentrated under reduced pressure at 40° C. in order to produce the expected compound in the form of the free base (275 mg; 94% yield).

MS/LC: calculated MM=511.6; m/z=512.3 (MH+)

NMR ($^1$H, 400 MHz, DMSO-$d_6$): δ0.82 (m, 12H), 1.87 (m, 4H), 2.58 (m, 2H), 3.21 (m, 4H), 3.62 (s, 3H), 3.78 (s, 6H), 4.25 (t, 2H), 7.0 (AB, 1H), 7.20 (s, 2H), 7.26 (s, 1H), 7.34 (AB, 1H).

Stage 2: N,N-diisobutyl-1-[3-(neopentylamino)propyl]-2-[(3,4,5-trimethoxyphenyl)amino]-1H-benzimidazole-6-carboxamide dihydrochloride A solution of 1-(3-aminopropyl)-N,N-diisobutyl-2-[(3,4,5-trimethoxyphenyl)amino]-1H-benzimidazole-6-carboxamide (100 mg, 1 eq) and trimethylacetaldehyde (25 mg, 1.5 eq) in dichloromethane (1 ml) is stirred for 4 hours at a temperature of approximately 20° C. The mixture is diluted with methanol (1 ml) then sodium triacetoxyborohydride is added (41 mg, 2 eq). After 1 hour at a temperature of approximately 20° C., dichloromethane (20 ml) and water saturated with sodium hydrogen carbonate (10 ml) are added to the mixture. After decantation and extractions, the combined organic phases are washed with salt water, dried over $Na_2SO_4$ then concentrated under reduced pressure at 40° C. Purification of the residue by flash chromatography on silica gel (eluent:100% dichloromethane to dichloromethane/methanol 9:1) produces the expected compound in the form of a base. The corresponding hydrochloride salt is formed by adding a 1N solution of hydrochloric acid in ether. The precipitate obtained is filtered and dried in order to produce the expected dihydrochloride compound (83 mg, 65% yield).

MS/LC: calculated MM=581.8; m/z=582.3 (MH+)

NMR ($^1$H, 400 MHz, DMSO-$d_6$): δ0.67 (m, 6H), 0.95 (m, 6H), 0.99 (s, 9H), 1.82 (m, 1H), 2.06 (m, 1H), 2.27 (m, 2H), 2.71 (m, 2H), 3.10 (m, 4H), 3.28 (m, 2H), 3.70 (s, 3H), 3.81 (s, 6H), 4.58 (t, 2H), 6.99 (m, 2H), 7.22 (AB, 1H), 7.41 (AB, 1H), 7.69 (s, 1H), 8.72 (m, 2H), 11.42 (m, 1H), 13.02 (m, 1H).

Preparation According to Reaction Diagram C':

The compounds (14) for which s=3 can also be prepared according to the following diagram C':

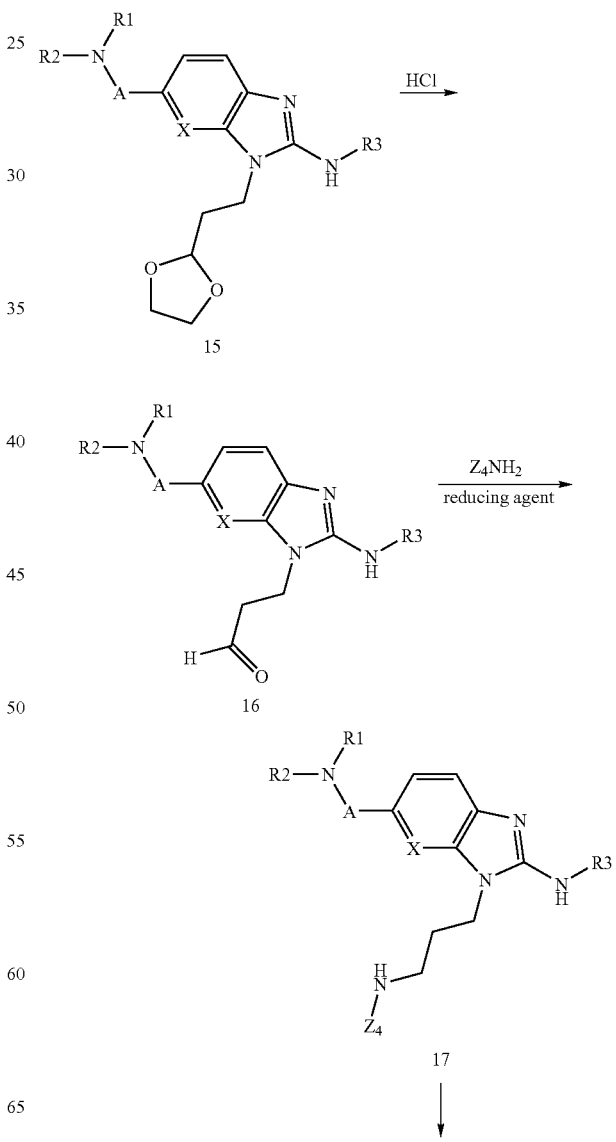

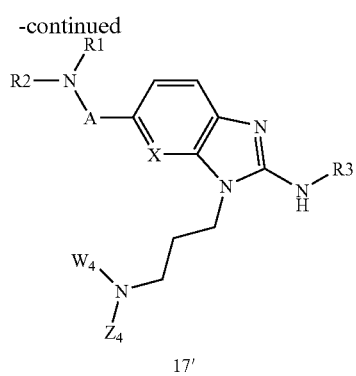

As described in diagram C', the derivative (15) prepared according to reaction diagram A can be treated either with an organic acid such as pyridinium tosylate or paratoluenesulphonic acid in an aprotic solvent such as acetone in the presence of water, at a temperature of 20-70° C. for 2 to 12 hours, or by an inorganic acid such as aqueous hydrogen chloride in an aprotic solvent such as tetrahydrofuran at a temperature of 0-20° C. for 6 to 18 hours in order to produce compound (16). The aldehyde (16) can then be treated with an amine in a protic 6 or aprotic solvent such as dichloromethane, tetrahydrofuran or methanol for 1 to 18 hours at a temperature of 20° C. The resultant imine is then reduced in situ by a reducing agent, preferably sodium triacetoxyborohydride or sodium cyanoborohydride, in the presence or absence of an acid such as acetic acid, at a temperature of 20-50° C. for a duration of 0.2 to 6 hours, in order to produce compound (17). The secondary amine (17) can optionally undergo a second reducing amination under the same operating conditions as those described previously in order to produce the tertiary amine (17').

EXAMPLE C1'

2-[(4-acetylphenyl)amino]-1-{3-[cyclohexylmethyl amino]propyl}-N,N-bis(3-methylbutyl)-1H-benzimidazole-6-carboxamide dihydrochloride

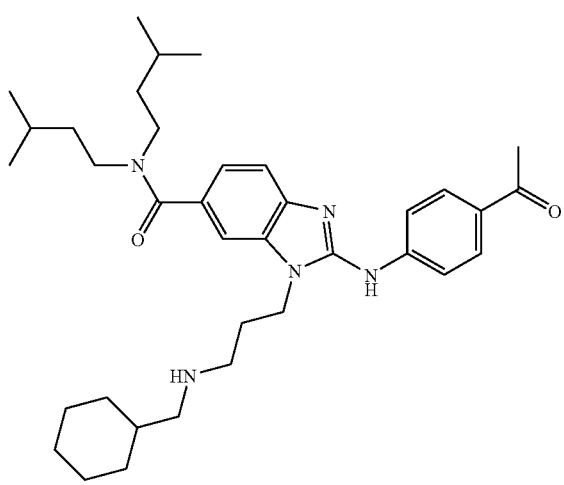

Stage 1: 3-{[2-(1,3-dioxolan-2-yl)ethyl]amino}-N,N-bis(3-methylbutyl)-4-nitrobenzamide A mixture of 3-fluoro-N,N-bis(3-methylbutyl)-4-nitrobenzamide prepared according to Example A1 (1.86 g, 1 eq), 2-(2-aminoethyl)-1,3-dioxolane (0.8 g, 1.2 eq) and potassium carbonate (1.58 g, 2 eq) in acetonitrile (150 ml) is heated under reflux for 3 hours then concentrated under reduced pressure at 40° C. The residue is taken up in dichloromethane (150 ml) and water (60 ml). After decantation and extractions, the combined organic phases are washed with salt water, dried over $Na_2SO_4$ then concentrated under reduced pressure at 40° C. Purification of the residue by flash chromatography on silica gel (eluent:heptane/ethyl acetate 8:2 to 7:3) produces the expected compound in the form of an orange-yellow oil (2.4 g; 98% yield).

MS/LC: calculated MM=421.5; m/z=422.2 (MH+)

NMR ($^1$H, 400 MHz, DMSO-$d_6$): δ0.68 (d, 6H), 0.92 (d, 6H), 1.31-1.50 (m, 5H), 1.61 (m, 1H), 1.97 (m, 2H), 3.10 (m, 2H), 3.37-3.48 (m, 4H), 3.80 (m, 2H), 3.91 (m, 2H), 4.94 (t, 1H), 6.55 (d, 1H), 6.89 (s, 1H), 8.10 (d, 1H), 8.39 (t, 1H).

Stage 2: 4-amino-3-{[2-(1,3-dioxolan-2-yl)ethyl] amino}-N,N-bis(3-methylbutyl)benzamide 3-{[2-(1,3-dioxolan-2-yl)ethyl]amino}-N,N-bis(3-methylbutyl)-4-nitrobenzamide (2.4 g) in solution in a mixture of ethyl acetate/methanol 2:1 (100 ml), and 10% palladium on carbon (240 mg) are introduced into an autoclave. After stirring for 4 hours under a hydrogen atmosphere (3 bar) at a temperature of approximately 20° C., the catalyst is eliminated by filtration on celite and the filtrate is concentrated under reduced pressure at 40° C. in order to produce the expected compound in the form of an oil (2.02 g; 89% yield).

MS/LC: calculated MM=391.5; m/z=392.2 (MH+)

NMR ($^1$H, 400 MHz, DMSO-$d_6$): δ0.80 (m, 12H), 1.40 (m, 6H), 1.90 (m, 2H), 3.10 (m, 2H), 3.29 (m, 4H), 3.77 (m, 2H), 3.90 (m, 2H), 4.54 (m, 1H), 4.78 (s, 2H), 4.93 (t, 1H), 6.36-6.52 (m, 1H).

Stage 3: 2-[(4-acetylphenyl)amino]-1-[2-(1,3-dioxolan-2-yl)ethyl]-N,N-bis(3-methylbutyl)-1H-benzimidazole-6-carboxamide 4-acetylphenyl isothiocyanate (1.1 g, 1.2 eq) and diisopropylcarbodiimide (1.95 g, 3 eq) are successively added to a solution of 4-amino-3-{[2-(1,3-dioxolan-2-yl)ethyl]amino}-N,N-bis(3-methylbutyl)benzamide (2 g, 1 eq) in tetrahydrofuran (50 ml). The mixture is heated under reflux for 18 hours then cooled down to ambient temperature and concentrated under reduced pressure at 40° C. Water (100 ml) and dichloromethane (200 ml) are added to the residue obtained. After decantation and extractions, the combined organic phases are washed with salt water, dried over $Na_2SO_4$ then concentrated under reduced pressure at 40° C. Purification of the residue by flash chromatography on silica gel (eluent:heptane/ethyl acetate 4:6) produces the expected compound in the form of a white foam (1.8 g; 66% yield).

MS/LC: calculated MM=534.7; m/z=535.3 (MH+)

NMR ($^1$H, 400 MHz, DMSO-$d_6$): δ0.80 (m, 12H), 1.44 (m, 6H), 2.01 (m, 2H), 2.52 (s, 3H), 3.30 (t, 4H), 3.72 (t, 2H), 3.85 (m, 2H), 4.39 (t, 2H), 4.83 (t, 1H), 7.05 (AB, 1H), 7.30 (s, 1H), 7.44 (AB, 1H), 7.96 (s, 4H), 9.37 (s, 1H).

Stage 4: 2-[(4-acetylphenyl)amino]-N,N-bis(3-methylbutyl)-1-(3-oxopropyl)-1H-benzimidazole-6-carboxamide A solution of 2-[(4-acetylphenyl)amino]-1-[2-(1,3-dioxolan-2-yl)ethyl]-N,N-bis(3-methylbutyl)-1H-benzimidazole-6-carboxamide (900 mg) in a mixture of tetrahydrofuran (30 ml) and aqueous hydrochloric acid (3N, 40 ml) is stirred for 18 hours at a temperature of approximately 20° C. then concentrated under reduced pressure at 40° C. Dichloromethane (100 ml) is added to the remaining aqueous phase. After decantation and extractions, the combined organic phases are washed with salt water, dried over $Na_2SO_4$ then concentrated under reduced pressure at 40° C. in order to produce the expected compound in the form of a beige foam (820 mg, 99% yield).

MS/LC: calculated MM=490.6; m/z=491.3 (MH+)

NMR ($^1$H, 400 MHz, DMSO-$d_6$): δ0.68-0.99 (m, 12H), 1.35 (m, 6H), 2.39 (m, 2H), 2.64 (s, 3H), 3.10-3.49 (m, 4H), 3.72 (m, 2H), 4.15 (m, 1H), 4.15 (m, 1H), 5.54 (s, 1H), 7.27 (AB, 1H), 7.39 (AB, 1H), 7.64 (s, 1H), 7.82 (AB, 1H), 8.15 (AB, 1H).

Stage 5: 2-[(4-acetylphenyl)amino]-1-{3-[(cyclohexylmethyl)amino]propyl}-N,N-bis(3-methylbutyl)-1H-benzimidazole-6-carboxamide dihydrochloride A solution of 2-[(4-acetylphenyl)amino]-N,N-bis(3-methylbutyl)-1-(3-oxopropyl)-1H-benzimidazole-6-carboxamide (100 mg, 1 eq) and aminomethylcyclohexane (46 mg, 2 eq) is stirred for 4 hours at a temperature of approximately 20° C. The mixture is diluted with methanol (1 ml), then sodium triacetoxyborohydride (86 mg, 2 eq) and a few drops of acetic acid are added to produce a pH of 5. After 1 hour at a temperature of approximately 20° C., dichloromethane (20 ml) and water saturated with sodium hydrogen carbonate (10 ml) are added to the mixture. After decantation and extractions, the combined organic phases are washed with salt water, dried over $Na_2SO_4$ then concentrated under reduced pressure at 40° C. Purification of the residue by flash chromatography on silica gel (eluent:100% dichloromethane to dichloromethane/methanol 9:1) produces the expected compound in the form of a base. The corresponding hydrochloride salt is formed by adding a 1N solution of hydrochloric acid in ether. The precipitate obtained is filtered and dried in order to produce the expected dihydrochloride compound (83 mg, 62% yield).

MS/LC: calculated MM=587.8; m/z=588.3 (MH+)

NMR ($^1$H, 400 MHz, DMSO-$d_6$): δ0.68-0.99 (m, 14H), 1.19 (m, 3H), 1.29-1.82 (m, 12H), 2.59 (s, 3H), 2.73 (m, 2H), 3.07 (t, 2H), 3.21 (m, 2H), 3.43 (m, 2H), 4.64 (t, 2H), 7.24 (AB, 1H), 7.47 (AB, 1H), 7.37 (s, 1H), 7.84 (d, 2H), 8.06 (d, 2H), 8.89 (m, 2H), 11.42 (m, 1H).

According to reaction diagram C or C' and in a fashion analogous to the procedure described for the synthesis of N,N-diisobutyl-1-[3-(neopentylamino)propyl]-2-[(3,4,5-trimethoxyphenyl)amino]-1H-benzimidazole-6-carboxamide dihydrochloride or 2-[(4-acetylphenyl)amino]-1-{3-[(cyclohexylmethyl)amino]propyl}-N,N-bis(3-methyl butyl)-1H-benzimidazole-6-carboxamide dihydrochloride, the following compounds were prepared:

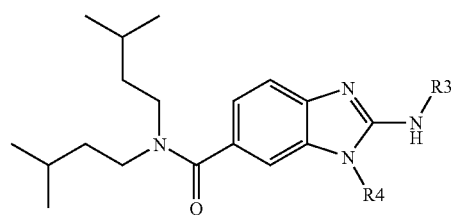

in which $R_3$ represents one of the radicals below:

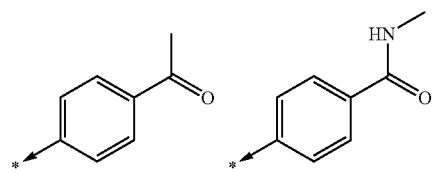

and $R_4$ represents one of the radicals below:

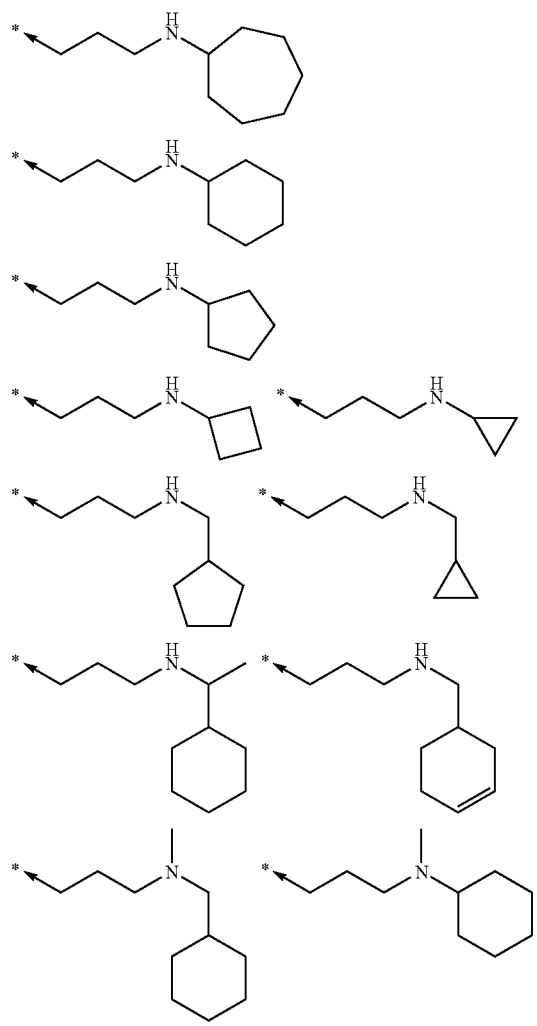

-continued
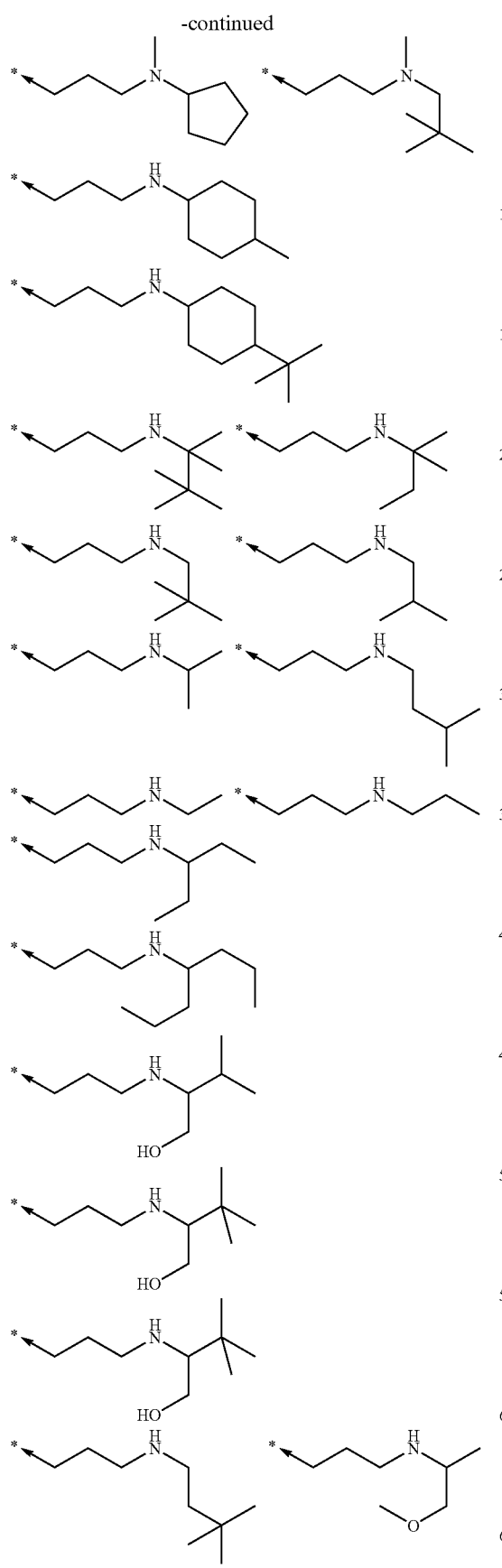
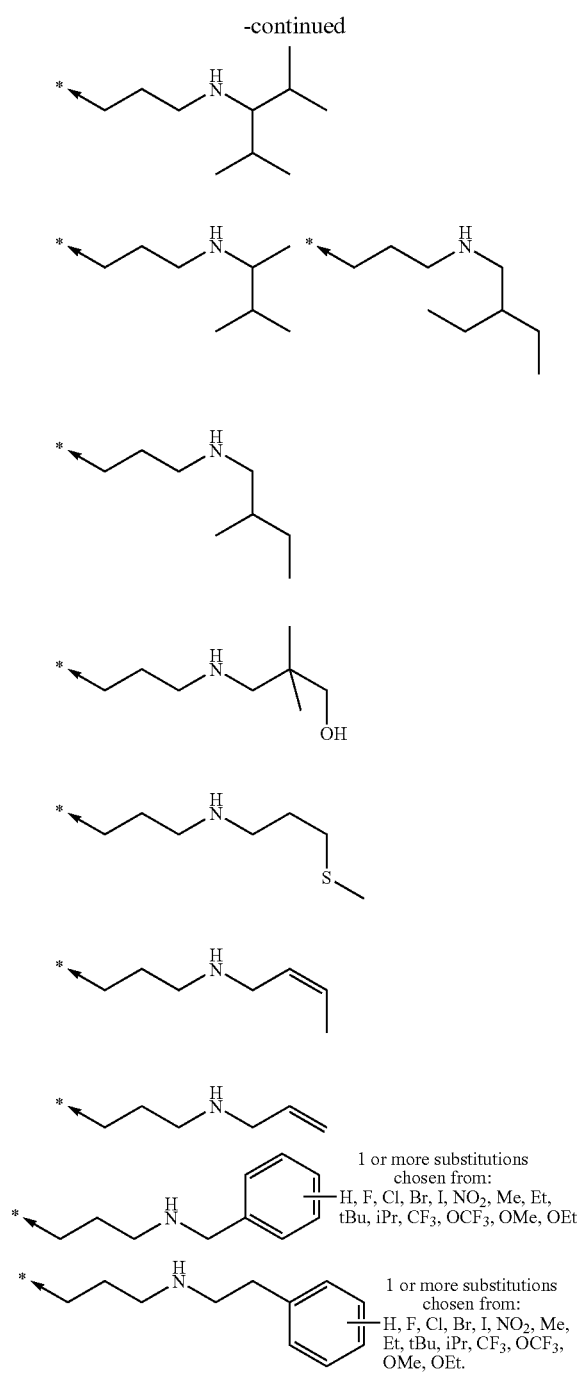
D. Preparation According to the Reaction Diagram D:
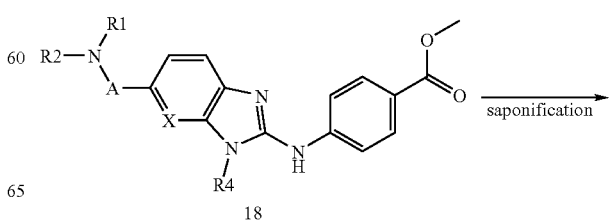

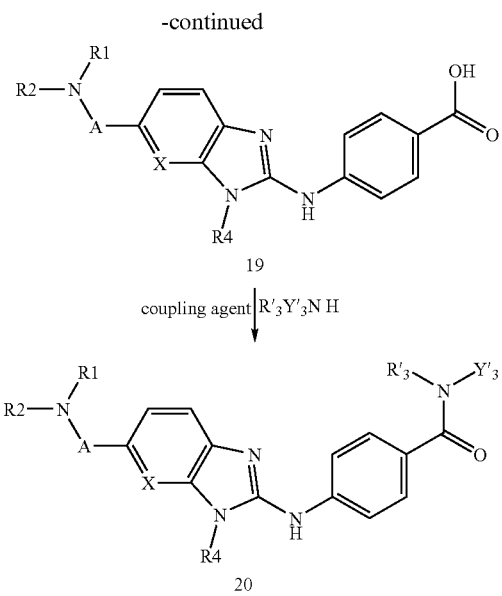

As described in diagram D, the derivative (18) prepared according to reaction diagram A, can be saponified in the presence of an inorganic base such as lithium hydroxide dihydrate in a mixture of polar solvents such as water and tetrahydrofuran at a temperature of 20 to 70° C. for 3 to 17 hours. The resultant carboxylic acid (19) can be coupled with a primary or secondary amine in the presence of a coupling agent such as diisopropylcarbodiimide (DIC), dicyclohexylcarbodiimide (DCC), 1-(3-dimethylaminopropyl)-3-ethylcarbodiimide hydrochloride (EDC) or carbonyldiimidazole (CDI), with or without 1-hydroxybenzotriazole (HOBt) in an inert organic solvent such as methylene chloride, tetrahydrofuran or dimethylformamide at ambient temperature for 3 to 24 hours in order to produce compound (20).

EXAMPLE D1

1-(3-aminopropyl)-2-({4-[(methylamino)carbonyl]phenyl}amino)-N,N-bis(3-methylbutyl)-1H-benzimidazole-6-carboxamide dihydrochloride

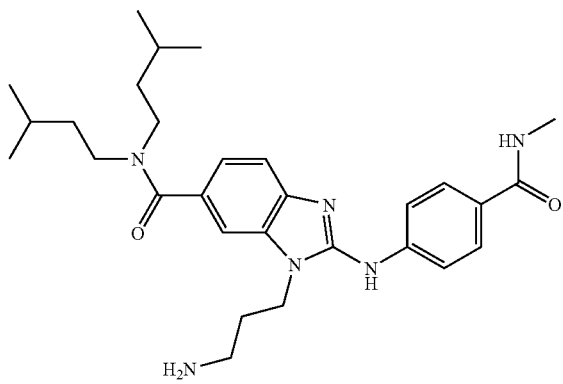

Stage 1: 4-[(6-{[bis(3-methylbutyl)amino]carbonyl}-1-{3-[(tert-butoxycarbonyl)amino]propyl}-1H-benzimidazol-2-yl)amino]benzoic acid Lithium hydroxide (141 mg, 5 eq) is added to methyl 4-[(6-{[bis(3-methylbutyl)amino]carbonyl}-1-{3-[(tert-butoxycarbonyl)amino]propyl}-1H-benzimidazol-2-yl)amino]benzoate prepared according to reaction diagram A, Example A1, (405 mg, 1 eq) in a mixture of tetrahydrofuran (4 ml) and water (3 ml). The mixture is heated under reflux for 18 hours then cooled down to ambient temperature and concentrated under reduced pressure at 40° C. Dichloromethane (50 ml) and water (20 ml) are added to the residue. The mixture is acidified by the addition of acetic acid to pH 5. After decantation and extractions, the combined organic phases are dried over sodium sulphate and concentrated under reduced pressure. The solid obtained is taken up in ethyl ether in order to produce the expected compound (309 mg; 79%).

MS/LC: calculated MM=593.8; m/z=594.3 (MH+)

NMR ($^1$H, 400 MHz, DMSO-$d_6$): 0.77 (m, 12H), 1.22-1.55 (m, 6H), 1.36 (s, 9H), 1.83 (m, 2H), 3.03 (m, 2H), 3.33 (m, 4H), 4.28 (m, 2H), 6.95-7.90 (m, 8H), 9.24 (s, 1H).

Stage 2: 1-(3-aminopropyl)-2-({4-[(methylamino)carbonyl]phenyl}amino)-N,N-bis(3-methylbutyl)-1H-benzimidazole-6-carboxamide dihydrochloride A solution of 1-(3-dimethylaminopropyl)-3-ethylcarbodiimide hydrochloride (EDC) (18 mg, 1.1 eq) in chloroform (1 ml) and a solution of 1-hydroxybenzotriazole (HOBt) (13 mg, 1.1 eq) in tetrahydrofuran (1 ml) are successively added to 4-[(6-{[bis(3-methylbutyl)amino]carbonyl}-1-{3-[(tert-butoxycarbonyl)amino]propyl}-1H-benzimidazol-2-yl)amino]benzoic acid (50 mg, 1 eq) in anhydrous tetrahydrofuran (1 ml). The mixture is stirred for 1 hour at a temperature of approximately 20° C. then the methylamine is added (2M in THF; 0.86 ml, 2 eq). After stirring for 17 hours at a temperature of approximately 20° C., the mixture is diluted with dichloromethane (3 ml) followed by the addition of aminomethylpolystyrene resin (2 eq), TBD-methyl polystyrene resin (2 eq) and methylisothiocyanate-polystyrene resin (4 eq). After stirring for 6 hours at approximately 20° C., the mixture is filtered and the filtrate is concentrated under reduced pressure at 40° C. The residue obtained is dissolved in dichloromethane (3 ml) and washed with a saturated aqueous solution of sodium hydrogen carbonate. The organic phase is dried over sodium sulphate and concentrated at a temperature of approximately 40° C. The residue obtained is dissolved in ethyl acetate (0.5 ml) and a solution of hydrochloric acid (4N in dioxane, 2 ml) is added. After stirring for 1 hour a temperature of approximately 20° C., the precipitate obtained is filtered and dried in order to produce the expected compound (29 mg; 60% yield).

MS/LC: calculated MM=506.7; m/z=507.2 (MH+)

NMR ($^1$H, 400 MHz, DMSO-$d_6$): 0.78 (m, 12H), 1.46 (m, 6H), 2.0 (m, 2H), 2.77 (d, 3H), 2.89 (m, 2H), 3.33 (m, 4H), 4.45 (m, 2H), 7.07 (d, 1H), 7.43 (d, 1H), 7.48 (s, 1H), 7.84 (m, 5H), 7.97 (m, 2H), 8.28 (m, 2H), 9.49 (m, 1H).

According to reaction diagram D and in a fashion analogous to the procedure described for the synthesis of 1-(3-aminopropyl)-2-({4-[(methylamino)carbonyl]phenyl}amino)-N,N-bis(3-methylbutyl)-1H-benzimidazole-6-carboxamide dihydrochloride, the following compounds were prepared

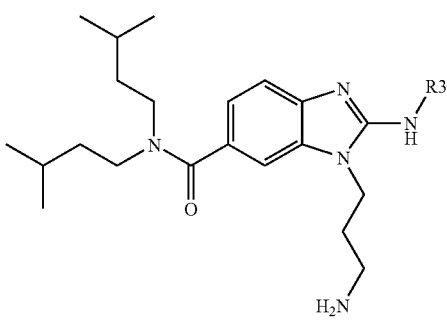

in which R₃ represents one of the radicals below:

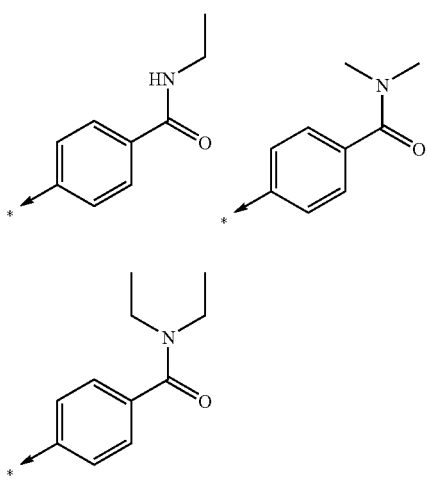

E. Preparation According to Reaction Diagram E:

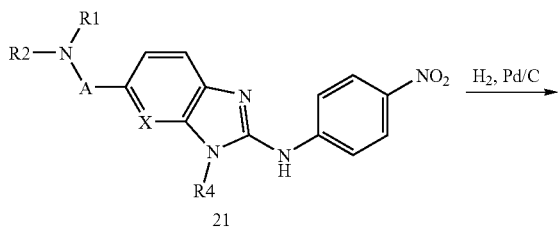

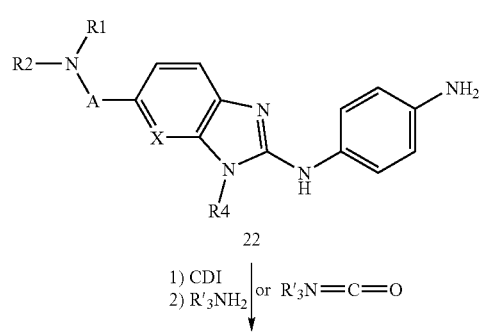

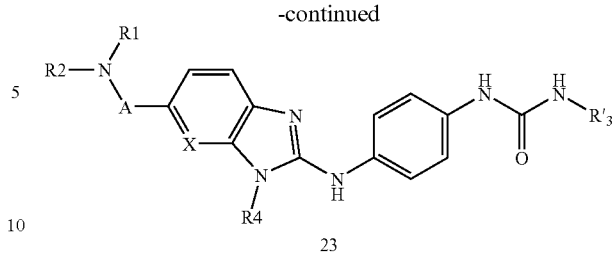

As described in diagram E, the derivative (21) prepared according to reaction diagram A, can be reduced by treatment with tin chloride dihydrate in an inert solvent such as ethyl acetate or dimethylformamide, at a temperature of 60-80° C. for 3 to 15 hours, or by catalytic hydrogenation in the presence of 10% palladium on carbon in an inert solvent such as methanol, ethanol, ethyl acetate or a mixture of these solvents, at a temperature of 18-25° C., for 2 to 8 hours, in order to produce aniline (22). Compound 23 can be treated with an isocyanate in an aprotic solvent such as dichloromethane or tetrahydrofuran at a temperature of 20-60° C. for 2 to 24 hours or alternatively with carbonyldiimidazole (CDI) in an aprotic solvent such as dichloromethane or tetrahydrofuran at a temperature of 0-60° C. for 6 to 24 hours, followed by a primary amine at a temperature of 20-60° C. for 2 to 24 hours, in order to produce the urea (23).

EXAMPLE E1

1-(3-aminopropyl)-2-[(4-{[(methylamino)carbonyl]amino}phenyl)amino]-N,N-bis(3-methylbutyl)-1H-benzimidazole-6-carboxamide

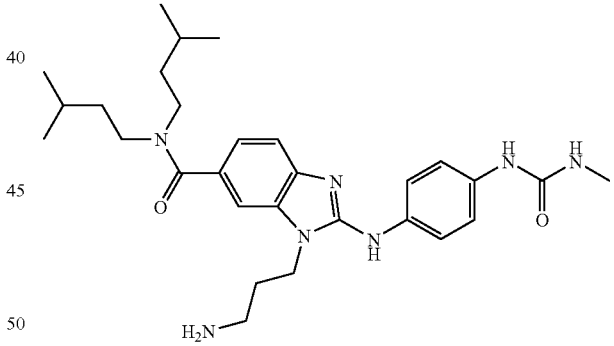

Stage 1: tert-butyl 3-{6-{[bis(3-methylbutyl)amino]carbonyl}-2-[(4-nitrophenyl)amino]-1H-benzimidazol-1-yl}propylcarbamate 4-nitrophenyl isothiocyanate (305 mg, 1.5 eq) and N-methylcyclohexylcarbodiimide-N-methyl-polystyrene resin (acquired from Novabiochem; charge 1.9 mmol/g; 1.75 g, 3 eq) are successively added to a solution of tert-butyl-3-[(2-amino-5-{[bis(3-methylbutyl)amino]carbonyl}phenyl)amino]propylcarbamate prepared according to Example A1 (500 mg, 1 eq) in tetrahydrofuran (30 ml). The mixture is heated under reflux for 18 hours then cooled down to ambient temperature and filtered on frit. The filtrate is concentrated under reduced pressure at 40° C. Purification of the residue by flash chromatography on silica gel (eluent:heptane/ethyl acetate 7:3 to 2:8) produces the expected compound in the form of a yellow solid (584 mg; 88% yield).

MS/LC: calculated MM=594.7; m/z=595.3 (MH+)

NMR ($^1$H, 400 MHz, DMSO-$d_6$): δ0.64-0.95 (m, 12H), 1.36 (s, 9H), 1.31-1.65 (m, 6H), 1.82 (m, 2H), 3.0 (m, 2H), 3.15-3.39 (m, 4H), 4.32 (t, 2H), 6.95 (m, 1H), 7.05 (d, 1H), 7.40 (s, 1H), 7.48 (d, 1H), 8.11 (AB, 2H), 8.26 (AB, 2H), 9.71 (s, 1H).

Stage 2: tert-butyl 3-(2-[(4-aminophenyl)amino]-6-{[bis(3-methylbutyl)amino]carbonyl}-1H-benzimidazol-1-yl)propylcarbamate Tert-butyl 3-{6-{[bis(3-methylbutyl)amino]carbonyl}-2-[(4-nitrophenyl)amino]-1H-benzimidazol-1-yl}propylcarbamate (580 mg) in solution in a mixture of ethyl acetate/methanol 3:1 (40 ml), and 10% palladium on carbon (58 mg) are introduced into an autoclave. After stirring for 15 hours under a hydrogen atmosphere (3 bar) at a temperature of approximately 20° C., the catalyst is eliminated by filtration on celite and the filtrate is concentrated under reduced pressure at 40° C. in order to produce the expected compound in the form of a foam (480 mg; 87% yield).

MS/LC: calculated MM=564.7; m/z=565.3 (MH+)

NMR ($^1$H, 400 MHz, DMSO-$d_6$): δ0.86 (m, 12H), 1.37 (s, 9H), 1.31-1.58 (m, 6H), 1.79 (m, 2H), 3.01 (m, 2H), 3.15-3.39 (m, 4H), 4.15 (t, 2H), 4.80 (m, 2H), 6.56 (m, 2H), 6.94 (d, 2H), 7.21 (AB, 2H), 7.40 (AB, 2H), 8.45 (s, 1H).

Stage 3: tert-butyl 3-{6-{[bis(3-methylbutyl)amino]carbonyl}-2-[(4-{[(methylamino)carbonyl]amino}phenyl)amino]-1H-benzimidazol-1-yl}propyl carbamate dihydrochloride A solution of carbonyldiimidazole (CDI) (29 mg, 2 eq) in dichloromethane (2 ml) is added to a solution of tert-butyl 3-(2-[(4-aminophenyl)amino]-6-{[bis (3-methylbutyl) amino]carbonyl}-1H-benzimidazol-1-yl)propylcarbamate (50 mg, 1 eq) in dichloromethane (2 ml). The mixture is stirred for 18 hours at a temperature of approximately 20° C. then methylamine is added (2M in THF, 0.440 ml, 10 eq). The mixture is stirred for 4 hours at a temperature of approximately 20° C. then concentrated under reduced pressure at 40° C. The residue is taken up in dichloromethane (7 ml) and a saturated aqueous solution of sodium hydrogen carbonate (3 ml). After decantation and extractions the combined organic phases are washed with salt water then concentrated under reduced pressure at 40° C. Purification of the residue by flash chromatography on silica gel (eluent:heptane/ethyl acetate 1:1 to 1:9) produces a compound in the form of foam which is dissolved in ethyl acetate (0.5 ml). A solution of hydrochloric acid (2N in diethyl ether, 2 ml) is added and the mixture is stirred for 1 hour at a temperature of approximately 20° C. then the precipitate obtained is filtered and dried in order to produce the expected compound (28 mg, 55% yield).

MS/LC: calculated MM=521.7; m/z=522.3 (MH$^+$)

According to reaction diagram E and in a fashion analogous to the procedure described for the synthesis of tert-butyl 3-{6-{[bis(3-methylbutyl)amino]carbonyl}-2-[(4-{[(methylamino)carbonyl]amino}phenyl)amino]-1H-benzimidazol-1-yl}propyl carbamate dihydrochloride, the following compounds were prepared:

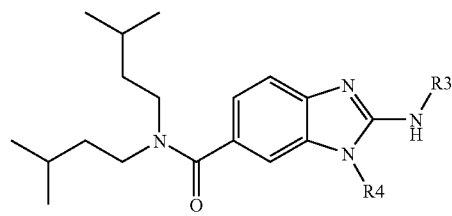

in which $R_3$ represents one of the radicals below:

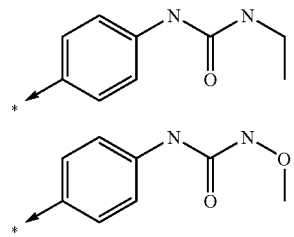

and $R_4$ represents one of the radicals below:

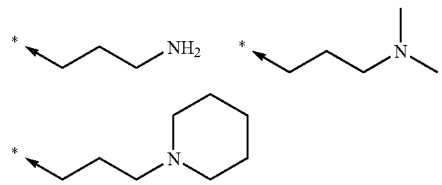

F. Preparation According to Reaction Diagram F:

The compounds of formula (I) according to the invention in which A represents —$CH_2$—, can be prepared according to the following diagrams F and F':

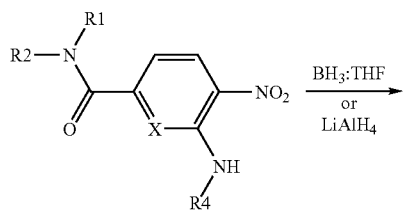

-continued

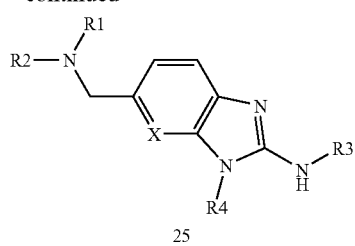

25

As described in diagram F, the derivative (4) prepared according to reaction diagram A, can be reduced to compound (24) using borane or lithium aluminium hydride in an aprotic solvent such as tetrahydrofuran or diethyl ether at a temperature of 0 to 70° C., for 18 to 24 hours. The dianiline (24) can then be treated by an isothiocyanate in the presence of a coupling agent supported or not supported on a resin such as diisopropylcarbodiimide or dicyclohexylcarbodiimide or N-methylcyclohexylcarbodiimide N-methyl polystyrene resin in an inert solvent such as tetrahydrofuran, methylene chloride, or chloroform at a temperature of 20-70° C. for 2 to 72 hours in order to produce derivative (25).

Preparation According to Reaction Diagram F':

The compounds (25) can also be prepared according to the following diagram F':

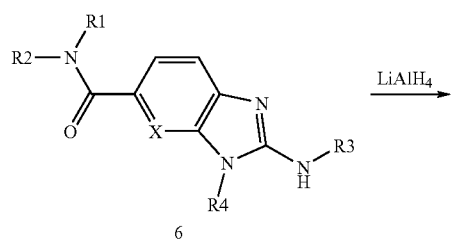

6

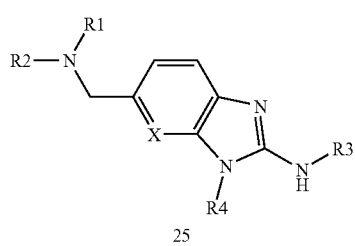

25

As described in diagram F', the amide (6) prepared according to reaction diagrams A or B, can be reduced to the corresponding amine (25) using borane or lithium aluminium hydride in an aprotic solvent such as tetrahydrofuran or diethyl ether at a temperature of 0 to 70° C., for 1 to 6 hours.

EXAMPLE F'1

6-{[bis(3-methylbutyl)amino]methyl}-1-[3-(dimethylamino)propyl]-N-(4-methoxyphenyl)-1H-benzimidazol-2-amine hydrochloride

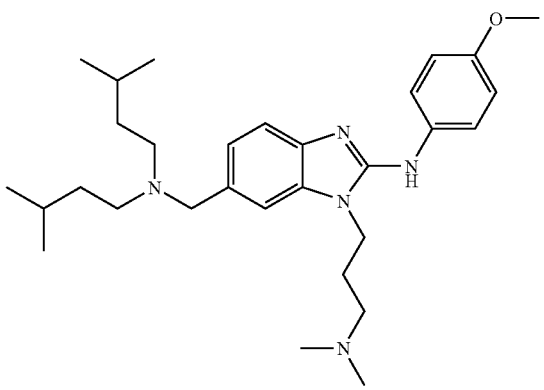

A solution of lithium aluminium hydride (0.785 ml; 1 M in THF) is added dropwise to a solution cooled down to 0° C. of 1-[3-(dimethylamino)propyl]-2-[(4-methoxyphenyl)amino]-N,N-bis(3-methylbutyl)-1H-benzimidazole-6-carboxamide prepared according to reaction diagram A (80 mg, 1 eq) in anhydrous tetrahydrofuran (2 ml). The mixture is taken to a temperature of 20° C. then heated at 60° C. for 3 hours. After cooling down to 0° C., the reaction medium is hydrolyzed. After the addition of ethyl acetate, decantation and extractions, the combined organic phases are washed with salt water, dried over sodium sulphate and concentrated under reduced pressure. Purification by flash chromatography on silica gel (eluent:100% dichloromethane to dichloromethane/methanol 9:1) produces the expected compound in the form of a base. The corresponding hydrochloride salt is formed by adding a 1N solution of hydrochloric acid in diethyl ether (61 mg; 55% yield).

MS/LC: calculated MM=493.7; m/z=494.4 (MH+)

NMR ($^1$H, 400 MHz, DMSO-$d_6$): $\delta$0.83 (m, 12H), 1.50-1.72 (m, 6H), 2.29 (m, 2H), 2.78 (m, 6H), 2.99 (m, 4H), 3.30 (m, 2H), 3.80 (s, 3H), 4.41 (m, 4H), 6.90-8.50 (m, 7H), 10.5 (m, 1H), 10.85 (m, 1H), 12.9 (m, 1H).

The following compounds were prepared according to reaction diagrams F or F':

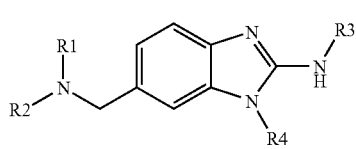

in which $R_1R_2N$ represents one of the radicals below:
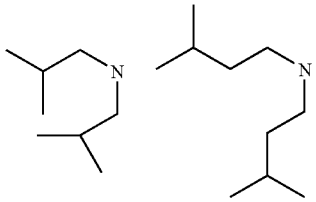
in which $R_3$ represents one of the radicals below:
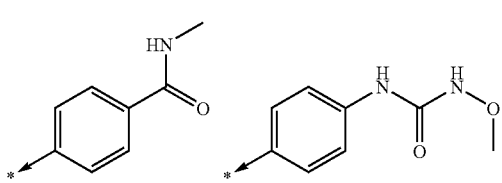
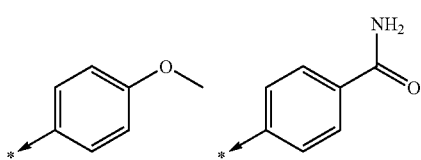
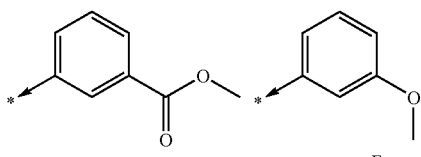
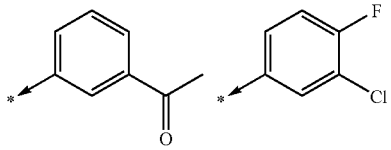
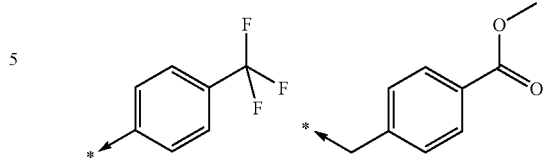
-continued
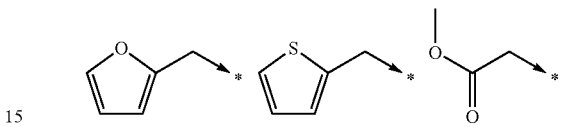
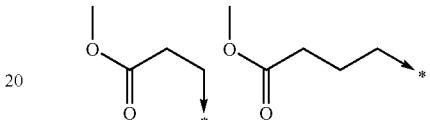
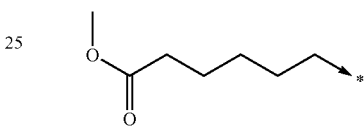
and $R_4$ represents one of the radicals below:
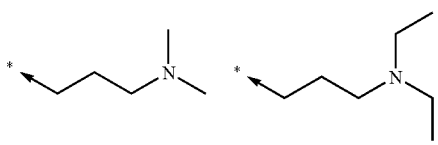
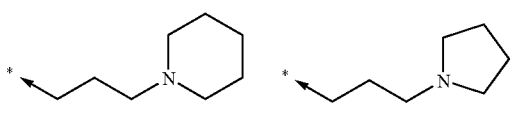
G. Preparation According to Reaction Diagram G:
The compounds of formula (I) according to the invention in which A represents —C(O)—C($R_a$)($R_b$)—, can be prepared according to the following diagram G:
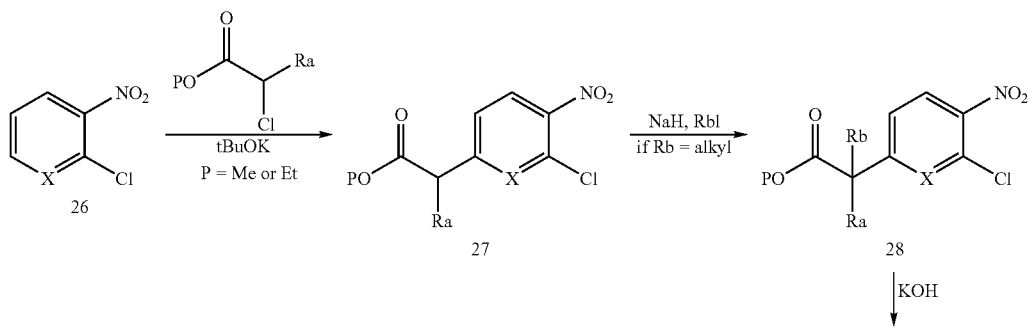

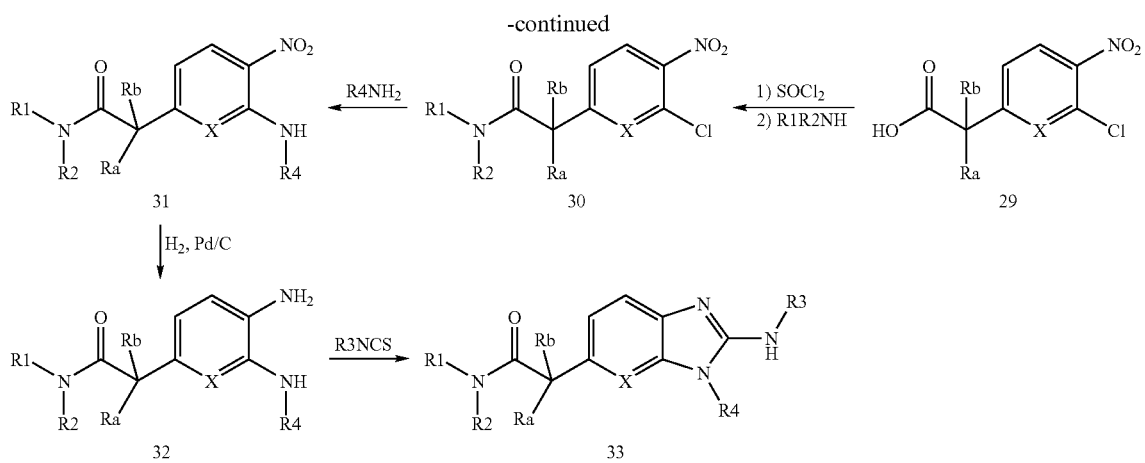

As described in diagram G, the derivative (26) can be alkylated in the presence of a strong base such as potassium tertbutylate, by an α-chloroester derivative, in an aprotic polar solvent such as dimethylformamide at a temperature of 0-20° C. for 0.5-2 hours, in order to produce compound (27). The derivative (27) can be optionally alkylated in the presence of a strong base such as sodium hydride and an alkylating agent such as an alkyl iodide in an aprotic solvent such as dimethylformamide at a temperature of 0-20° C. for 1-4 hours, in order to produce compound (28). The ester (28) can be saponified in the presence of an inorganic base such as lithium or potassium hydroxide in a mixture of polar solvents such as water and methanol at a temperature of 20-80° C. for 1-6 hours. The resultant carboxylic acid (29) can be coupled with a primary or secondary amine in the presence of a coupling agent such as diisopropylcarbodiimide (DIC), dicyclohexylcarbodiimide (DCC), 1-(3-dimethylaminopropyl)-3-ethylcarbodiimide hydrochloride (EDC) or carbonyldiimidazole (CDI), with or without 1-hydroxybenzotriazole (HOBt) in an inert organic solvent such as methylene chloride, tetrahydrofuran or dimethylformamide at ambient temperature for 3 to 24 hours. Alternatively the acid (29) can be treated with thionyl or oxalyl chloride in an aprotic solvent such as dichloromethane or toluene at a temperature of 40-60° C. for 2-16 hours then the acid chloride thus obtained can react with a primary or secondary amine, in the presence of a tertiary base such as triethylamine, diisopropylethylamine in an aprotic solvent such as dichloromethane or tetrahydrofuran at a temperature of 0-20° C. over 0.5-4 hours in order to produce the amide (30). Treatment of the fluorinated or chlorinated derivative (30) with a primary amine in the presence of an inorganic base such as caesium or potassium carbonate in an inert organic solvent such as dimethylformamide or acetonitrile at a temperature of 20-100° C. for 2 to 48 hours leads to the derivative (31). The nitro function of compound (31) is reduced by treatment with tin chloride dihydrate in an inert solvent such as ethyl acetate or dimethylformamide at a temperature of 60-80° C. for 3 to 15 hours, or by catalytic hydrogenation in the presence of 10% palladium on carbon in an inert solvent such as methanol, ethanol, ethyl acetate or a mixture of these solvents, at a temperature of 18-25° C., for 2 to 8 hours in order to produce the dianiline (32). The derivative (32) is then treated with an isothiocyanate in the presence of a coupling agent supported or not supported on a resin such as diisopropylcarbodiimide or dicyclohexylcarbodiimide or N-methylcyclohexylcarbodiimide N-methyl polystyrene resin in an inert solvent such as tetrahydrofuran, methylene chloride, or chloroform at a temperature of 20-70° C. for 2 to 72 hours in order to produce the derivative (33). Alternatively, the derivative (32) can be treated with an isothiocyanate in an inert solvent such as tetrahydrofuran, methylene chloride, chloroform or ethanol at a temperature of 20-80° C. for 1-16 hours then the resultant thiourea can be treated with methyl iodide or yellow mercury (II) oxide in the presence of a catalytic quantity of sulphur in a polar solvent such as methanol or ethanol for 2 to 24 hours at a temperature of 20-80° C. in order to produce (33). Compound (6) can be isolated either by flash chromatography on silica gel, or by the addition to the reaction mixture of a nucleophilic reagent supported on a polymer such as for example an aminomethylpolystyrene resin and/or an electrophilic reagent supported on a polymer such as for example methylisothiocyanate-polystyrene resin, followed by filtration and evaporation of the filtrate.

EXAMPLE G1

2-{2-[(4-acetylphenyl)amino]-1-[3-(dimethylamino)propyl]-1H-benzimidazol-6-yl}-N,N-diisobutyl-2-methylpropanamide dihydrochloride

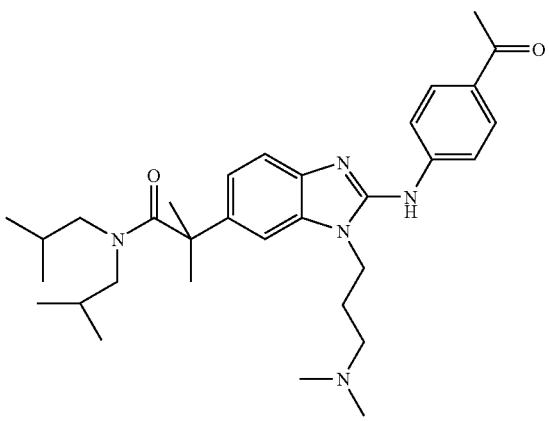

Stage 1: ethyl 2-(3-chloro-4-nitrophenyl)propanoate

Potassium tert-butylate (11.22 g, 2 eq) is added to a solution of DMF (80 ml) cooled down to 0° C. A solution of 1-chloro-2-nitrobenzene (7.87 g, 1 eq) and ethyl 2-chloropropanoate (7 ml, 1.1 eq) is added dropwise over 45 minutes to the mixture whilst keeping the reaction temperature below 5° C. At the end of the addition, stirring is maintained for 2 hours at 0° C., then the mixture is hydrolyzed at this temperature with a 1N solution of hydrochloric acid and ethyl acetate is added. After decantation and extractions, the combined organic phases are washed with salt water, dried over $Na_2SO_4$ and concentrated under reduced pressure. Purification by flash chromatography on silica gel (eluent:heptane/dichloromethane 8:2 to 6:4) produces the expected compound in the form of a yellow oil (8.28 g; 64% yield).

NMR ($^1$H, 400 MHz, DMSO-$d_6$): δ 1.14 (t, 3H), 1.42 (d, 3H), 3.99 (q, 1H), 4.08 (m, 2H), 7.52 (AB, 1H), 7.71 (s, 1H), 8.05 (AB, 1H).

Stage 2: ethyl 2-(3-chloro-4-nitrophenyl)-2-methylpropanoate

A solution of ethyl 2-(3-chloro-4-nitrophenyl)propanoate (14.1 g) is added dropwise to a suspension of sodium hydride (60% in oil, 2.4 g, 1.1 eq) in DMF (15 ml), cooled down to 0° C. After stirring for 1 hour at this temperature, a solution of methyl iodide (3.72 ml, 1.1 eq) in DMF (40 ml) is added dropwise to the mixture. Stirring is continued for 3 hours at ambient temperature. The reaction medium is cooled down to 0° C. then ethyl acetate, water saturated with sodium hydrogen carbonate are added dropwise, then water. After decantation and extractions, the combined organic phases are washed with salt water, dried over $Na_2SO_4$ and concentrated under reduced pressure in order to produce the expected compound in the form of an oil which crystallizes. The crystals are washed with heptane and dried (13.8 g; 94% yield).

NMR ($^1$H, 400 MHz, DMSO-$d_6$): δ1.12 (t, 3H), 1.54 (s, 6H), 4.09 (q, 1H), 7.50 (AB, 1H), 7.66 (s, 1H), 8.04 (AB, 1H).

Stage 3: 2-(3-chloro-4-nitrophenyl)-2-methylpropanoic acid

A 2N solution of potassium hydroxide (18 ml) is added at a temperature of approximately 20° C. to a solution of ethyl 2-(3-chloro-4-nitrophenyl)-2-methylpropanoate (1 g) in methanol (20 ml). The mixture is then heated at 80° C. for 1.5 hours then cooled down to ambient temperature. The methanol is evaporated by concentration of the mixture under reduced pressure. The remaining aqueous phase is washed with dichloromethane then cooled down to 0° C. and acidified with acetic acid. After the addition of dichloromethane, decantation and extractions, the combined organic phases are washed with salt water, dried over $Na_2SO_4$ and concentrated under reduced pressure in order to produce the expected compound in the form of an oil which crystallizes (852 mg, 95% yield).

NMR ($^1$H, 400 MHz, DMSO-$d_6$): δ1.52 (s, 6H), 7.53 (AB, 1H), 7.66 (s, 1H), 8.04 (AB, 1H), 12.72 (s, 1H).

Stage 4: 2-(3-chloro-4-nitrophenyl)-N,N-diisobutyl-2-methylpropanamide

Thionyl chloride (0.54 ml, 4 eq) is added to a solution of 2-(3-chloro-4-nitrophenyl)-2-methylpropanoic acid (500 mg) in dichloromethane (1 ml). The mixture is heated under reflux for 16 hours then cooled down to ambient temperature. The solvent is evaporated off under reduced pressure at 40° C. (co-evaporation with toluene). Diisopropylethylamine (0.42 ml, 1.2 eq) and diisobutylamine (0.36 ml, 1 eq) are successively added to a solution of the acid chloride thus obtained in dichloromethane (1 ml), cooled down to 0° C. At the end of the addition, stirring is continued for 3 hours at ambient temperature then the mixture is concentrated under reduced pressure at 40° C. The residue is dissolved in ethyl ether and the organic phase is washed successively with 1N soda, a saturated solution of sodium hydrogen carbonate, salt water then dried over $Na_2SO_4$ and concentrated under reduced pressure at 40° C. Purification by flash chromatography on silica gel (eluent:heptane/ethyl acetate 8:2 to 7:3) produces the expected compound in the form of an oil which crystallizes (0.585 g; 82% yield).

MS/LC: calculated MM=354.9; m/z=355.2 (MH+)

NMR ($^1$H, 400 MHz, CDCl$_3$): δ0.58 (d, 6H), 0.90 (d, 6H), 1.58 (m, 6H), 1.74 (m, 1H), 1.95 (m, 1H), 2.65 (d, 2H), 3.27 (d, 2H), 7.30 (AB, 1H), 7.44 (s, 1H), 7.91 (AB, 1H).

Stage 5: 2-(3-{[3-(dimethylamino)propyl]amino}-4-nitrophenyl)-N,N-diisobutyl-2-methylpropanamide A mixture of 2-(3-chloro-4-nitrophenyl)-N,N-diisobutyl-2-methylpropanamide (78 mg, 1 eq), 3-dimethylaminopropylamine (45 mg, 2 eq) and potassium carbonate (62 mg, 2 eq) in DMF (2 ml) is heated under reflux for 3 hours then cooled down to ambient temperature. The residue is taken up in ethyl acetate (20 ml) and water (8 ml). After decantation and extractions, the combined organic phases are washed with salt water, dried over $Na_2SO_4$ then concentrated under reduced pressure at 40° C. Purification of the residue by flash chromatography on silica gel (eluent:100% dichloromethane to dichloromethane/methanol 8:2) produces the expected compound in the form of a yellow oil (44 mg; 48% yield).

MS/LC: calculated MM=420.6; m/z=421.3 (MH+)

NMR ($^1$H, 400 MHz, CDCl$_3$): δ0.60 (d, 6H), 0.90 (d, 6H), 1.57 (m, 6H), 1.75 (m, 1H), 1.88 (m, 2H), 1.97 (m, 1H), 2.28 (s, 6H), 2.45 (t, 1H), 2.75 (d, 2H), 3.26 (d, 2H), 3.34 (m, 2H), 6.57 (m, 1H), 6.68 (s, 1H), 8.15 (m, 1H), 8.49 (m, 1H).

Stage 6: 2-(4-amino-3-{[3-(dimethylamino)propyl]amino}phenyl)-N,N-diisobutyl-2-methylpropanamide 2-(3-{[3-(dimethylamino)propyl]amino}-4-nitrophenyl)-N,N-diisobutyl-2-methylpropanamide (44 mg) in solution in a mixture of ethyl acetate/ethanol 2:1 (3 ml), and 10% palladium on carbon (5 mg) are introduced into an autoclave. After stirring for 4 hours under a hydrogen atmosphere (3 bar) at a temperature of approximately 20° C., the catalyst is eliminated by filtration on celite and the filtrate is concentrated under reduced pressure at 40° C. in order to produce the expected compound in the form of an oil (39 mg; 95% yield).

MS/LC: calculated MM=390.6; m/z=391.3 (MH+)

NMR ($^1$H, 400 MHz, DMSO-$d_6$): δ0.49 (m, 6H), 0.81 (m, 6H), 1.36 (s, 6H), 1.65 (m, 1H), 1.72 (m, 2H), 1.87 (m, 1H), 2.20 (s, 6H), 2.39 (t, 2H), 2.81 (m, 2H), 2.97 (t, 2H), 3.11 (m, 2H), 4.56 (m, 2H), 6.18 (s, 1H), 6.30 (AB, 1H), 6.48 (AB, 1H).

Stage 7: 2-{2-[(4-acetylphenyl)amino]-1-[3-(dimethylamino)propyl]-1H-benzimidazol-6-yl}-N,N-diisobutyl-2-methylpropanamide dihydrochloride 4-acetylphenyl isothiocyanate (14 mg, 1.2 eq) and N-methylcyclohexylcarbodiimide-N-methyl-polystyrene resin (acquired from Novabiochem; charge 1.9 mmol/g; 210 mg, 4 eq) are successively added to a solution of 2-(4-amino-3-{[3-(dimethylamino)propyl]amino}phenyl)-N,N-diisobutyl-2-methylpropanamide (39 mg, 1 eq) in tetrahydrofuran (2 ml). The mixture is heated under reflux for 17 hours then cooled down to ambient temperature and filtered. The filtrate is concentrated under reduced pressure at 40° C. Purification of the residue by flash chromatography on silica gel (eluent:100% dichloromethane to dichloromethane/methanol 9:1) produces the expected compound in form of a base (409 mg; 60% yield). The corresponding hydrochloride salt is formed by adding a 1N solution of hydrochloric acid in ether. The precipitate obtained is filtered and dried in order to produce the expected dihydrochloride compound (51 mg, 85% yield).

MS/LC: calculated MM=533.7; m/z=534.4 (MH+)

NMR ($^1$H, 400 MHz, DMSO-$d_6$): δ0.40 (m, 6H), 0.82 (m, 6H), 1.53 (s, 6H), 1.64 (m, 1H), 1.89 (m, 1H), 2.21 (m, 2H), 2.59 (s, 3H), 2.75 (m, 8H), 3.15 (m, 2H), 3.25 (m, 2H), 4.60 (t, 2H), 7.10 (AB, 1H), 7.41 (AB, 1H), 7.56 (s, 1H), 7.82 (m, 2H), 8.05 (m, 2H), 10.79 (m, 1H), 11.4 (m, 1H).

According to reaction diagram G, the following compounds were prepared:

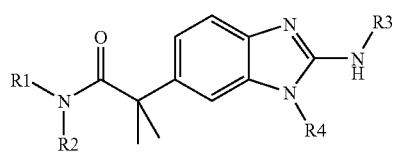

in which $R_1R_2N$ represents one of the radicals below:

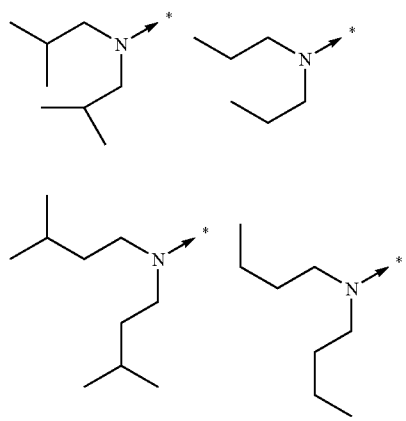

$R_3$ represents one of the radicals below:

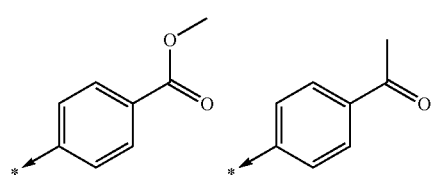

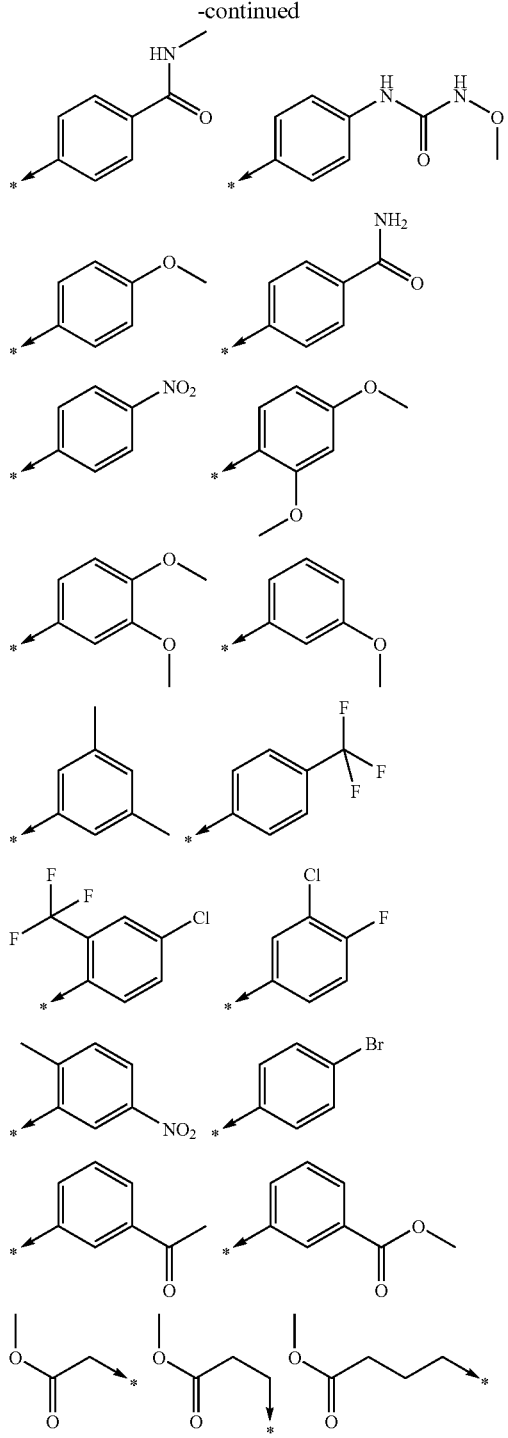

and $R_4$ represents one of the radicals below:

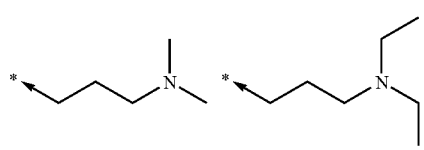

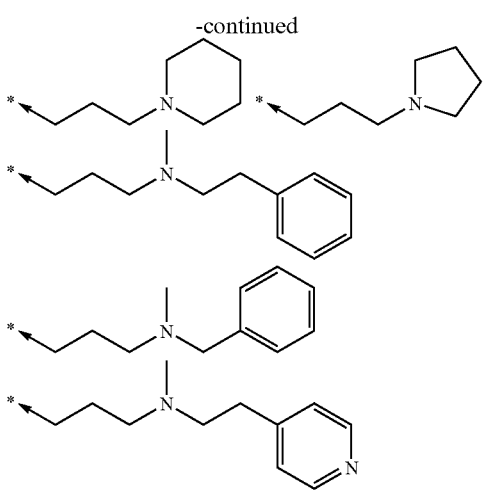

A subject of the invention is also a process for the preparation of a compound of formula (I) as defined above, characterized in that the compound of general formula:

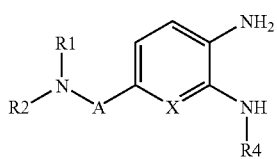

in which A, X, $R_1$, $R_2$, $R_4$ have the meaning indicated above, is treated with an isothiocyanate of general formula $R_3N=C=S$ in which $R_3$ has the meaning indicated above, in the presence of a coupling agent or of yellow mercury (II) oxide in the presence of sulphur, for a period of 3 to 48 hours, in a protic or aprotic solvent, at a temperature of 50 to 80° C.

The coupling agent can be supported such as N-methylcyclohexyl carbodiimide N-methyl polystyrene resin or not supported such as diisopropylcarbodiimide, diethylcarbodiimide or dicyclohexylcarbodiimide. A protic solvent such as methanol or ethanol or an aprotic solvent such as tetrahydrofuran or acetonitrile can be used.

A subject of the invention is also a compound of general formula (II)

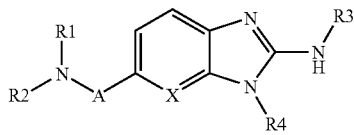

(II)

in racemic or enantiomeric form or any combinations of these forms and in which:
A represents —$CH_2$—, —C(O)—, —C(O)—C($R_a$)($R_b$)—;
X represents —C— or —N—;
$R_a$ and $R_b$ represent, independently, the hydrogen atom or a ($C_1$-$C_6$)alkyl radical;
$R_1$ and $R_2$ represent, independently, the hydrogen atom, a ($C_1$-$C_8$)alkyl radical optionally substituted by hydroxy, ($C_2$-$C_6$)alkenyl or a radical of formula —$(CH_2)_n$—$X_1$;

$X_1$ represents ($C_1$-$C_6$)alkoxy, ($C_3$-$C_7$)cycloalkyl, adamantyl, heterocycloalkyl, aryl or heteroaryl,
the ($C_3$-$C_7$)cycloalkyl, heterocycloalkyl, aryl and heteroaryl radicals being optionally substituted by one or more identical or different substituents chosen from: —$(CH_2)_{n'}$—$V_1$—$Y_1$, halo, nitro and cyano;
$V_1$ represents —O—, —S— or a covalent bond;
$Y_1$ represents a ($C_1$-$C_6$)alkyl radical optionally substituted by one or more identical or different halo radicals; or aryl;
n represents an integer from 0 to 6 and n' an integer from 0 to 2 (it being understood that when n is equal to 0, then $X_1$ represents neither the hydroxy radical nor the alkoxy radical);

or $R_1$ and $R_2$ form together with the nitrogen atom to which they are attached, a heterobicycloalkyl or a heterocycloalkyl optionally substituted by one or more identical or different substituents chosen from: hydroxy, ($C_1$-$C_6$)alkyl, ($C_1$-$C_6$)hydroxyalkyl, ($C_1$-$C_6$)alkoxy-carbonyl, —C(O)N$V_1'Y_1'$ with $V_1'$ and $Y_1'$ independently representing the hydrogen atom or a ($C_1$-$C_6$)alkyl, and heterocycloalkyl; or $R_1$ and $R_2$ form together a radical of formula:

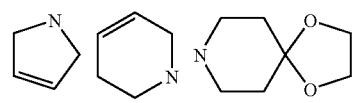

$R_3$ represents —$(CH_2)_p$-$Z_3$ or —C(O)-$Z'_3$
$Z_3$ represents a ($C_1$-$C_6$)alkyl, ($C_2$-$C_6$)alkenyl, ($C_1$-$C_6$) alkoxy, ($C_1$-$C_6$)alkoxy-carbonyl, ($C_3$-$C_7$)cycloalkyl, heterocycloalkyl, aryl or heteroaryl radical,
the ($C_3$-$C_7$) cycloalkyl and heterocycloalkyl radicals being optionally substituted by ($C_1$-$C_6$)alkyl,
the aryl radical being optionally substituted by one or more identical or different substituents chosen from: halo, nitro, azido or —$(CH_2)_{p'}$—$V_3$—$Y_3$;
$V_3$ represents —O—, —S—, —C(O)—, —C(O)—O—, —NH—C(O)—, —C(O)—NR'$_3$—, —NH—C(O)—NR'$_3$— or a covalent bond;
$Y_3$ represents the hydrogen atom or a ($C_1$-$C_6$)alkyl radical optionally substituted by one or more identical or different halo radicals;
or $Z_3$ represents a radical of formula

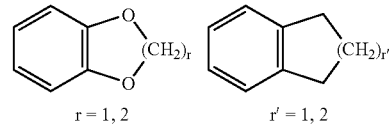

$Z'_3$ represents an aryl radical optionally substituted by one or more identical or different substituents chosen from: halo, nitro and —$(CH_2)_{p''}$—$V'_3$—$Y'_3$;
$V'_3$ represents —O—, —C(O)—, —C(O)—O—, —C(O)—NR'$_3$—, —NH—C(O)—, —NH—C(O)—NR'$_3$— or a covalent bond;
$Y'_3$ represents the hydrogen atom or a ($C_1$-$C_6$)alkyl radical optionally substituted by one or more identical or different halo radicals;
R'$_3$ represents the hydrogen atom, a ($C_1$-$C_6$)alkyl or ($C_1$-$C_6$)alkoxy radical;
p, p' and p" represent, independently, an integer from 0 to 4;
$R_4$ represents a radical of formula —$(CH_2)_r$—$R'_4$ R'$_4$ represents a heterocycloalkyl containing at least one nitrogen atom and optionally substituted by (C$_1$-C$_6$)alkyl or aralkyl; a heteroaryl containing at least one nitrogen atom and optionally substituted by (C$_1$-C$_6$)alkyl; or a radical of formula —NW$_4$W'$_4$ W$_4$ represents the hydrogen atom or (C$_1$-C$_8$)alkyl;

W'$_4$ represents a radical of formula —(CH$_2$)$_s$-Z$_4$;

Z$_4$ represents the hydrogen atom, (C$_1$-C$_8$)alkyl optionally substituted by one or more identical or different substituents chosen from: (C$_1$-C$_6$)alkoxy, (C$_1$-C$_6$)alkylthio and hydroxy; (C$_2$-C$_6$)alkenyl; (C$_3$-C$_7$)cycloalkyl optionally substituted by one or more identical or different (C$_1$-C$_6$)alkyl substituents; cyclohexene; heteroaryl; aryl optionally substituted by one or more identical or different radicals chosen from: —(CH$_2$)$_{s''}$—V$_4$—Y$_4$, hydroxy, halo, nitro and cyano;

V$_4$ represents —O—, —S—, —NH—C(O)—, —NV$_4$'— or a covalent bond;

Y$_4$ represents a hydrogen atom or a (C$_1$-C$_6$)alkyl radical optionally substituted by one or more identical or different halo radicals;

V$_4$' represents a hydrogen atom or a (C$_1$-C$_6$)alkyl;

s" represents an integer from 0 to 4;

or Z$_4$ represents a radical of formula

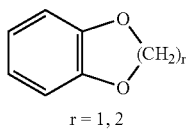

r = 1, 2 s and s' represent, independently, an integer from 0 to 6;

and when R$_3$ represents —C(O)-Z'$_3$ and R$_4$ represents a radical of formula —(CH$_2$)$_s$—NW$_4$W'$_4$ and W$_4$ and W'$_4$ represent, independently, the hydrogen atom or the (C$_1$-C$_6$)alkyl radical, then —(CH$_2$)$_s$ represents neither the ethylene radical nor the —(CH$_2$)—CH((C$_1$-C$_4$)alkyl)-radical;

Preferably, the invention relates to compounds of formula II as defined above and in which A represents —C(O)— and X represents —C—;

R$_1$ and R$_2$ represent, independently, a hydrogen atom, a (C$_1$-C$_8$)alkyl radical optionally substituted by hydroxy, (C$_2$-C$_6$)alkenyl or a radical of formula —(CH$_2$)$_n$—X$_1$;

X$_1$ represents (C$_1$-C$_6$)alkoxy, (C$_3$-C$_7$)cycloalkyl, aryl or heteroaryl, the aryl radical being optionally substituted by one or more identical or different substituents chosen from: —(CH$_2$)$_{n'}$—V$_1$—Y$_1$, halo;

V$_1$ represents —O— or a covalent bond;

Y$_1$ represents a (C$_1$-C$_6$)alkyl radical optionally substituted by one or more identical or different halo radicals; or aryl;

or R$_1$ and R$_2$ form together with the nitrogen atom to which they are attached, a heterocycloalkyl optionally substituted by one or more identical or different substituents chosen from: hydroxy, (C$_1$-C$_6$)alkyl, (C$_1$-C$_6$)hydroxyalkyl, (C$_1$-C$_6$) alkoxy-carbonyl, —C(O)NV$_1$'Y$_1$' with V$_1$' and Y$_1$' independently representing the hydrogen atom or a (C$_1$-C$_6$)alkyl, and heterocycloalkyl; or R$_1$ and R$_2$ form together a radical of formula:

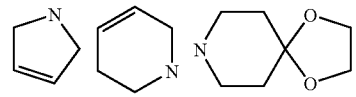

R$_3$ represents —(CH$_2$)$_p$-Z$_3$ or —C(O)-Z'$_3$

Z$_3$ represents a (C$_1$-C$_6$)alkoxy-carbonyl, (C$_3$-C$_7$)cycloalkyl, heteroaryl, or aryl radical optionally substituted by one or more identical or different substituents chosen from: halo, nitro or —(CH$_2$)$_{p'}$V$_3$—Y$_3$;

V$_3$ represents —O—, —S—, —C(O)—, —C(O)—O—, —C(O)—NR'$_3$—, —NH—C(O)—, —NH—C(O)—NR'$_3$— or a covalent bond;

Y$_3$ represents the hydrogen atom or a (C$_1$-C$_6$)alkyl radical optionally substituted by one or more identical or different halo radicals;

or Z$_3$ represents a radical of formula

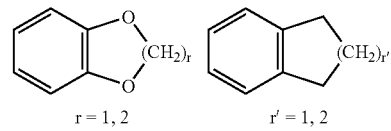

r = 1, 2    r' = 1, 2

Z'$_3$ represents an aryl radical optionally substituted by one or more identical or different substituents chosen from: halo, nitro and —(CH$_2$)$_{p''}$V'$_3$—Y'$_3$;

V'$_3$ represents —O— or a covalent bond;

Y'$_3$ represents the hydrogen atom or a (C$_1$-C$_6$)alkyl radical optionally substituted by one or more identical or different halo radicals;

R'$_3$ represents the hydrogen atom, a (C$_1$-C$_6$)alkyl or (C$_1$-C$_6$)alkoxy radical;

p is equal to 0 or 1, and p' and p" are equal to 0;

R$_4$ represents a radical of formula —(CH$_2$),—R'$_4$

R'$_4$ represents a heterocycloalkyl containing at least one nitrogen atom and optionally substituted by (C$_1$-C$_6$) alkyl or benzyl; a heteroaryl containing at least one nitrogen atom; or a radical of formula —NW$_4$W'$_4$;

W$_4$ represents the hydrogen atom or (C$_1$-C$_8$)alkyl;

W'$_4$ represents a radical of formula —(CH$_2$)$_s$-Z$_4$;

Z$_4$ represents the hydrogen atom, (C$_1$-C$_8$)alkyl, (C$_3$-C$_7$) cycloalkyl or aryl;

and more particularly the cycloalkyl radical is chosen from the cyclopropyl, cyclohexyl and cycloheptyl radicals, the heterocycloalkyl radical is chosen from the pyrrolidinyl, piperidinyl, morpholinyl, piperazinyl, azacycloheptyl, azacyclooctyl and decahydro-isoquinolinyl radicals, the aryl radical is the phenyl radical, the heteroaryl radical is chosen from the furyl, pyridyl and imidazolyl radicals, or a pharmaceutically acceptable salt thereof.

Very preferably, the invention also relates to compounds of formula II as defined above and in which A represents —C(O)— and X represents —C—;

R$_1$ and R$_2$ represent, independently, a (C$_1$-C$_8$)alkyl radical;

R$_3$ represents —(CH$_2$)$_p$-Z$_3$

Z$_3$ represents a phenyl radical optionally substituted by one or more identical or different substituents chosen from: nitro or —(CH$_2$)$_{p'}$V$_3$—Y$_3$;

$V_3$ represents —O—, —C(O)—, —C(O)—O—, —C(O)—NR'$_3$—, NH—C(O)—, —NH—C(O)—NR'$_3$—;

$Y_3$ represents the hydrogen atom or a ($C_1$-$C_6$)alkyl radical;

R'$_3$ represents the hydrogen atom or a ($C_1$-$C_6$)alkoxy radical;

p is equal to 0 or 1; p' is equal to 0;

$R_4$ represents a radical of formula —(CH$_2$)$_s$—R'$_4$

R'$_4$ represents a heterocycloalkyl containing at least one nitrogen atom and optionally substituted by ($C_1$-$C_6$)alkyl; or a radical of formula —NW$_4$W'$_4$;

$W_4$ represents the hydrogen atom or ($C_1$-$C_8$)alkyl;

W'$_4$ represents a radical of formula —(CH$_2$)$_{s'}$-Z$_4$;

$Z_4$ represents the hydrogen atom or ($C_3$-$C_7$)cycloalkyl;

s represents an integer from 2 to 4; s' represents an integer from 0 to 4;

and more particularly the heterocycloalkyl radical represented by R'$_4$ is the pyrrolidinyl, piperidinyl, morpholinyl or piperazinyl radical, and the cycloalkyl represented by $Z_4$ is cyclohexyl;

or a pharmaceutically acceptable salt thereof.

Preferably also, the invention relates to compounds of formula II as defined above and in which A represents —C(O)—C($R_a$)($R_b$)—; X represents —C—;

$R_a$ and $R_b$ represent, independently, a ($C_1$-$C_6$)alkyl radical;

$R_1$ and $R_2$ represent, independently, a ($C_1$-$C_8$)alkyl radical;

$R_3$ represents —(CH$_2$)$_p$-Z$_3$ $Z_3$ represents a phenyl radical optionally substituted by one or more identical or different substituents of formula —(CH$_2$)$_{p'}$V$_3$—Y$_3$;

$V_3$ represents —O—, —C(O)—, —C(O)—O—, —C(O)—NR'$_3$—, —NH—C(O)—NR'$_3$—;

$Y_3$ represents the hydrogen atom or a ($C_1$-$C_6$)alkyl radical;

R'$_3$ represents a ($C_1$-$C_6$)alkyl or ($C_1$-$C_6$)alkoxy radical;

p and p' are equal to 0;

$R_4$ represents a radical of formula —(CH$_2$),—R'$_4$

R'$_4$ represents a heterocycloalkyl containing at least one nitrogen atom and optionally substituted by ($C_1$-$C_6$)alkyl; or a radical of formula —NW$_4$W'$_4$ $W_4$ represents the hydrogen atom or ($C_1$-$C_8$)alkyl;

W'$_4$ represents a radical of formula —(CH$_2$)$_{s'}$-Z$_4$;

$Z_4$ represents the hydrogen atom, the phenyl radical or a heteroaryl;

s represents an integer from 2 to 4; s' represents an integer from 0 to 4;

or a pharmaceutically acceptable salt thereof.

Preferably also, the invention relates to compounds of formula II as defined above and in which A represents —CH$_2$—; X represents —C—;

$R_1$ and $R_2$ represent, independently, a ($C_1$-$C_8$)alkyl radical;

$R_3$ represents —(CH$_2$)$_p$-Z$_3$ $Z_3$ represents a phenyl radical optionally substituted by one or more identical or different substituents of formula —(CH$_2$)$_{p'}$—V$_3$—Y$_3$;

$V_3$ represents —O—, —C(O)—, —C(O)—O—, —C(O)—NR'$_3$—, —NH—C(O)—NR'$_3$—;

$Y_3$ represents the hydrogen atom or a ($C_1$-$C_6$)alkyl radical;

R'$_3$ represents a ($C_1$-$C_6$)alkyl or ($C_1$-$C_6$)alkoxy radical;

p and p' are equal to 0;

$R_4$ represents a radical of formula —(CH$_2$), —R'$_4$

R'$_4$ represents a heterocycloalkyl containing at least one nitrogen atom and optionally substituted by ($C_1$-$C_6$)alkyl; or a radical of formula —NW$_4$W'$_4$ $W_4$ represents the hydrogen atom or ($C_1$-$C_8$)alkyl;

W'$_4$ represents a radical of formula —(CH$_2$)$_{s'}$-Z$_4$;

$Z_4$ represents the hydrogen atom;

s represents an integer from 2 to 4; s' represents an integer from 0 to 4;

or a pharmaceutically acceptable salt thereof.

The compounds I and II of the present invention have useful pharmacological properties. It has thus been discovered that the compounds I and II of the present invention have a good affinity for certain sub-types of melanocortin receptors, in particular the MC4 receptors.

The compounds of the present invention can thus be used in different therapeutic applications. They can advantageously be used for treating the pathological states or diseases in which one or more melanocortin receptors are involved such as inflammatory conditions, weight disorders (obesity, cachexia, anorexia), sexual activity disorders (erective disorders), pain, but also mental health problems (anxiety, depression), drug addiction, skin diseases (acne, dermatoses, melanomas). Hereafter, in the experimental part, an illustration will be found of the pharmacological properties of the compounds of the invention.

A subject of the present application is also pharmaceutical compositions containing, as active ingredient, at least one product of formula I as defined above, as well as the pharmaceutically acceptable salts of said product of formula I, in combination with a pharmaceutically acceptable support.

By pharmaceutically acceptable salt, is understood in particular addition salts of inorganic acids such as hydrochloride, hydrobromide, hydroiodide, sulphate, phosphate, diphosphate and nitrate or of organic acids such as acetate, maleate, fumarate, tartrate, succinate, citrate, lactate, methanesulphonate, p-toluenesulphonate, pamoate and stearate. Also within the scope of the present invention, when they can be used, the salts formed from bases such as sodium or potassium hydroxide. For other examples of pharmaceutically acceptable salts, reference can be made to "Salt selection for basic drugs", *Int. J. Pharm.* (1986), 33, 201-217.

A subject of the present application is also the use of the compounds according to the present invention, for the preparation of a medicament for the treatment of weight disorders such as obesity, cachexia and more particularly cancerous cachexia, AIDS cachexia, old-age cachexia, cardiac cachexia, renal cachexia, cachexia in rheumatoid arthritis, and anorexia, the treatment of pain and more particularly neuropathic pain, mental health problems such as anxiety and depression, sexual activity disorders such as erective disorders.

The pharmaceutical composition can be in the form of a solid, for example, powders, granules, tablets, gelatin capsules or suppositories. Appropriate solid supports can be, for example, calcium phosphate, magnesium stearate, talc, sugars, lactose, dextrin, starch, gelatin, cellulose, methyl cellulose, sodium carboxymethyl cellulose, polyvinylpyrrolidine and wax.

A subject of the present invention is also the use of a compound of general formula (I')

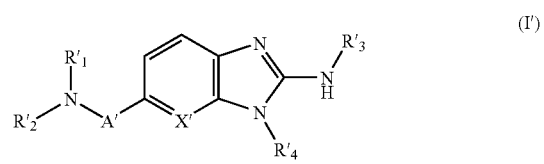

in racemic or enantiomeric form or any combinations of these forms and in which:

A' represents —$CH_2$—, —$C(O)$—, —$C(O)$—$C(R_a)(R_b)$—;

X' represents —CH—;

$R_a$ and $R_b$ represent, independently, the hydrogen atom or a ($C_1$-$C_6$)alkyl radical;

$R'_1$ represents the hydrogen atom; a ($C_1$-$C_8$)alkyl radical optionally substituted by hydroxy or one or more identical or different halo radicals; ($C_2$-$C_6$)alkenyl; or a radical of formula —$(CH_2)_n$—$X_1$;

$R'_2$ represents a ($C_1$-$C_8$)alkyl radical optionally substituted by hydroxy or one or more identical or different halo radicals; ($C_2$-$C_6$)alkenyl; or a radical of formula —$(CH_2)_n$—$X_1$;

each $X_1$ independently represents ($C_1$-$C_6$)alkoxy, ($C_3$-$C_7$)cycloalkyl, adamantyl, heterocycloalkyl, aryl or heteroaryl, the ($C_3$-$C_7$)cycloalkyl, heterocycloalkyl, aryl and heteroaryl radicals being optionally substituted by one or more identical or different substituents chosen from: —$(CH_2)_{n'}V_1$—$Y_1$, halo, nitro, cyano and aryl;

$V_1$ represents —O—, —S— or a covalent bond;

$Y_1$ represents a ($C_1$-$C_6$)alkyl radical optionally substituted by one or more identical or different halo radicals;

n represents an integer from 0 to 6 and n' an integer from 0 to 2 (it being understood that when n is equal to 0, then $X_1$ does not represent the alkoxy radical)

or $R_1$ and $R_2$ form together with the nitrogen atom to which they are attached, a heterobicycloalkyl or a heterocycloalkyl optionally substituted by one or more identical or different substituents chosen from: hydroxy, ($C_1$-$C_6$)alkyl optionally substituted by hydroxy, ($C_1$-$C_6$)alkoxy-carbonyl, heterocycloalkyl and —$C(O)NV_1'Y_1'$ with $V_1'$ and $Y_1'$ independently representing the hydrogen atom or a ($C_1$-$C_6$)alkyl; or $R_1$ and $R_2$ form together a radical of formula:

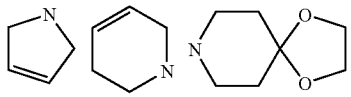

$R'_3$ represents -$Z_3$, $C(R_{Z3})(R'_{Z3})$-$Z_3$, —$C(R_{Z3})(R'_{Z3})$—$(CH_2)_p$-$Z_3$ or —$C(O)$-$Z'_3$ $R_{Z3}$ and $R'_{Z3}$ represent, independently, the hydrogen atom or a ($C_1$-$C_6$)alkyl radical;

$Z_3$ represents $Z_{3a}$, $Z_{3b}$, $Z_{3c}$, $Z_{3d}$, or $Z_{3e}$;

$Z_{3a}$ represents a ($C_1$-$C_6$)alkyl radical;

$Z_{3b}$ represents a ($C_1$-$C_6$)alkoxy, ($C_1$-$C_6$)alkylthio, ($C_1$-$C_6$)alkylamino or di(($C_1$-$C_6$)alkyl)amino radical;

$Z_{3c}$ represents an aryl or heteroaryl radical;

$Z_{3d}$ represents a ($C_1$-$C_6$)alkoxy-carbonyl, amino-carbonyl, ($C_1$-$C_6$)alkylamino-carbonyl, di(($C_1$-$C_6$)alkyl)amino-carbonyl, ($C_1$-$C_6$)alkyl-C(O)—NH—, ($C_3$-$C_7$)cycloalkyl, heterocycloalkyl radical;

the ($C_3$-$C_7$) cycloalkyl and heterocycloalkyl radicals being optionally substituted by one or more identical or different substituents chosen from: halo, nitro, ($C_1$-$C_6$)alkoxy optionally substituted by one or more identical or different halo radicals, ($C_1$-$C_6$)alkyl optionally substituted by one or more identical or different halo radicals, ($C_1$-$C_6$) alkyl-carbonyl, ($C_1$-$C_6$)alkoxy-carbonyl, amino-carbonyl, ($C_1$-$C_6$)alkylamino-carbonyl, di(($C_1$-$C_6$)alkyl) amino-carbonyl and oxy;

the aryl and heteroaryl radicals being optionally substituted by one or more identical or different substituents chosen from: halo, cyano, nitro, azido, oxy, ($C_1$-$C_6$) alkoxy-carbonyl-($C_1$-$C_6$)alkenyl, ($C_1$-$C_6$)alkylamino-carbonyl-($C_1$-$C_6$)alkenyl, —$SO_2$—$NR_{31}R_{32}$, heterocycloalkyl, heteroaryl or —$(CH_2)_p$—$V_3$—$Y_3$;

$R_{31}$ and $R_{32}$ form together with the nitrogen atom to which they are attached, a heterocycloalkyl;

$V_3$ represents —O—, —S—, —$C(O)$—, —$C(O)$—O—, —O—$C(O)$—, —$SO_2$—, —$SO_2NH$—, —$NR'_3$—$SO_2$—, —$NR'_3$—, —$NR'_3$—$C(O)$—, —$C(O)$—$NR'_3$—, —NH—$C(O)$—$NR'_3$— or a covalent bond;

$Y_3$ represents the hydrogen atom; a ($C_1$-$C_6$)alkyl radical optionally substituted by one or more identical or different halo radicals; an aryl radical optionally substituted by one or more identical or different substituents chosen from: halo, nitro, ($C_1$-$C_6$)alkyl and ($C_1$-$C_6$)alkoxy; or an aryl-($C_1$-$C_6$)alkyl radical optionally substituted by one or more identical or different substituents chosen from: halo, nitro, ($C_1$-$C_6$)alkyl and ($C_1$-$C_6$)alkoxy;

$Z_{3e}$ represents a radical of formula

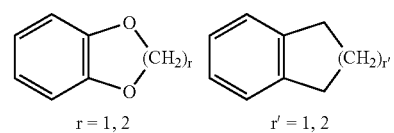

$Z'_3$ represents an aryl radical optionally substituted by one or more identical or different substituents chosen from: halo, nitro and —$(CH_2)_{p''}$—$V'_3$—$Y'_3$;

$V'_3$ represents —O—, —$C(O)$—, —$C(O)$—O—, —$C(O)$—$NR'_3$, —NH—$C(O)$—$NR'_3$ or a covalent bond;

$Y'_3$ represents the hydrogen atom or a ($C_1$-$C_6$)alkyl radical optionally substituted by one or more identical or different halo radicals;

$R'_3$ represents the hydrogen atom, a ($C_1$-$C_6$)alkyl or ($C_1$-$C_6$)alkoxy radical;

p represents an integer from 1 to 4; p' and p" represent, independently, an integer from 0 to 4;

$R_4$ represents a radical of formula —$(CH_2)_s$—$R'_4$;

$R'_4$ represents the guanidine radical; a heterocycloalkyl containing at least one nitrogen atom and optionally substituted by ($C_1$-$C_6$)alkyl or aralkyl; a heteroaryl containing at least one nitrogen atom and optionally substituted by ($C_1$-$C_6$)alkyl; or a radical of formula —$NW_4W'_4$ $W_4$ represents the hydrogen atom or ($C_1$-$C_8$)alkyl;

$W'_4$ represents a radical of formula —$(CH_2)_{s'}$-$Z_4$;

$Z_4$ represents the hydrogen atom, ($C_1$-$C_8$)alkyl optionally substituted by one or more identical or different substituents chosen from: ($C_1$-$C_6$)alkoxy, ($C_1$-$C_6$)alkylthio and hydroxy; ($C_2$-$C_6$)alkenyl; ($C_3$-$C_7$)cycloalkyl optionally substituted by one or more identical or different ($C_1$-$C_6$)alkyl substituents; cyclohexene; heteroaryl and aryl;

the aryl and heteroaryl radicals being optionally substituted by one or more identical or different radicals chosen from formula —$(CH_2)_{s''}$—$V_4$—$Y_4$, hydroxy, halo, nitro and cyano;

$V_4$ represents —O—, —S—, —NH—$C(O)$—, —$NV'_4$ or a covalent bond;

$Y_4$ represents a hydrogen atom or a ($C_1$-$C_6$)alkyl radical optionally substituted by one or more identical or different halo radicals;

$V'_4$ represents a hydrogen atom or a ($C_1$-$C_6$)alkyl;

s" represents an integer from 0 to 4;

or $Z_4$ represents a radical of formula

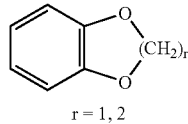

r = 1, 2 s and s' represent, independently, an integer from 0 to 6; or a pharmaceutically acceptable salt thereof;

for the preparation of a medicament for the treatment of weight disorders, mental health problems, pain, or sexual activity disorders.

A subject of the present invention is more particularly the use of a compound of general formula (I') as defined above, characterized in that $R_1$ and $R_2$ represent, independently, a $(C_1-C_8)$alkyl radical;

$R_3$ represents $Z_{3c}$ and $Z_{3c}$ represents a phenyl or naphthyl radical, each substituted at least by cyano;

$R_4$ represents a radical of formula $—(CH_2)_s—R'_4$ with $R'_4$ representing the pyrrolidinyl or piperidinyl radical; or a radical of formula $—NW_4W'_4$;

$W_4$ represents the hydrogen atom or $(C_1-C_8)$alkyl;

$W'_4$ represents a radical of formula $—(CH_2)_{s'}-Z_4$ with $Z_4$ representing the hydrogen atom;

s represents an integer from 2 to 4; s' represents an integer from 0 to 4;

or a pharmaceutically acceptable salt thereof.

The pharmaceutical compositions containing a compound of the invention can also be presented in liquid form, for example, solutions, emulsions, suspensions or syrups. Appropriate liquid supports can be, for example, water, organic solvents such as glycerol or the glycols, as well as their mixtures, in varying proportions, in water, added to pharmaceutically acceptable oils or greases. The sterile liquid compositions can be used for intramuscular, intraperitoneal or sub-cutaneous injections and the sterile compositions can also be administered by intravenous route.

All the technical and scientific terms used in the present text have the meaning known to a person skilled in the art. Moreover, all the patents (or patent applications) as well as the other bibliographical references are incorporated by way of reference.

Experimental Part:

The compounds according to the invention obtained according to the procedures of Examples A, B, C, C', D, E, F, F' and G described previously, are set out in the table below.

The compounds are characterized by their retention times (rt) and their molecular peak determined by mass spectrometry (MH+).

For the mass spectrometry, a single quadripole mass spectrometer (Micromass, Platform model) equipped with an electrospray source is used with a resolution of 0.8 Da at 50% valley. A calibration is carried out monthly between the masses 80 and 1000 Da using a calibrating mixture of sodium iodide and rubidium iodide in solution in an isopropanol/water mixture (1/1 Vol.).

For the liquid chromatography, a Waters system including an in-line degasser, a Waters 600 quaternary pump, a Gilson 233 plate sampling injector and a Waters PAD 996 UV detector, is used.

The elution conditions used are the following:
Eluent: A water+0.04% trifluoroacetic acid; B acetonitrile

| T (minutes) | A % | B % |
| --- | --- | --- |
| 1 | 95 | 5 |
| 8.5 | 5 | 95 |
| 10.5 | 5 | 95 |
| 10.6 | 95 | 5 |
| 14.9 | 95 | 5 |
| 15.0 | 95 | 5 |

Flow rate: 1 ml/min; Injection: 10 µl; Column: Uptisphere ODS 3 µm 75*4.6 mm i.d.

These examples are presented in order to illustrate the procedures above and should in no event be considered as a limit to the scope of the invention.

| Examples | Molecular structures | [M + H]+ | rt (min) |
| --- | --- | --- | --- |
| 1 | 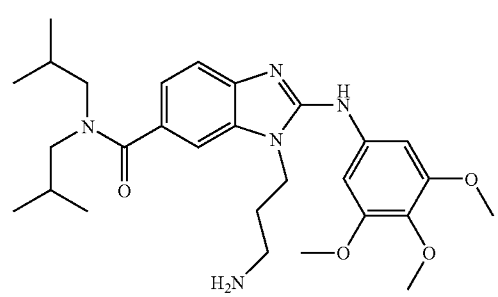 | 512.3 | 7.8 |

-continued
| Examples | Molecular structures | [M + H]+ | rt (min) |
|---|---|---|---|
| 2 | 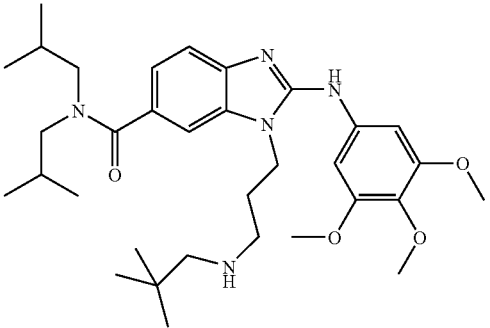 | 582.3 | 8.0 |
| 3 | 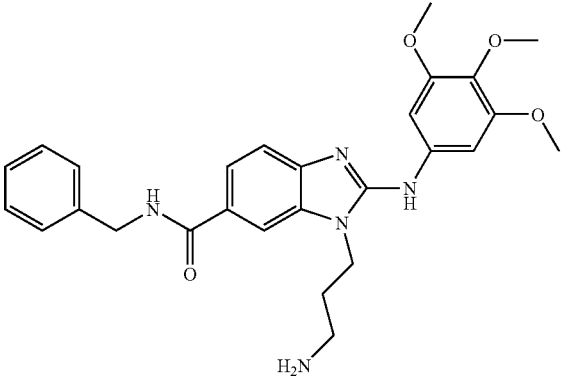 | 490.5 | 7.5 |
| 4 | 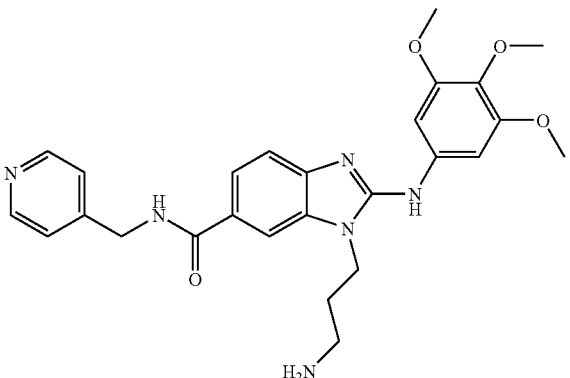 | 491.4 | 6.9 |
| 5 | 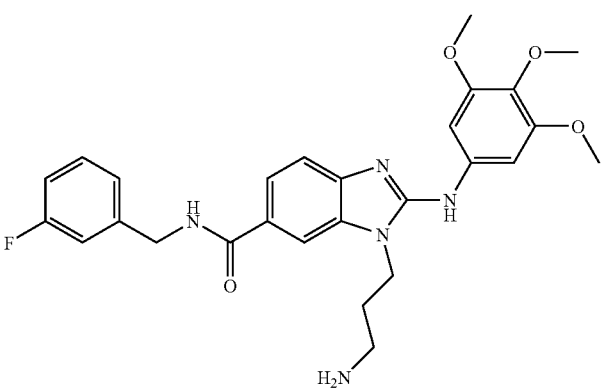 | 508.4 | 7.6 |

-continued

| Examples | Molecular structures | [M + H]+ | rt (min) |
|---|---|---|---|
| 6 | 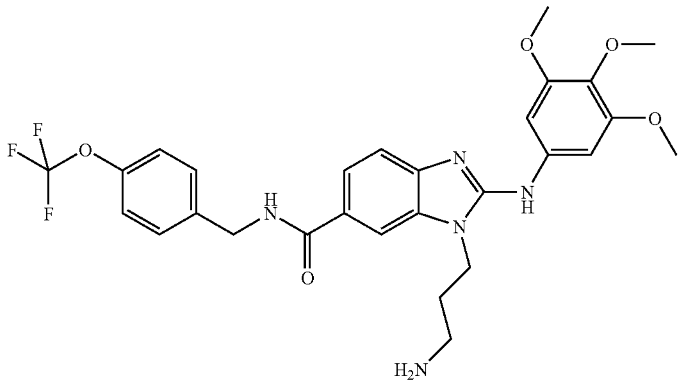 | 574.4 | 8.0 |
| 7 | 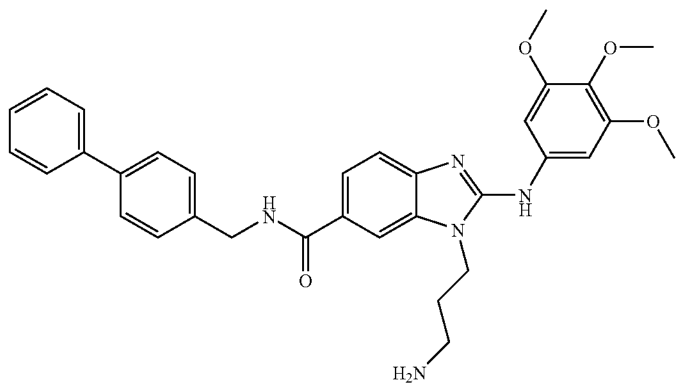 | 566.4 | 8.1 |
| 8 | 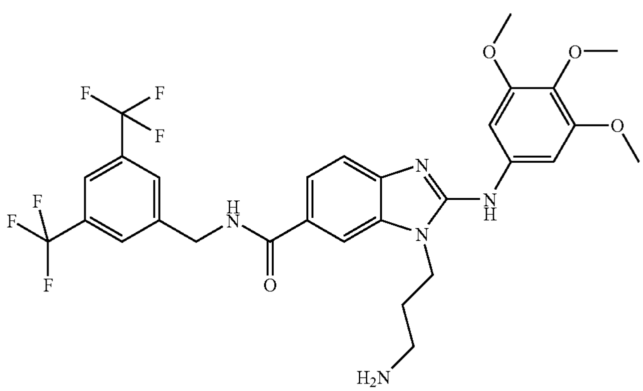 | 626.4 | 8.2 |
| 9 | 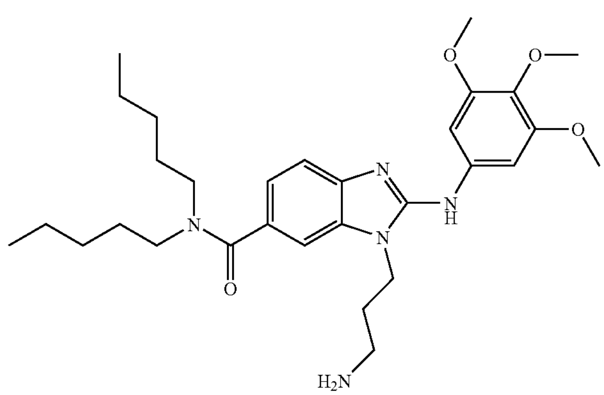 | 540.3 | 8.2 |

-continued

| Examples | Molecular structures | [M + H]+ | rt (min) |
|---|---|---|---|
| 10 | 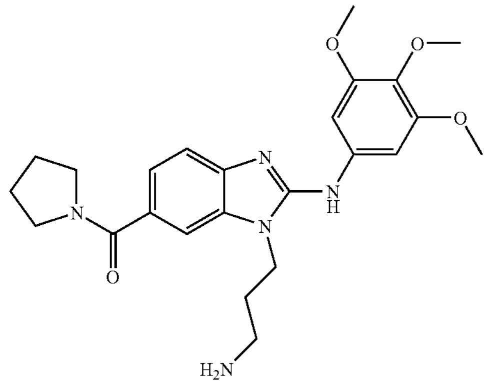 | 454.3 | 7.2 |
| 11 | 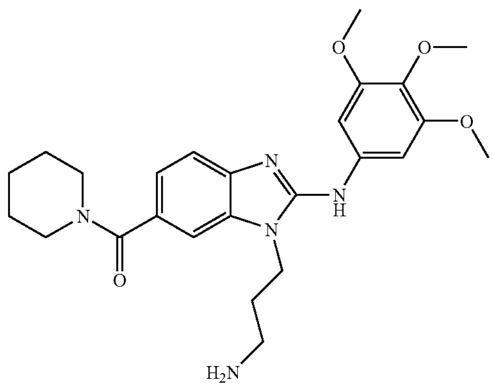 | 467.9 | 7.3 |
| 12 | 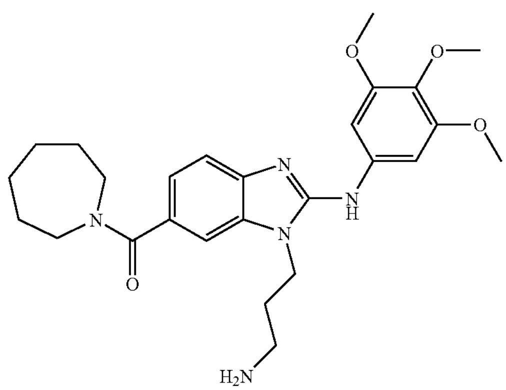 | 482.3 | 7.4 |
| 13 | 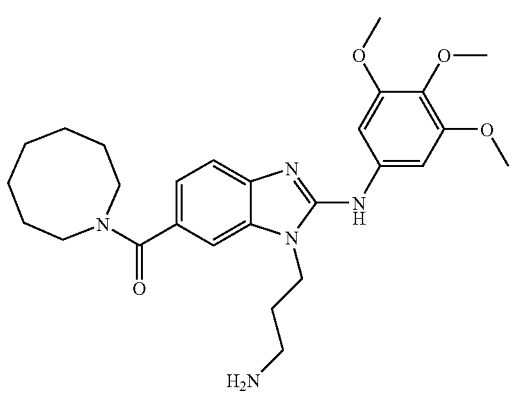 | 496.1 | 7.5 |

-continued

| Examples | Molecular structures | [M + H]+ | rt (min) |
|---|---|---|---|
| 14 | 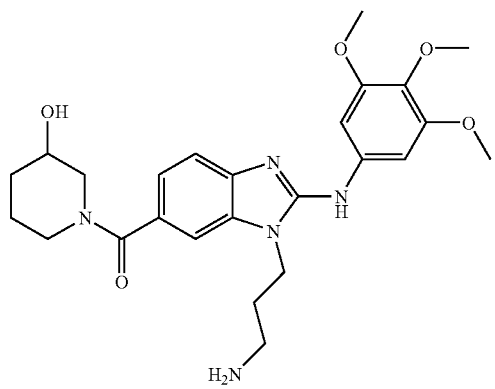 | 484.5 | 7.0 |
| 15 | 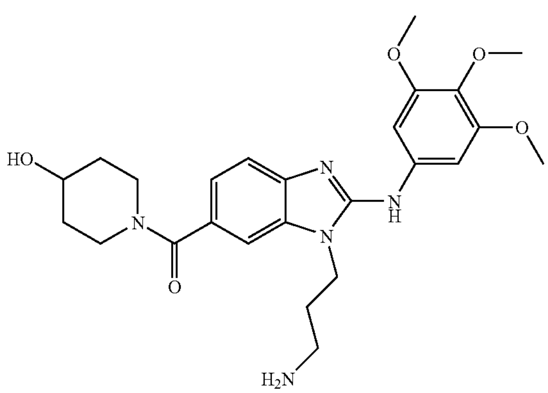 | 484.3 | 7.0 |
| 16 | 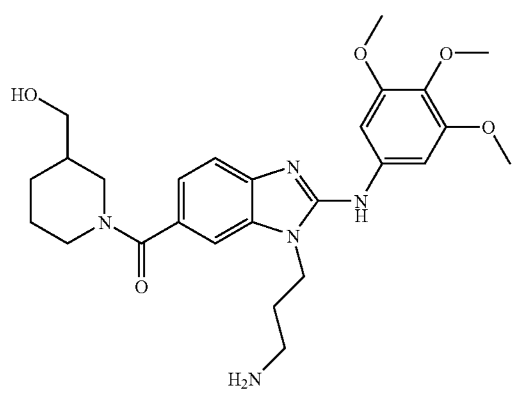 | 498.3 | 7.1 |
| 17 | 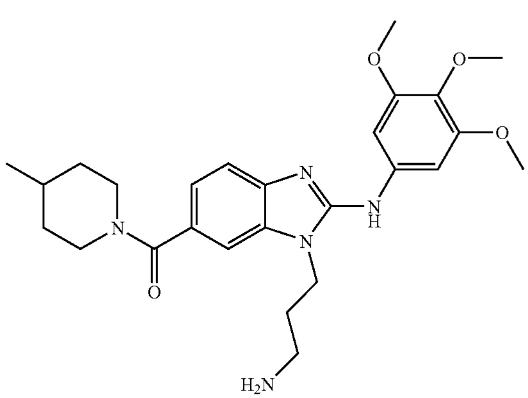 | 482.3 | 7.5 |

-continued
| Examples | Molecular structures | [M + H]+ | rt (min) |
|---|---|---|---|
| 18 | 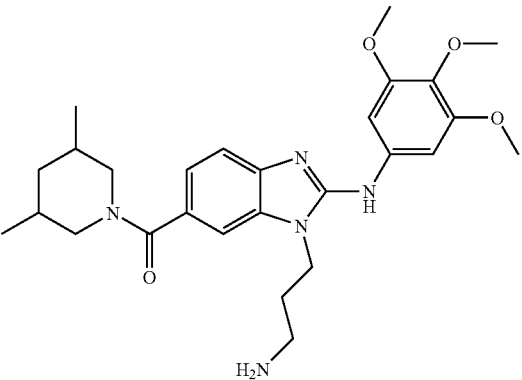 | 496.2 | 7.6 |
| 19 | 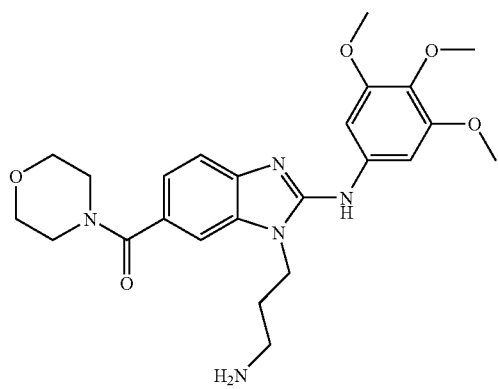 | 470.2 | 7.0 |
| 20 | 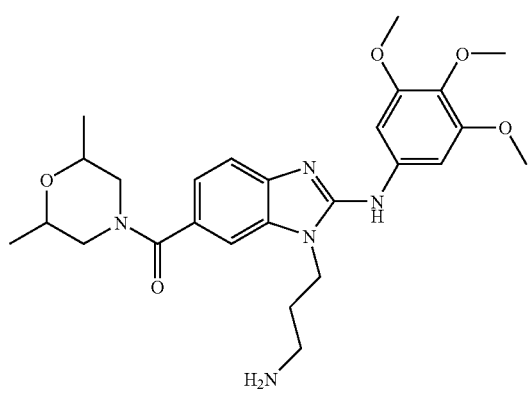 | 498.3 | 7.2 |
| 21 | 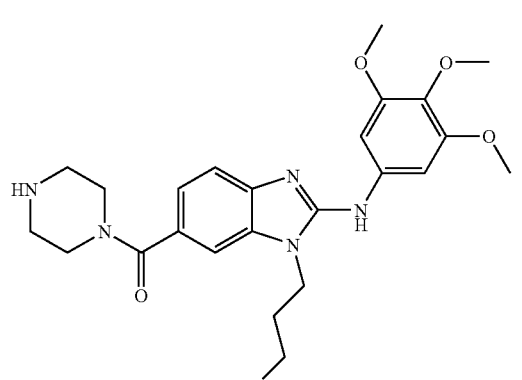 | 469.1 | 6.2 |

| Examples | Molecular structures | [M + H]+ | rt (min) |
|---|---|---|---|
| 22 | 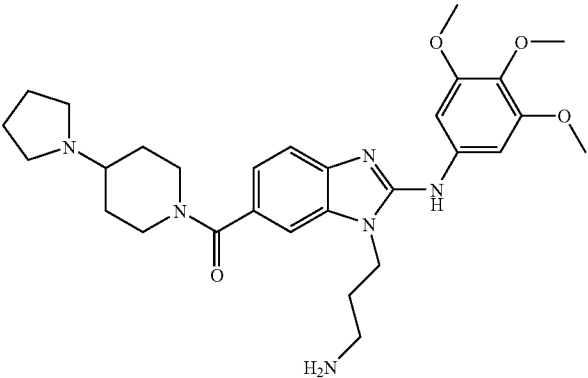 | 537.1 | 6.8 |
| 23 | 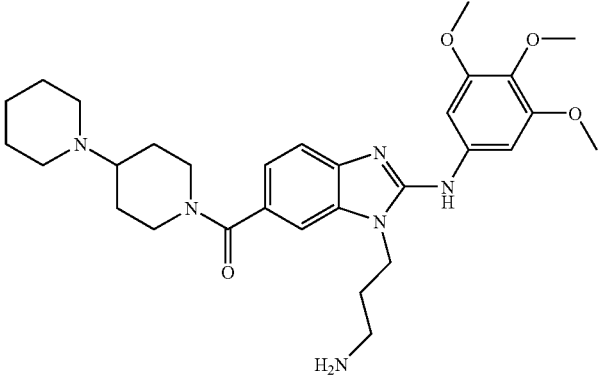 | 551.0 | 6.9 |
| 24 | 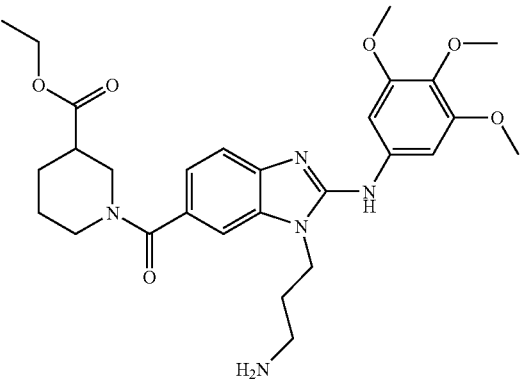 | 540.2 | 7.4 |
| 25 | 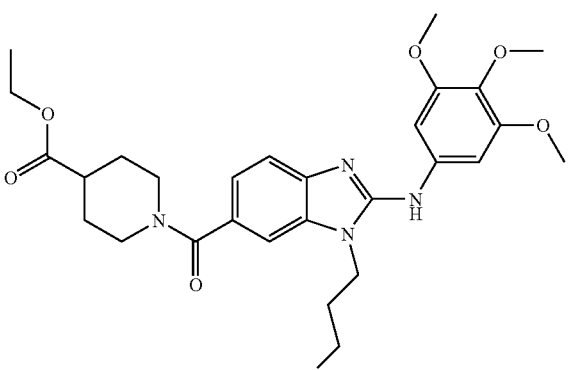 | 540.0 | 7.4 |

-continued

| Examples | Molecular structures | [M + H]+ | rt (min) |
|---|---|---|---|
| 26 | 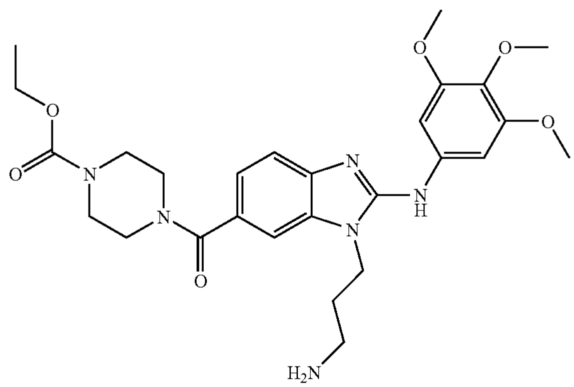 | 541.0 | 7.3 |
| 27 | 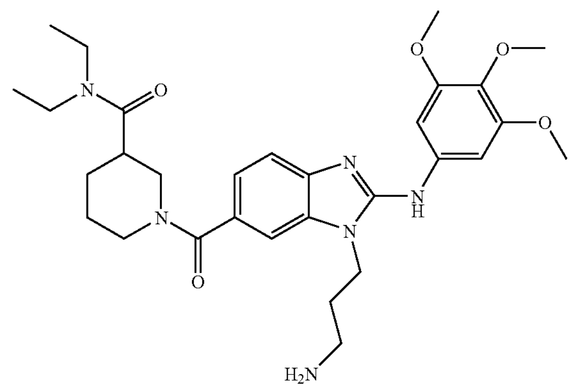 | 566.9 | 7.3 |
| 28 | 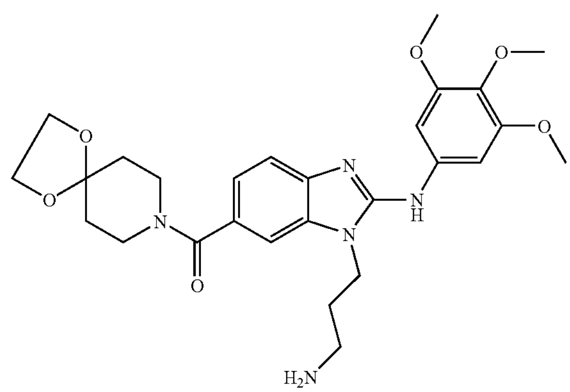 | 526.0 | 7.2 |
| 29 | 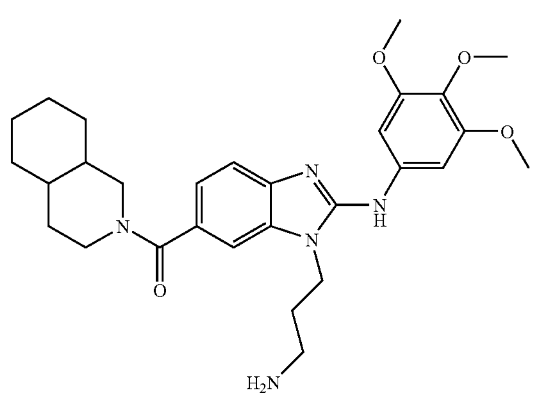 | 522.3 | 7.7 |

-continued
| Examples | Molecular structures | [M + H]+ | rt (min) |
|---|---|---|---|
| 30 | 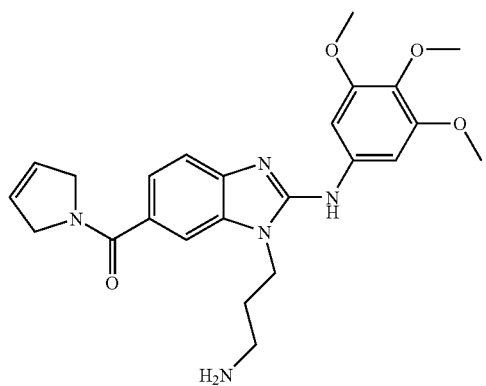 | 452.2 | 7.2 |
| 31 | 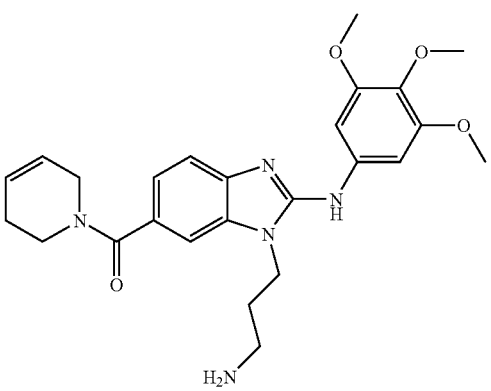 | 466.1 | 7.3 |
| 32 | 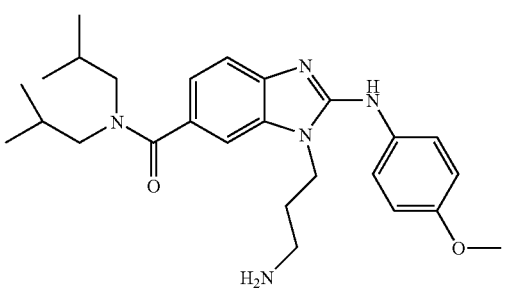 | 452.3 | 7.8 |
| 33 | 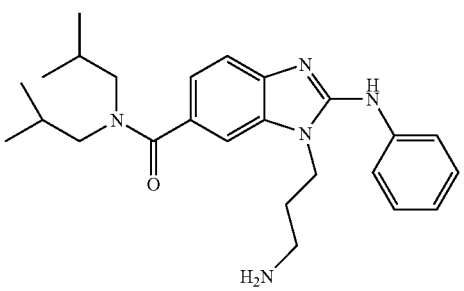 | 422.3 | 7.7 |

| Examples | Molecular structures | [M + H]+ | rt (min) |
| --- | --- | --- | --- |
| 34 | 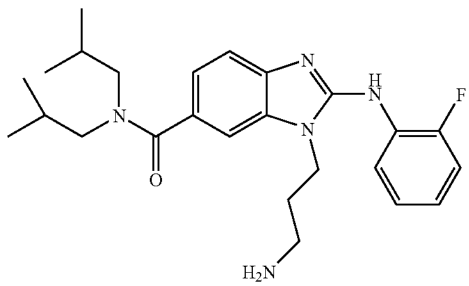 | 440.3 | 7.8 |
| 35 | 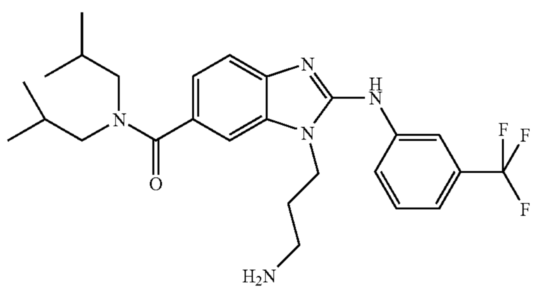 | 490.3 | 8.3 |
| 36 | 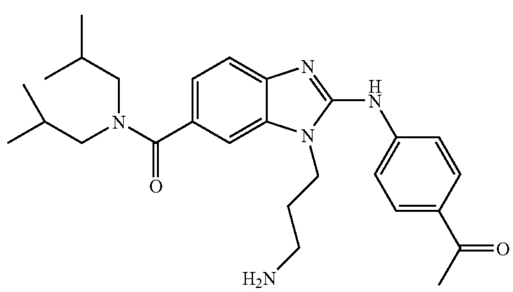 | 464.3 | 8.0 |
| 37 | 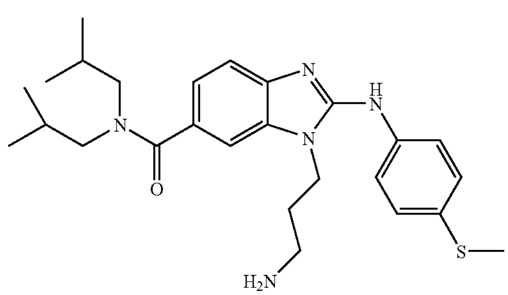 | 468.3 | 7.9 |
| 38 | 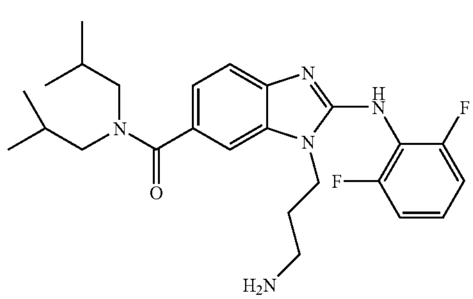 | 458.3 | 8.0 |

-continued

| Examples | Molecular structures | [M + H]+ | rt (min) |
|---|---|---|---|
| 39 | 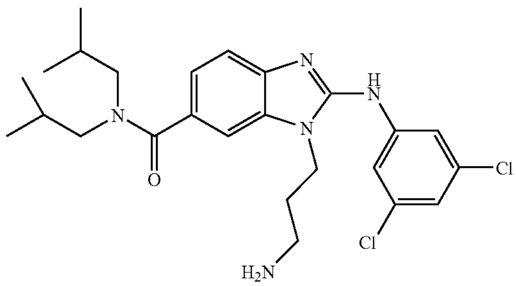 | 490.3 | 8.9 |
| 40 | 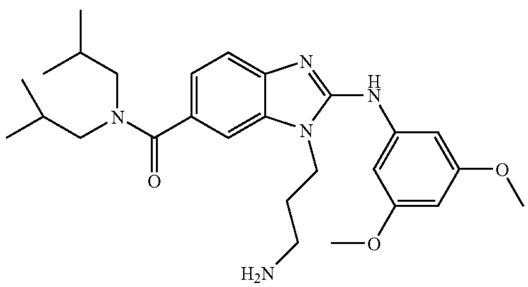 | 482.3 | 7.9 |
| 41 | 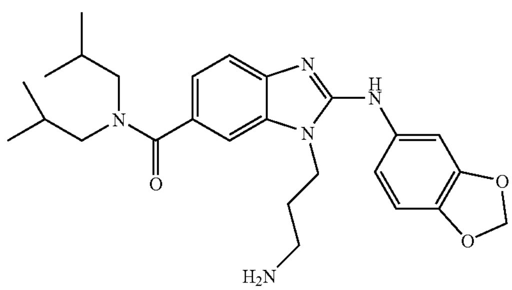 | 466.3 | 7.8 |
| 42 | 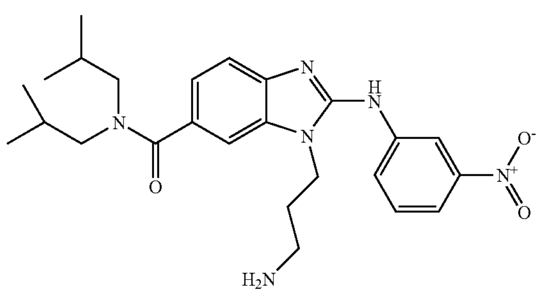 | 467.3 | 8.3 |
| 43 | 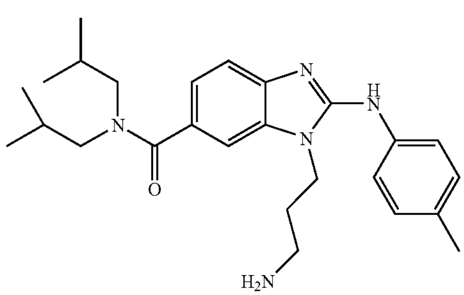 | 436.3 | 7.8 |

-continued

| Examples | Molecular structures | [M + H]+ | rt (min) |
|---|---|---|---|
| 44 | 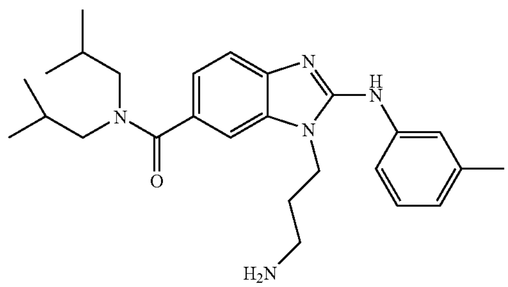 | 436.3 | 7.8 |
| 45 | 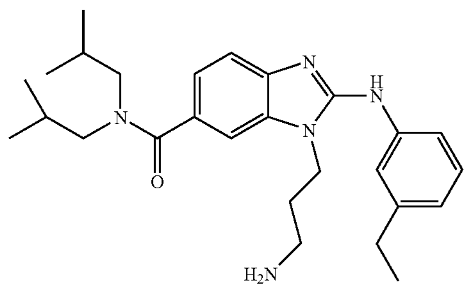 | 450.3 | 8.0 |
| 46 | 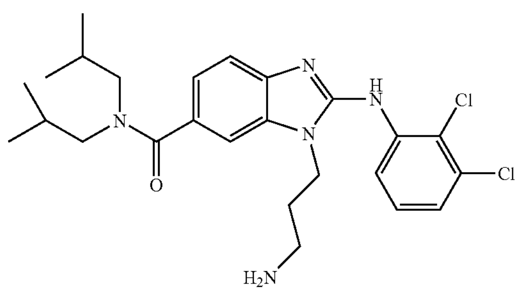 | 490.3 | 8.2 |
| 47 | 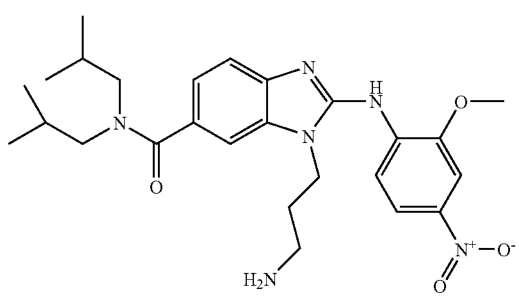 | 497.3 | 8.5 |
| 48 | 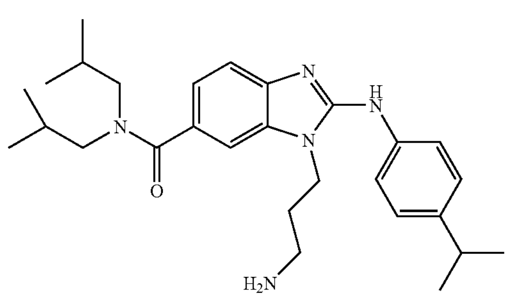 | 464.3 | 8.1 |

-continued
| Examples | Molecular structures | [M + H]+ | rt (min) |
|---|---|---|---|
| 49 | 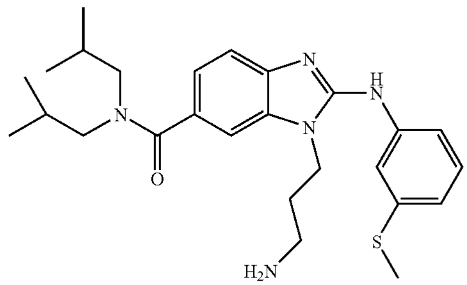 | 468.3 | 8.0 |
| 50 | 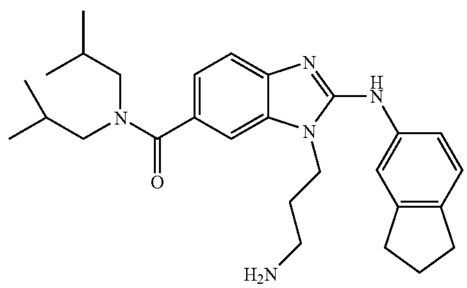 | 462.4 | 8.0 |
| 51 | 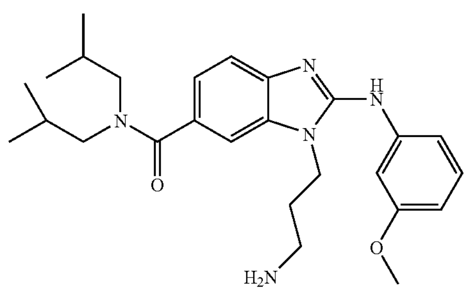 | 452.4 | 7.8 |
| 52 | 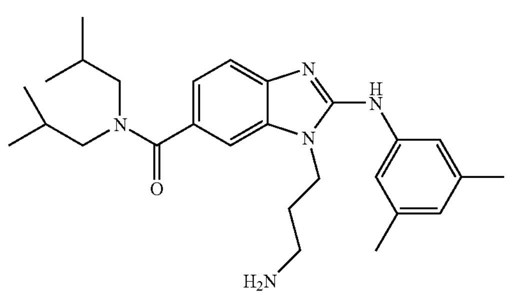 | 450.4 | 8.0 |
| 53 | 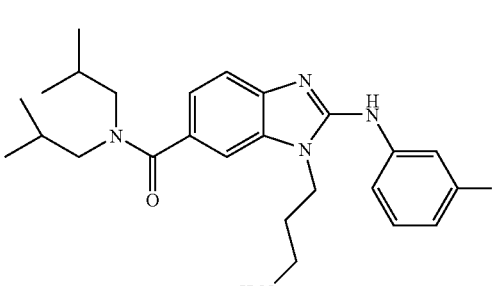 | 500.2 | 8.2 |

-continued

| Examples | Molecular structures | [M + H]+ | rt (min) |
|---|---|---|---|
| 54 | 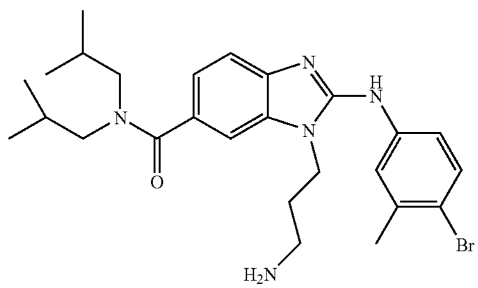 | 514.3 | 8.2 |
| 55 | 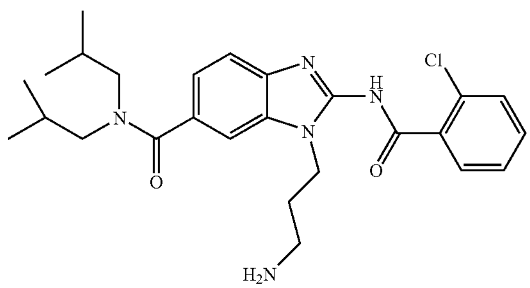 | 484.2 | 8.7 |
| 56 | 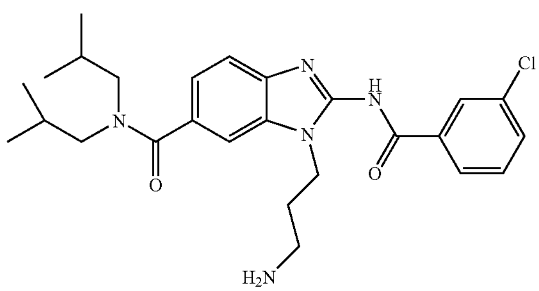 | 484.2 | 9.1 |
| 57 | 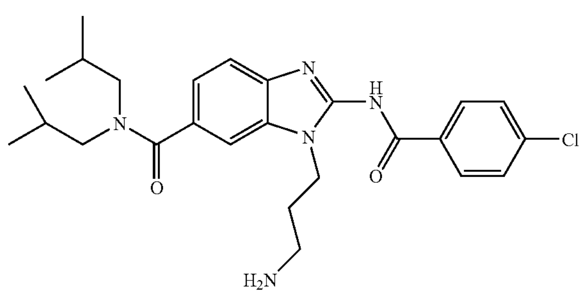 | 484.2 | 9.0 |
| 58 | 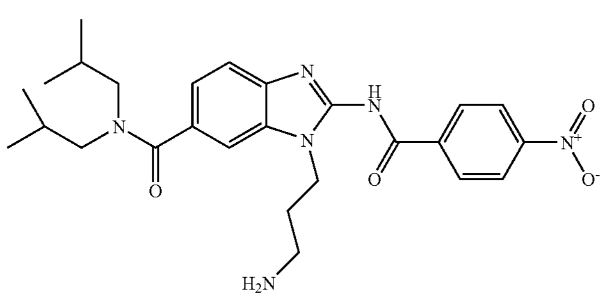 | 495.3 | 8.9 |

-continued

| Examples | Molecular structures | [M + H]+ | rt (min) |
|---|---|---|---|
| 59 | 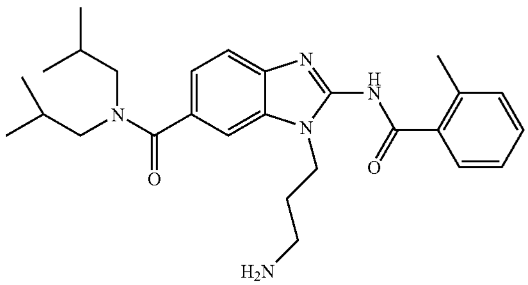 | 464.3 | 8.7 |
| 60 | 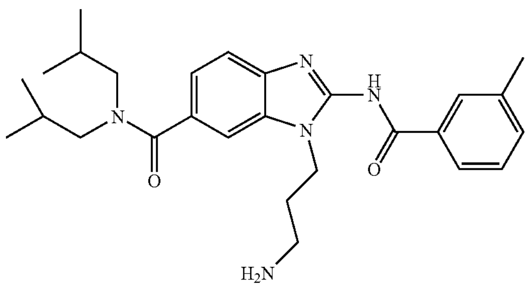 | 464.3 | 8.9 |
| 61 | 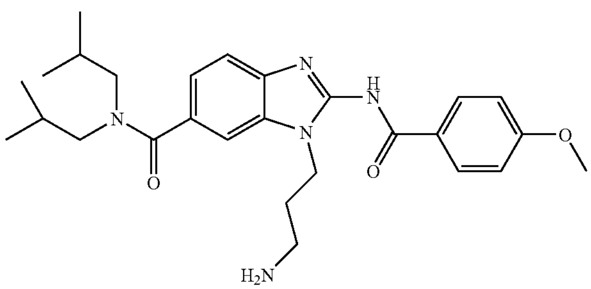 | 480.3 | 8.7 |
| 62 | 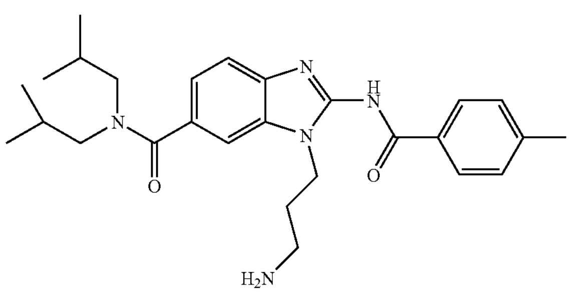 | 464.3 | 8.9 |
| 63 | 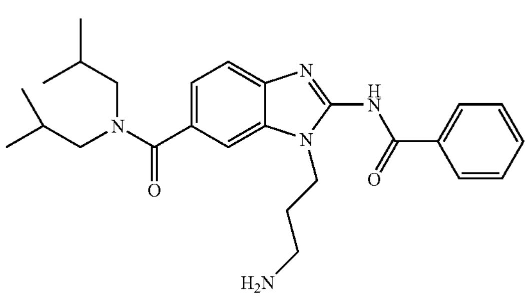 | 450.3 | 8.7 |

-continued
| Examples | Molecular structures | [M + H]+ | rt (min) |
|---|---|---|---|
| 64 | 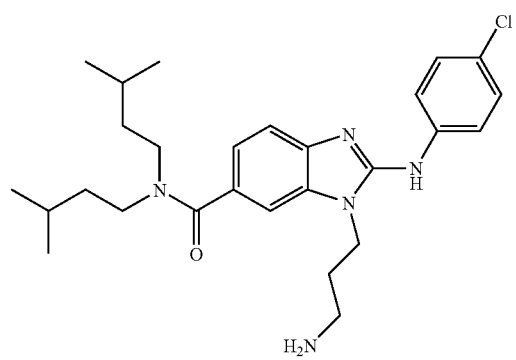 | 484.2 | 8.4 |
| 65 | 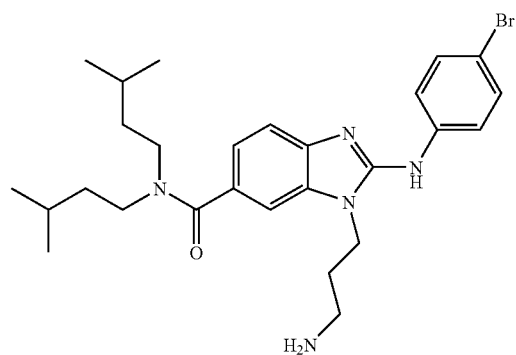 | 528.2 | 8.5 |
| 66 | 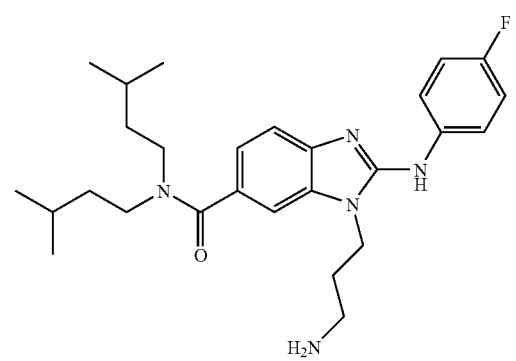 | 468.3 | 8.2 |
| 67 | 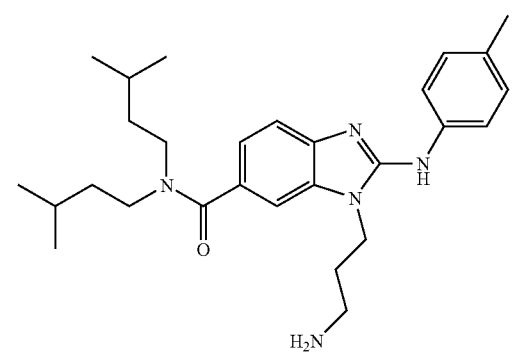 | 464.3 | 8.1 |

| Examples | Molecular structures | [M + H]+ | rt (min) |
| --- | --- | --- | --- |
| 68 | 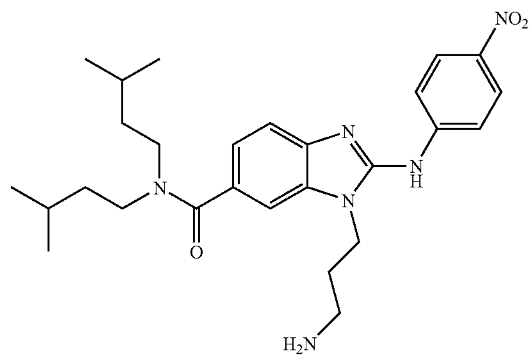 | 495.3 | 9.1 |
| 69 | 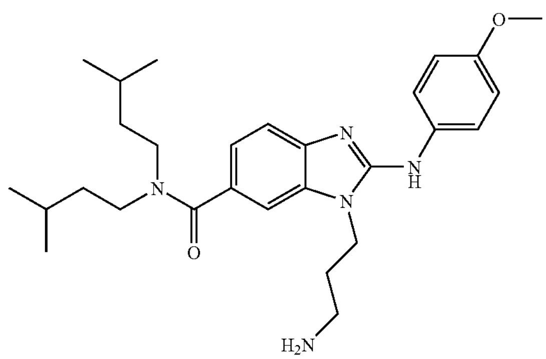 | 480.3 | 8.1 |
| 70 | 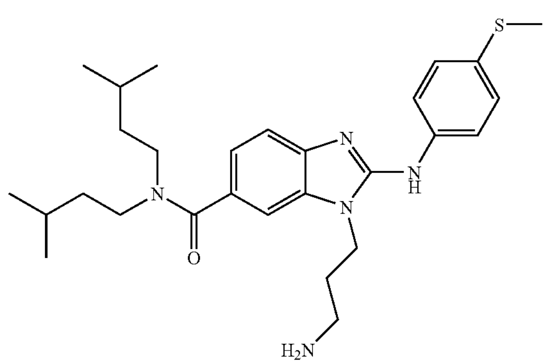 | 496.3 | 8.3 |
| 71 | 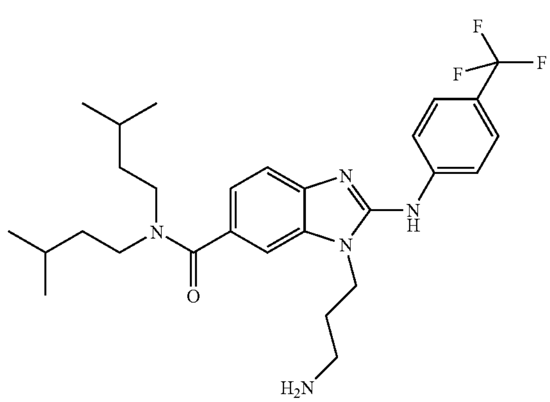 | 518.2 | 9.0 |

-continued
| Examples | Molecular structures | [M + H]+ | rt (min) |
|---|---|---|---|
| 72 | 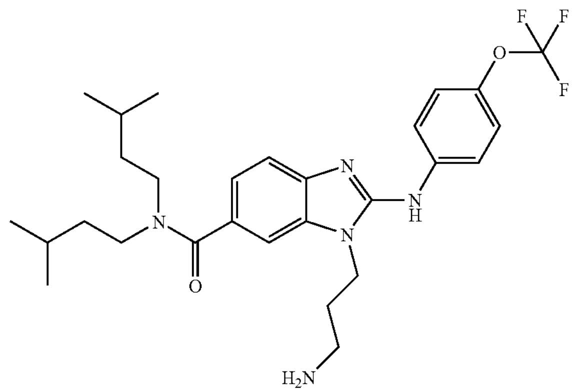 | 534.2 | 8.7 |
| 73 | 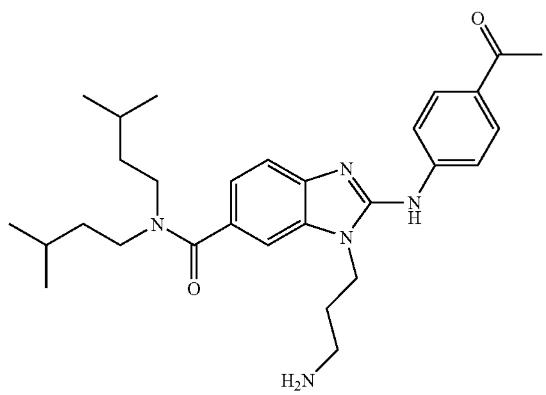 | 492.3 | 8.4 |
| 74 | 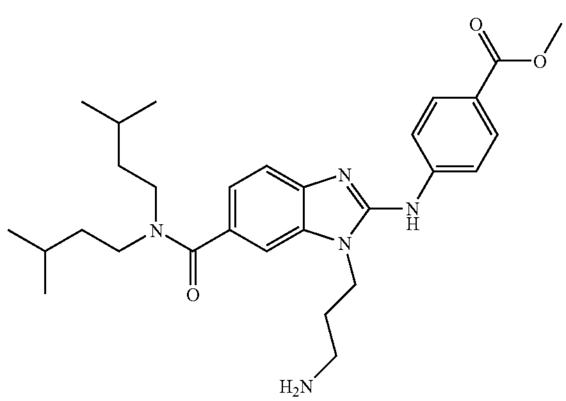 | 508.3 | 8.5 |
| 75 | 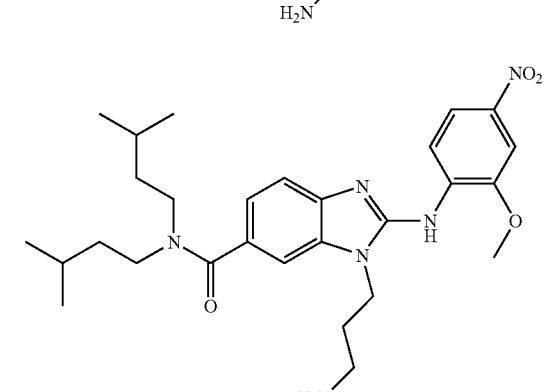 | 525.3 | 8.9 |

-continued
| Examples | Molecular structures | [M + H]+ | rt (min) |
|---|---|---|---|
| 76 | 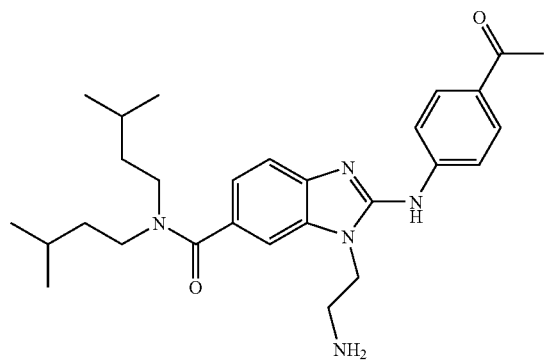 | 478.2 | 8.5 |
| 77 | 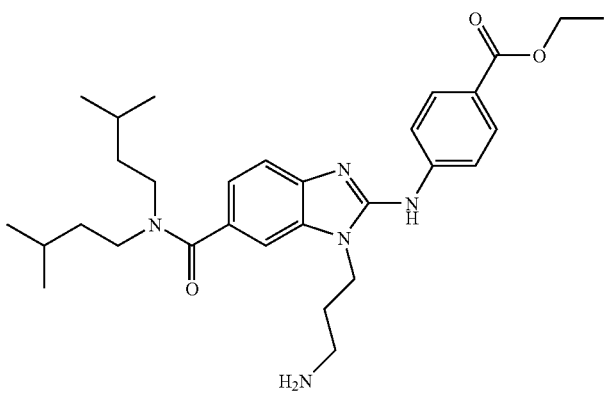 | 522.2 | 8.6 |
| 78 | 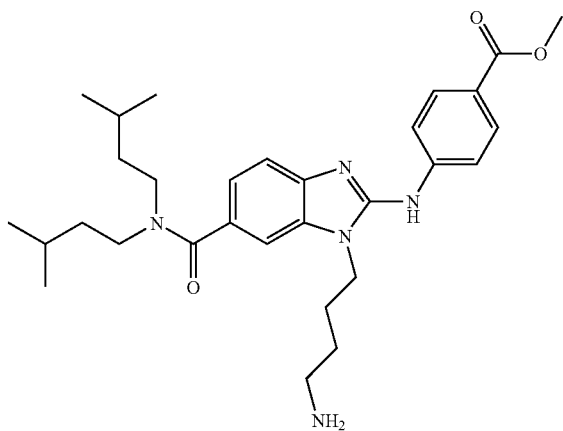 | 522.2 | 8.4 |

-continued
| Examples | Molecular structures | [M + H]+ | rt (min) |
|---|---|---|---|
| 79 | 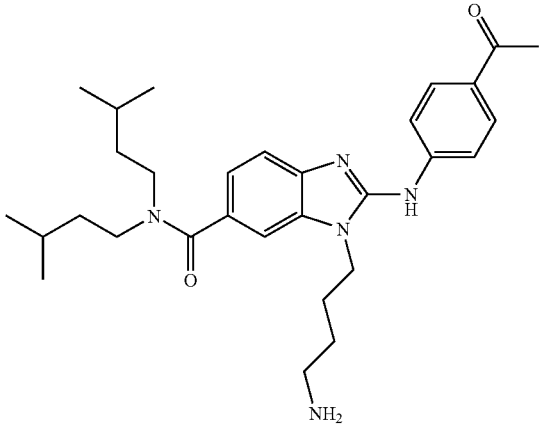 | 506.2 | 8.2 |
| 80 | 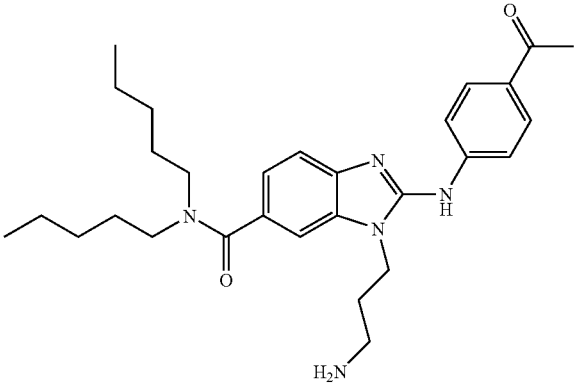 | 492.2 | 8.5 |
| 81 | 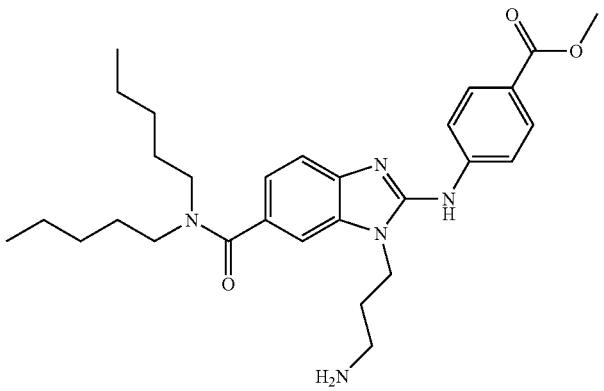 | 508.2 | 8.6 |

-continued
| Examples | Molecular structures | [M + H]+ | rt (min) |
|---|---|---|---|
| 82 | 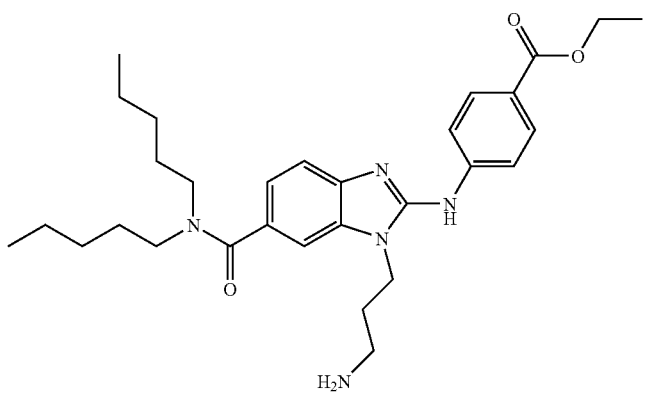 | 522.3 | 8.8 |
| 83 | 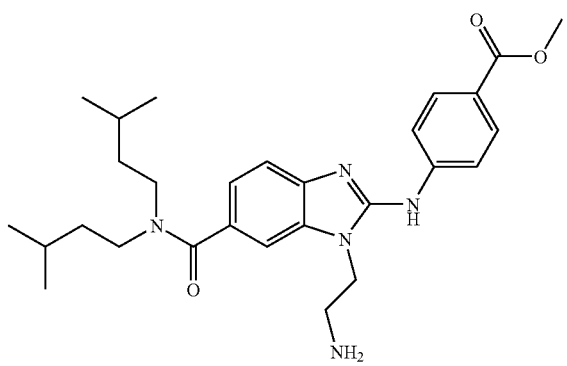 | 494.2 | 8.7 |
| 84 | 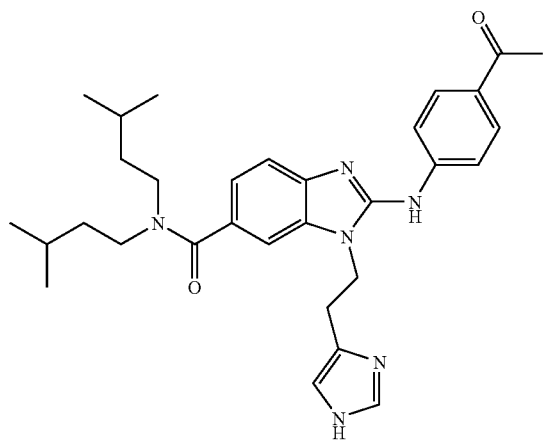 | 529.3 | 8.5 |

-continued
| Examples | Molecular structures | [M + H]+ | rt (min) |
|---|---|---|---|
| 85 | 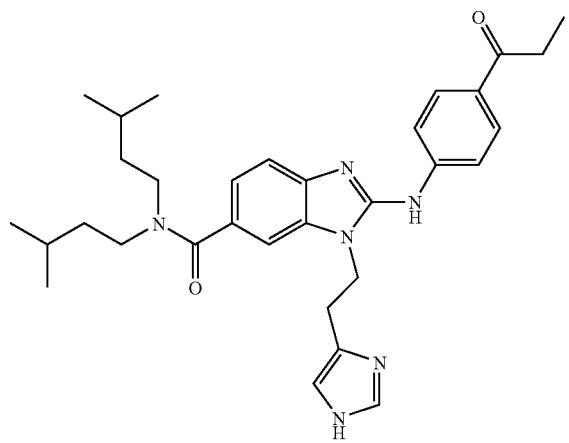 | 543.3 | 8.7 |
| 86 | 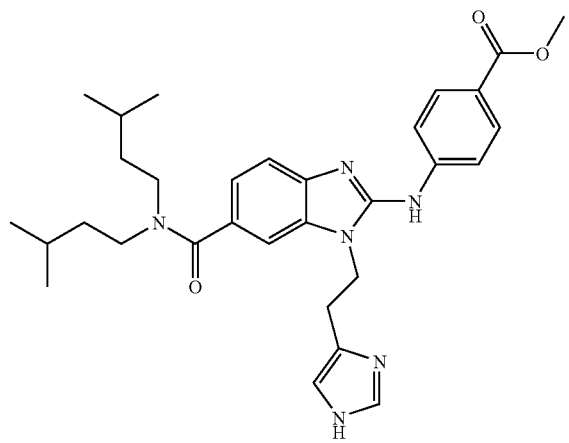 | 545.3 | 8.6 |
| 87 | 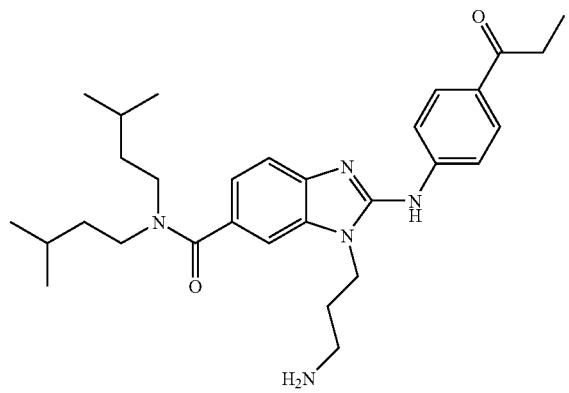 | 506.3 | 8.5 |

-continued
| Examples | Molecular structures | [M + H]+ | rt (min) |
|---|---|---|---|
| 88 | 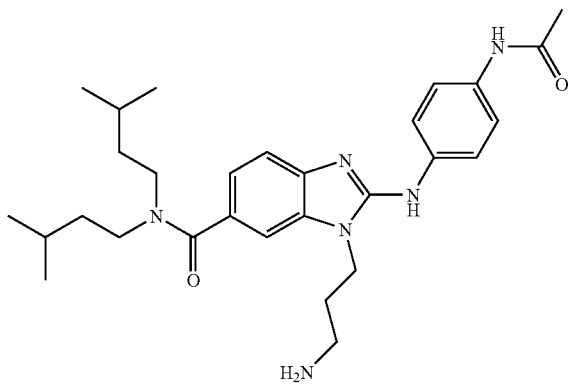 | 507.3 | 7.9 |
| 89 | 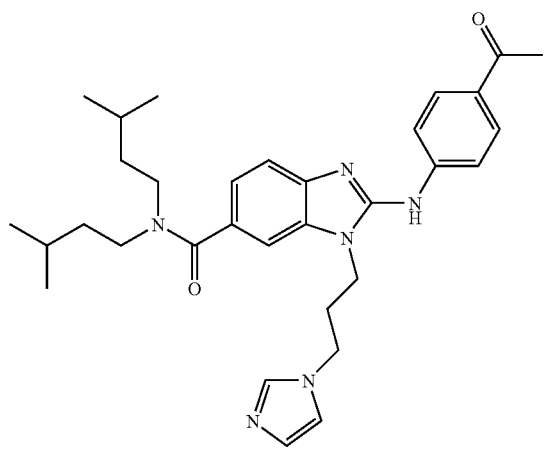 | 543.3 | 8.5 |
| 90 | 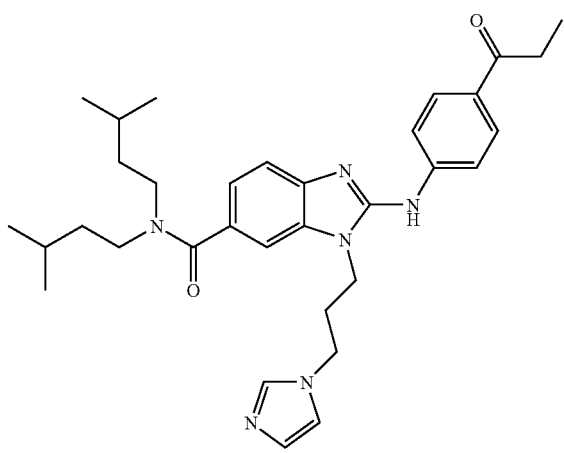 | 557.3 | 8.7 |

-continued
| Examples | Molecular structures | [M + H]+ | rt (min) |
|---|---|---|---|
| 91 | 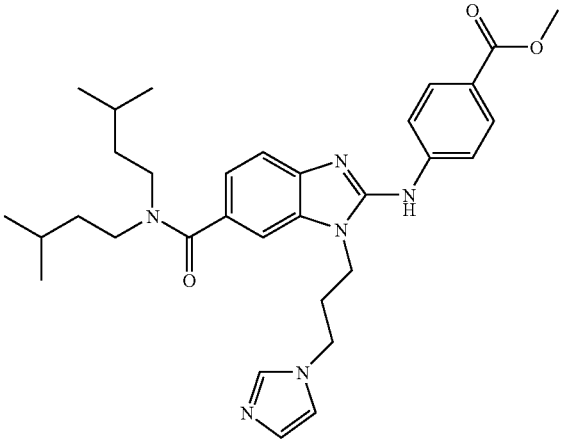 | 559.3 | 8.7 |
| 92 | 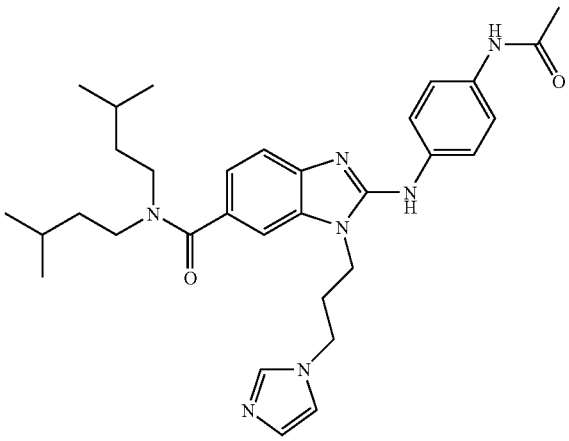 | 558.3 | 8.0 |
| 93 | 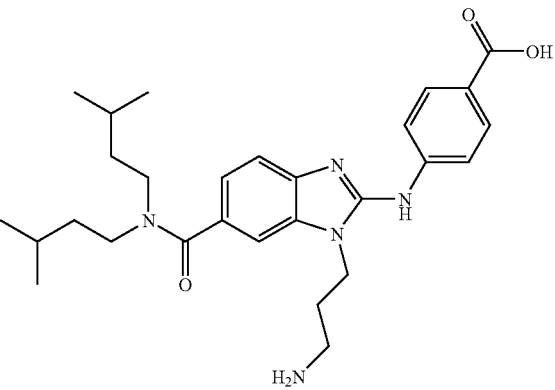 | 494.3 | 8.1 |

-continued
| Examples | Molecular structures | [M + H]+ | rt (min) |
|---|---|---|---|
| 94 | 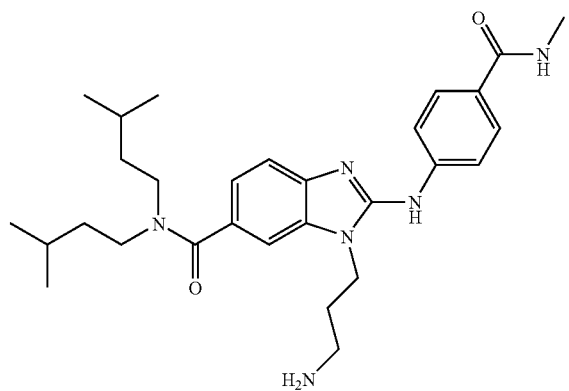 | 507.2 | 8.0 |
| 95 | 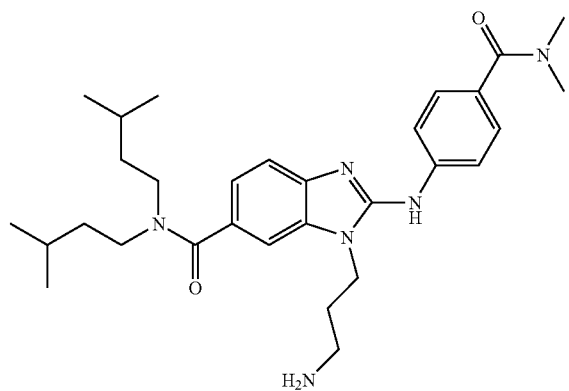 | 521.2 | 8.0 |
| 96 | 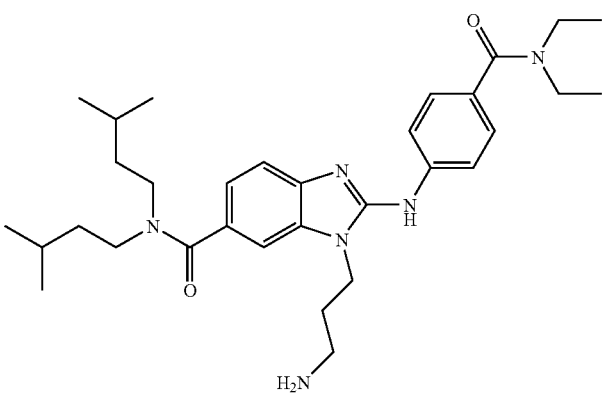 | 549.3 | 8.2 |

| Examples | Molecular structures | [M + H]+ | rt (min) |
|---|---|---|---|
| 97 | 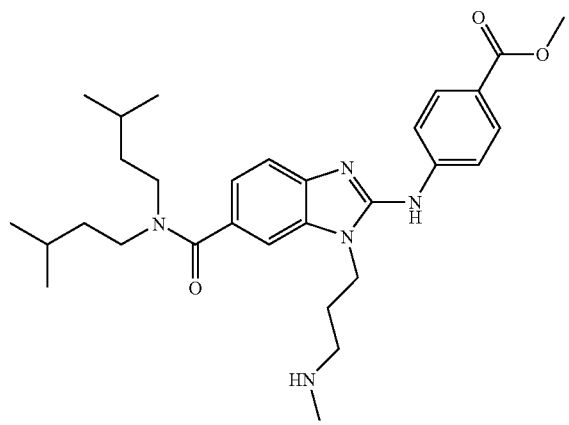 | 522.3 | 8.6 |
| 98 | 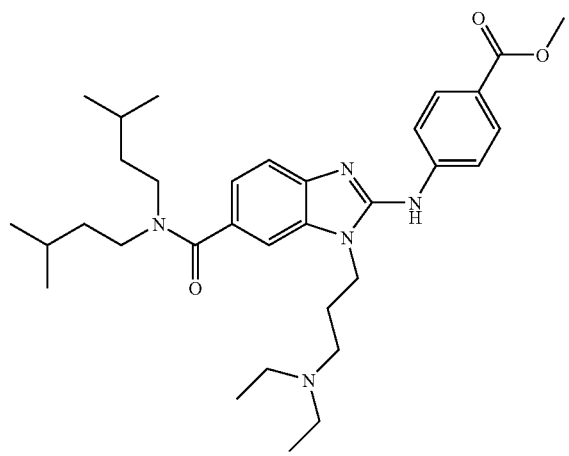 | 564.3 | 8.9 |
| 99 | 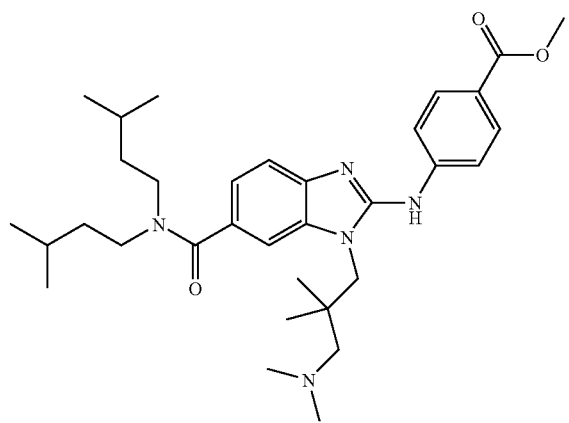 | 564.3 | 9.1 |

-continued
| Examples | Molecular structures | [M + H]+ | rt (min) |
|---|---|---|---|
| 100 | 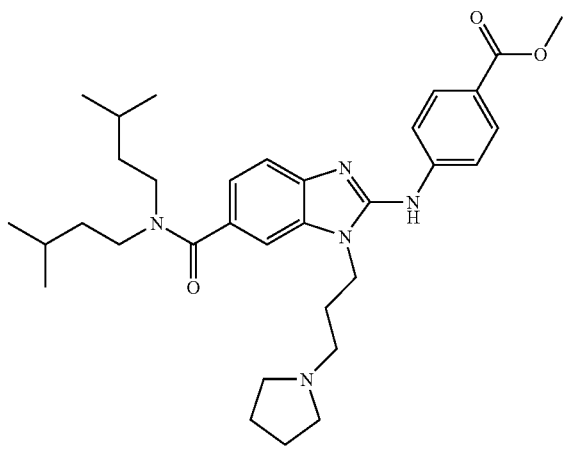 | 562.3 | 8.8 |
| 101 | 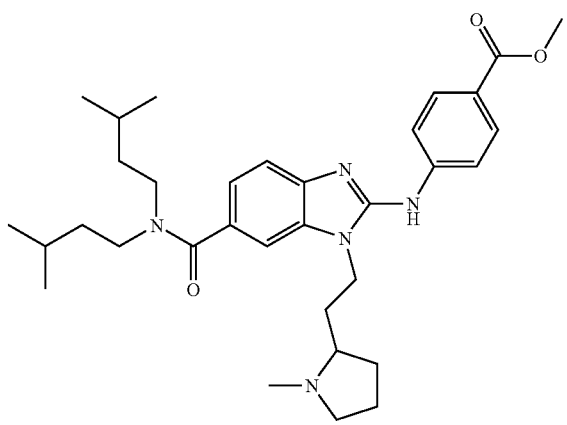 | 562.3 | 8.8 |
| 102 | 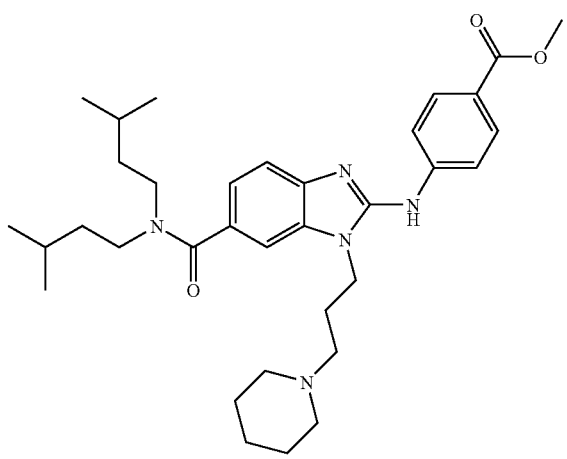 | 576.3 | 8.9 |

| Examples | Molecular structures | [M + H]+ | rt (min) |
|---|---|---|---|
| 103 | 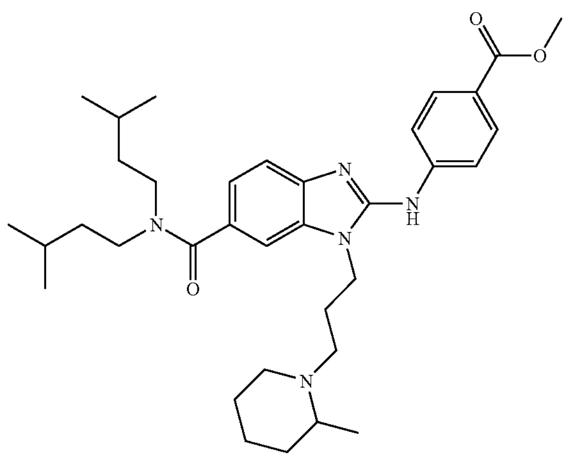 | 590.3 | 9.0 |
| 104 | 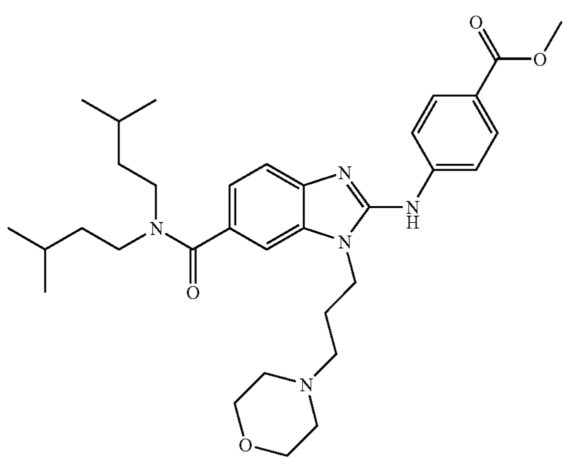 | 578.3 | 8.7 |
| 105 | 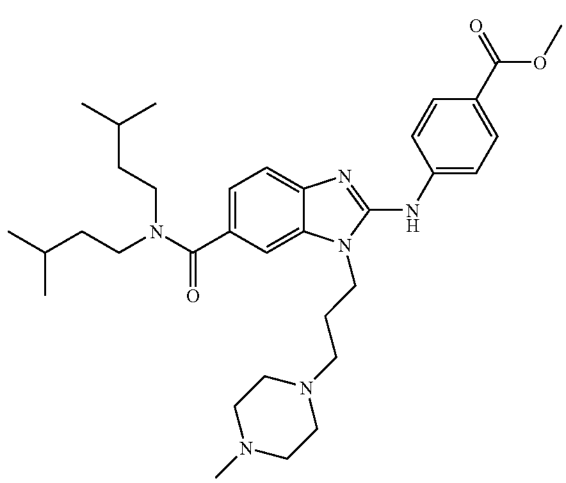 | 591.3 | 8.5 |

-continued
| Examples | Molecular structures | [M + H]+ | rt (min) |
|---|---|---|---|
| 106 | 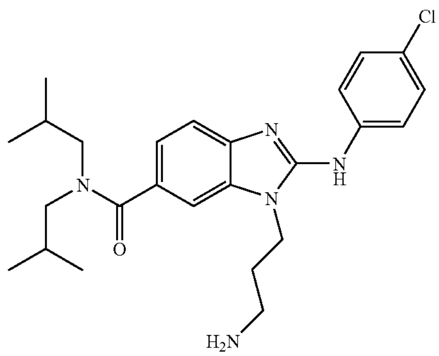 | 456.2 | 8.0 |
| 107 | 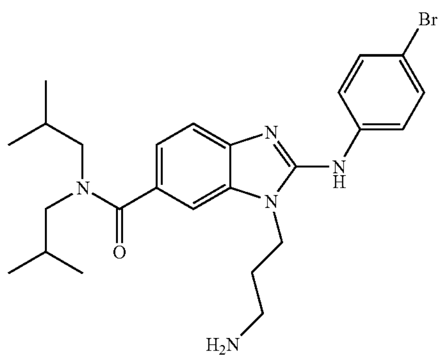 | 500.1 | 8.0 |
| 108 | 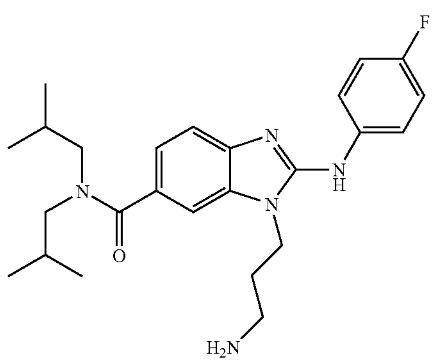 | 440.2 | 77 |
| 109 | 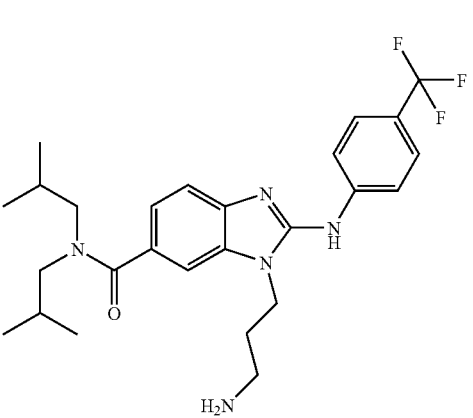 | 490.2 | 8.4 |

-continued

| Examples | Molecular structures | [M + H]+ | rt (min) |
|---|---|---|---|
| 110 | 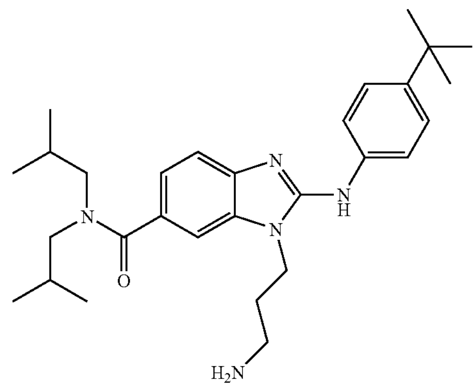 | 478.3 | 8.2 |
| 111 | 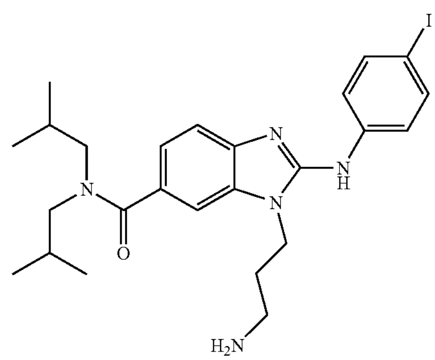 | 548.1 | 8.1 |
| 112 | 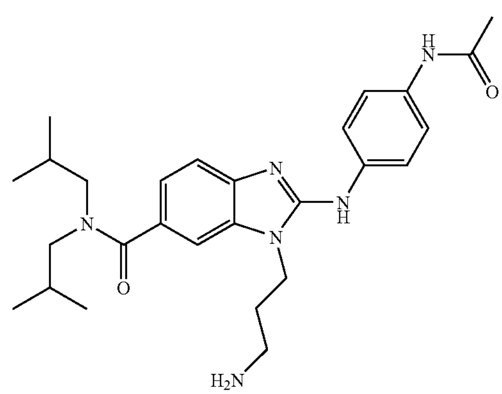 | 479.2 | 7.6 |
| 113 | 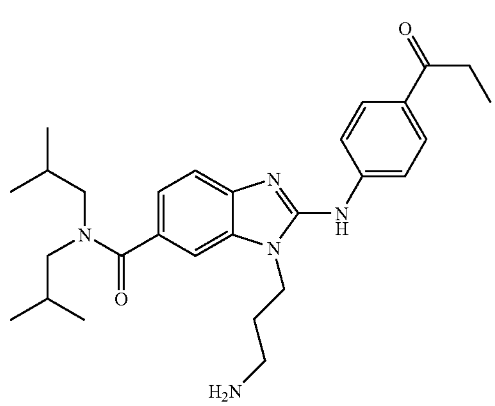 | 478.2 | 8.1 |

-continued

| Examples | Molecular structures | [M + H]+ | rt (min) |
| --- | --- | --- | --- |
| 114 | 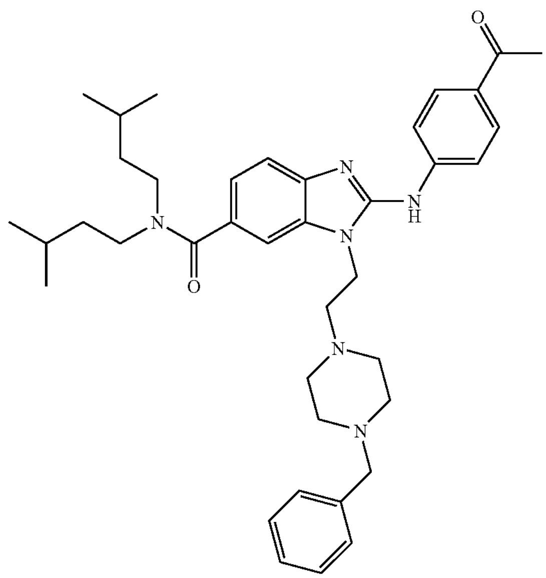 | 637.3 | 8.8 |
| 115 | 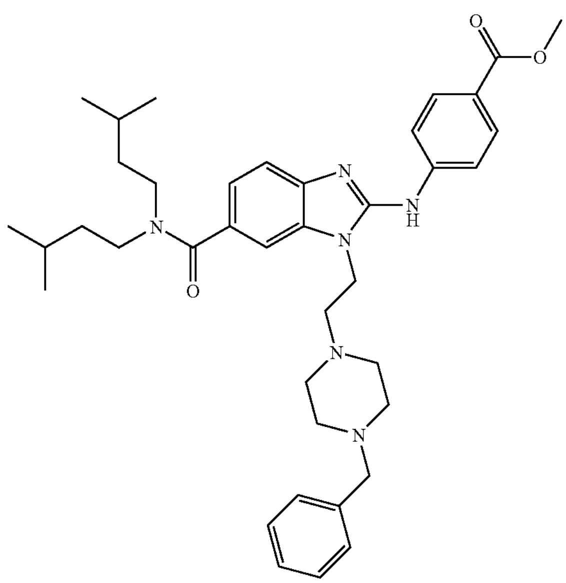 | 653.3 | 9.0 |
| 116 | 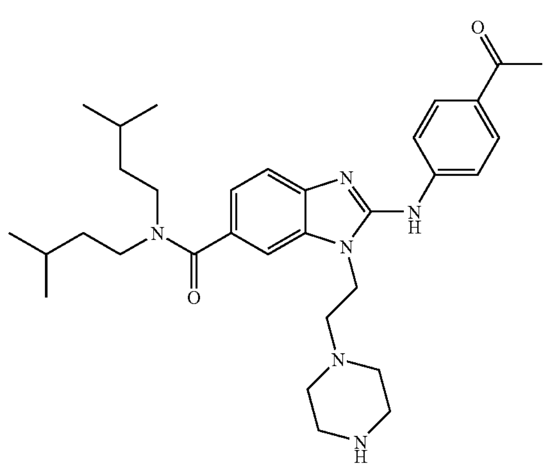 | 547.3 | 8.8 |

-continued
| Examples | Molecular structures | [M + H]+ | rt (min) |
|---|---|---|---|
| 117 | 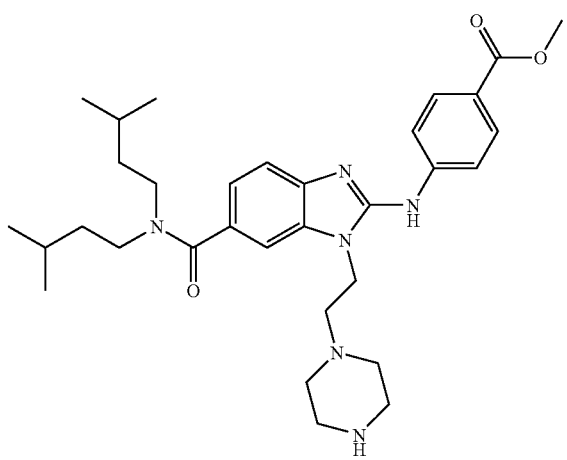 | 563.3 | 9.0 |
| 118 | 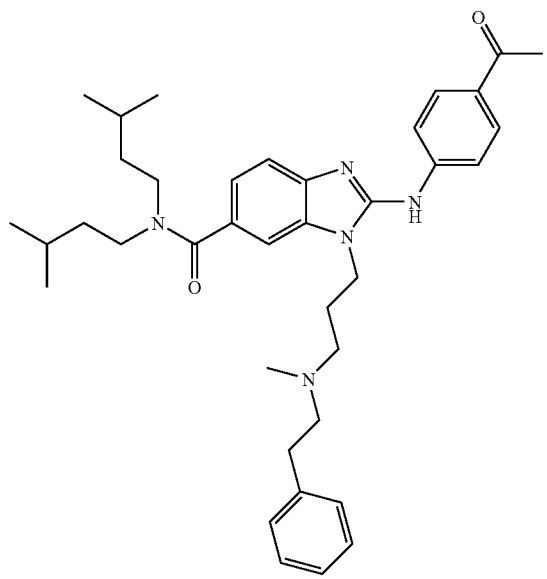 | 610.4 | 9.1 |

-continued
| Examples | Molecular structures | [M + H]+ | rt (min) |
|---|---|---|---|
| 119 | 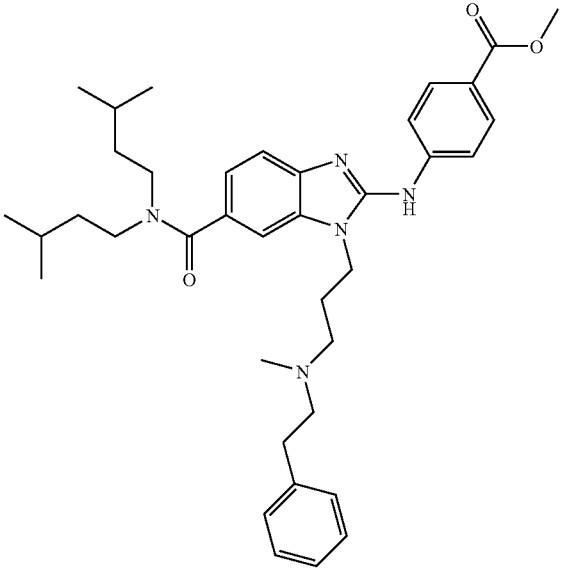 | 626.4 | 9.3 |
| 120 | 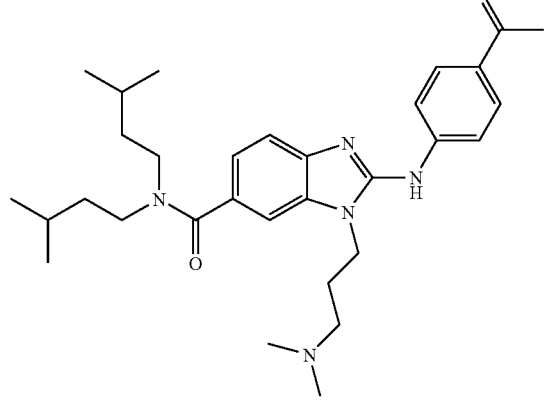 | 520.3 | 8.5 |
| 121 | 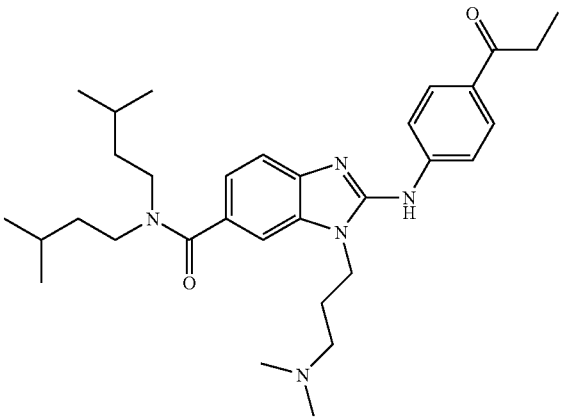 | 534.3 | 8.7 |

-continued
| Examples | Molecular structures | [M + H]+ | rt (min) |
|---|---|---|---|
| 122 | 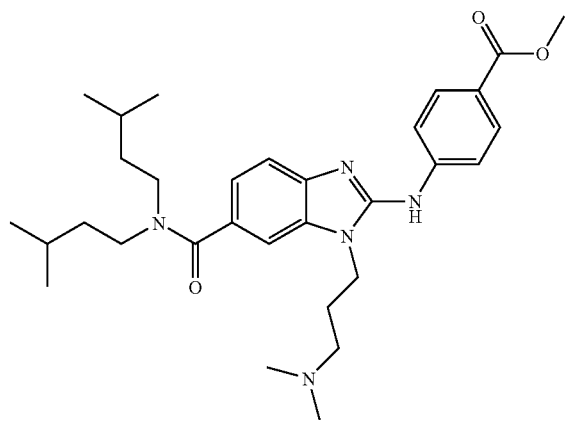 | 536.3 | 8.6 |
| 123 | 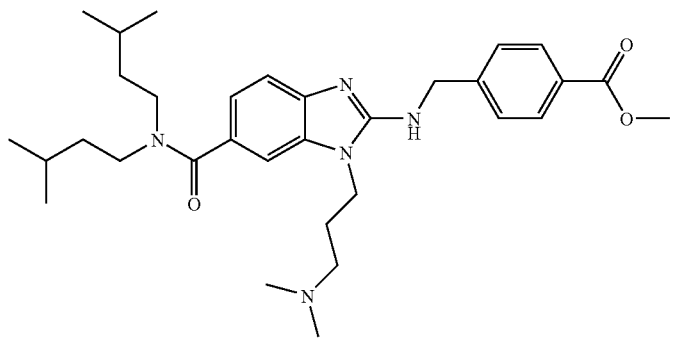 | 550.3 | 8.2 |
| 124 | 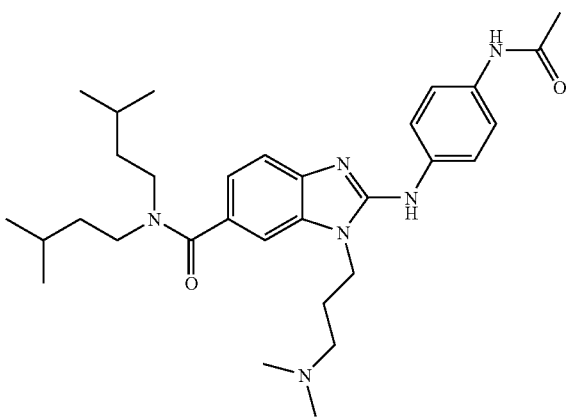 | 535.3 | 8.0 |

-continued

| Examples | Molecular structures | [M + H]+ | rt (min) |
|---|---|---|---|
| 125 | 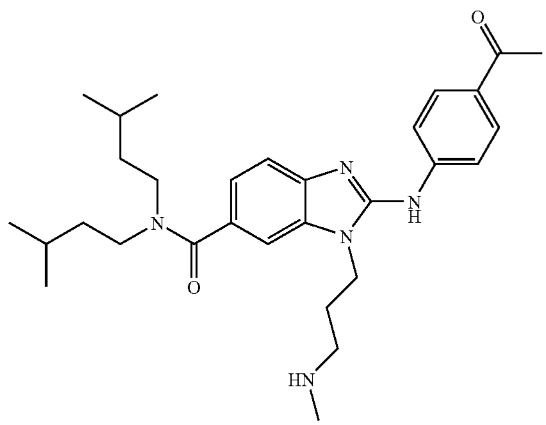 | 506.3 | 8.4 |
| 126 | 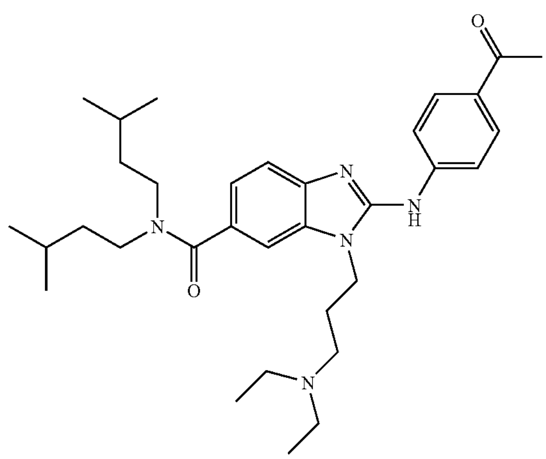 | 548.3 | 8.6 |
| 127 | 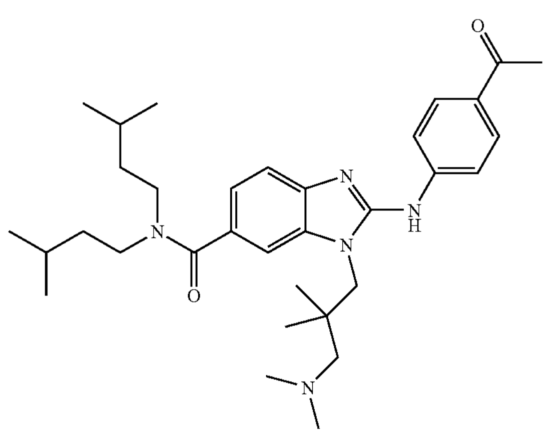 | 548.3 | 8.8 |

-continued
| Examples | Molecular structures | [M + H]+ | rt (min) |
|---|---|---|---|
| 128 | 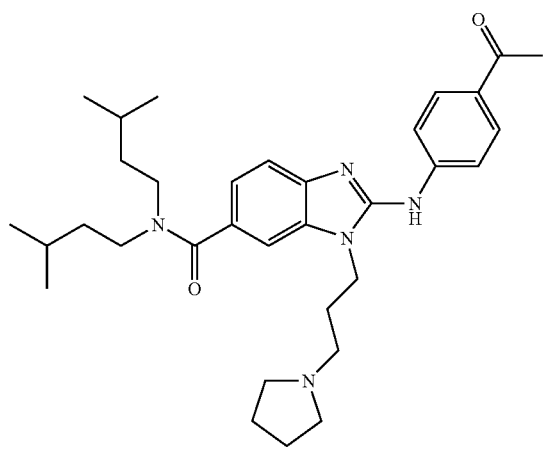 | 546.3 | 8.6 |
| 129 | 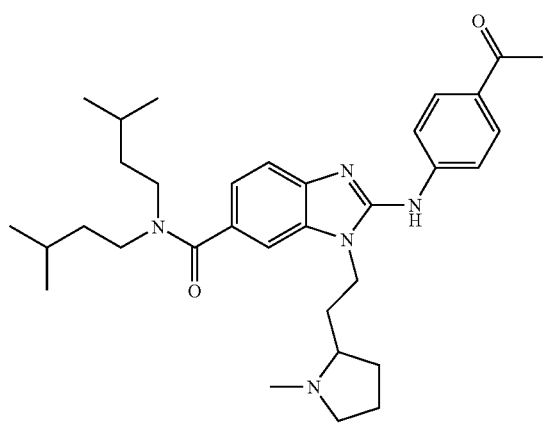 | 546.3 | 8.6 |
| 130 | 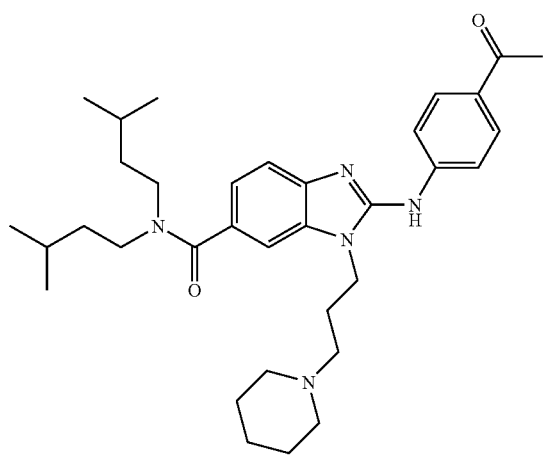 | 560.3 | 8.6 |

-continued

| Examples | Molecular structures | [M + H]+ | rt (min) |
|---|---|---|---|
| 131 | 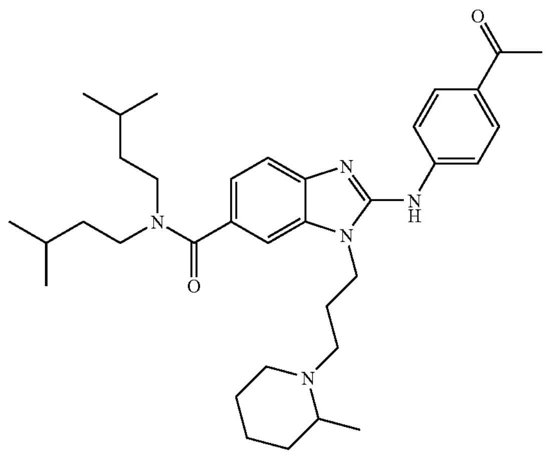 | 574.3 | 8.7 |
| 132 | 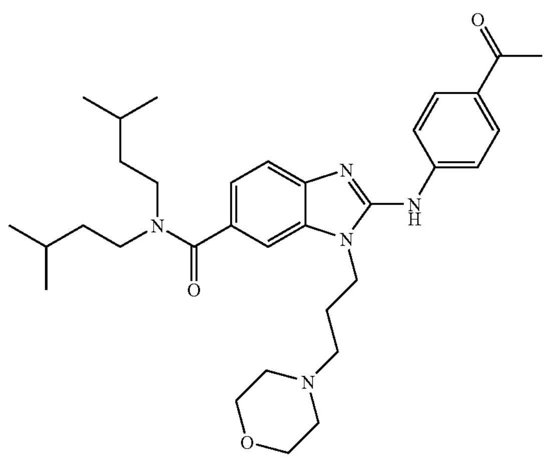 | 562.3 | 8.5 |
| 133 | 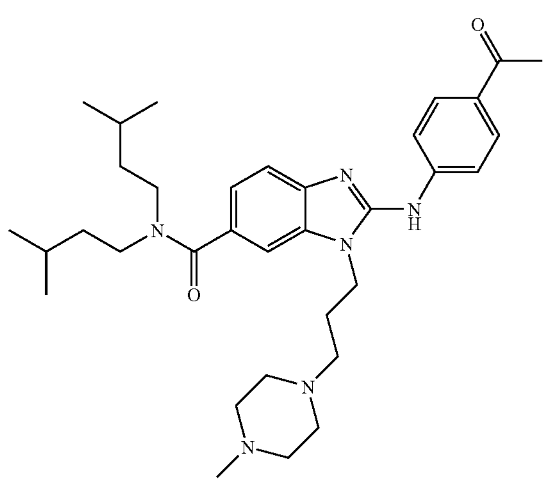 | 575.3 | 8.3 |

-continued
| Examples | Molecular structures | [M + H]+ | rt (min) |
|---|---|---|---|
| 134 | 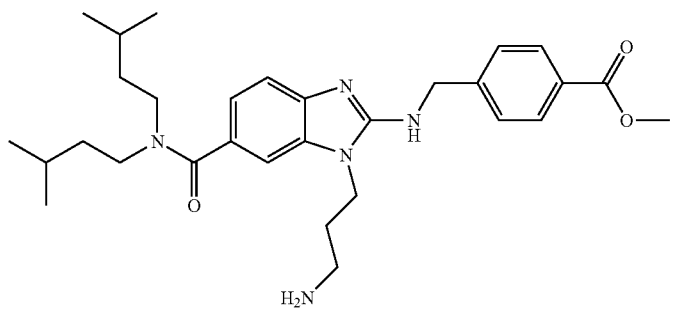 | 522.3 | 8.2 |
| 135 | 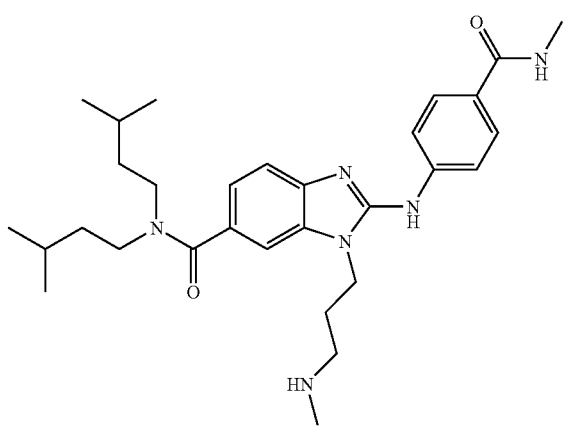 | 521.2 | 8.1 |
| 136 | 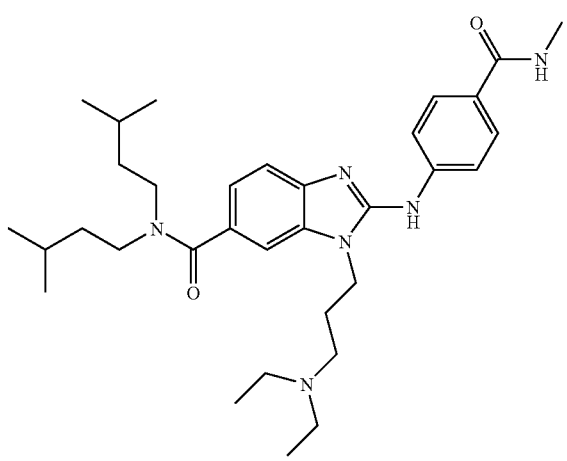 | 563.2 | 8.2 |

-continued

| Examples | Molecular structures | [M + H]+ | rt (min) |
|---|---|---|---|
| 137 | 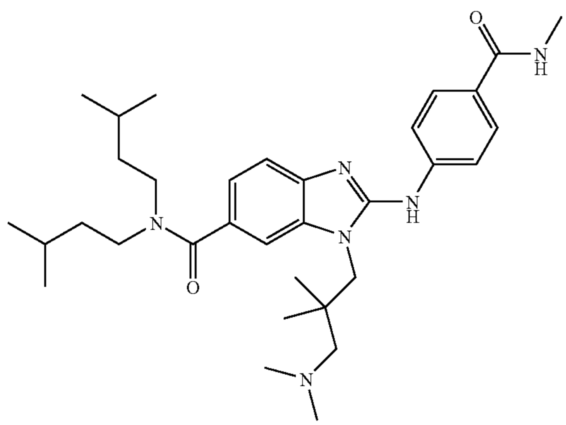 | 563.2 | 8.3 |
| 138 | 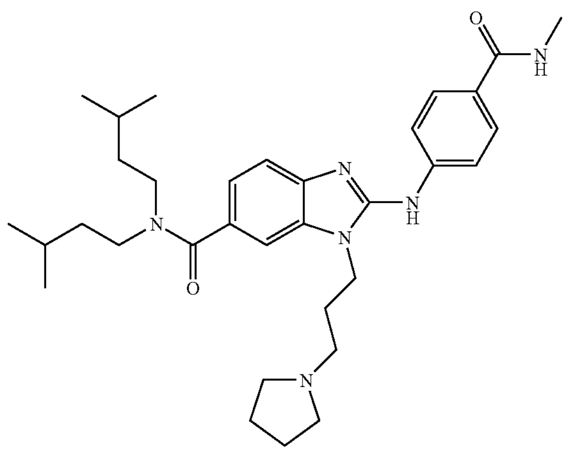 | 561.2 | 8.2 |
| 139 | 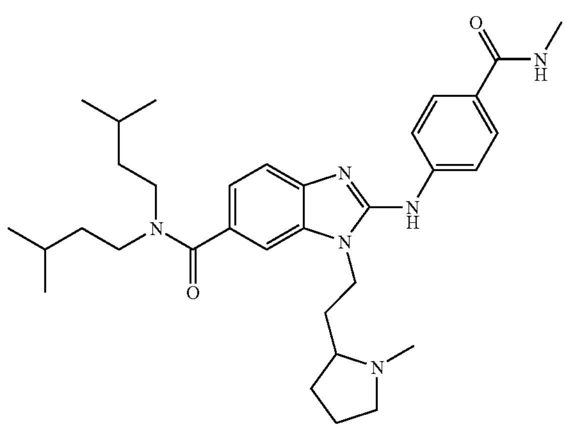 | 561.2 | 8.2 |

-continued

| Examples | Molecular structures | [M + H]+ | rt (min) |
|---|---|---|---|
| 140 | 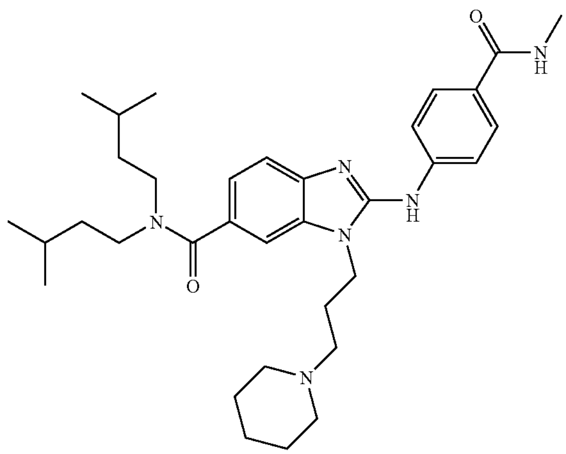 | 575.2 | 8.2 |
| 141 | 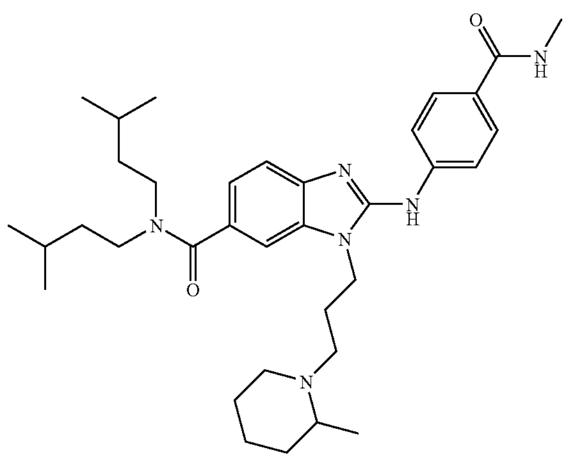 | 589.2 | 8.3 |
| 142 | 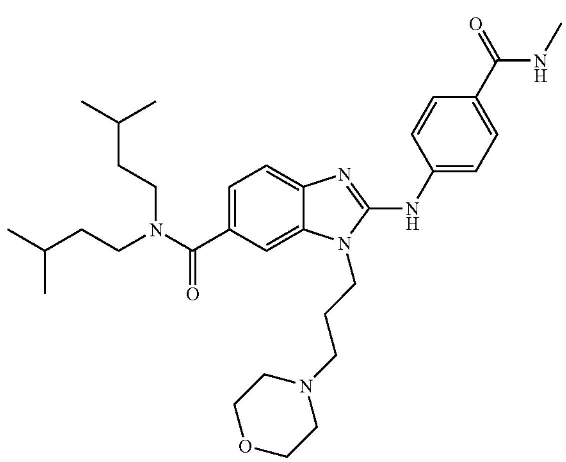 | 577.2 | 8.1 |

-continued
| Examples | Molecular structures | [M + H]+ | rt (min) |
|---|---|---|---|
| 143 | 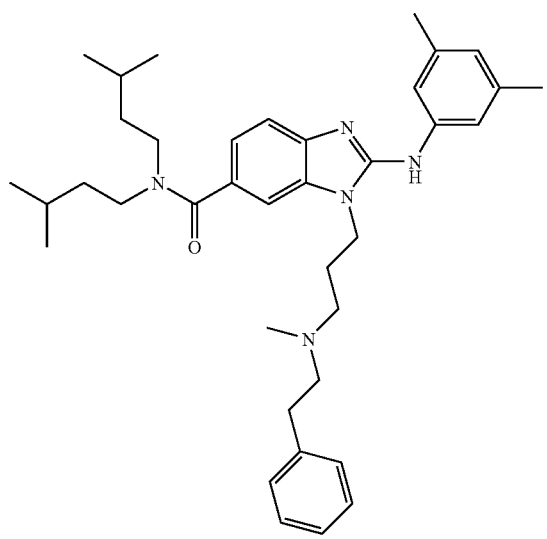 | 594.4 | 8.8 |
| 144 | 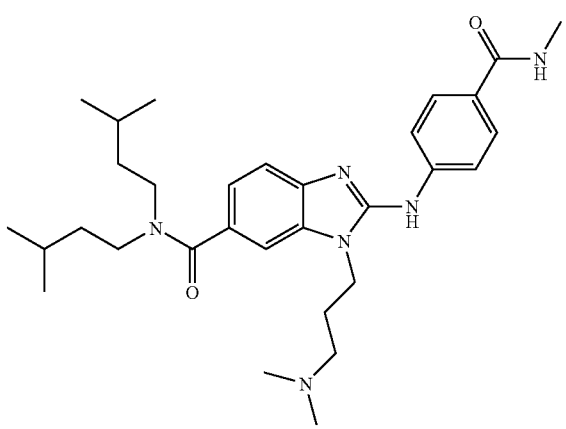 | 535.4 | 8.0 |
| 145 | 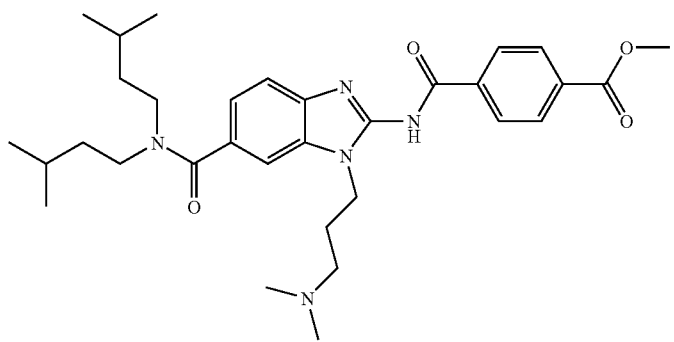 | 564.4 | 9.5 |

-continued

| Examples | Molecular structures | [M + H]+ | rt (min) |
|---|---|---|---|
| 146 | 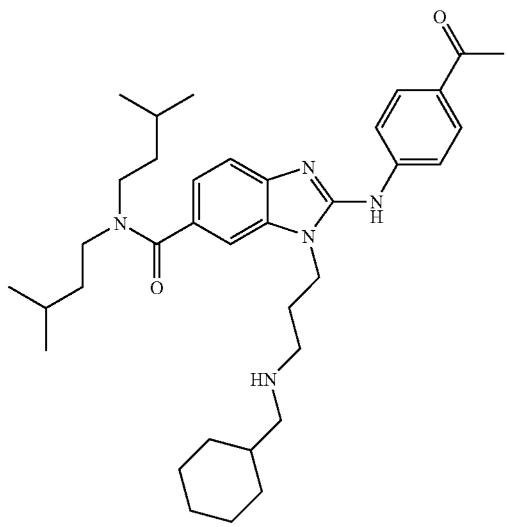 | 588.4 | 9.2 |
| 147 | 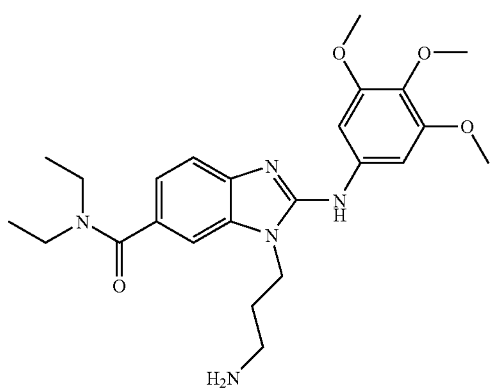 | 456.2 | 7.2 |
| 148 | 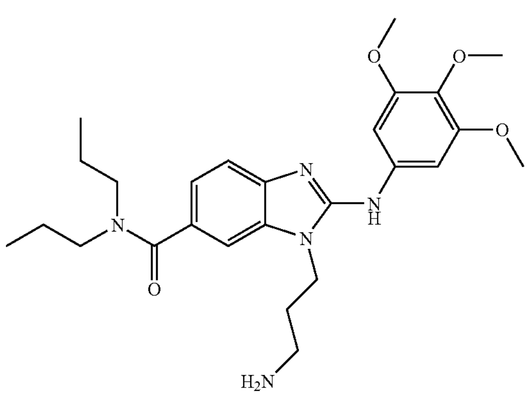 | 484.3 | 7.5 |

-continued

| Examples | Molecular structures | [M + H]+ | rt (min) |
|---|---|---|---|
| 149 | 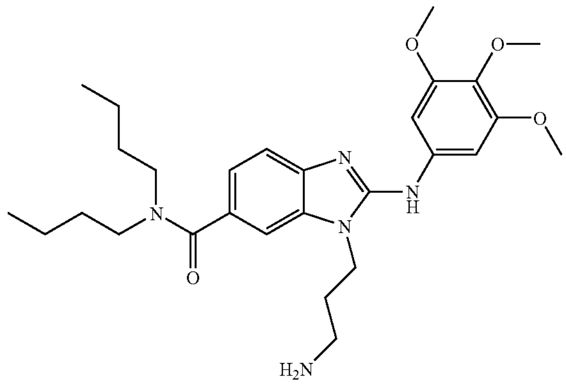 | 512.2 | 7.8 |
| 150 | 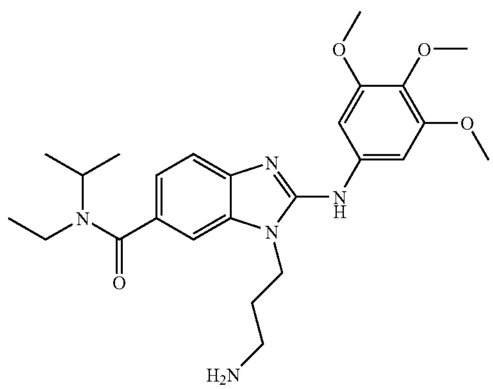 | 470.3 | 7.3 |
| 151 | 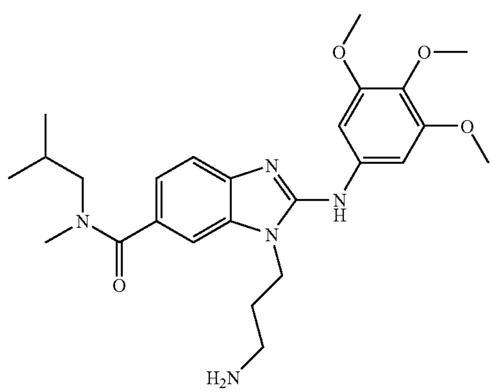 | 470.2 | 7.4 |
| 152 | 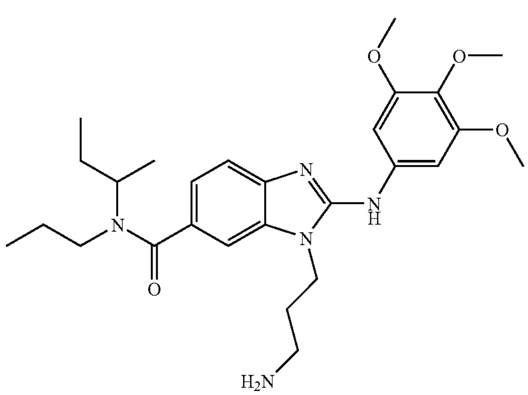 | 498.3 | 7.6 |

-continued
| Examples | Molecular structures | [M + H]+ | rt (min) |
|---|---|---|---|
| 153 | 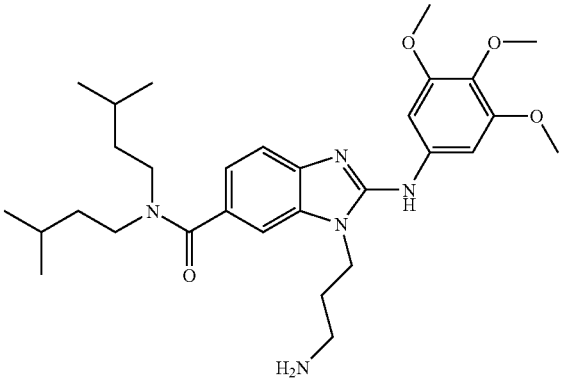 | 540.2 | 8.1 |
| 154 | 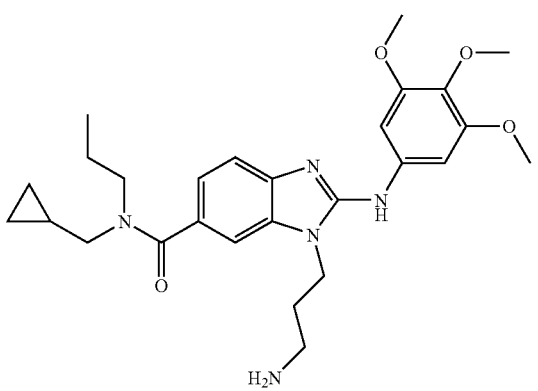 | 496.3 | 7.6 |
| 155 | 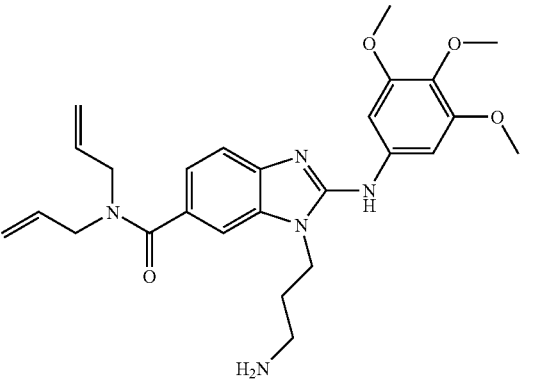 | 480.3 | 7.4 |
| 156 | 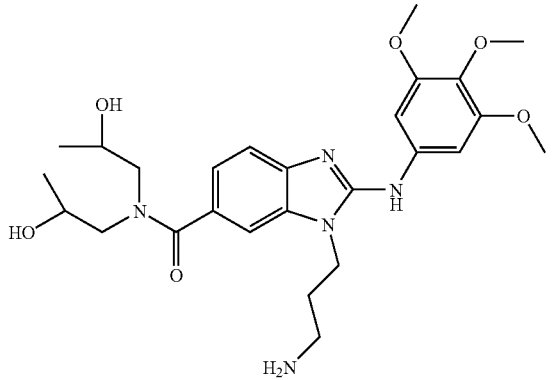 | 516.0 | 7.0 |

-continued
| Examples | Molecular structures | [M + H]+ | rt (min) |
|---|---|---|---|
| 157 | 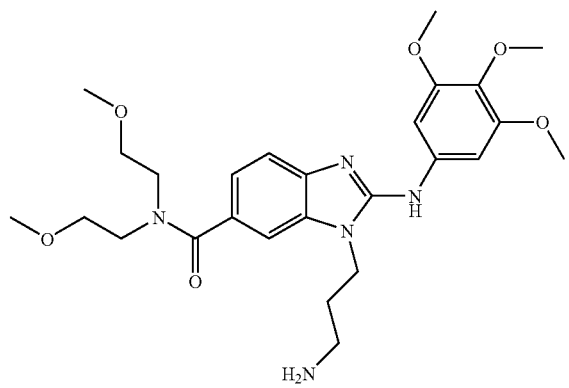 | 516.2 | 7.2 |
| 158 | 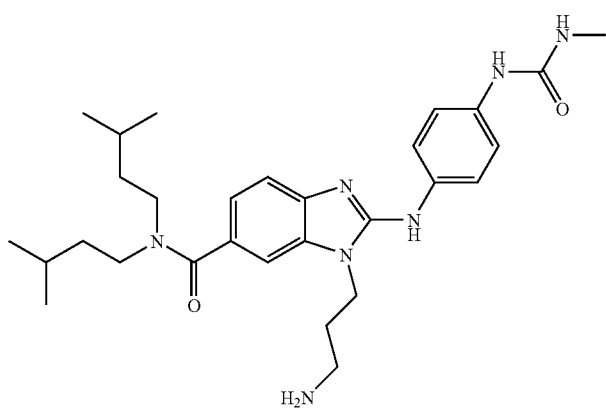 | 522.3 | 7.9 |
| 159 | 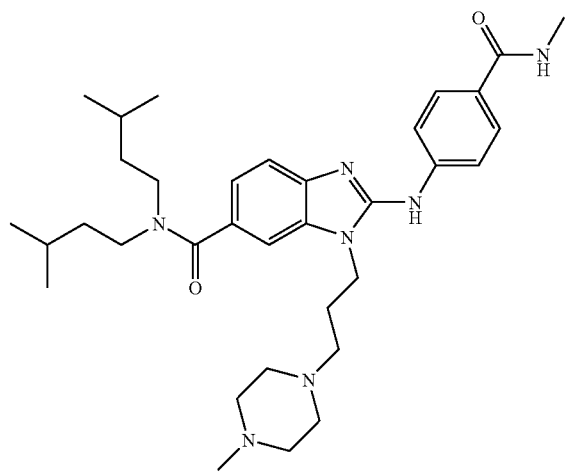 | 590.2 | 8.0 |

| Examples | Molecular structures | [M + H]+ | rt (min) |
|---|---|---|---|
| 160 | 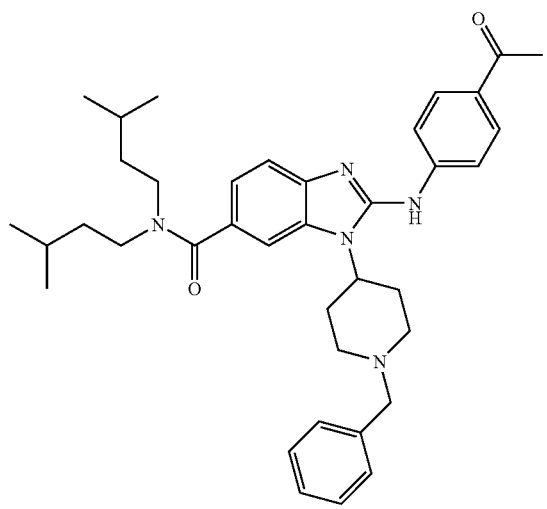 | 608.5 | 9.2 |
| 161 | 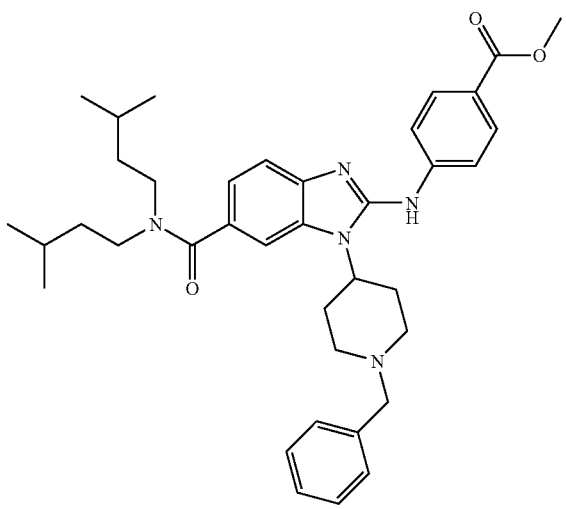 | 624.5 | 9.4 |
| 162 | 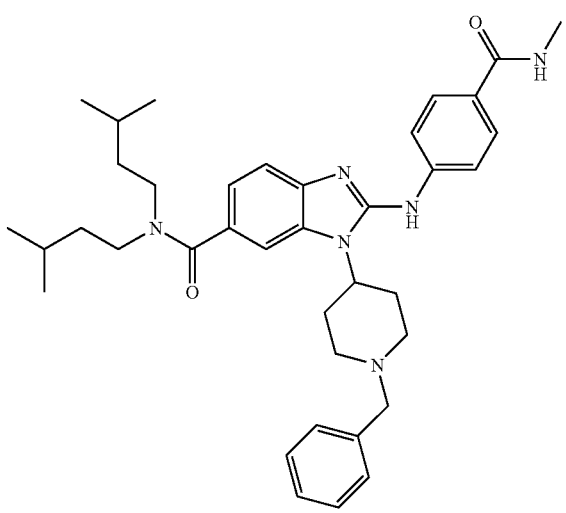 | 623.5 | 8.5 |

-continued
| Examples | Molecular structures | [M + H]+ | rt (min) |
|---|---|---|---|
| 163 | 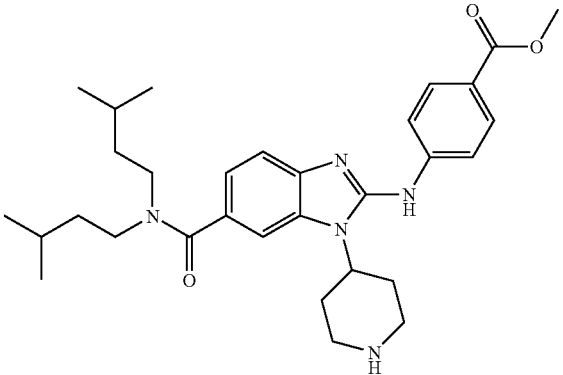 | 534.3 | 8.7 |
| 164 | 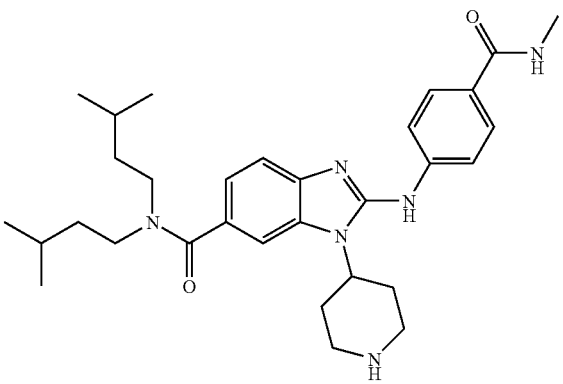 | 533.3 | 8.0 |
| 165 | 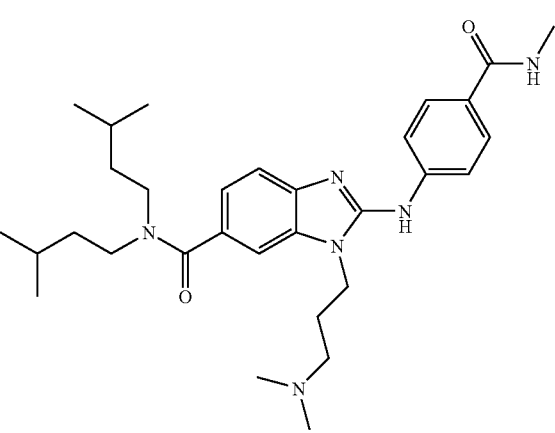 | 535.4 | 8.0 |
| 166 | 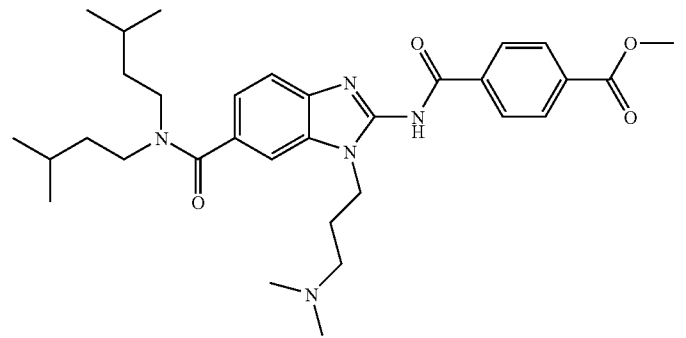 | 564.4 | 9.5 |

| Examples | Molecular structures | [M + H]+ | rt (min) |
|---|---|---|---|
| 167 | 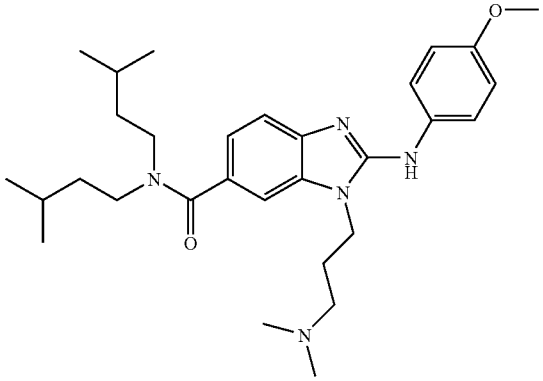 | 508.2 | 8.2 |
| 168 | 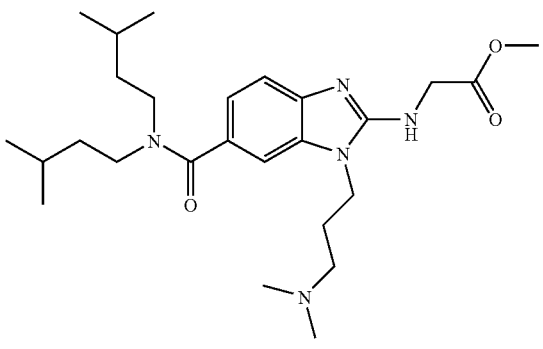 | 474.3 | 8.0 |
| 169 | 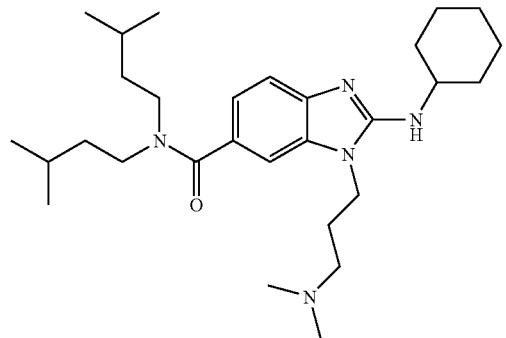 | 484.4 | 8.2 |
| 170 | 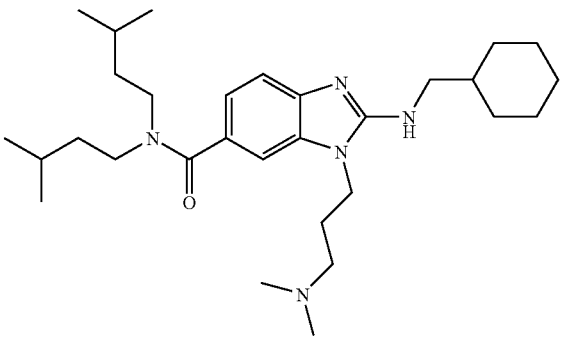 | 498.4 | 8.4 |

-continued

| Examples | Molecular structures | [M + H]+ | rt (min) |
|---|---|---|---|
| 171 | 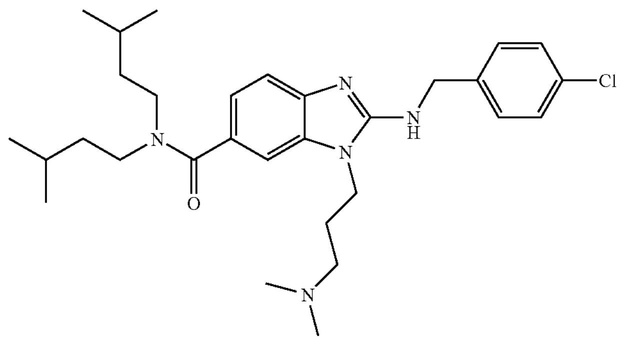 | 526.3 | 8.4 |
| 172 | 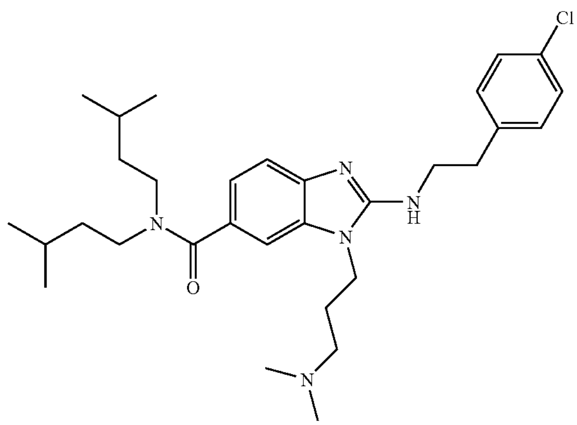 | 540.3 | 8.5 |
| 173 | 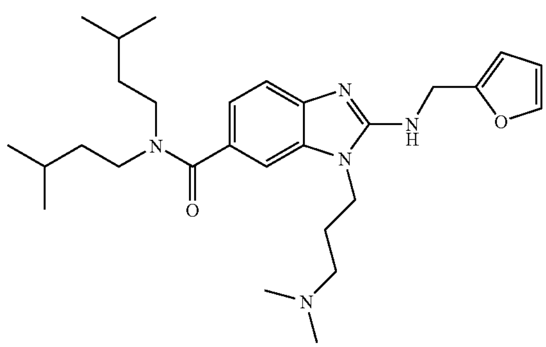 | 482.3 | 8.1 |
| 174 | 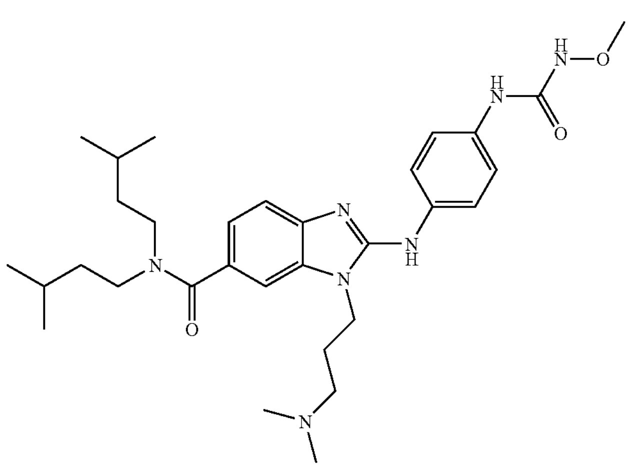 | 566.4 | 8.1 |

| Examples | Molecular structures | [M + H]+ | rt (min) |
|---|---|---|---|
| 175 | 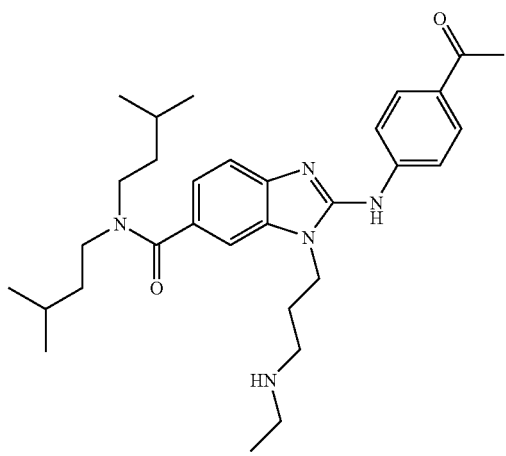 | 520.2 | 8.6 |
| 176 | 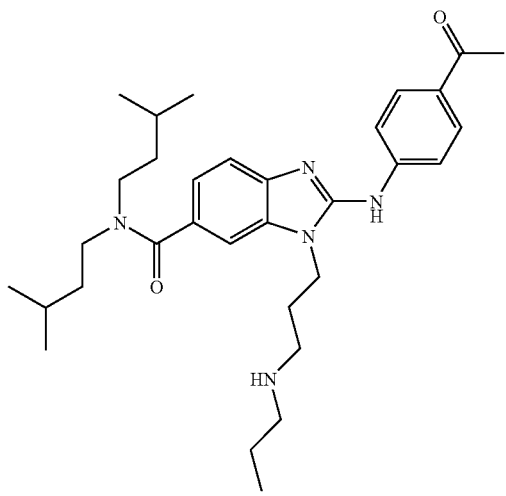 | 534.2 | 8.7 |
| 177 | 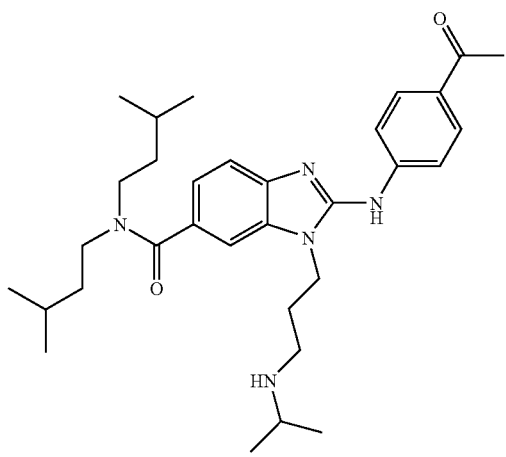 | 534.2 | 8.7 |

-continued
| Examples | Molecular structures | [M + H]+ | rt (min) |
|---|---|---|---|
| 178 | 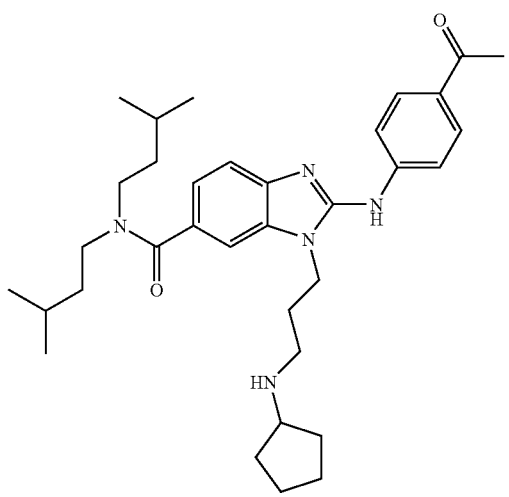 | 560.2 | 8.9 |
| 179 | 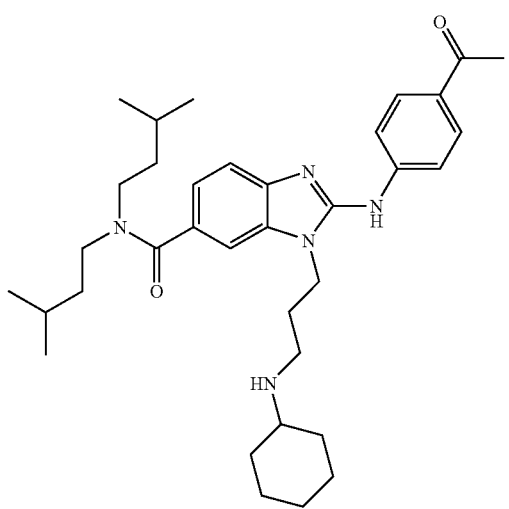 | 574.2 | 9.0 |
| 180 | 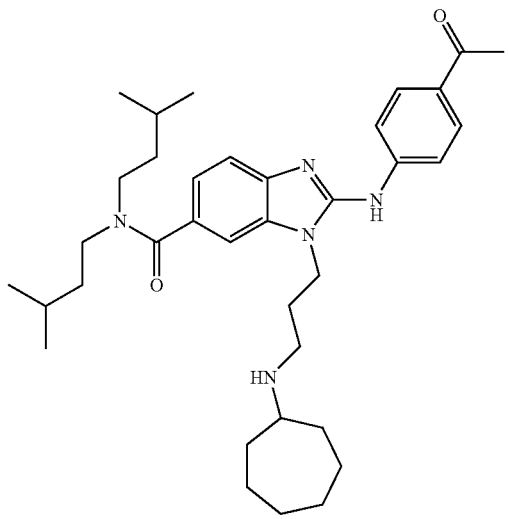 | 588.2 | 9.1 |

-continued

| Examples | Molecular structures | [M + H]+ | rt (min) |
|---|---|---|---|
| 181 | 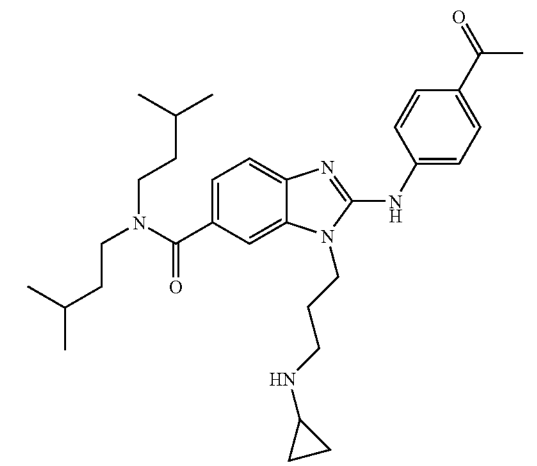 | 532.2 | 8.6 |
| 182 | 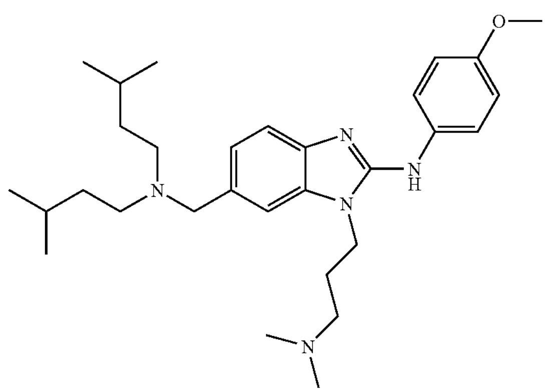 | 494.4 | 7.5 |
| 183 | 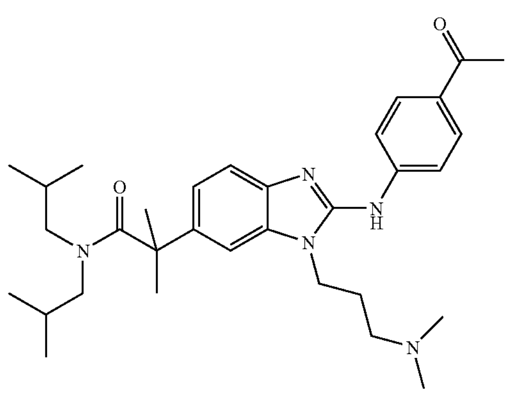 | 534.4 | 8.1 |
| 184 | 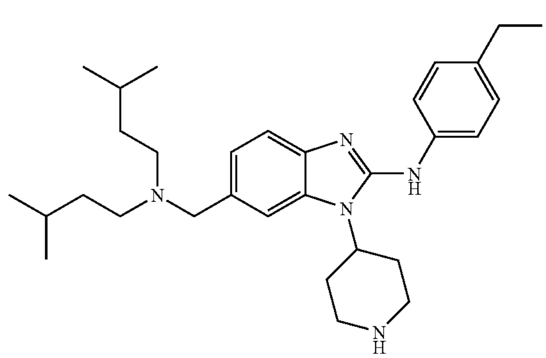 | 504.4 | 8.4 |

| Examples | Molecular structures | [M + H]+ | rt (min) |
|---|---|---|---|
| 185 | 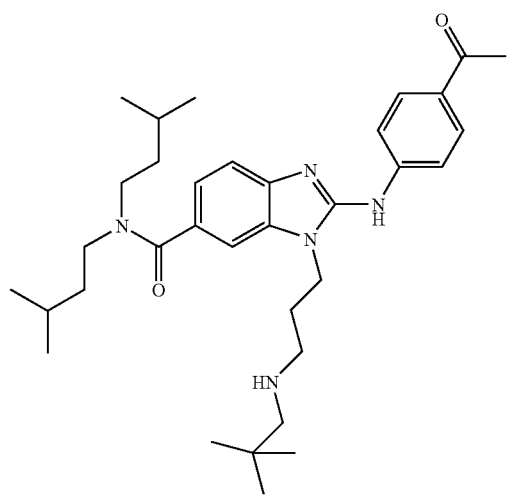 | 562.2 | 8.9 |
| 186 | 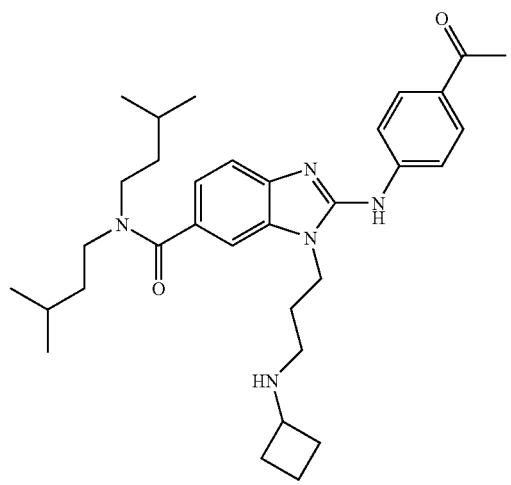 | 546.2 | 8.7 |
| 187 | 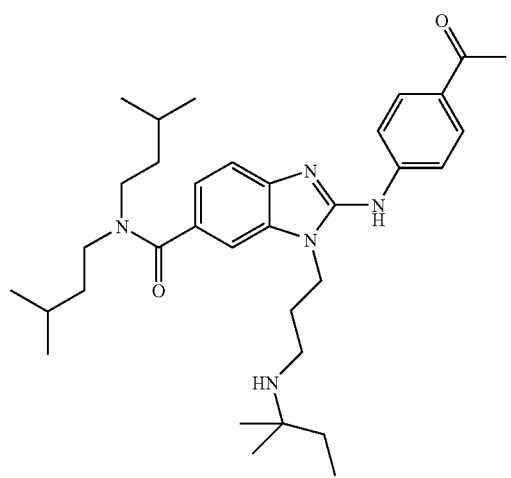 | 562.2 | 8.9 |

| Examples | Molecular structures | [M + H]+ | rt (min) |
|---|---|---|---|
| 188 | 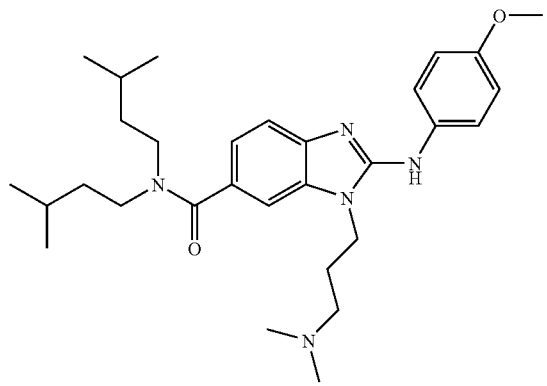 | 508.2 | 8.2 |
| 189 | 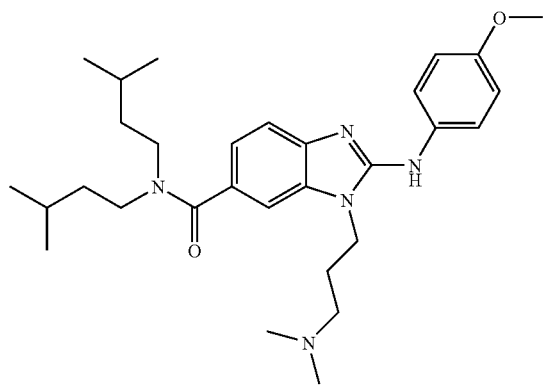 | 494.4 | 7.5 |
| 190 | 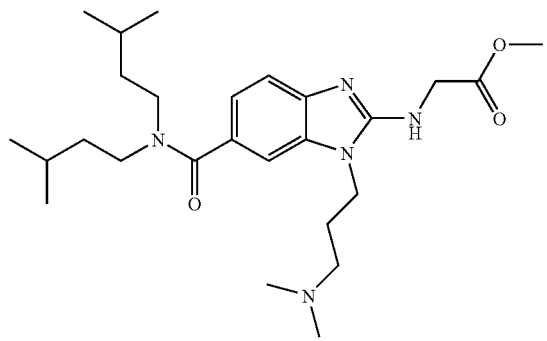 | 474.3 | 8.0 |
| 191 | 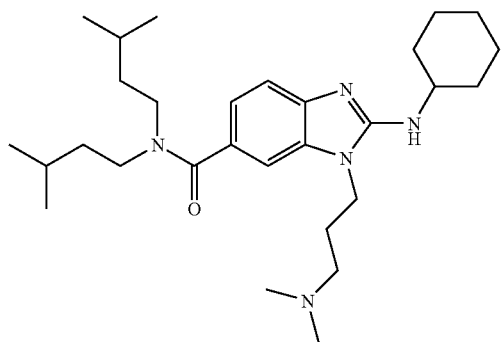 | 484.4 | 8.2 |

| Examples | Molecular structures | [M + H]+ | rt (min) |
|---|---|---|---|
| 192 | 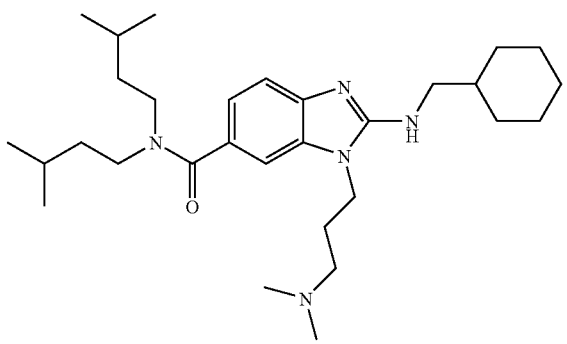 | 498.4 | 8.4 |
| 193 | 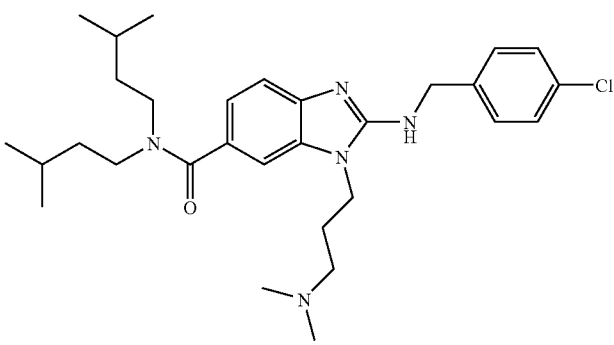 | 526.3 | 8.4 |
| 194 | 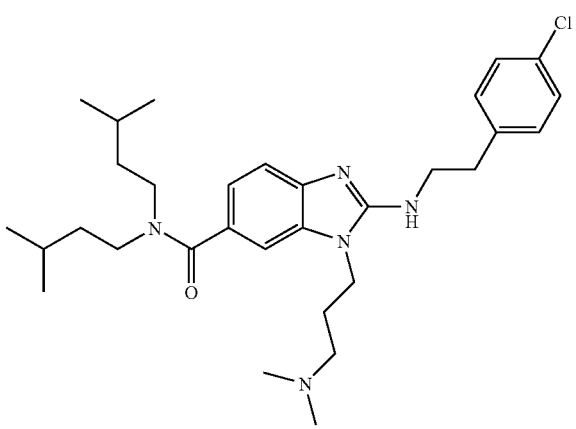 | 540.3 | 8.5 |
| 195 | 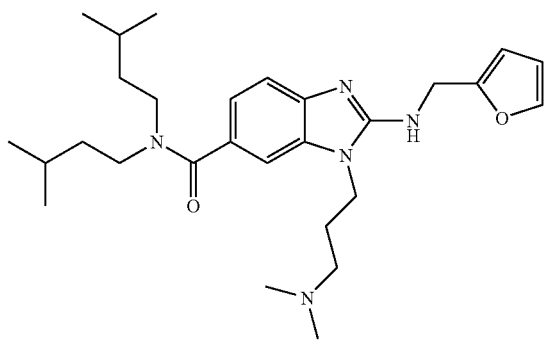 | 482.3 | 8.1 |

-continued

| Examples | Molecular structures | [M + H]+ | rt (min) |
|---|---|---|---|
| 196 | 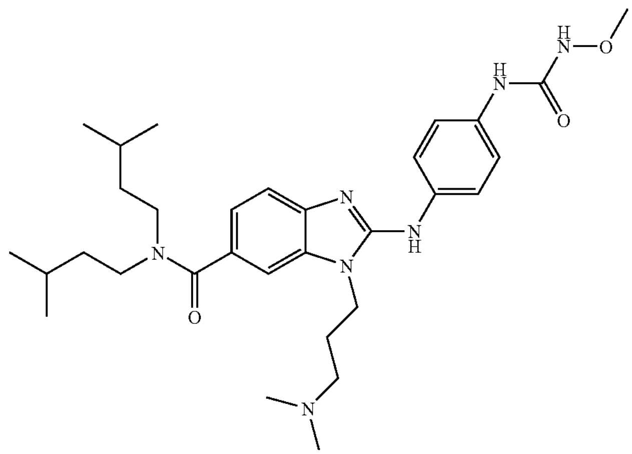 | 566.4 | 8.1 |
| 197 | 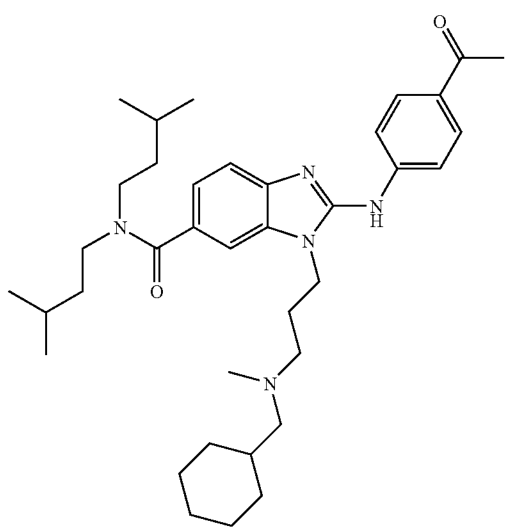 | 602.3 | 9.2 |
| 198 | 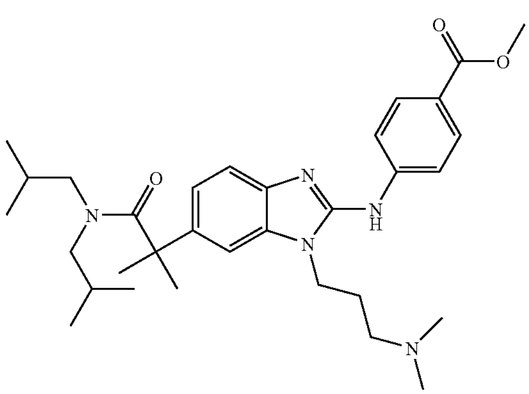 | 550.3 | 8.1 |

| Examples | Molecular structures | [M + H]+ | rt (min) |
|---|---|---|---|
| 199 | 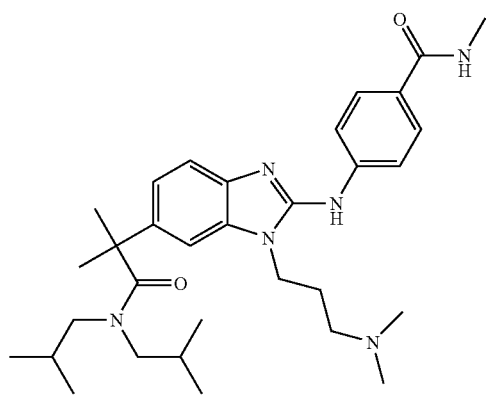 | 549.3 | 7.8 |
| 200 | 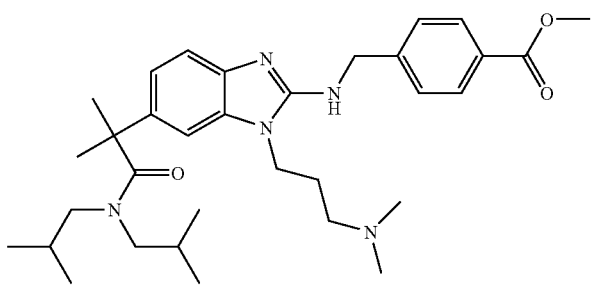 | 564.4 | 8.1 |
| 201 | 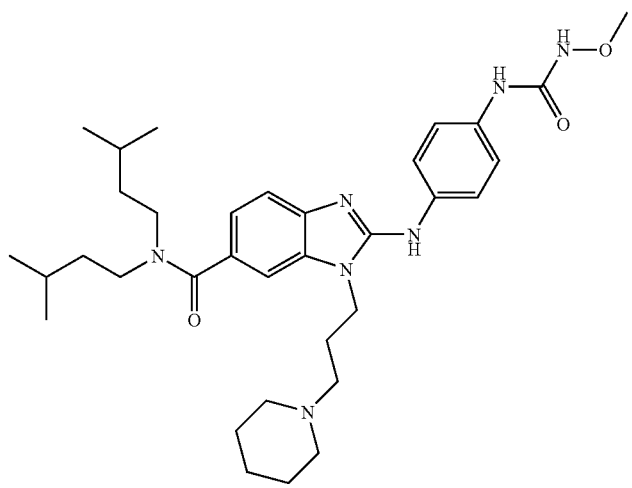 | 606.4 | 8.2 |

-continued
| Examples | Molecular structures | [M + H]+ | rt (min) |
|---|---|---|---|
| 203 | 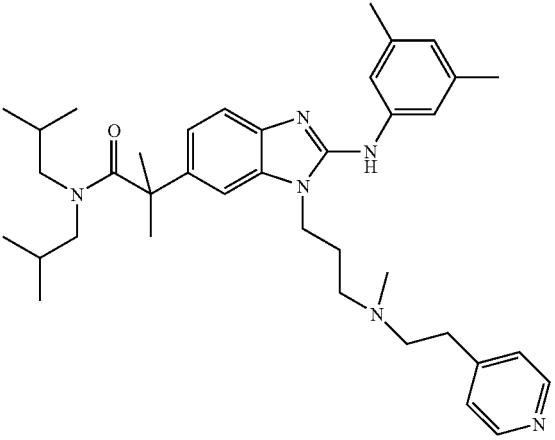 | 611.4 | 7.4 |
| 204 | 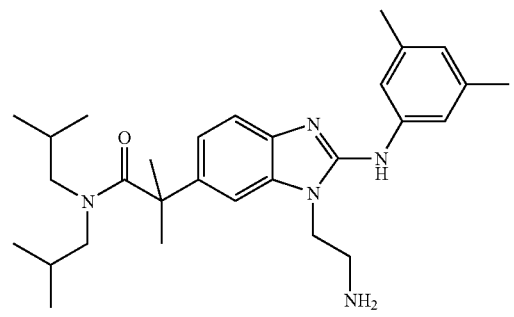 | 478.4 | 7.5 |
| 205 | 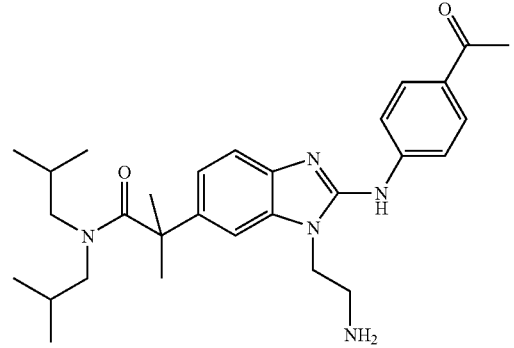 | 492.4 | 7.5 |
| 206 | 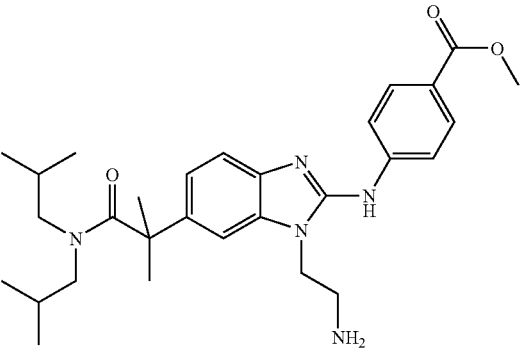 | 508.3 | 7.6 |

-continued

| Examples | Molecular structures | [M + H]+ | rt (min) |
| --- | --- | --- | --- |
| 207 | 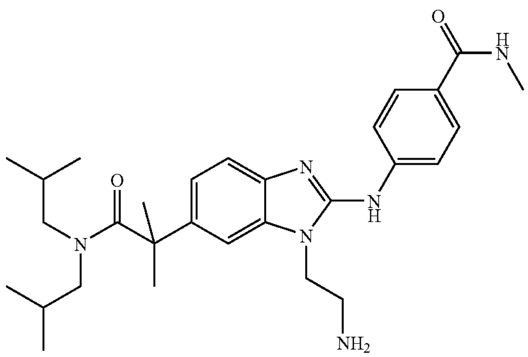 | 507.3 | 7.3 |
| 208 | 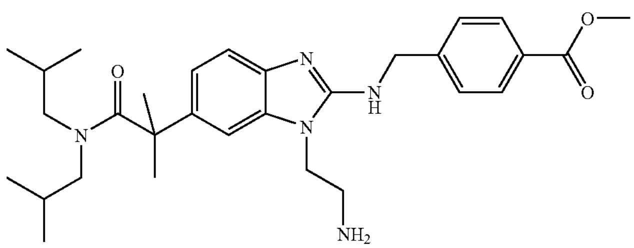 | 522.3 | 7.4 |
| 209 | 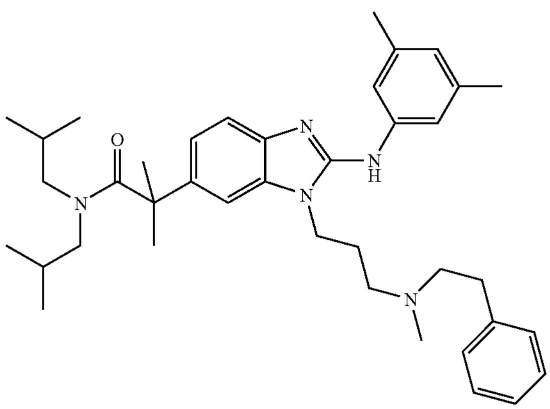 | 610.3 | 8.7 |
| 210 | 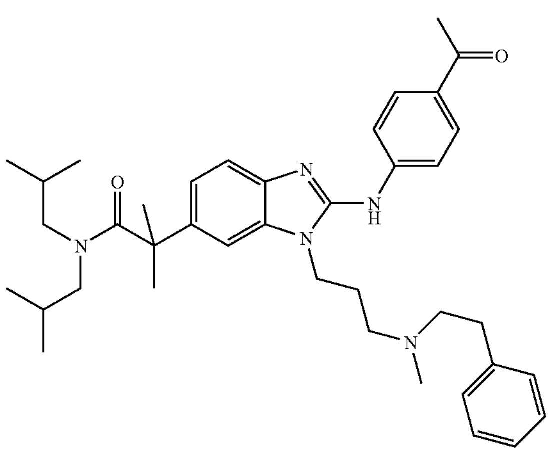 | 624.4 | 8.7 |

-continued
| Examples | Molecular structures | [M + H]+ | rt (min) |
|---|---|---|---|
| 211 | 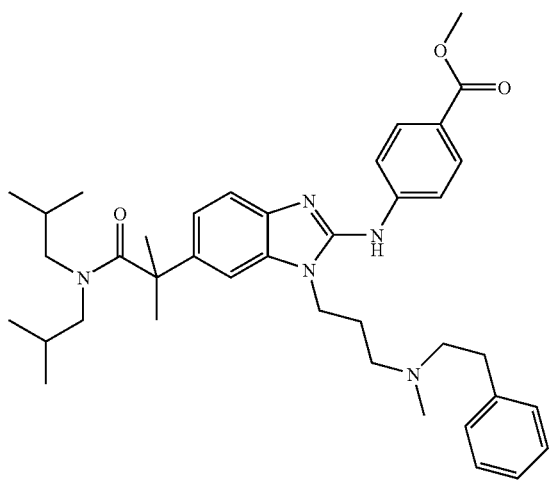 | 640.4 | 8.8 |
| 212 | 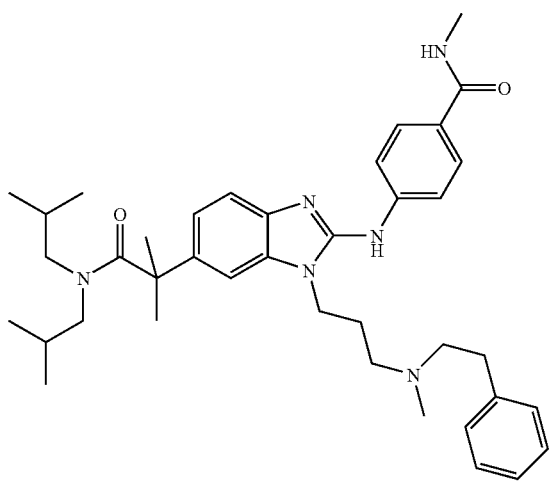 | 639.3 | 8.3 |
| 213 | 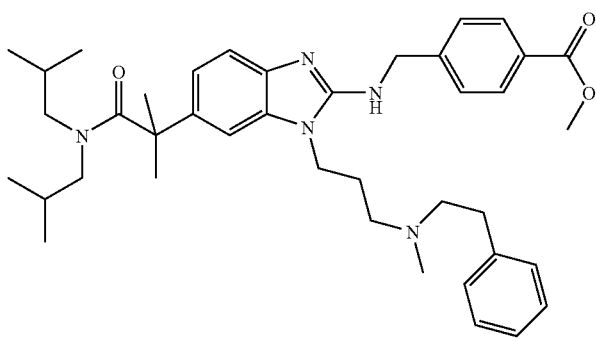 | 654.4 | 8.5 |

-continued
| Examples | Molecular structures | [M + H]+ | rt (min) |
|---|---|---|---|
| 214 | 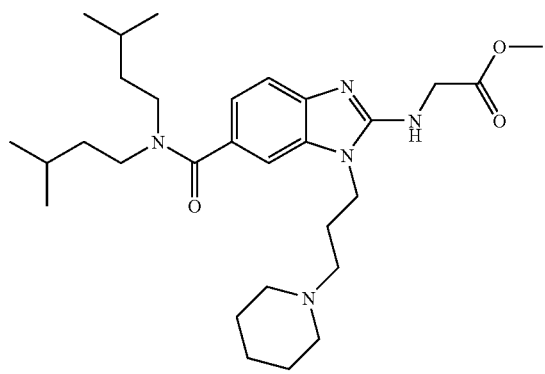 | 514.4 | 8.2 |
| 215 | 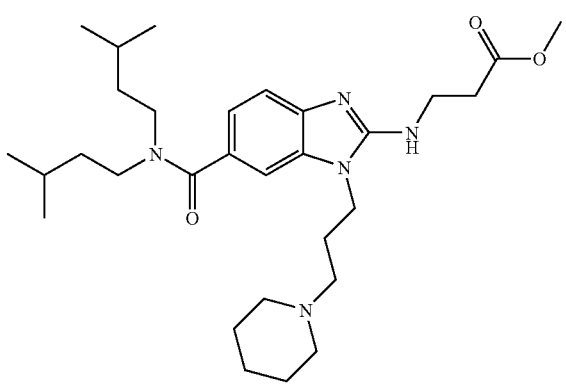 | 528.4 | 8.2 |
| 216 | 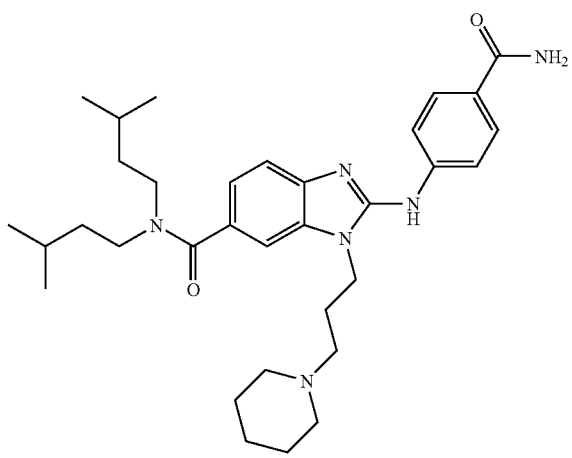 | 560.4 | 8.2 |

-continued
| Examples | Molecular structures | [M + H]+ | rt (min) |
|---|---|---|---|
| 217 | 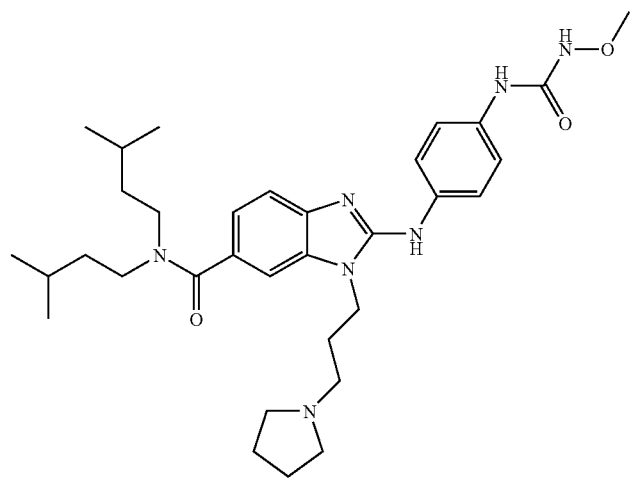 | 592.4 | 8.1 |
| 218 | 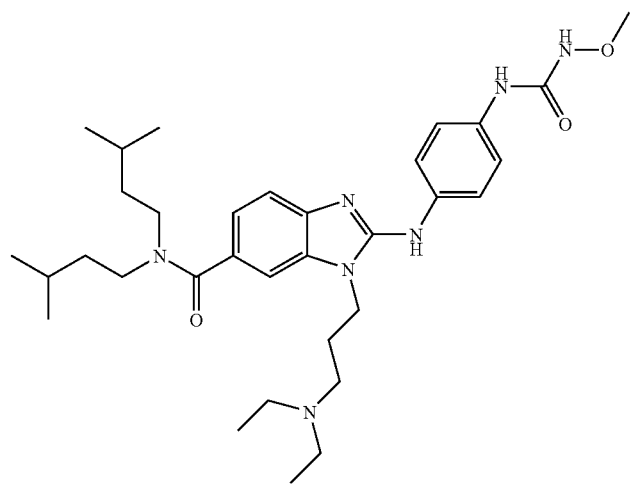 | 594.3 | 8.1 |
| 219 | 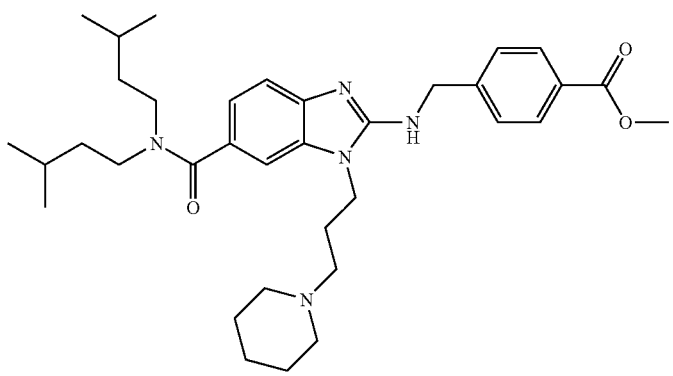 | 590.4 | 8.4 |

-continued
| Examples | Molecular structures | [M + H]+ | rt (min) |
|---|---|---|---|
| 220 | 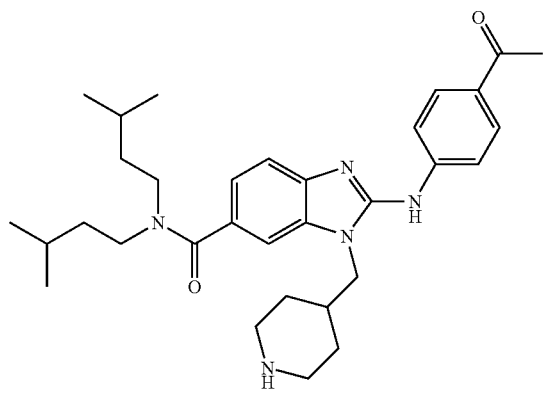 | 532.3 | 8.4 |
| 221 | 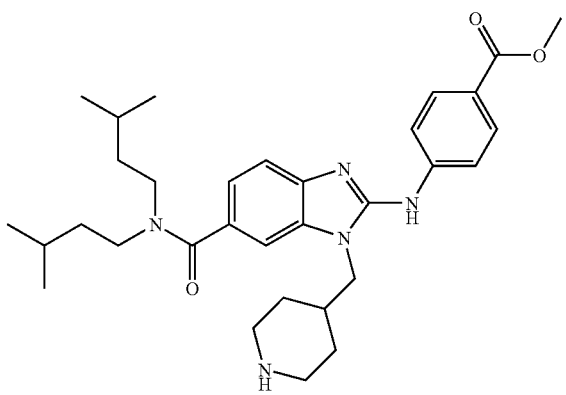 | 548.2 | 8.6 |
| 222 | 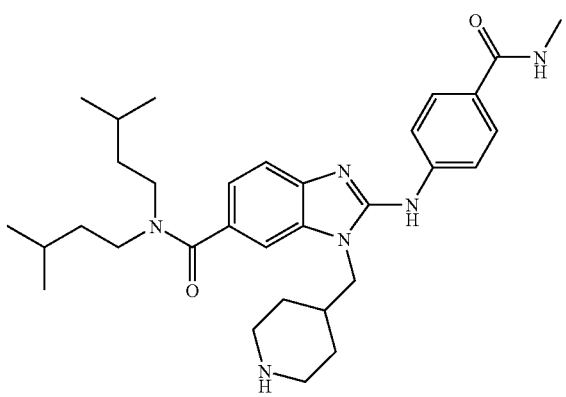 | 547.4 | 8.0 |

-continued
| Examples | Molecular structures | [M + H]+ | rt (min) |
|---|---|---|---|
| 223 | 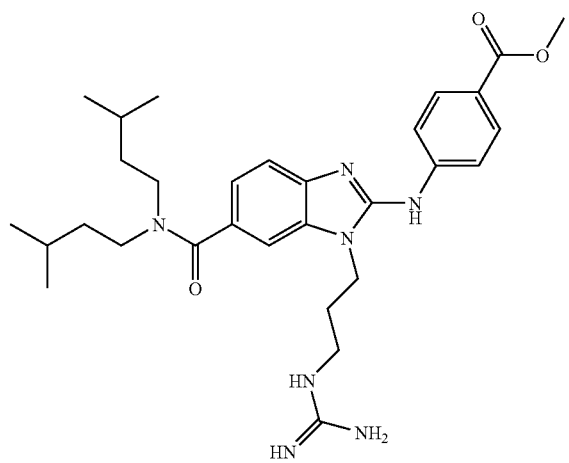 | 550.4 | 8.5 |
| 224 | 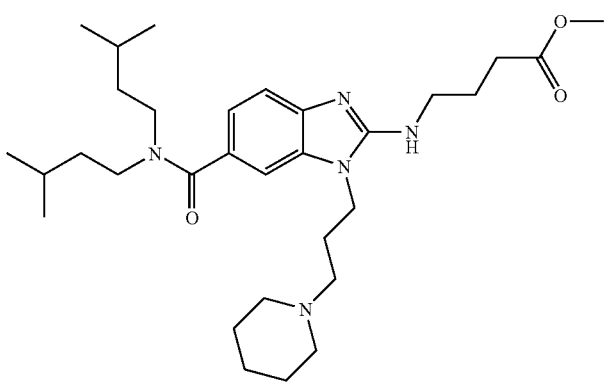 | 542.4 | 8.2 |
| 225 | 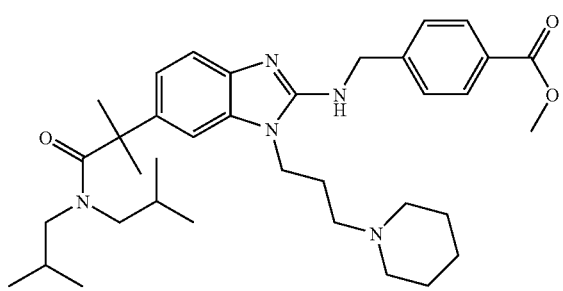 | 604.5 | 8.3 |
| 226 | 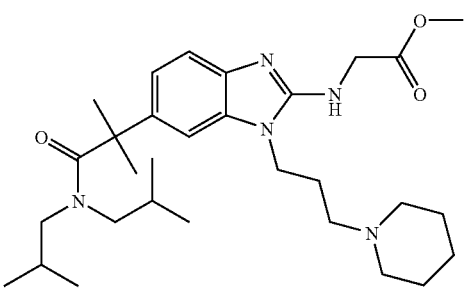 | 528.4 | 7.9 |

-continued
| Examples | Molecular structures | [M + H]+ | rt (min) |
|---|---|---|---|
| 227 | 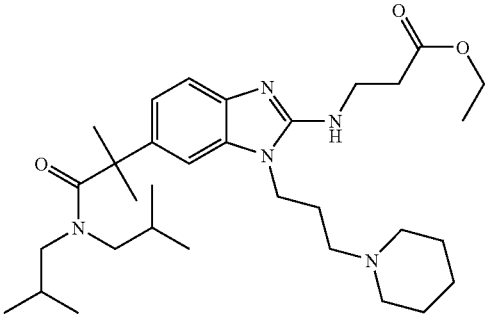 | 556.5 | 8.1 |
| 228 | 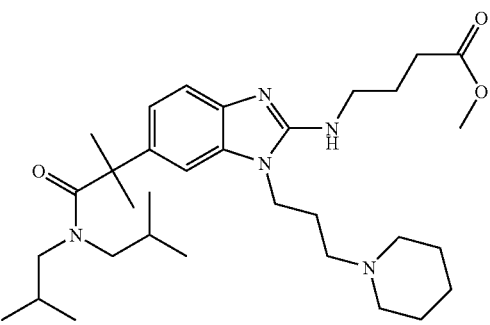 | 556.5 | 8.0 |
| 229 | 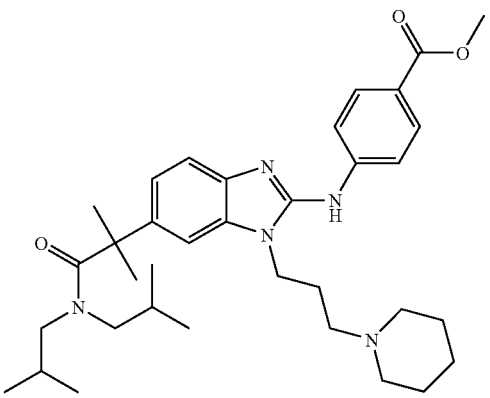 | 590.4 | 8.4 |
| 230 | 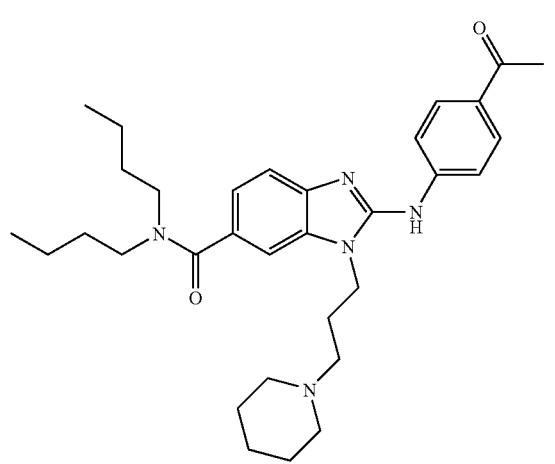 | 532.4 | 8.6 |

-continued

| Examples | Molecular structures | [M + H]+ | rt (min) |
|---|---|---|---|
| 231 | 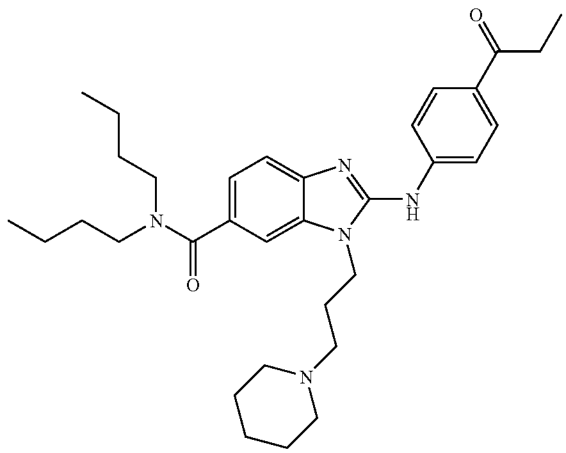 | 546.4 | 8.6 |
| 232 | 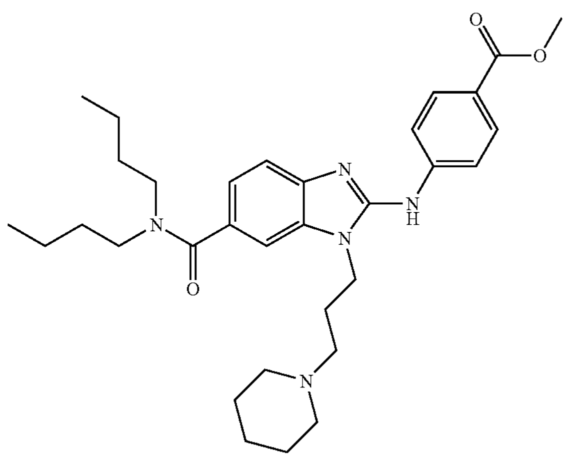 | 548.3 | 8.5 |
| 233 | 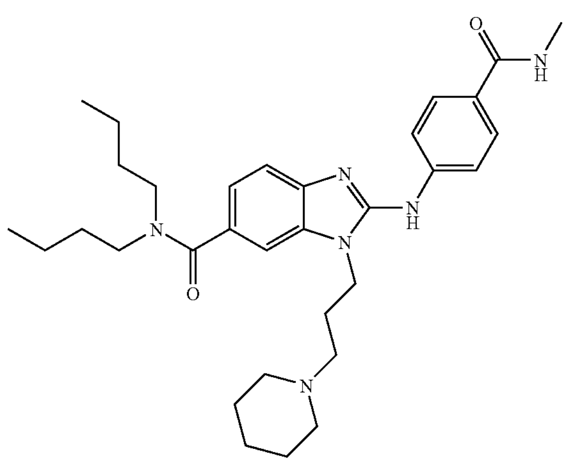 | 547.4 | 7.9 |

-continued

| Examples | Molecular structures | [M + H]+ | rt (min) |
|---|---|---|---|
| 234 | 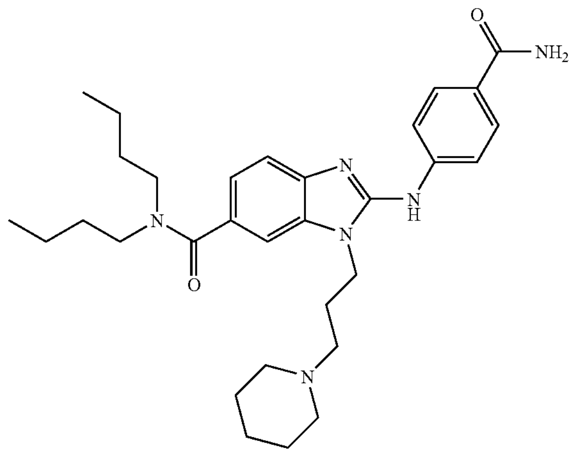 | 533.4 | 7.9 |
| 235 | 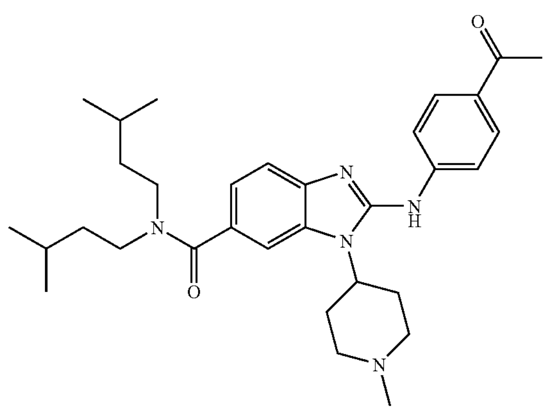 | 532.5 | 8.7 |
| 236 | 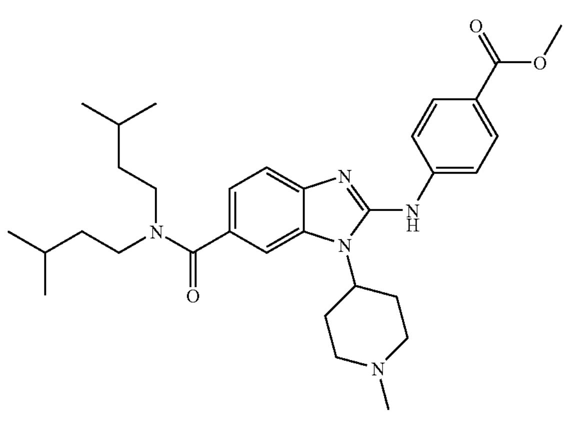 | 548.4 | 8.8 |

| Examples | Molecular structures | [M + H]+ | rt (min) |
|---|---|---|---|
| 237 | 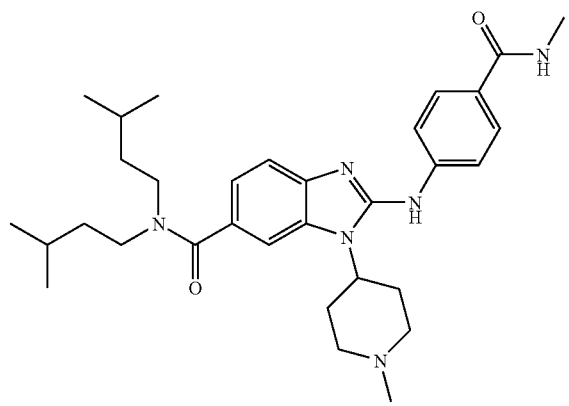 | 547.5 | 8.1 |
| 238 | 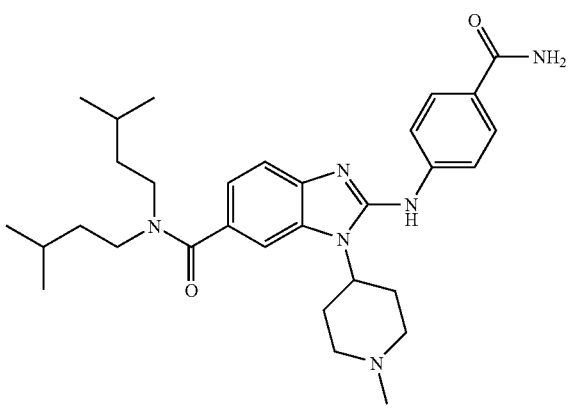 | 533.4 | 8.0 |
| 239 | 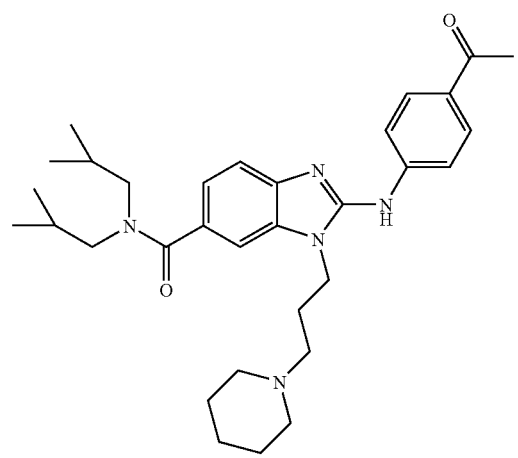 | 532.4 | 8.1 |

-continued
| Examples | Molecular structures | [M + H]+ | rt (min) |
|---|---|---|---|
| 240 | 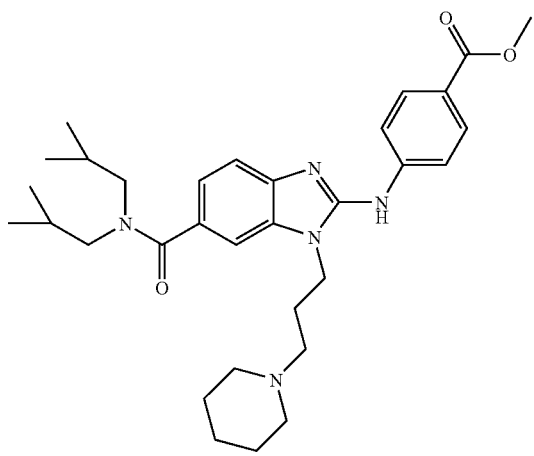 | 548.4 | 8.3 |
| 241 | 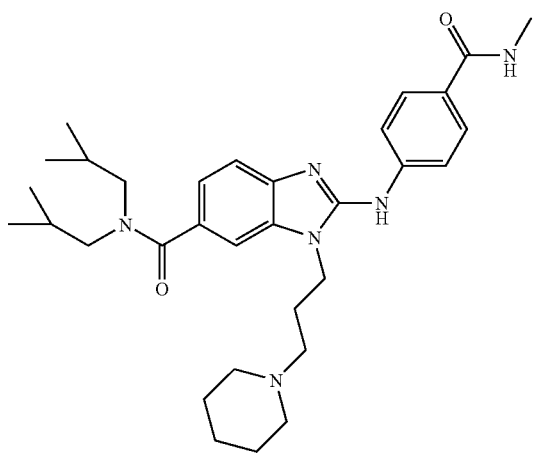 | 547.4 | 7.7 |
| 242 | 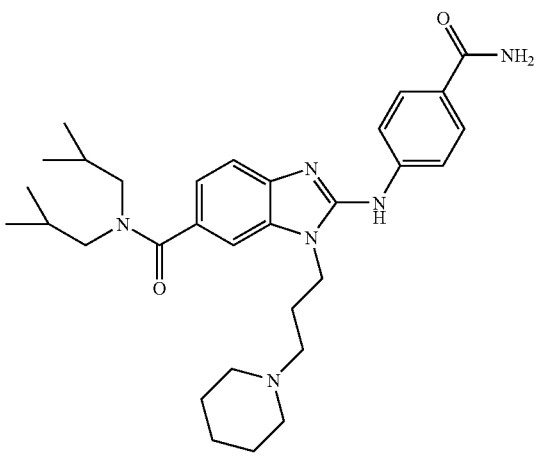 | 533.4 | 7.7 |

| Examples | Molecular structures | [M + H]+ | rt (min) |
|---|---|---|---|
| 243 | 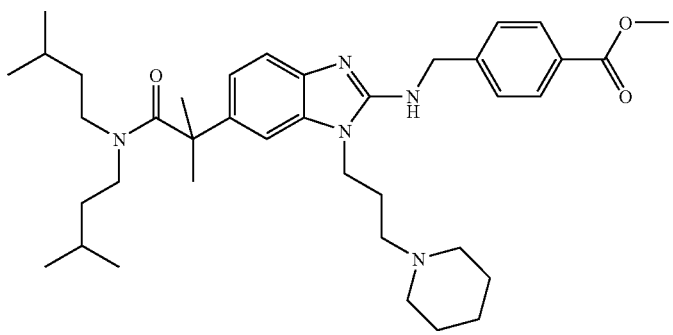 | 632.5 | 8.3 |
| 244 | 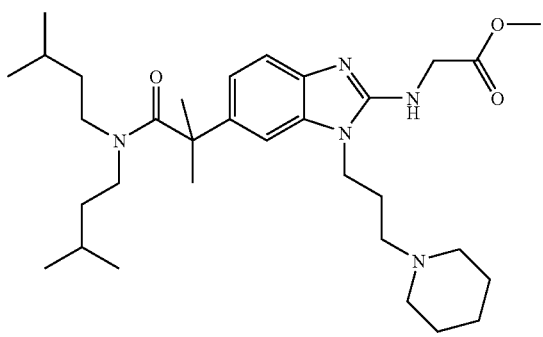 | 556.4 | 8.1 |
| 245 | 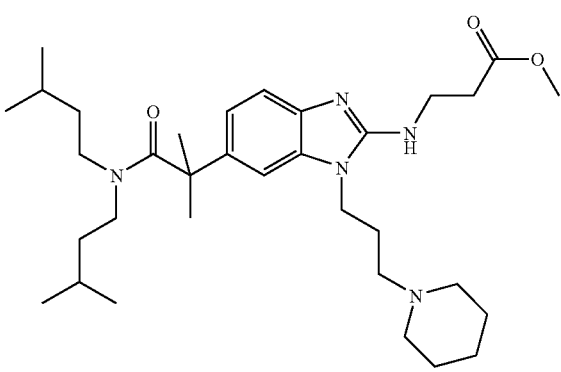 | 570.4 | 8.1 |
| 246 | 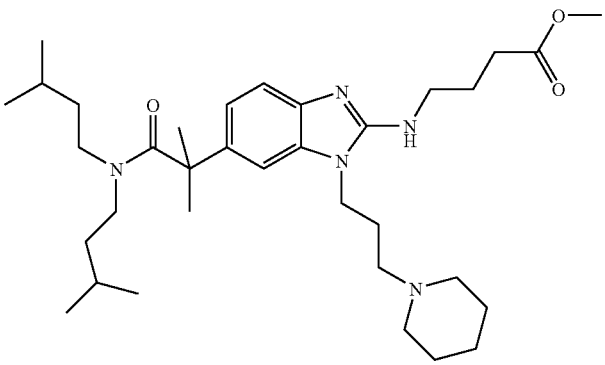 | 584.5 | 8.2 |

-continued

| Examples | Molecular structures | [M + H]+ | rt (min) |
|---|---|---|---|
| 247 | 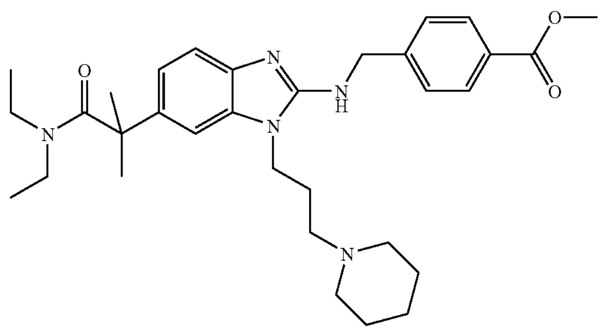 | 548.4 | 7.5 |
| 248 | 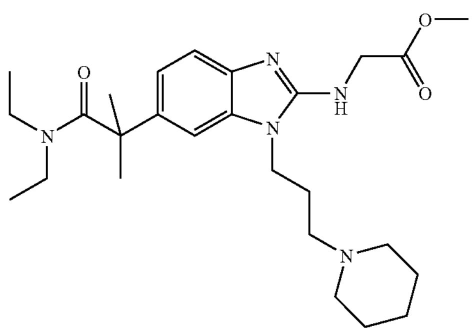 | 472.4 | 7.2 |
| 249 | 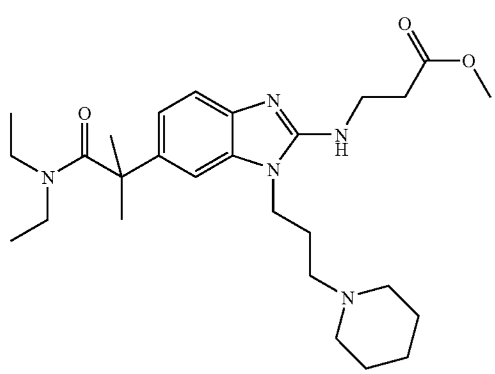 | 486.4 | 7.3 |
| 250 | 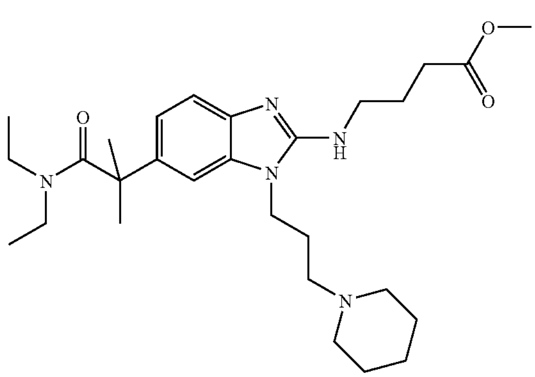 | 500.4 | 7.3 |

-continued
| Examples | Molecular structures | [M + H]+ | rt (min) |
|---|---|---|---|
| 251 | 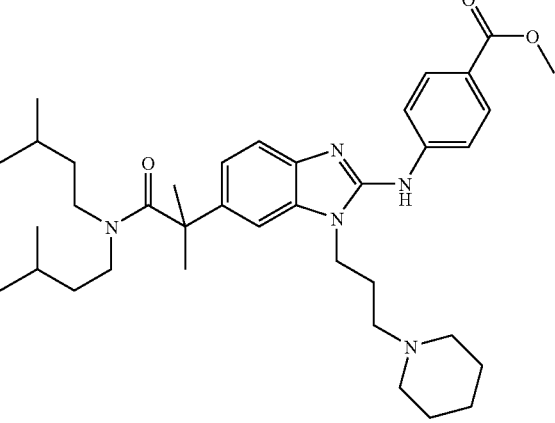 | 618.5 | 8.7 |
| 252 | 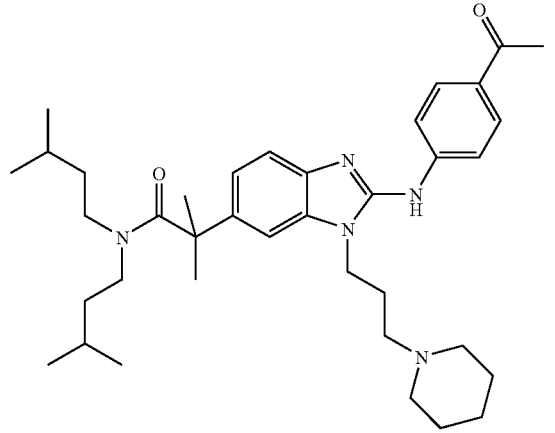 | 602.5 | 8.6 |
| 253 | 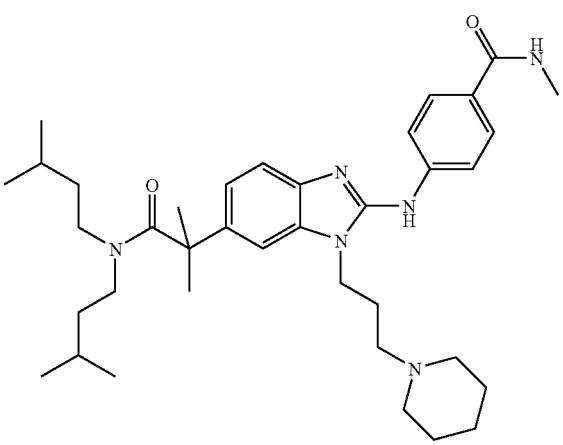 | 617.5 | 8.1 |

| Examples | Molecular structures | [M + H]+ | rt (min) |
|---|---|---|---|
| 254 | 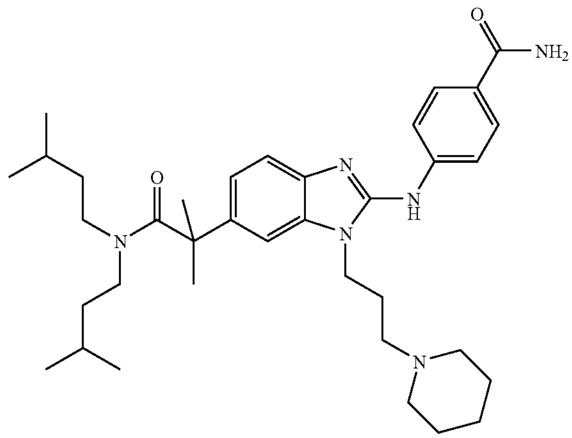 | 603.5 | 8.1 |
| 255 | 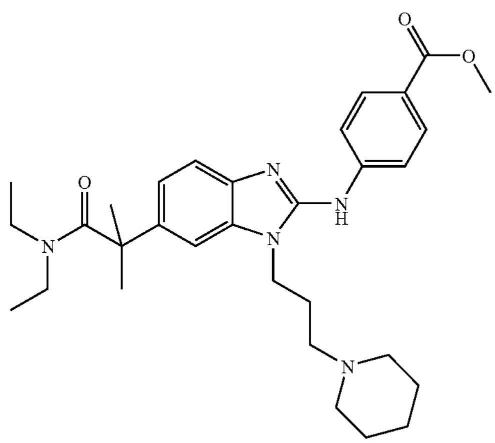 | 534.4 | 7.6 |
| 256 | 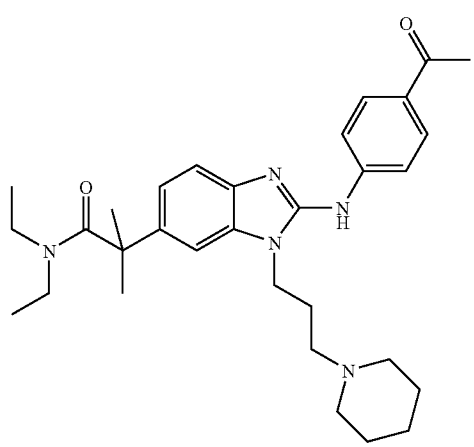 | 518.4 | 7.5 |

| Examples | Molecular structures | [M + H]+ | rt (min) |
|---|---|---|---|
| 257 | 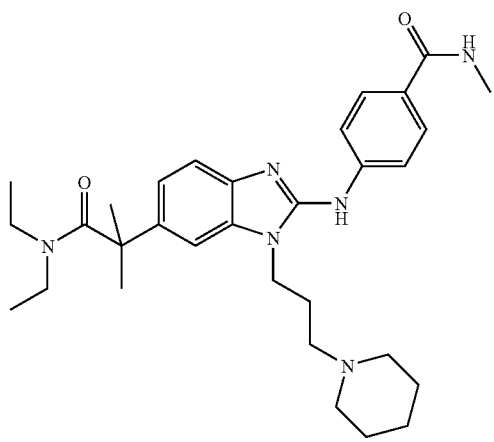 | 533.4 | 7.3 |
| 258 | 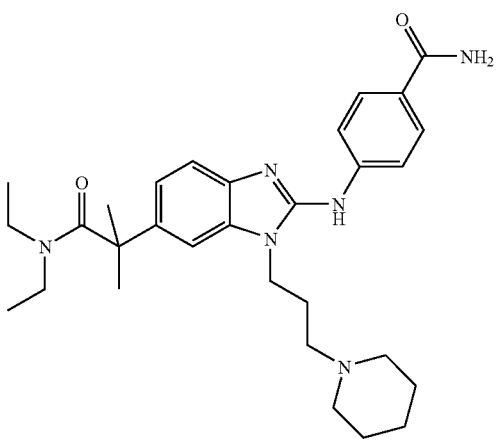 | 519.4 | 7.2 |
| 259 | 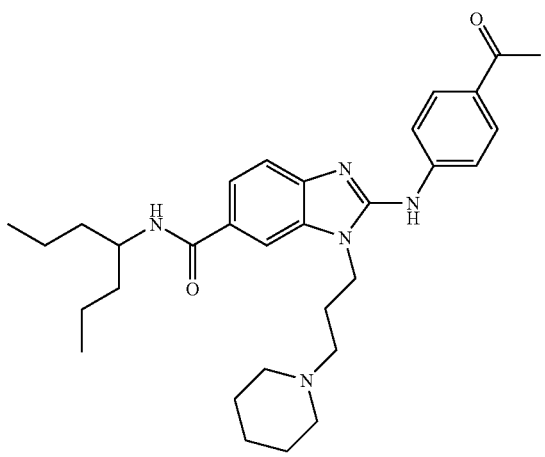 | 518.4 | 8.1 |

-continued
| Examples | Molecular structures | [M + H]+ | rt (min) |
|---|---|---|---|
| 260 | 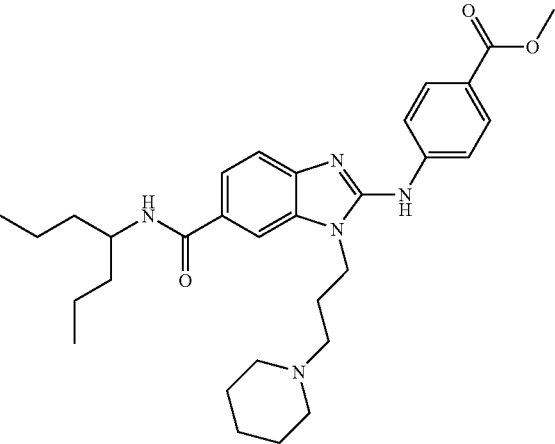 | 534.4 | 8.2 |
| 261 | 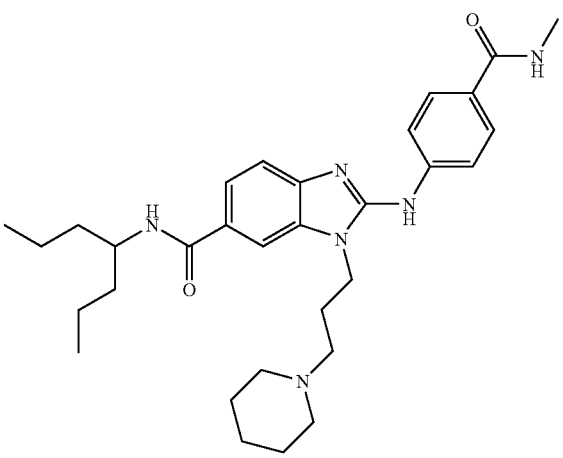 | 533.4 | 7.7 |
| 262 | 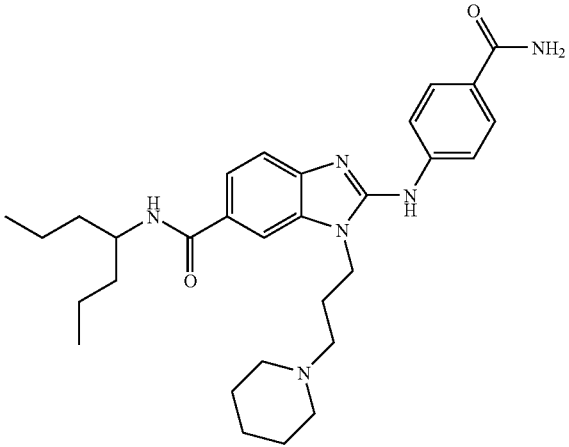 | 519.4 | 7.7 |

| Examples | Molecular structures | [M + H]+ | rt (min) |
|---|---|---|---|
| 263 | 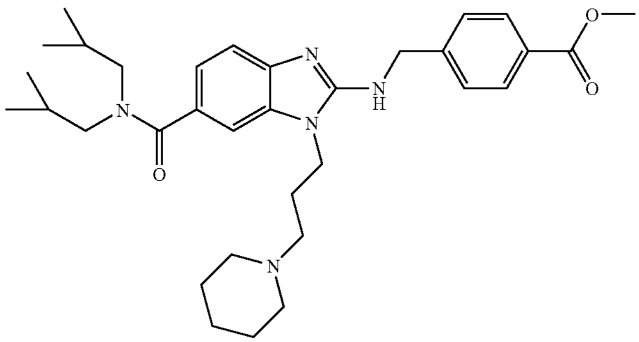 | 562.4 | 7.8 |
| 264 | 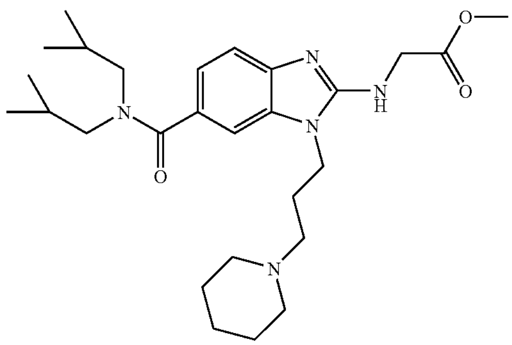 | 486.3 | 7.6 |
| 265 | 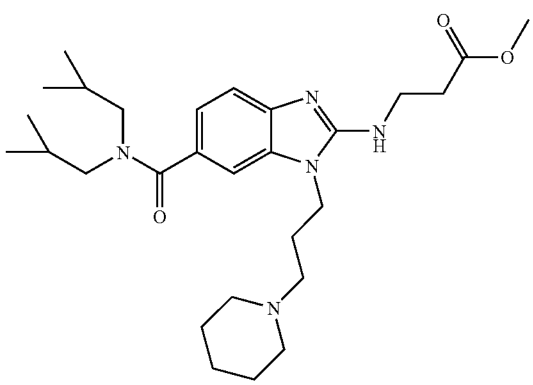 | 500.4 | 7.6 |
| 266 | 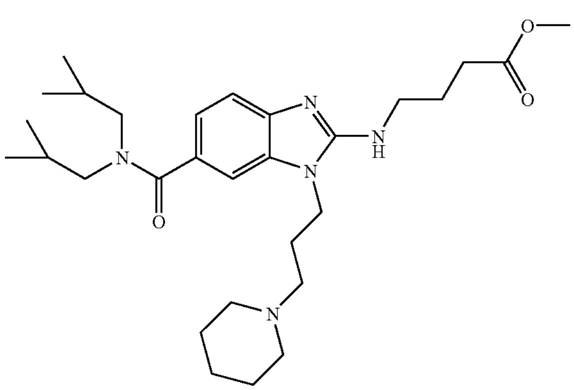 | 514.4 | 7.7 |

| Examples | Molecular structures | [M + H]+ | rt (min) |
|---|---|---|---|
| 267 | 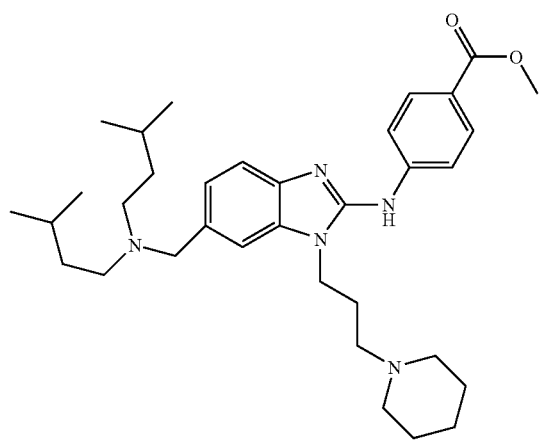 | 562.4 | 8.2 |
| 268 | 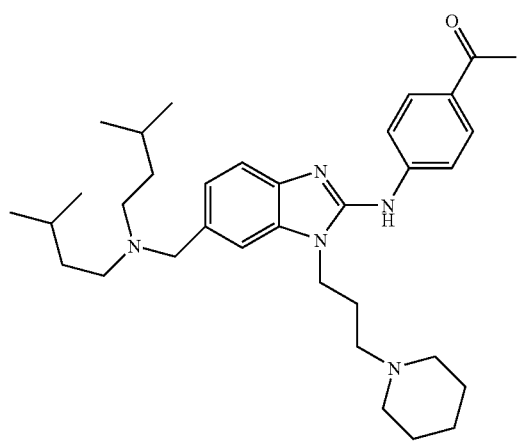 | 546.4 | 8.1 |
| 269 | 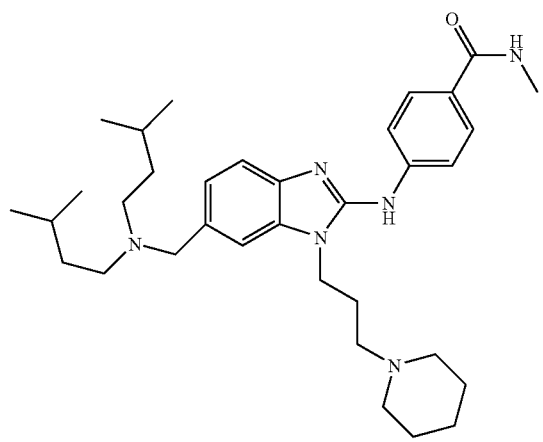 | 561.4 | 7.8 |

-continued
| Examples | Molecular structures | [M + H]+ | rt (min) |
|---|---|---|---|
| 270 | 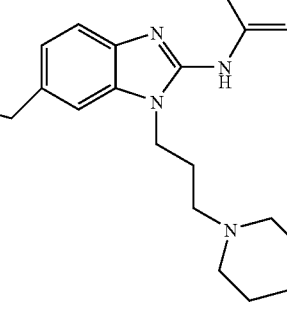 | 547.4 | 7.8 |
| 271 | 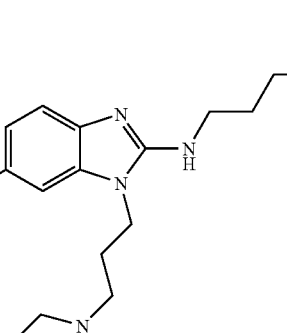 | 570.4 | 8.7 |
| 272 | 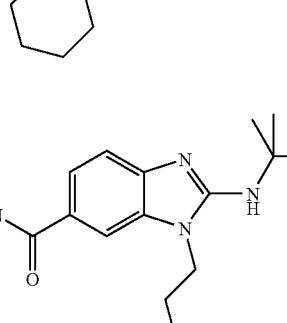 | 542.4 | 8.7 |
| 273 | 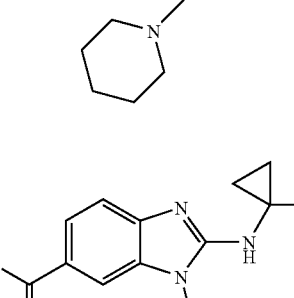 | 554.4 | 8.6 |

| Examples | Molecular structures | [M + H]+ | rt (min) |
|---|---|---|---|
| 274 | 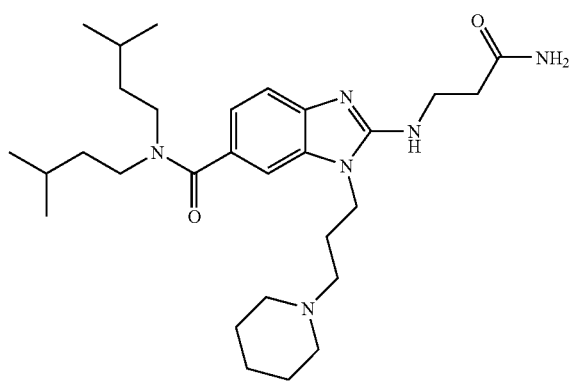 | 513.4 | 8.3 |
| 275 | 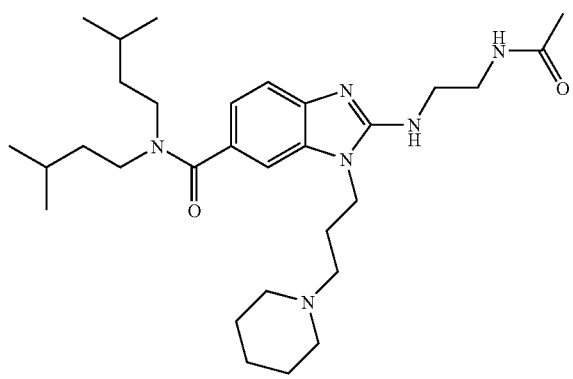 | 527.4 | 8.4 |
| 276 | 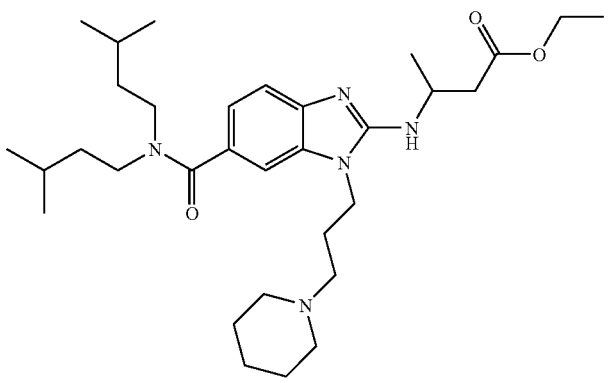 | 556.4 | 8.6 |
| 277 | 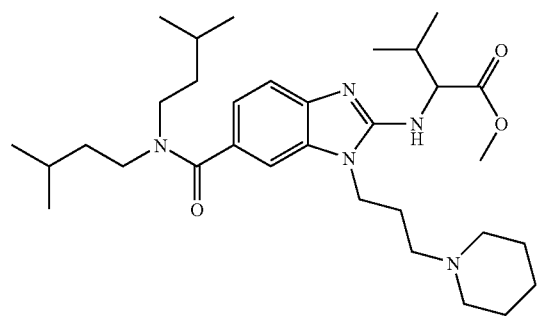 | 556.4 | 8.8 |

| Examples | Molecular structures | [M + H]+ | rt (min) |
|---|---|---|---|
| 278 | 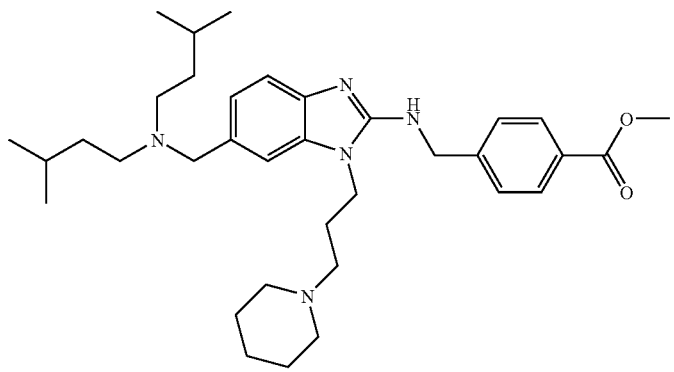 | 576.4 | 7.9 |
| 279 | 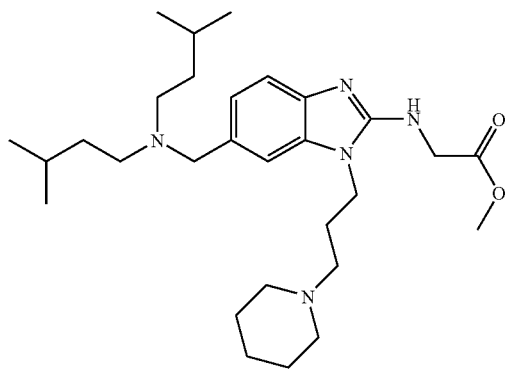 | 500.4 | 7.6 |
| 280 | 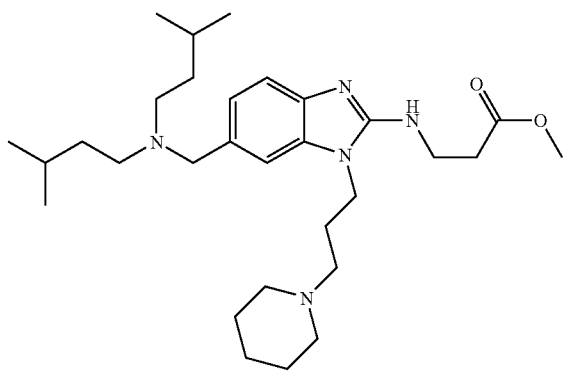 | 514.4 | 7.6 |
| 281 | 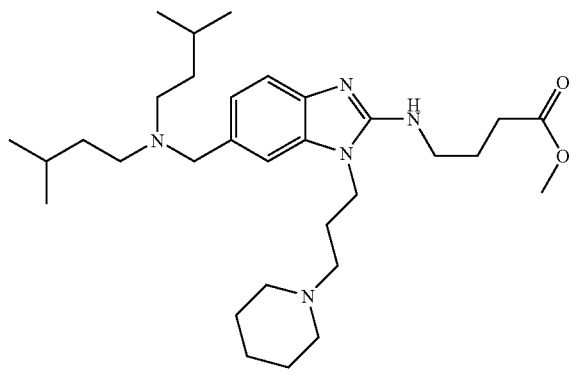 | 528.5 | 7.7 |

| Examples | Molecular structures | [M + H]+ | rt (min) |
|---|---|---|---|
| 282 | 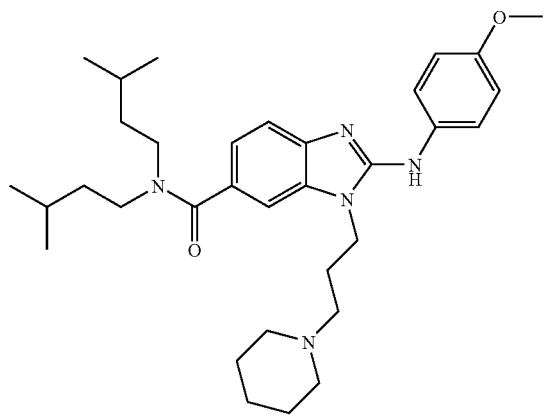 | 548.4 | 8.7 |
| 283 | 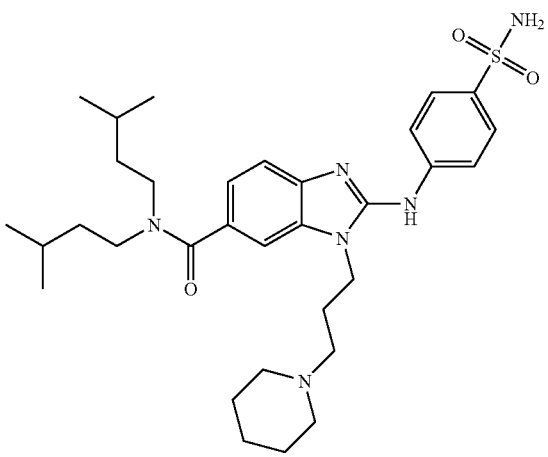 | 597.4 | 8.9 |
| 284 | 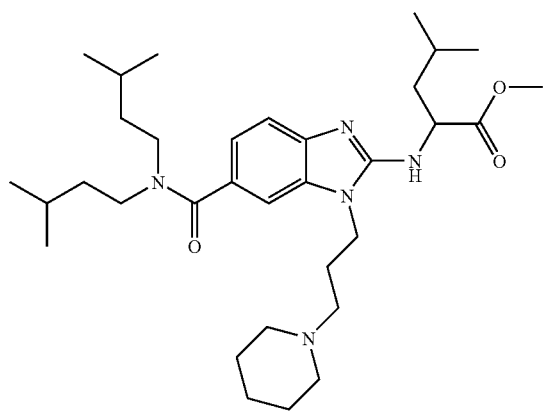 | 570.4 | 8.9 |

| Examples | Molecular structures | [M + H]+ | rt (min) |
|---|---|---|---|
| 285 | 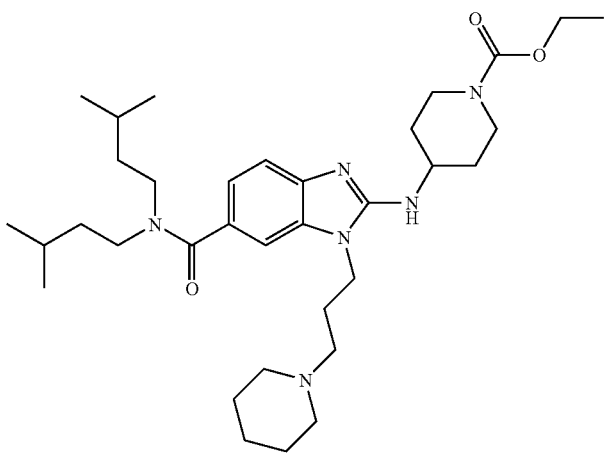 | 597.4 | 8.7 |
| 286 | 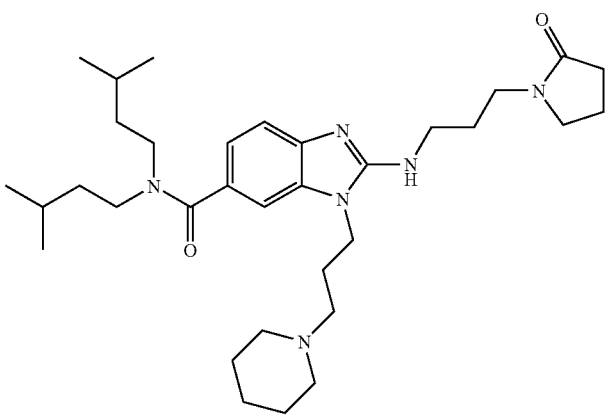 | 567.4 | 8.5 |
| 287 | 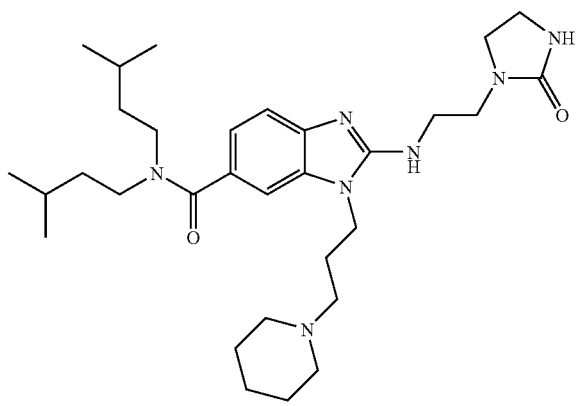 | 554.4 | 8.4 |

| Examples | Molecular structures | [M + H]+ | rt (min) |
|---|---|---|---|
| 288 | 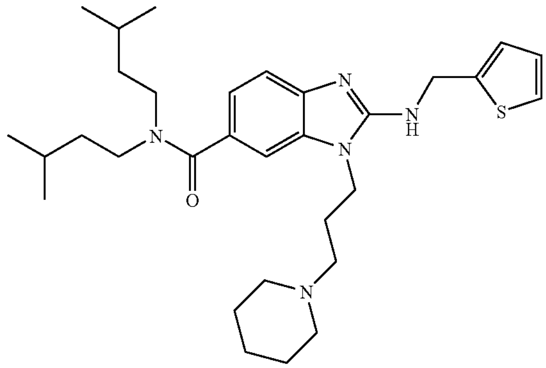 | 538.3 | 8.7 |
| 289 | 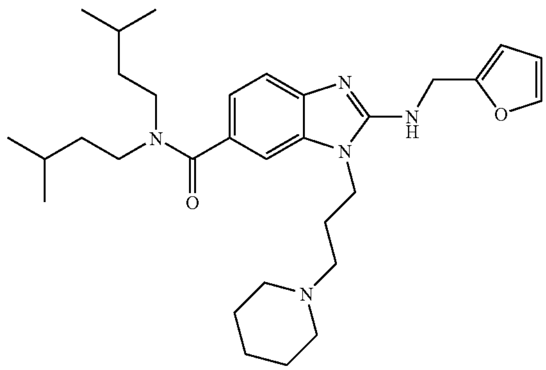 | 522.4 | 8.6 |
| 290 | 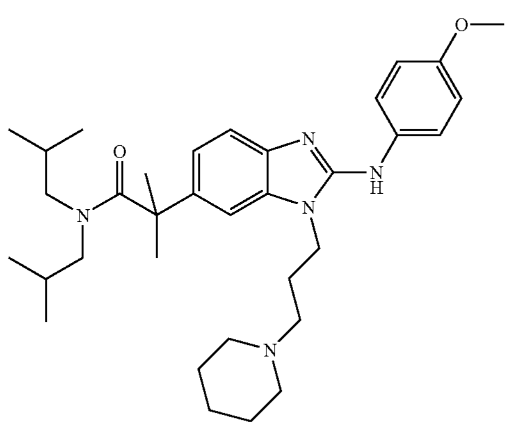 | 562.4 | 8.5 |
| 291 | 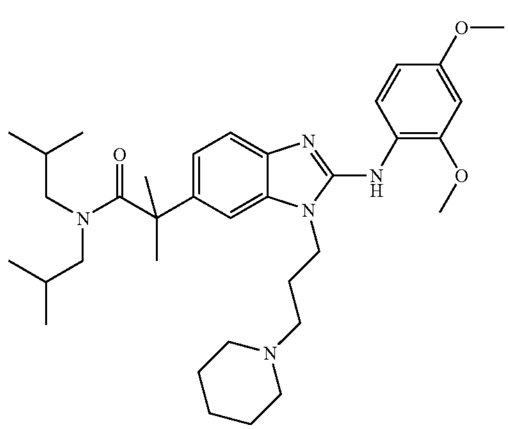 | 592.4 | 8.6 |

-continued
| Examples | Molecular structures | [M + H]+ | rt (min) |
|---|---|---|---|
| 292 | 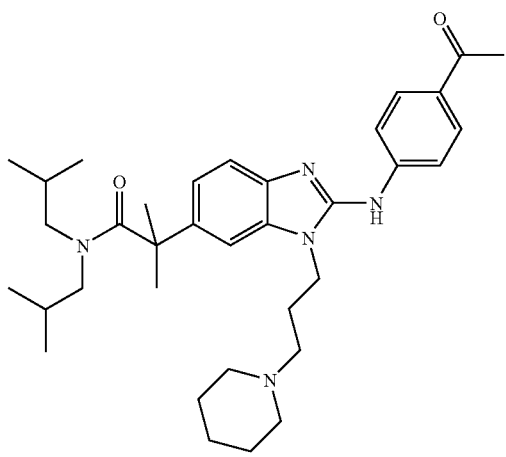 | 574.4 | 8.6 |
| 293 | 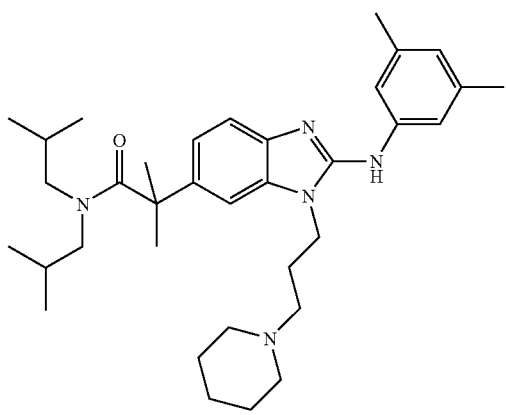 | 560.4 | 8.7 |
| 294 | 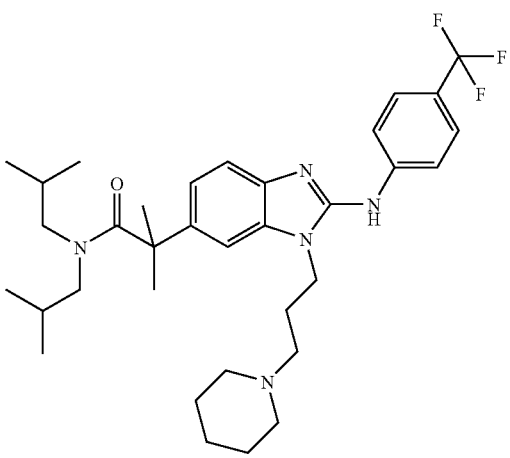 | 600.3 | 9.2 |

-continued
| Examples | Molecular structures | [M + H]+ | rt (min) |
|---|---|---|---|
| 295 | 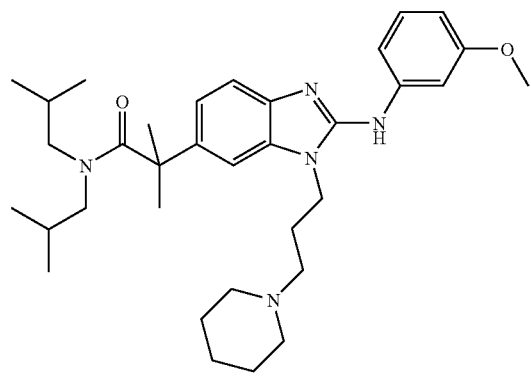 | 562.4 | 8.5 |
| 296 | 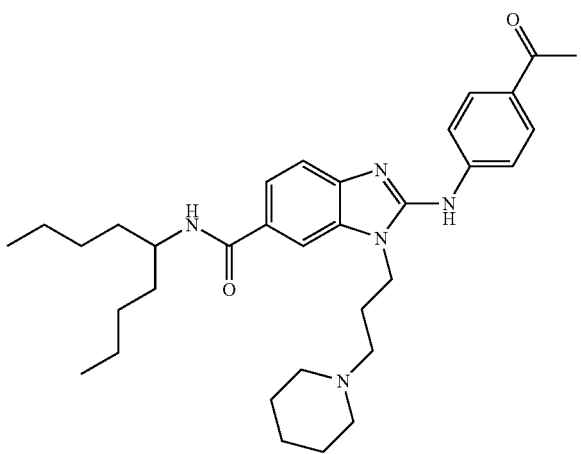 | 546.3 | 8.9 |
| 297 | 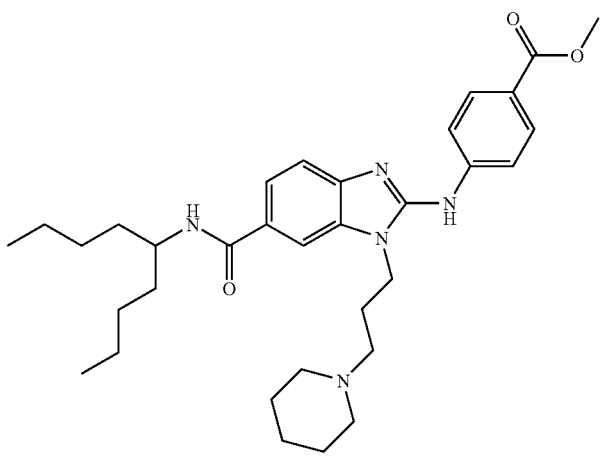 | 562.3 | 9.1 |

| Examples | Molecular structures | [M + H]+ | rt (min) |
|---|---|---|---|
| 298 | 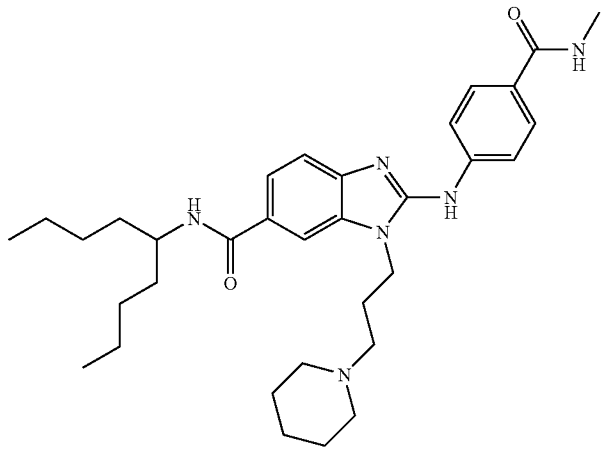 | 561.3 | 8.5 |
| 299 | 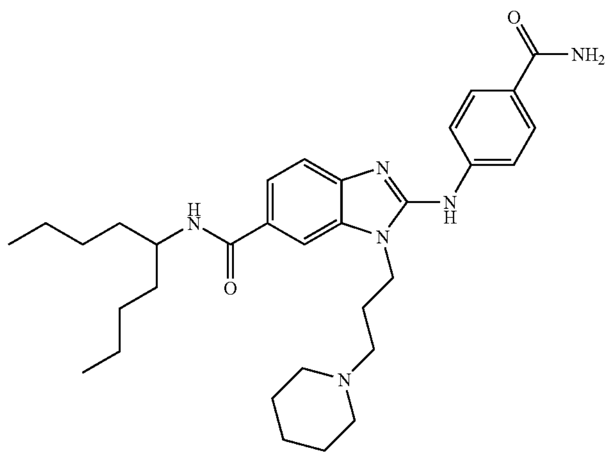 | 547.3 | 8.5 |
| 300 | 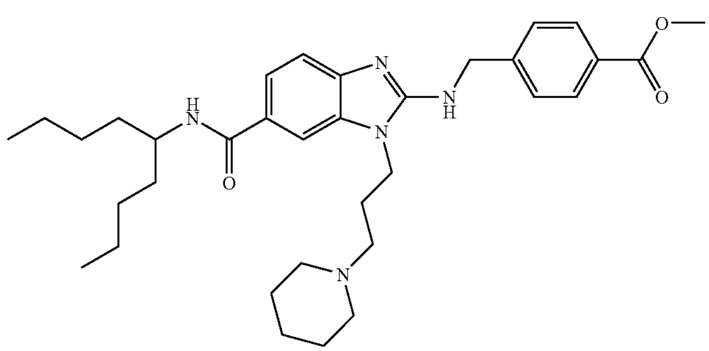 | 576.4 | 8.6 |
| 301 | 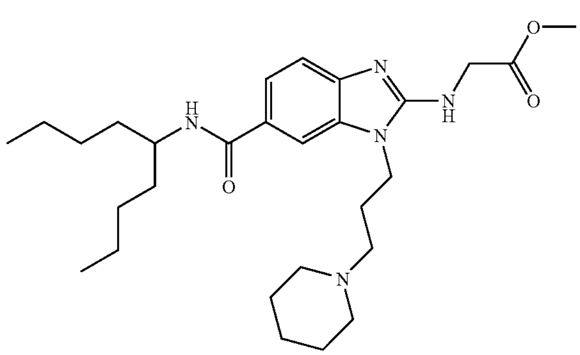 | 500.4 | 8.4 |

-continued

| Examples | Molecular structures | [M + H]+ | rt (min) |
|---|---|---|---|
| 302 | 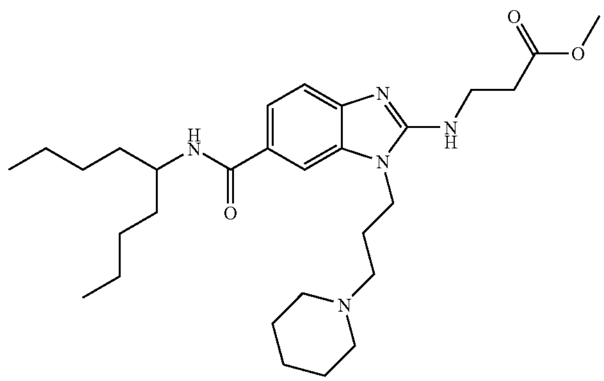 | 514.4 | 8.4 |
| 303 | 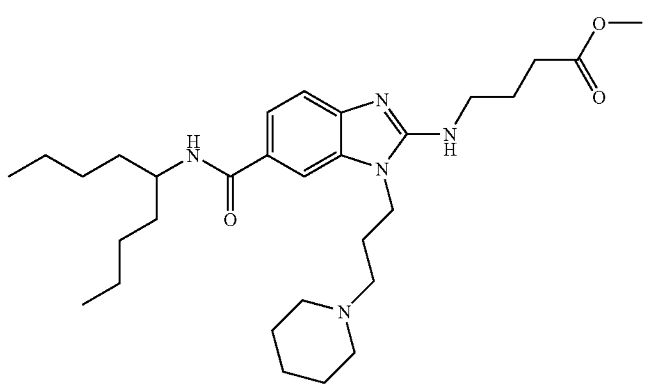 | 528.4 | 8.4 |
| 304 | 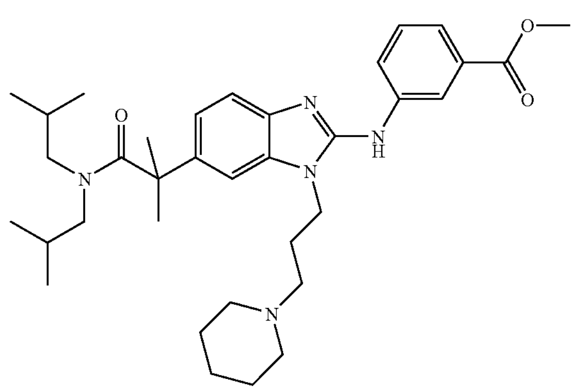 | 590.4 | 8.5 |

-continued

| Examples | Molecular structures | [M + H]+ | rt (min) |
|---|---|---|---|
| 305 | 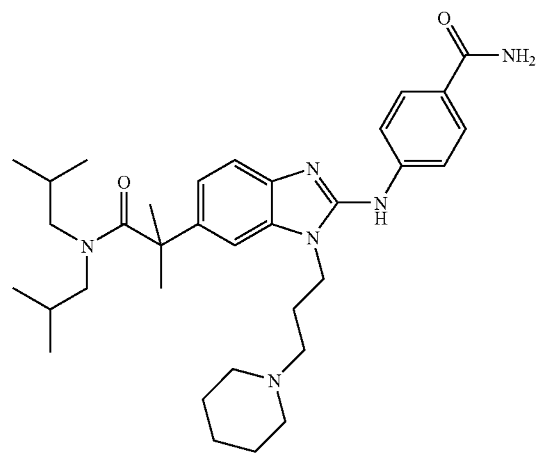 | 575.4 | 8.1 |
| 306 | 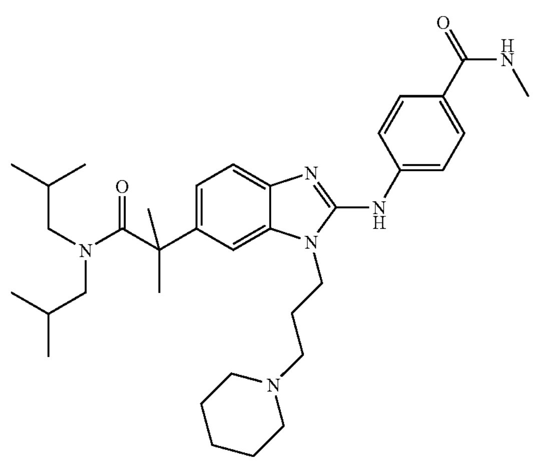 | 589.4 | 8.2 |
| 307 | 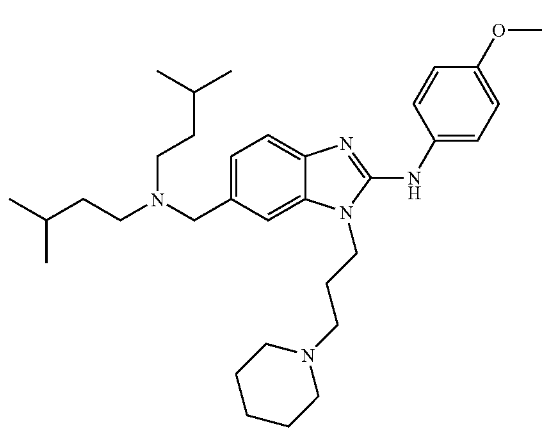 | 534.5 | 7.7 |

-continued

| Examples | Molecular structures | [M + H]+ | rt (min) |
|---|---|---|---|
| 308 | 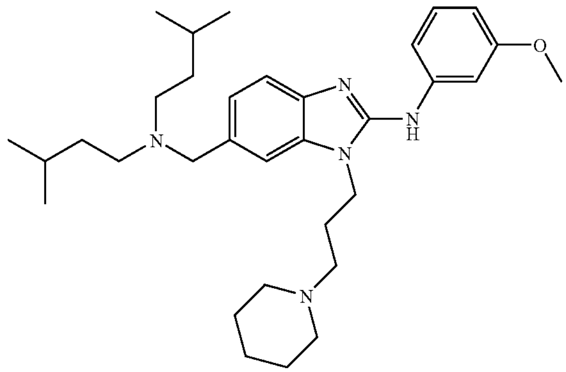 | 534.5 | 7.8 |
| 309 | 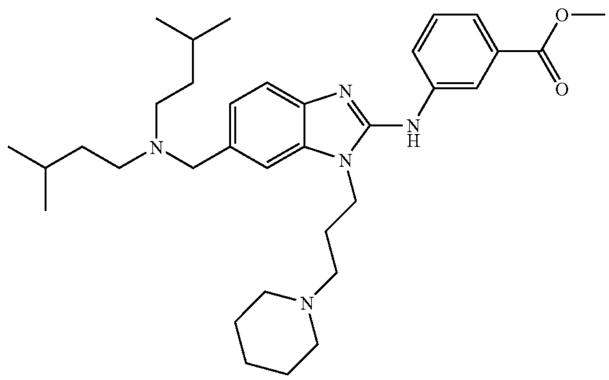 | 562.5 | 7.9 |
| 310 | 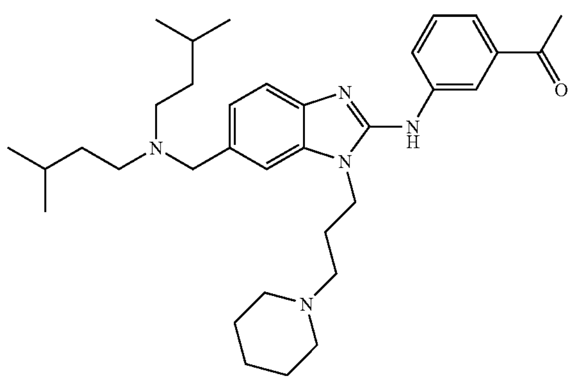 | 546.5 | 7.8 |
| 311 | 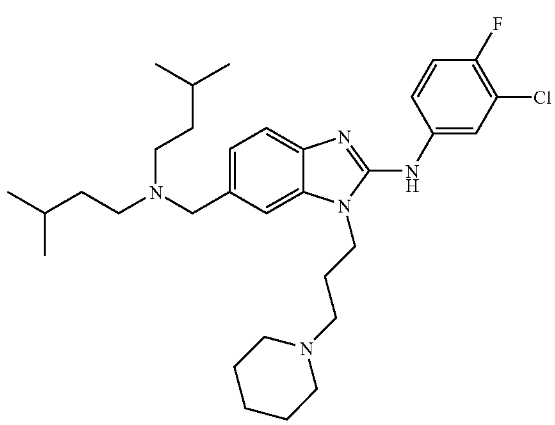 | 556.4 | 8.2 |

| Examples | Molecular structures | [M + H]+ | rt (min) |
|---|---|---|---|
| 312 | 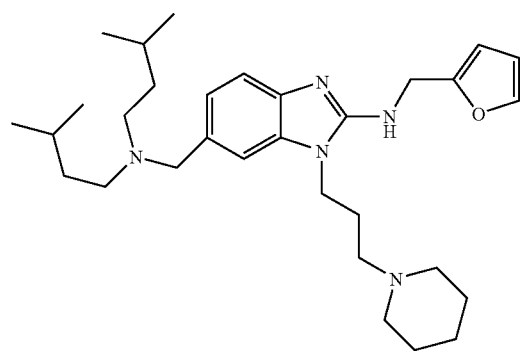 | 508.5 | 7.7 |
| 313 | 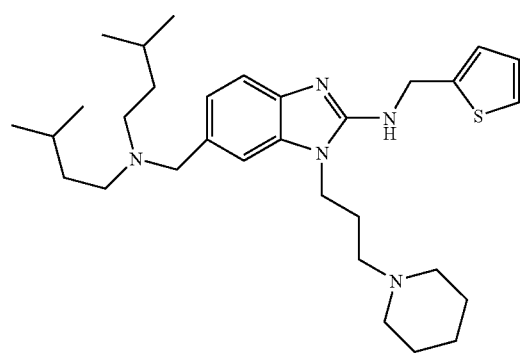 | 524.3 | 7.5 |
| 314 | 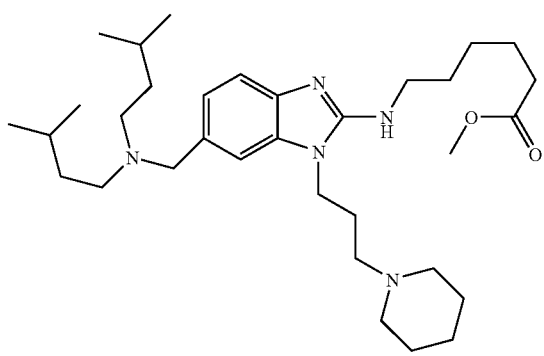 | 556.4 | 7.5 |
| 315 | 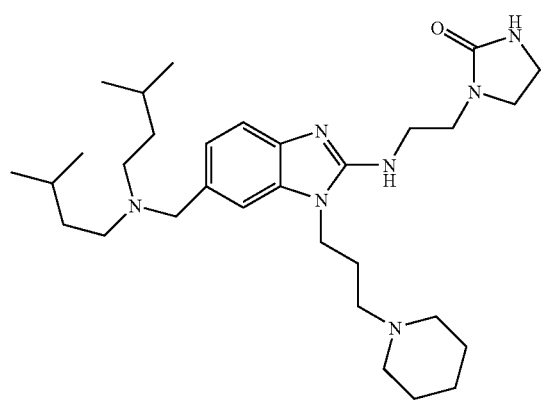 | 540.3 | 7.5 |

-continued
| Examples | Molecular structures | [M + H]+ | rt (min) |
|---|---|---|---|
| 316 | 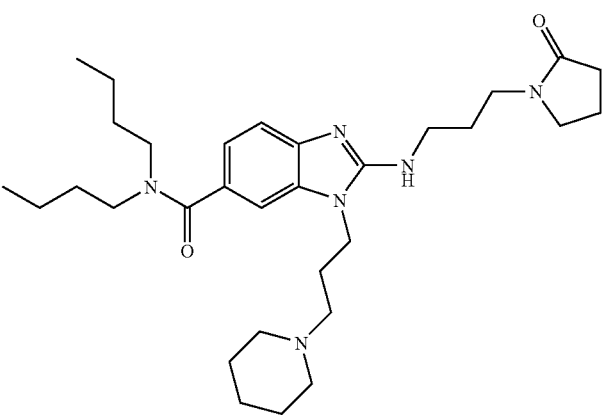 | 539.5 | 7.9 |
| 317 | 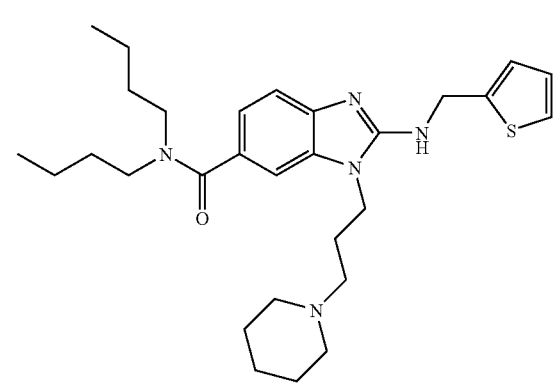 | 510.4 | 8.1 |
| 318 | 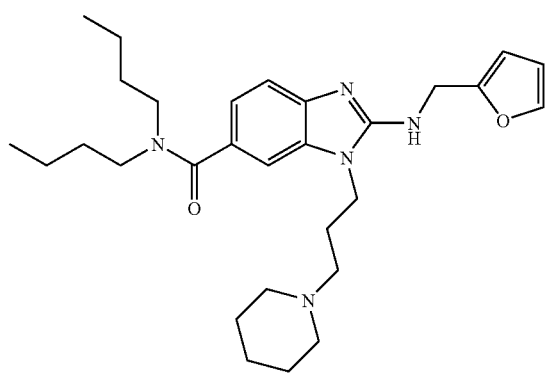 | 494.4 | 8.0 |
| 319 | 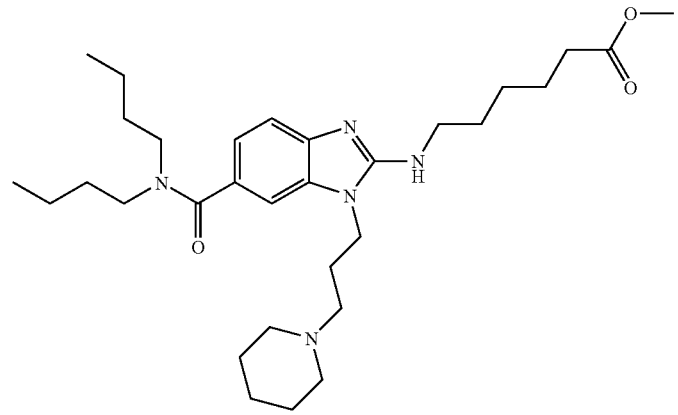 | 542.4 | 8.1 |

-continued

| Examples | Molecular structures | [M + H]+ | rt (min) |
|---|---|---|---|
| 320 | 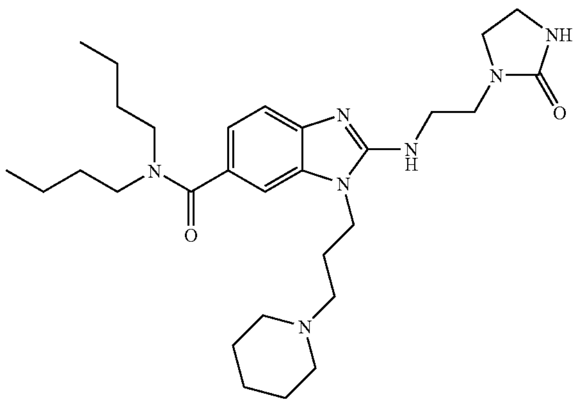 | 526.4 | 7.8 |
| 321 | 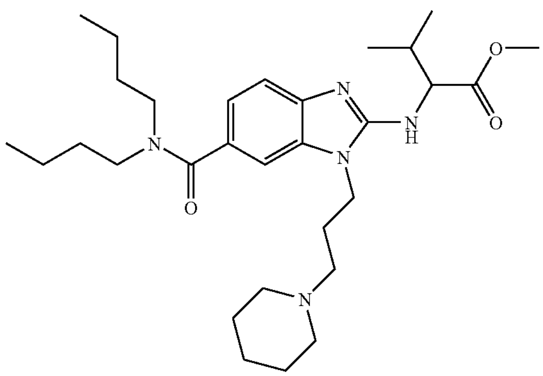 | 528.4 | 8.3 |
| 322 | 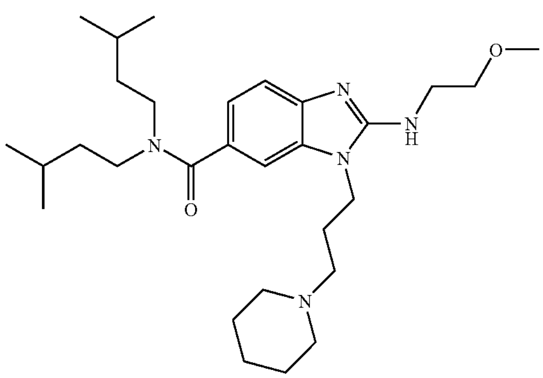 | 500.4 | 8.4 |
| 323 | 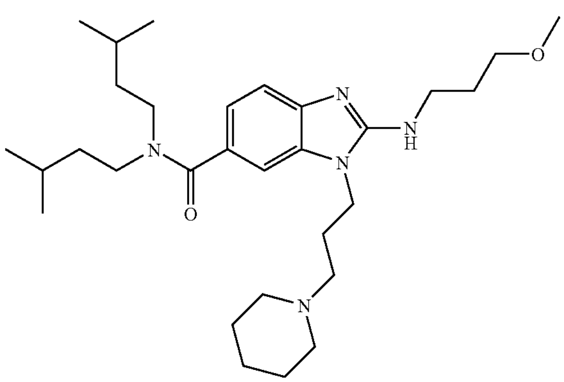 | 514.4 | 8.4 |

-continued
| Examples | Molecular structures | [M + H]+ | rt (min) |
|---|---|---|---|
| 324 | 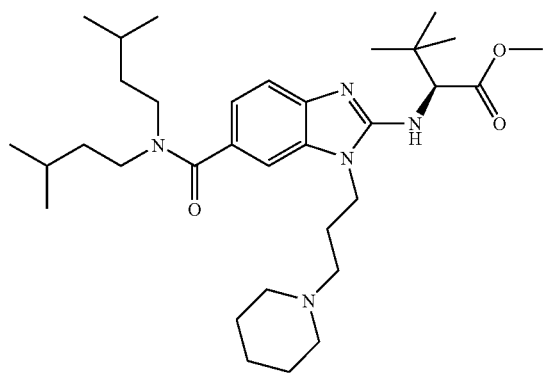 | 570.4 | 8.8 |
| 325 | 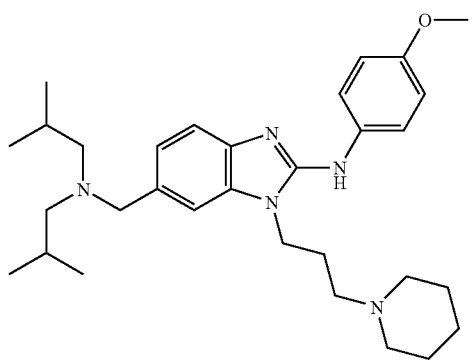 | 506.4 | 7.3 |
| 326 | 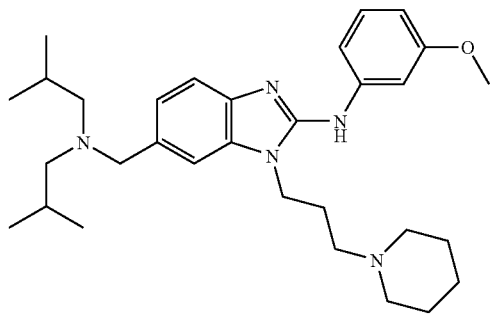 | 506.4 | 7.3 |
| 327 | 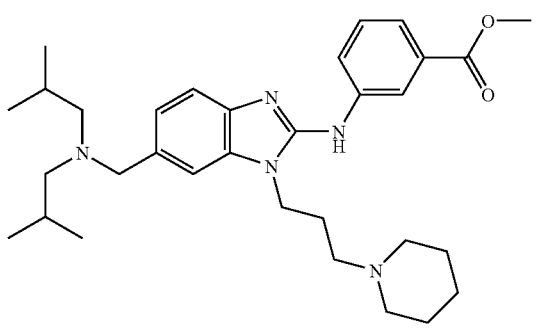 | 534.4 | 7.4 |

| Examples | Molecular structures | [M + H]+ | rt (min) |
|---|---|---|---|
| 328 | 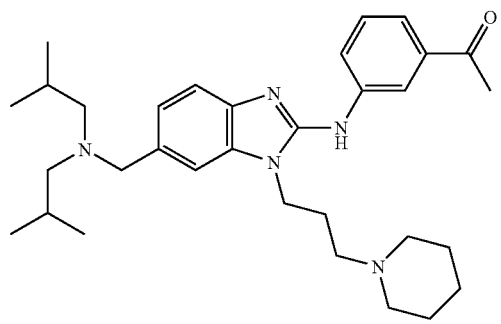 | 518.4 | 7.3 |
| 329 | 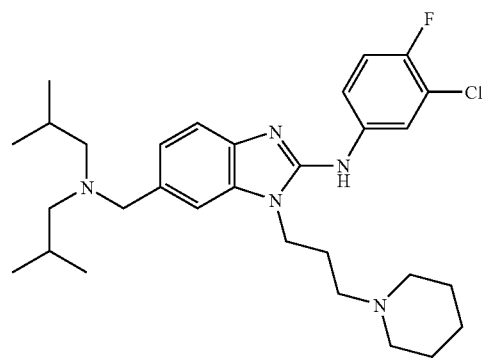 | 528.3 | 7.6 |
| 330 | 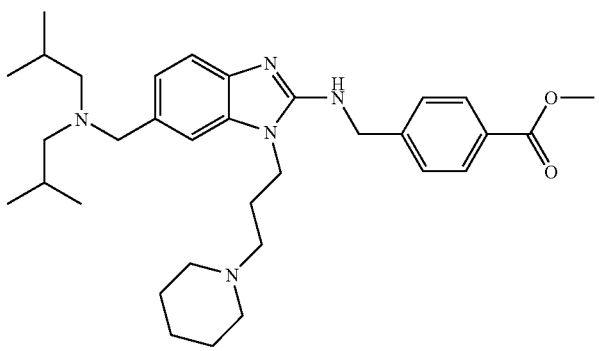 | 548.3 | 7.3 |
| 331 | 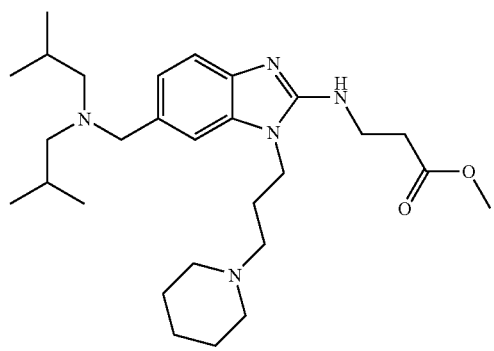 | 486.3 | 7.0 |

-continued

| Examples | Molecular structures | [M + H]+ | rt (min) |
| --- | --- | --- | --- |
| 332 | 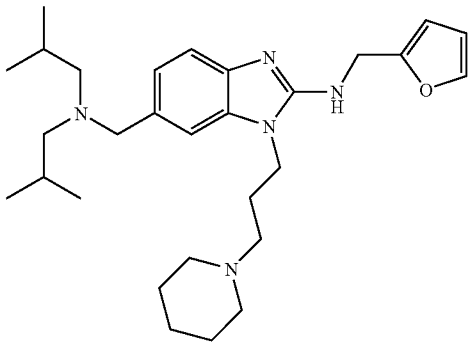 | 480.4 | 7.1 |
| 333 | 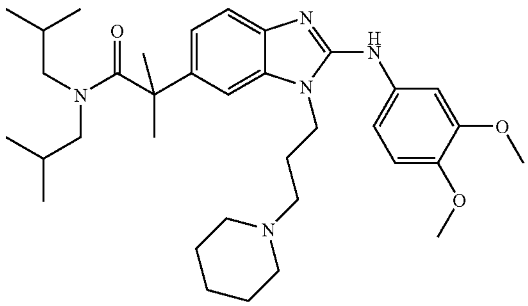 | 592.4 | 8.1 |
| 334 | 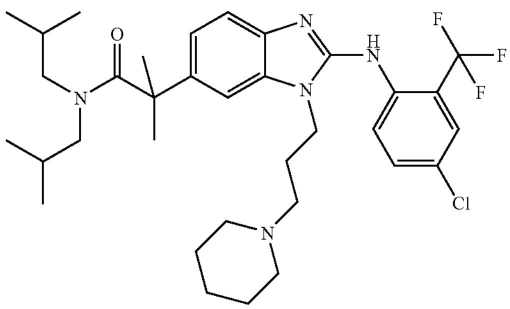 | 634.3 | 9.2 |
| 335 | 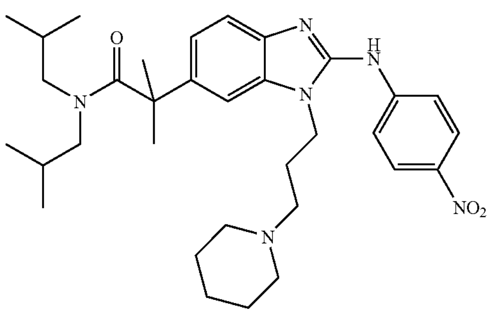 | 577.4 | 9.0 |
| 336 | 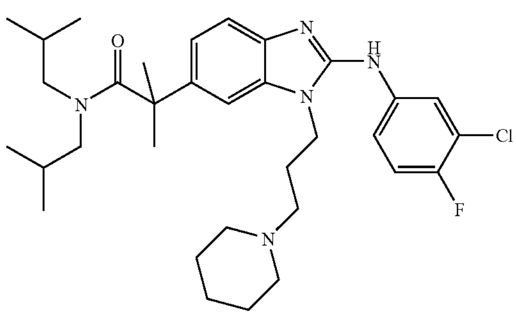 | 584.3 | 8.4 |

| Examples | Molecular structures | [M + H]+ | rt (min) |
|---|---|---|---|
| 337 | 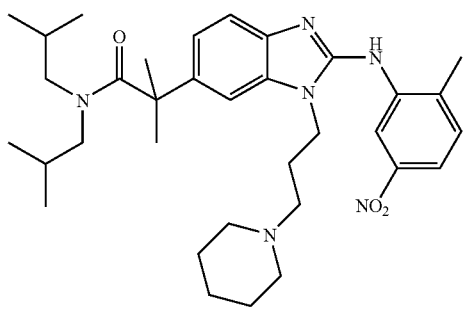 | 591.4 | 8.3 |
| 338 | 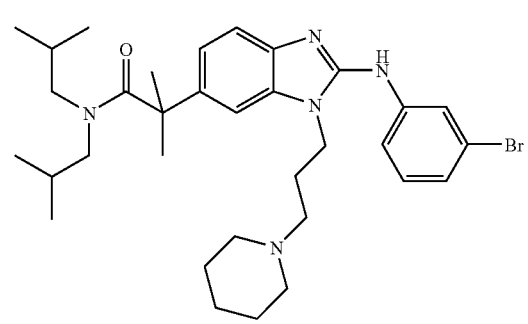 | 610.3 | 8.4 |
| 339 | 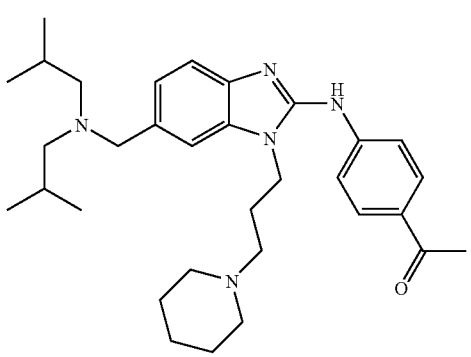 | 518.4 | 7.4 |
| 340 | 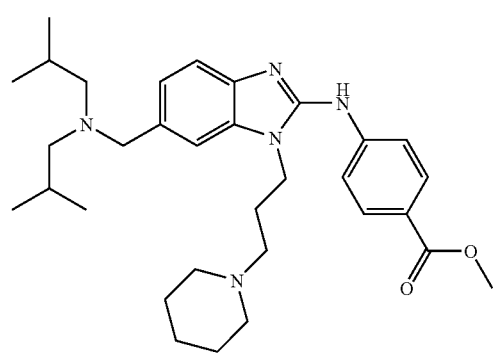 | 534.3 | 7.5 |

-continued
| Examples | Molecular structures | [M + H]+ | rt (min) |
|---|---|---|---|
| 341 | 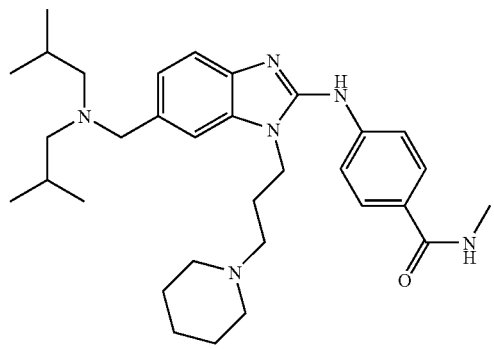 | 533.3 | 7.2 |
| 342 | 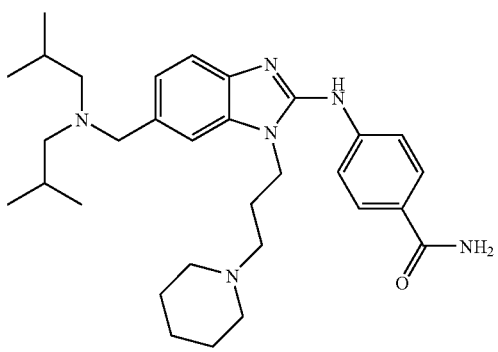 | 519.3 | 7.1 |
| 343 | 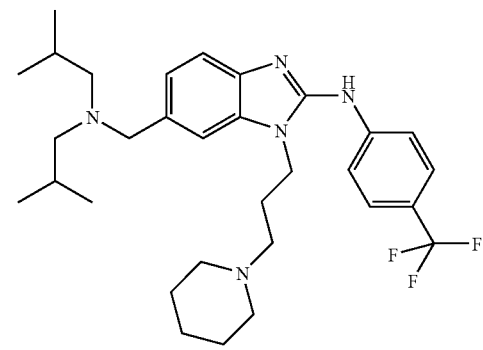 | 544.3 | 7.8 |
| 344 | 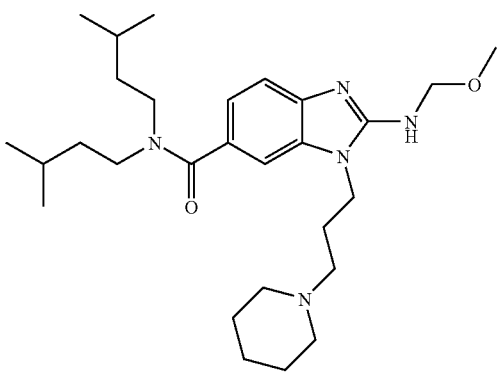 | 486.3 | 8.1 |

-continued
| Examples | Molecular structures | [M + H]+ | rt (min) |
|---|---|---|---|
| 345 | 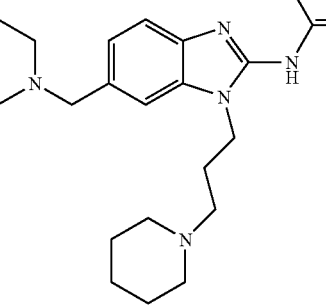 | 506.5 | 7.3 |
| 346 | 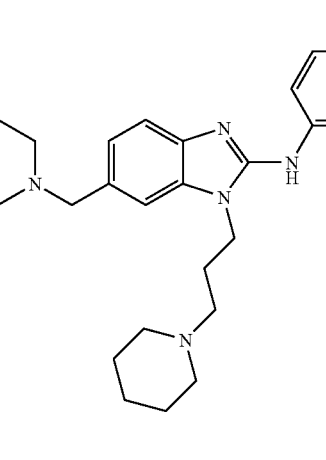 | 518.5 | 7.5 |
| 347 | 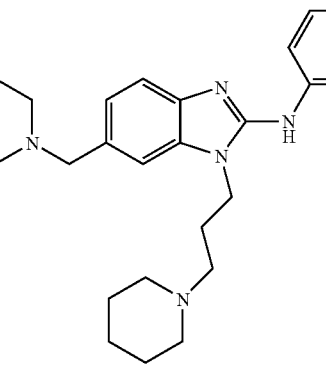 | 544.4 | 7.9 |

-continued
| Examples | Molecular structures | [M + H]+ | rt (min) |
|---|---|---|---|
| 348 | 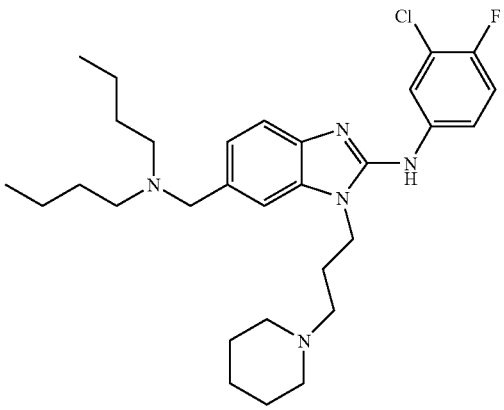 | 528.4 | 7.7 |
| 349 | 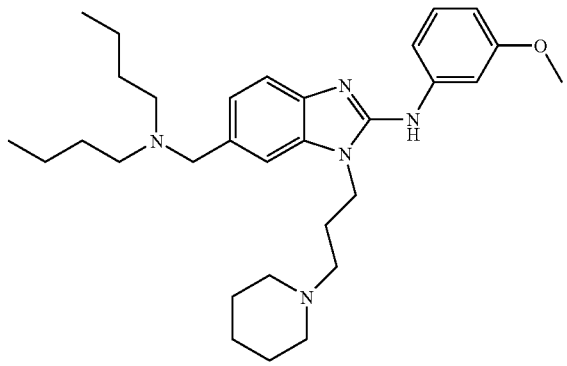 | 506.5 | 7.4 |
| 350 | 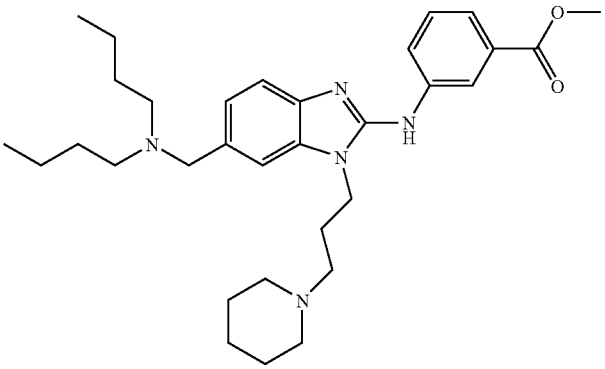 | 534.4 | 7.4 |
| 351 | 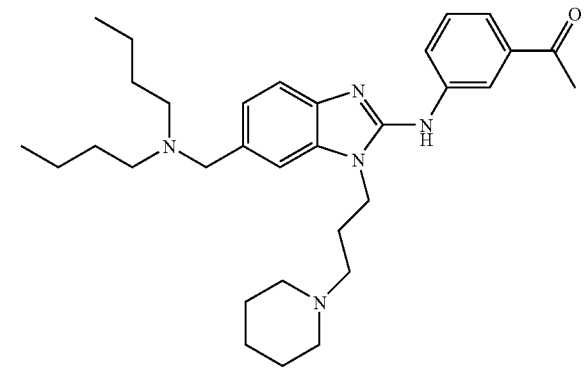 | 518.4 | 7.4 |

-continued
| Examples | Molecular structures | [M + H]+ | rt (min) |
|---|---|---|---|
| 352 | 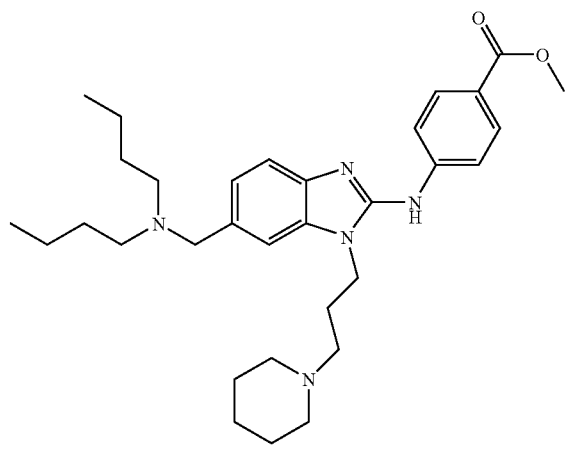 | 534.4 | 7.6 |
| 353 | 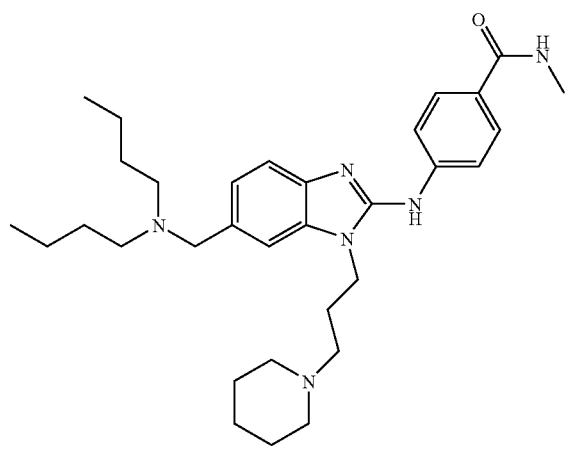 | 533.5 | 7.3 |
| 354 | 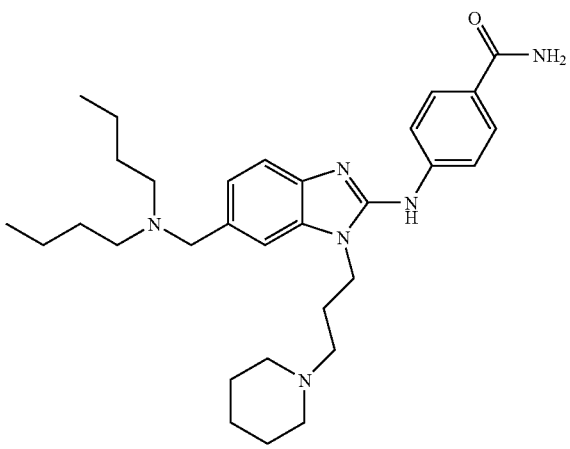 | 519.4 | 7.3 |

| Examples | Molecular structures | [M + H]+ | rt (min) |
|---|---|---|---|
| 355 | 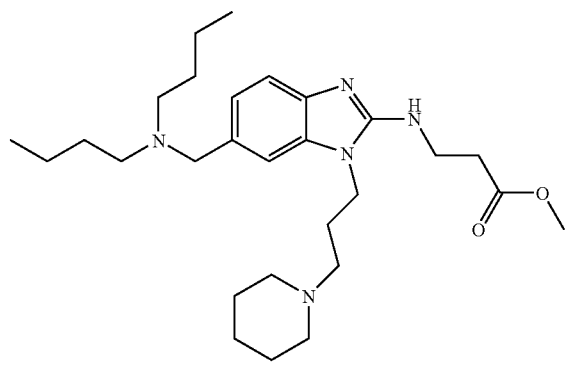 | 486.4 | 7.2 |
| 356 | 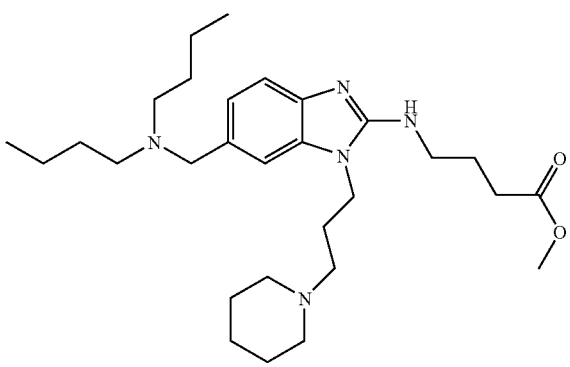 | 500.4 | 7.2 |
| 357 | 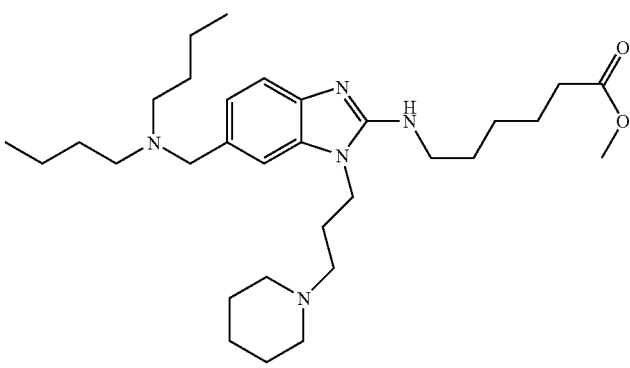 | 528.5 | 7.3 |
| 358 | 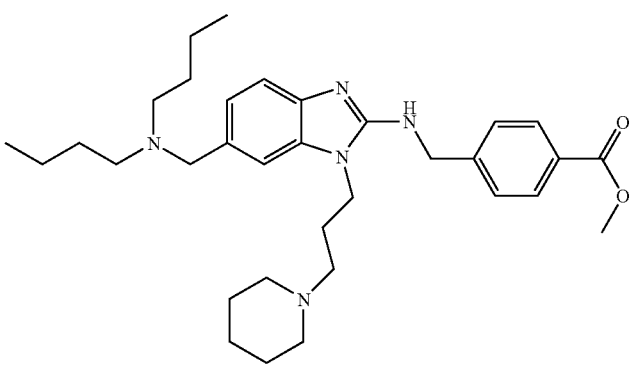 | 548.4 | 7.4 |

-continued
| Examples | Molecular structures | [M + H]+ | rt (min) |
|---|---|---|---|
| 359 | 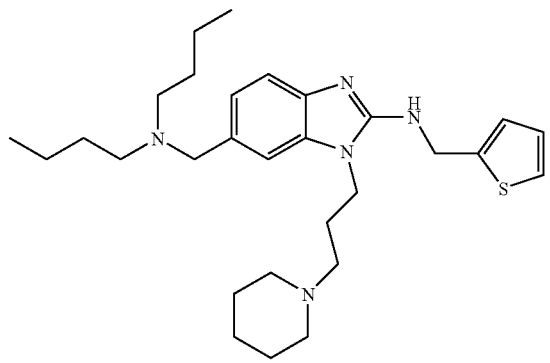 | 496.4 | 7.3 |
| 360 | 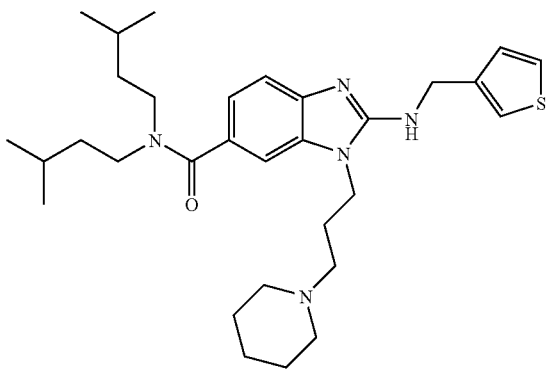 | 538.5 | 8.3 |
| 361 | 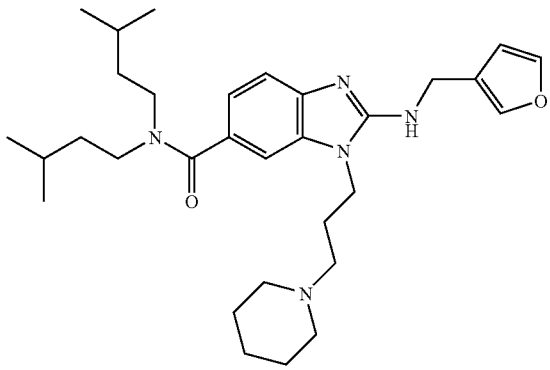 | 522.5 | 8.2 |
| 362 | 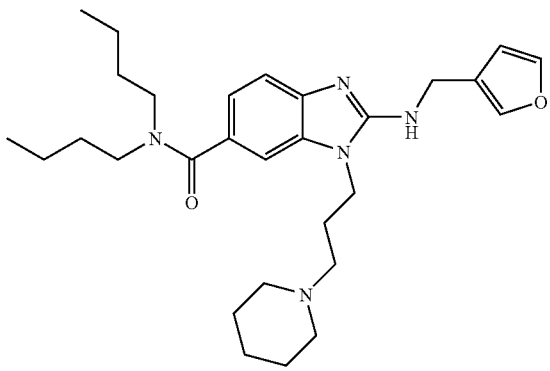 | 494.5 | 8.0 |

| Examples | Molecular structures | [M + H]+ | rt (min) |
|---|---|---|---|
| 363 | 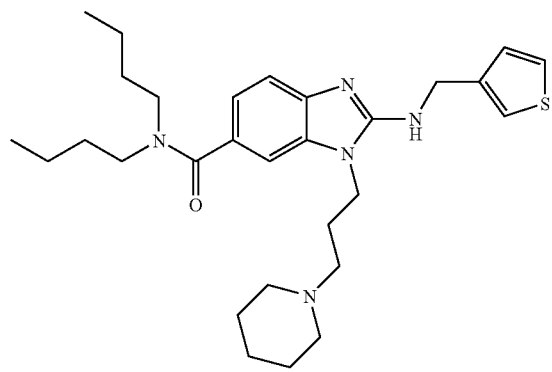 | 510.5 | 8.1 |
| 364 | 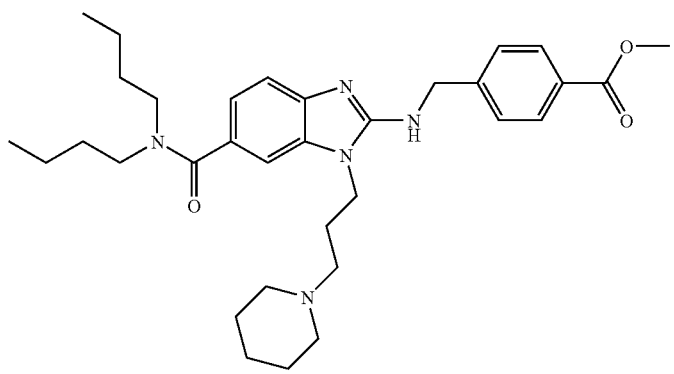 | 562.5 | 8.1 |
| 365 | 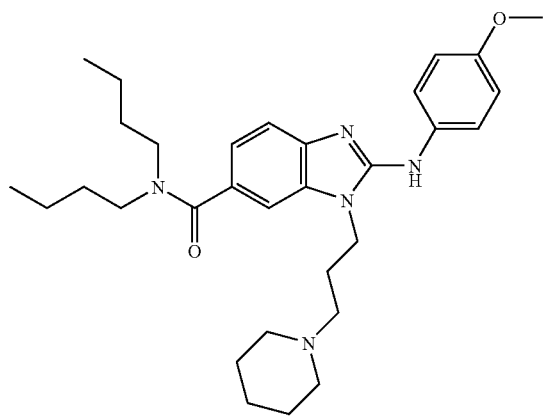 | 520.5 | 8.1 |

-continued
| Examples | Molecular structures | [M + H]+ | rt (min) |
|---|---|---|---|
| 366 | 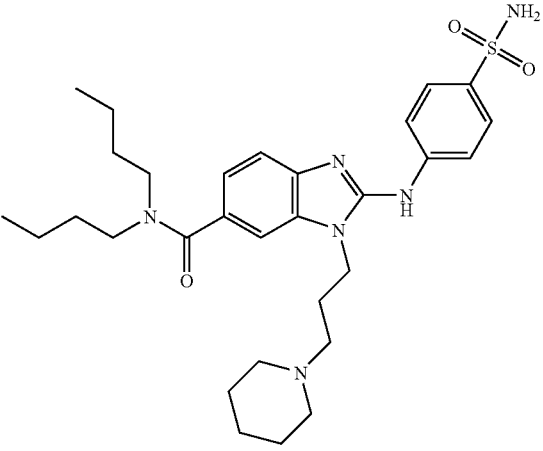 | 569.4 | 8.2 |
| 367 | 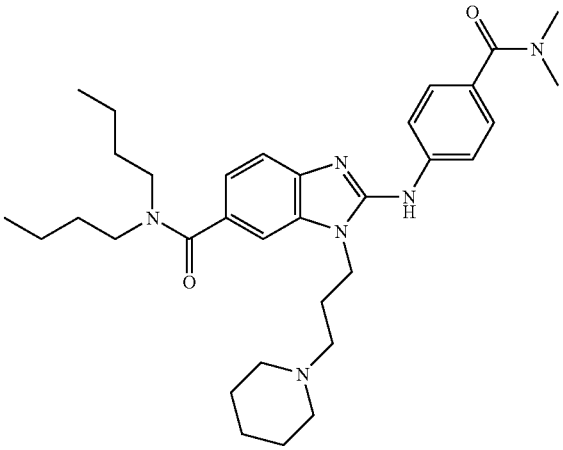 | 561.5 | 7.9 |
| 368 | 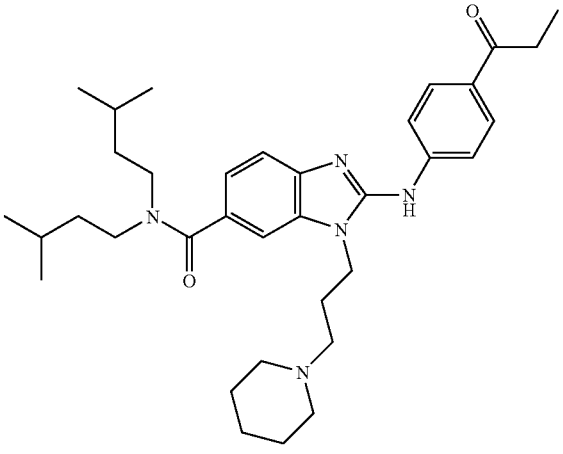 | 574.5 | 9.0 |

-continued
| Examples | Molecular structures | [M + H]+ | rt (min) |
|---|---|---|---|
| 369 | 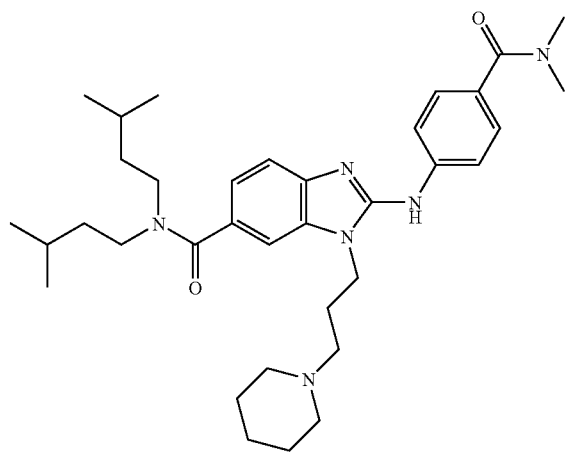 | 589.6 | 8.3 |
| 370 | 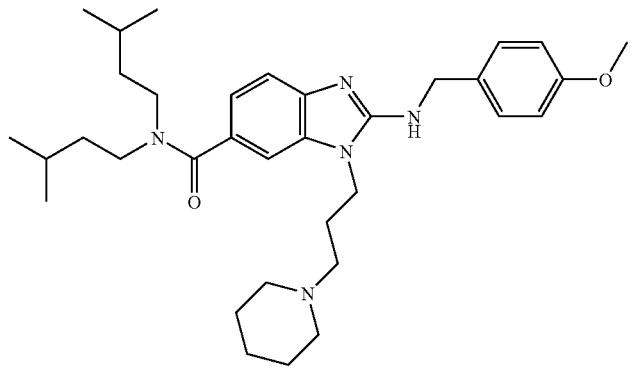 | 562.5 | 8.4 |
| 371 | 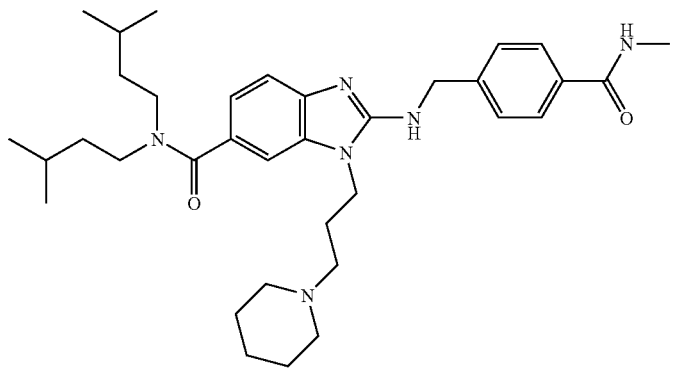 | 589.6 | 8.1 |

-continued
| Examples | Molecular structures | [M + H]+ | rt (min) |
|---|---|---|---|
| 372 | 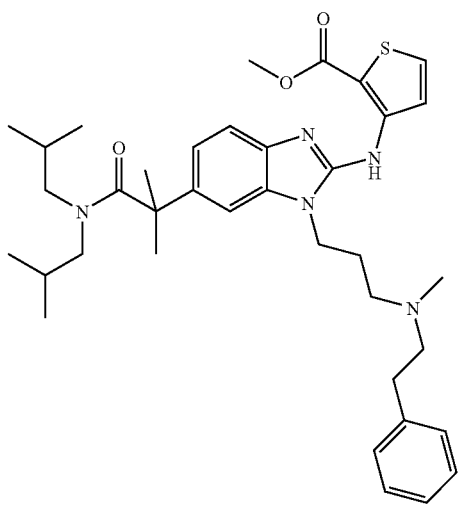 | 646.4 | 9.9 |
| 373 | 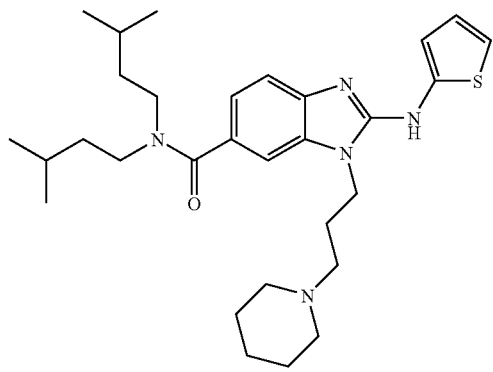 | 524.4 | 8.7 |
| 374 | 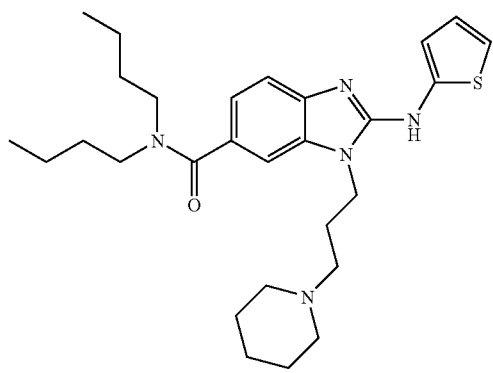 | 496.4 | 8.3 |

-continued
| Examples | Molecular structures | [M + H]+ | rt (min) |
|---|---|---|---|
| 375 | 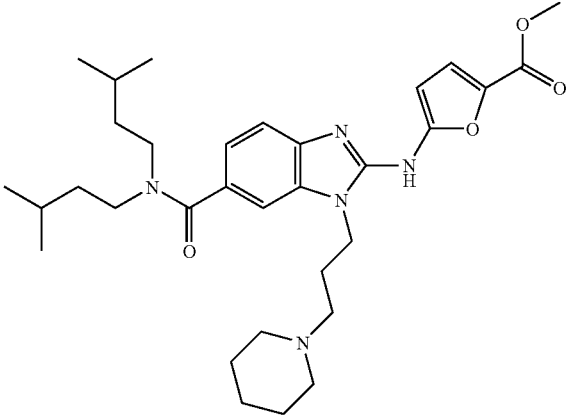 | 566.4 | 9.9 |
| 376 | 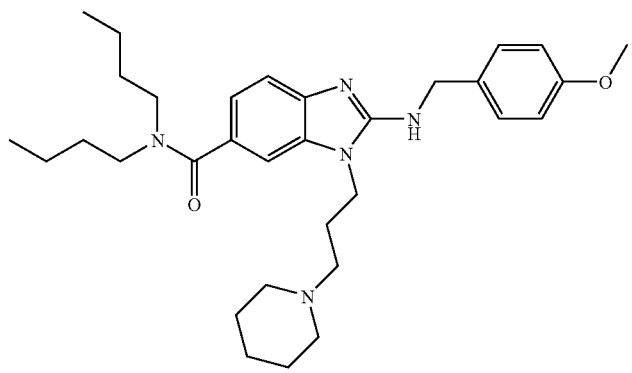 | 534.4 | 8.2 |
| 377 | 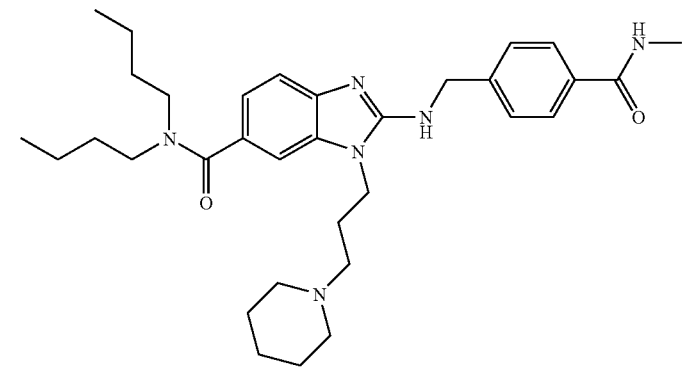 | 561.4 | 7.9 |
| 378 | 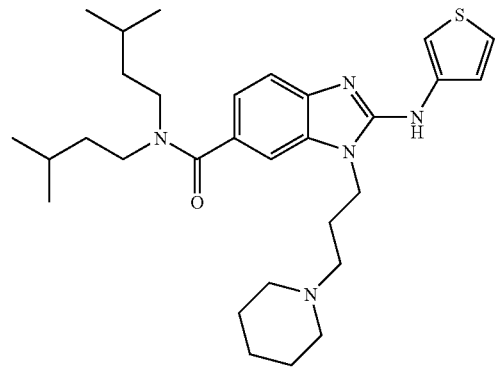 | 524.4 | 8.4 |

-continued

| Examples | Molecular structures | [M + H]+ | rt (min) |
|---|---|---|---|
| 379 | 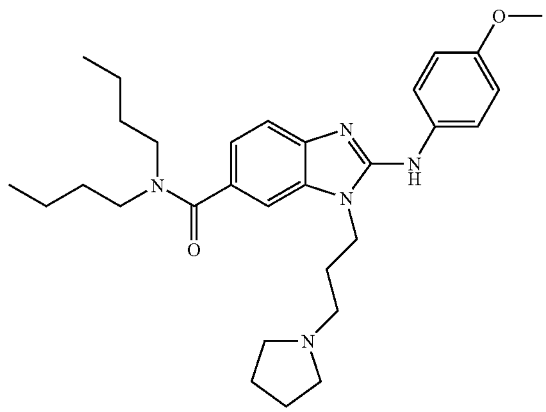 | 506.4 | 8.1 |
| 380 | 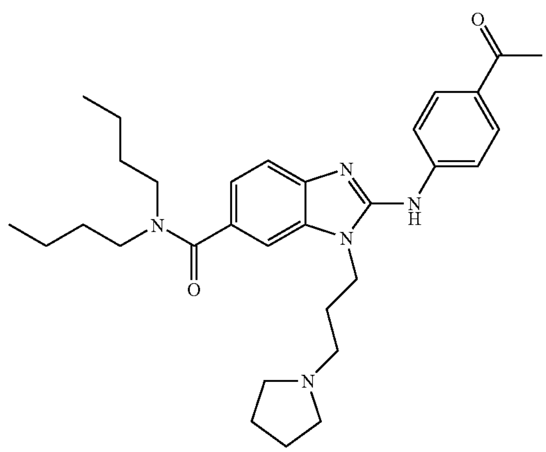 | 518.4 | 8.4 |
| 381 | 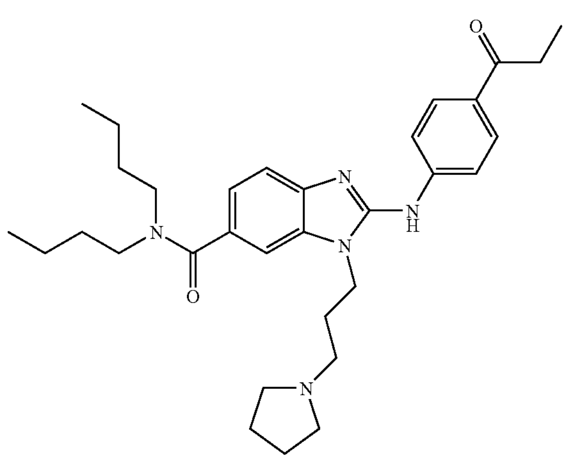 | 532.4 | 8.6 |

-continued
| Examples | Molecular structures | [M + H]+ | rt (min) |
|---|---|---|---|
| 382 | 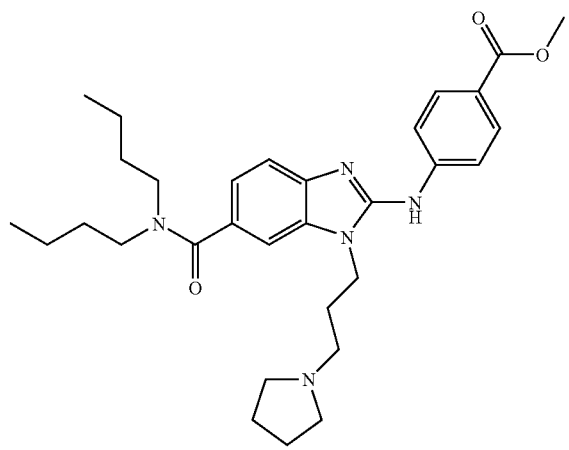 | 534.4 | 8.5 |
| 383 | 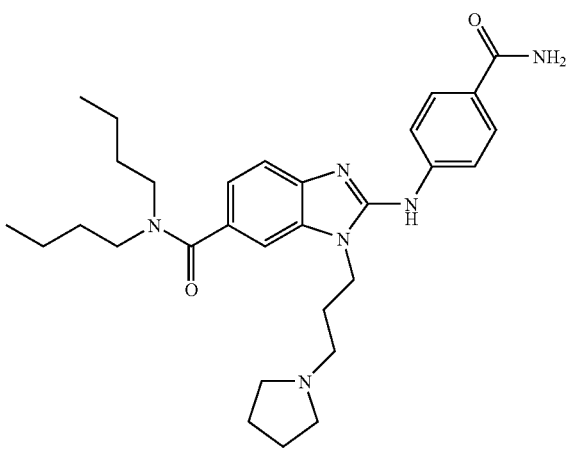 | 519.4 | 7.9 |
| 384 | 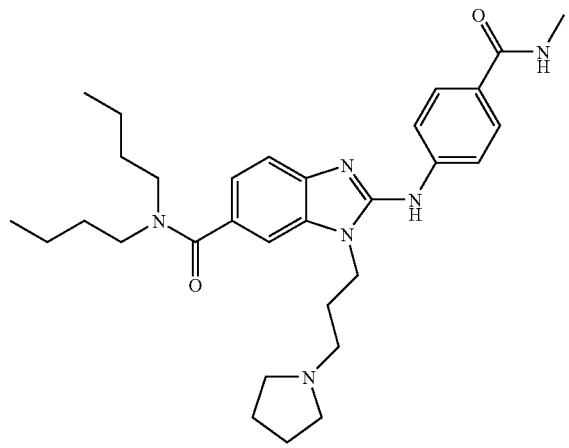 | 533.4 | 7.9 |

-continued
| Examples | Molecular structures | [M + H]+ | rt (min) |
|---|---|---|---|
| 385 | 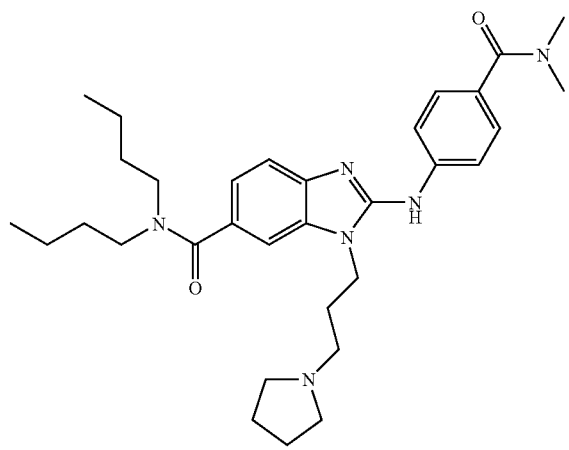 | 547.4 | 7.9 |
| 386 | 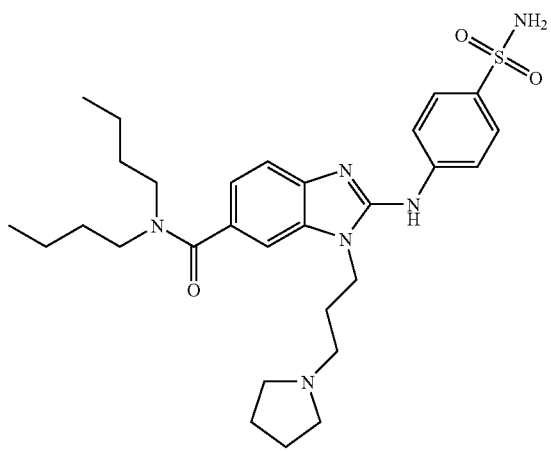 | 555.3 | 8.2 |
| 387 | 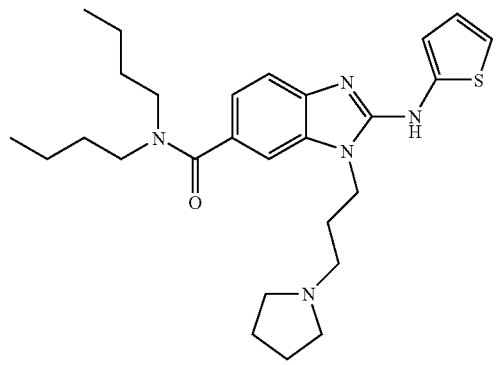 | 482.5 | 8.2 |

| Examples | Molecular structures | [M + H]+ | rt (min) |
|---|---|---|---|
| 388 | 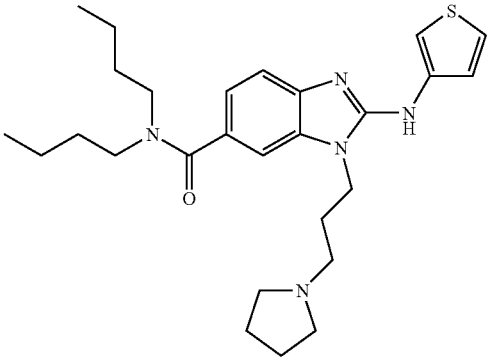 | 482.3 | 8.0 |
| 389 | 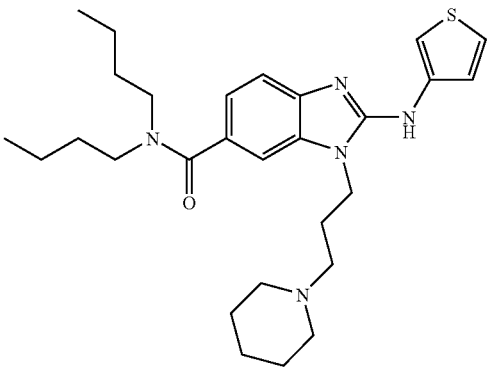 | 496.4 | 8.1 |
| 390 | 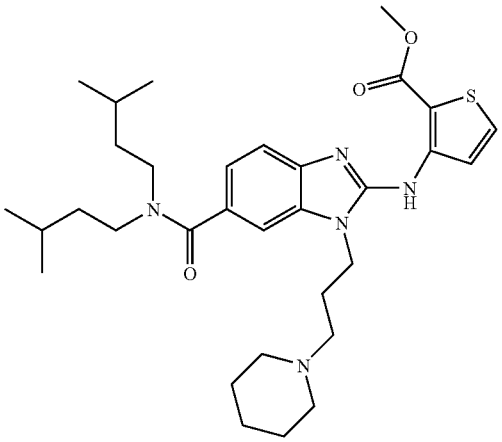 | 582.4 | 10.3 |
| 391 | 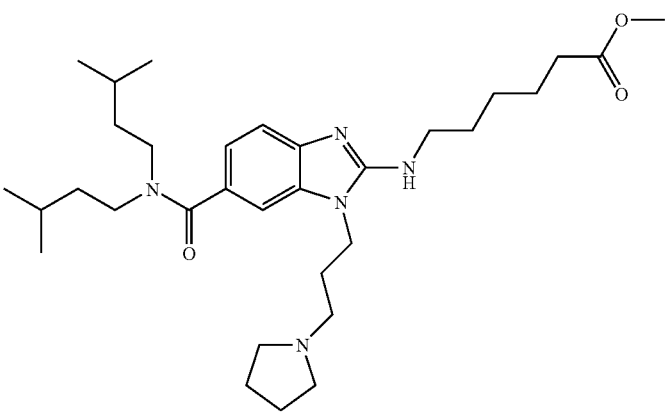 | 556.5 | 8.4 |

| Examples | Molecular structures | [M + H]+ | rt (min) |
|---|---|---|---|
| 392 | 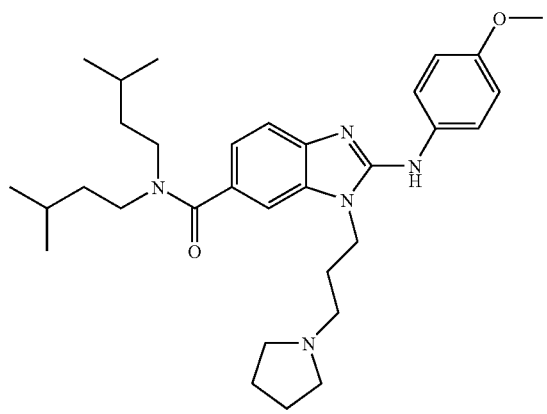 | 534.4 | 8.4 |
| 393 | 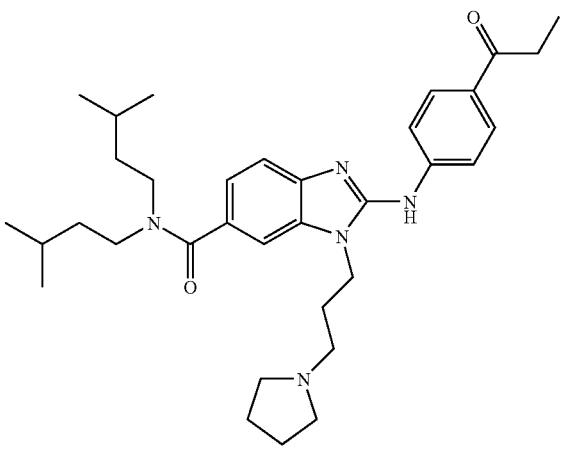 | 560.4 | 9.0 |
| 394 | 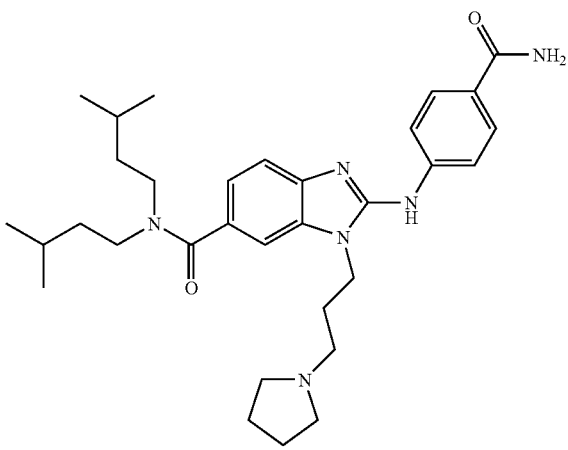 | 547.4 | 8.2 |

-continued
| Examples | Molecular structures | [M + H]+ | rt (min) |
|---|---|---|---|
| 395 | 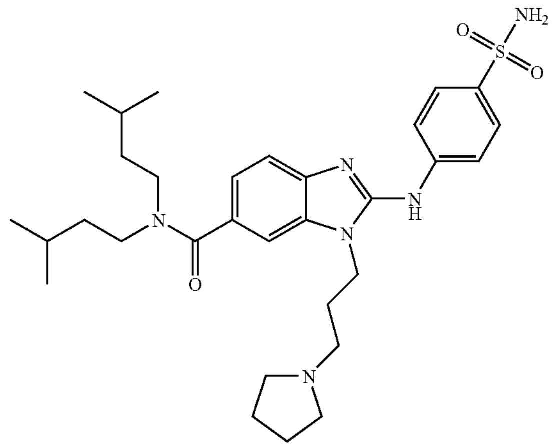 | 583.4 | 8.5 |
| 396 | 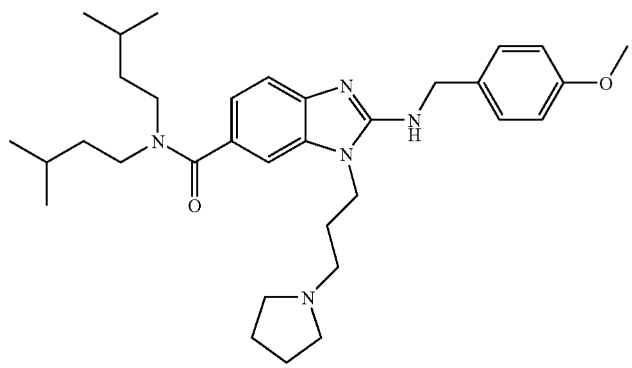 | 548.4 | 8.4 |
| 397 | 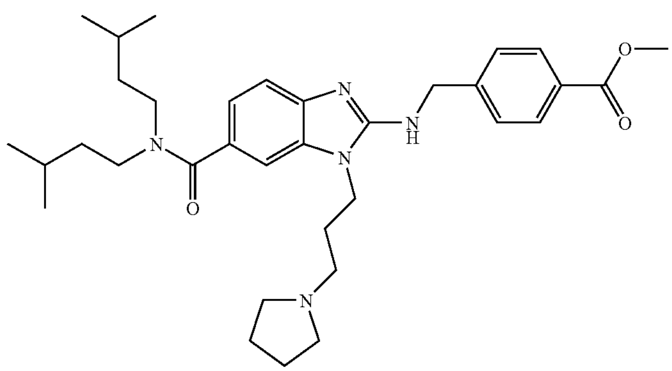 | 576.4 | 8.4 |
| 398 | 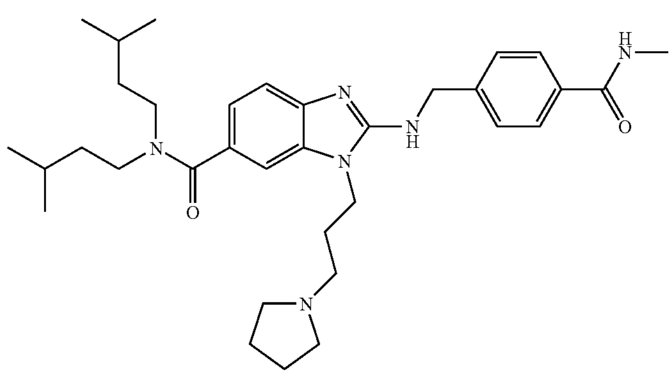 | 575.5 | 8.1 |

-continued
| Examples | Molecular structures | [M + H]+ | rt (min) |
|---|---|---|---|
| 399 | 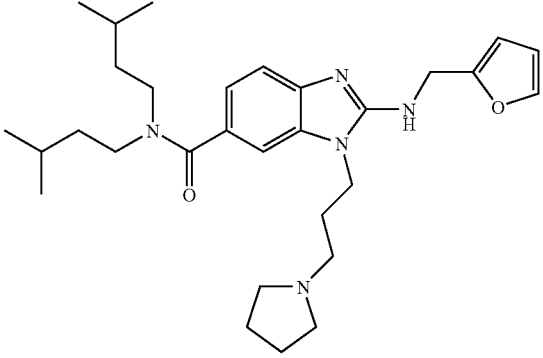 | 508.4 | 8.3 |
| 400 | 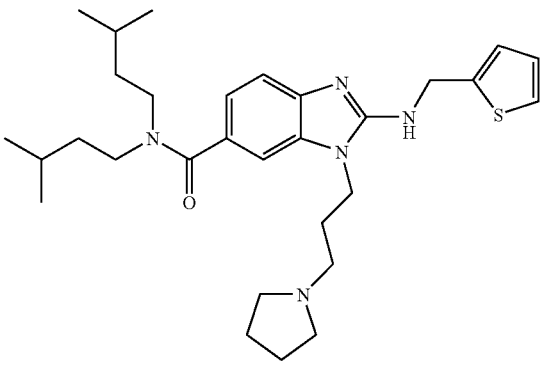 | 524.4 | 8.4 |
| 401 | 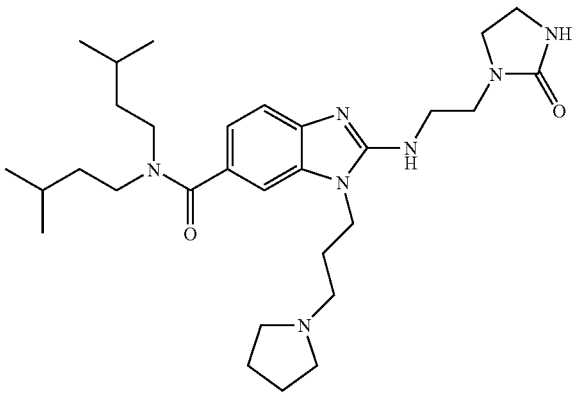 | 540.4 | 8.1 |
| 402 | 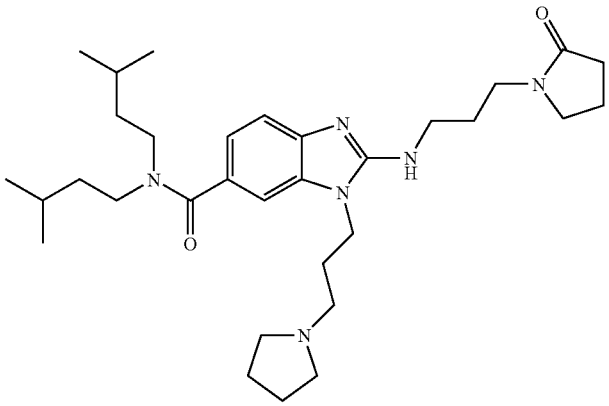 | 553.5 | 8.1 |

| Examples | Molecular structures | [M + H]+ | rt (min) |
|---|---|---|---|
| 403 | 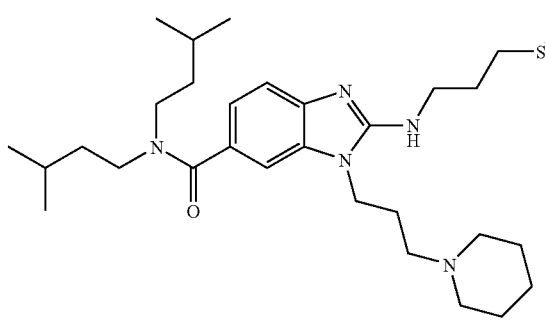 | 530.4 | 8.4 |
| 404 | 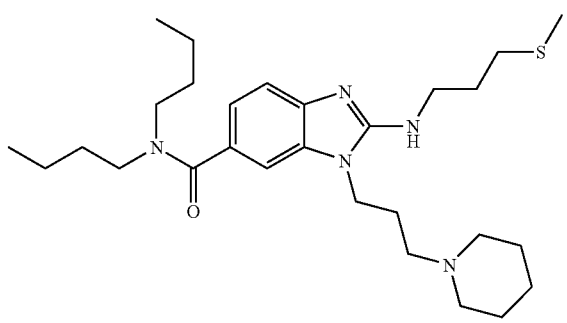 | 502.4 | 8.1 |
| 405 | 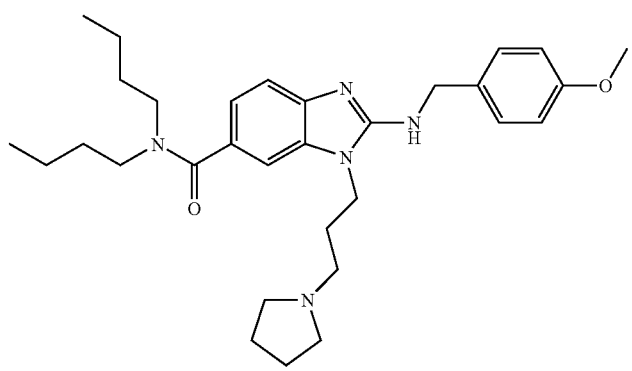 | 520.4 | 8.2 |
| 406 | 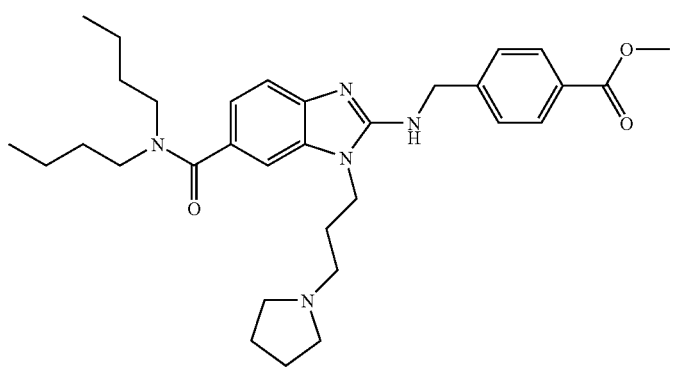 | 548.4 | 8.2 |

-continued
| Examples | Molecular structures | [M + H]+ | rt (min) |
|---|---|---|---|
| 407 | 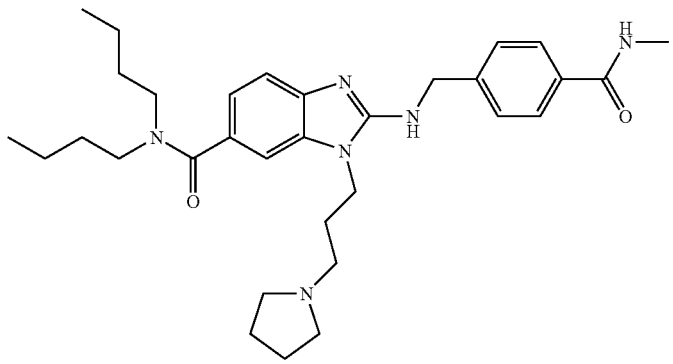 | 547.4 | 7.9 |
| 408 | 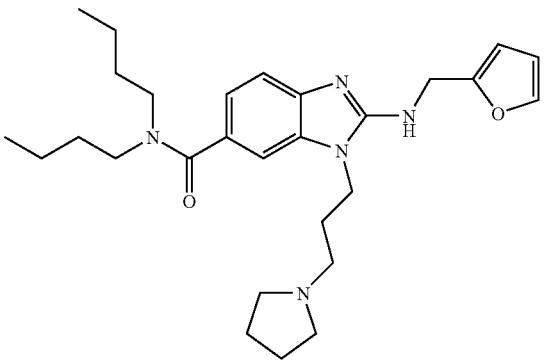 | 480.4 | 8.0 |
| 409 | 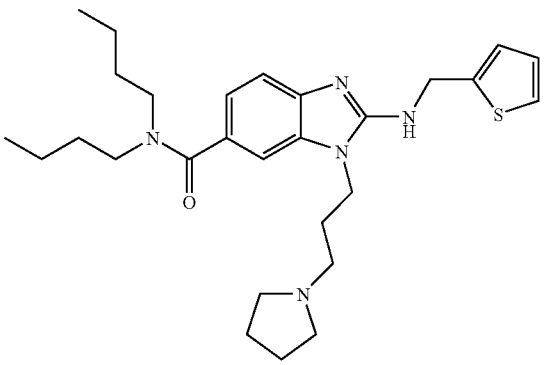 | 496.4 | 8.1 |
| 410 | 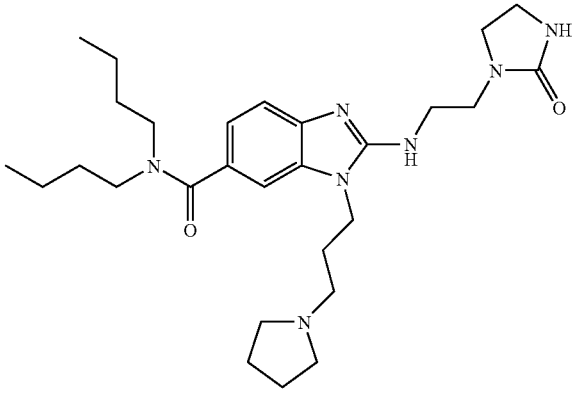 | 512.4 | 7.8 |

| Examples | Molecular structures | [M + H]+ | rt (min) |
|---|---|---|---|
| 411 | 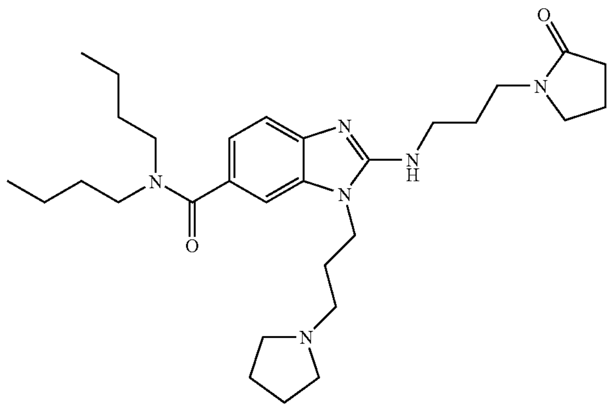 | 525.4 | 7.9 |
| 412 | 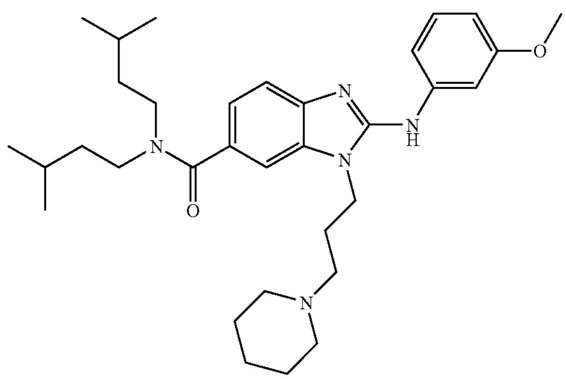 | 548.4 | 8.6 |
| 413 | 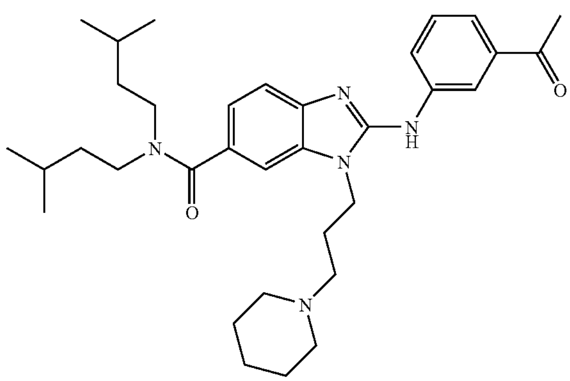 | 560.4 | 8.6 |
| 414 | 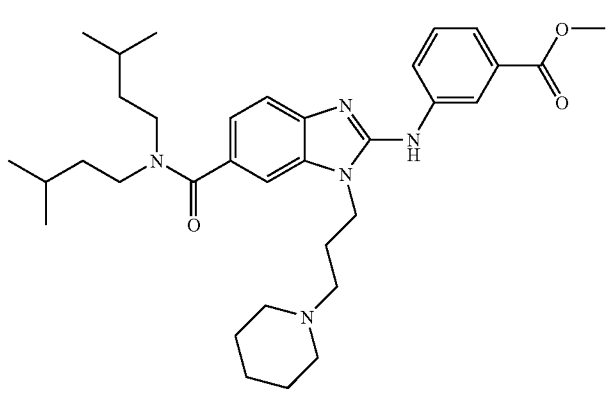 | 576.4 | 8.8 |

-continued
| Examples | Molecular structures | [M + H]+ | rt (min) |
|---|---|---|---|
| 415 | 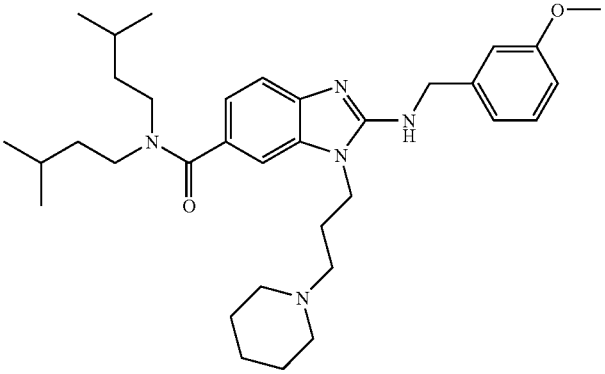 | 562.4 | 8.5 |
| 416 | 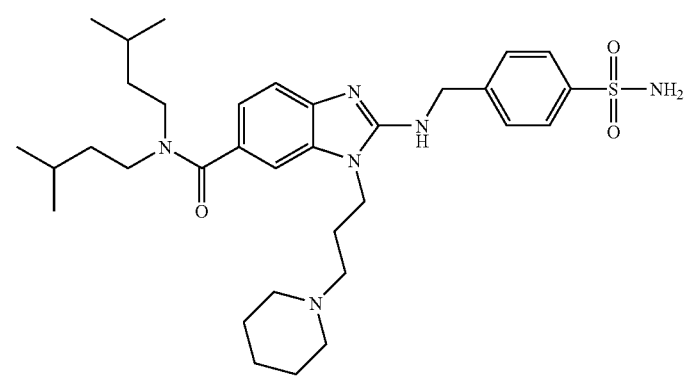 | 611.4 | 8.3 |
| 417 | 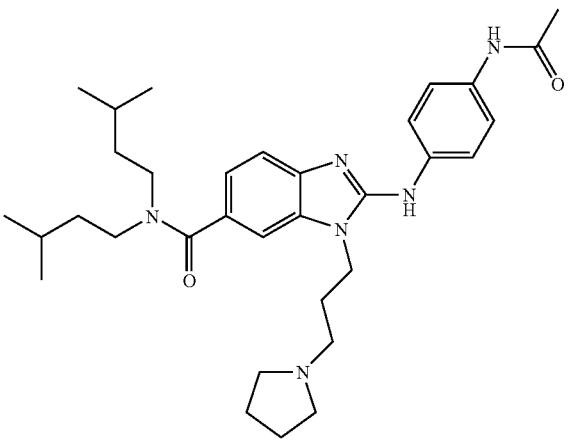 | 561.4 | 8.2 |
| 418 | 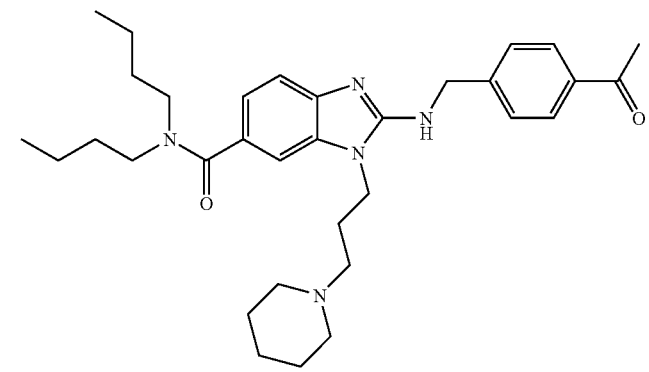 | 546.6 | 8.1 |

-continued

| Examples | Molecular structures | [M + H]+ | rt (min) |
|---|---|---|---|
| 419 | 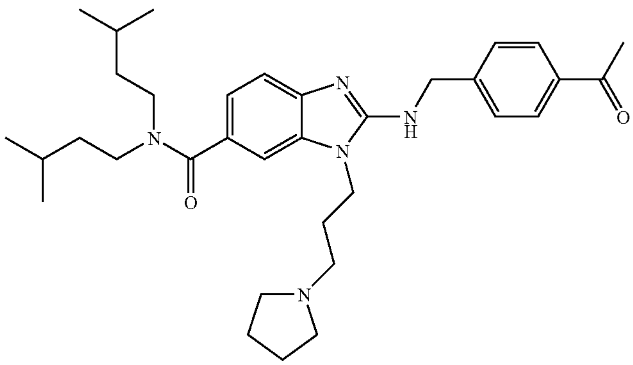 | 560.6 | 8.3 |
| 420 | 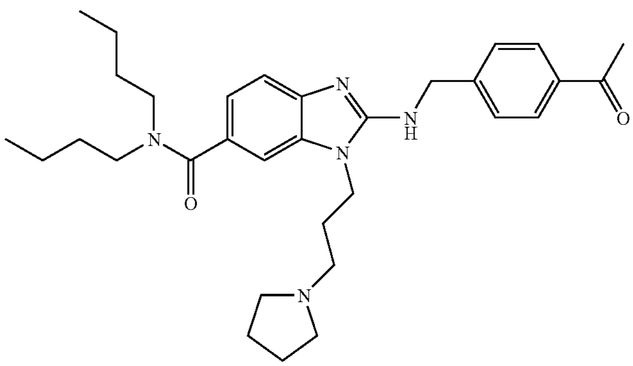 | 532.6 | 8.0 |
| 421 | 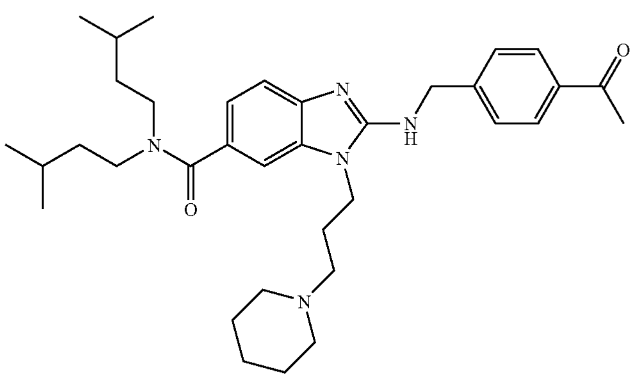 | 574.4 | 8.3 |
| 422 | 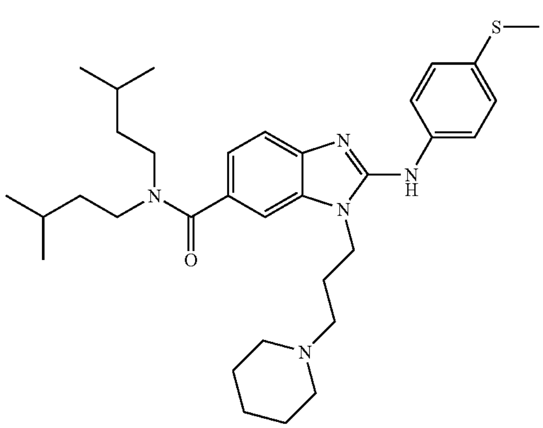 | 564.6 | 8.7 |

-continued

| Examples | Molecular structures | [M + H]+ | rt (min) |
|---|---|---|---|
| 423 | 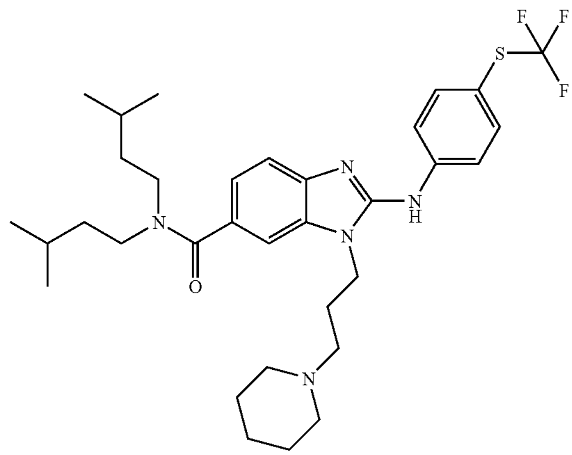 | 618.6 | 9.9 |
| 424 | 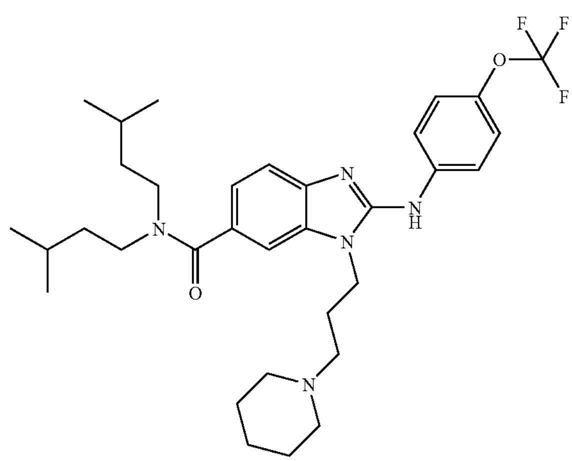 | 602.6 | 9.1 |
| 425 | 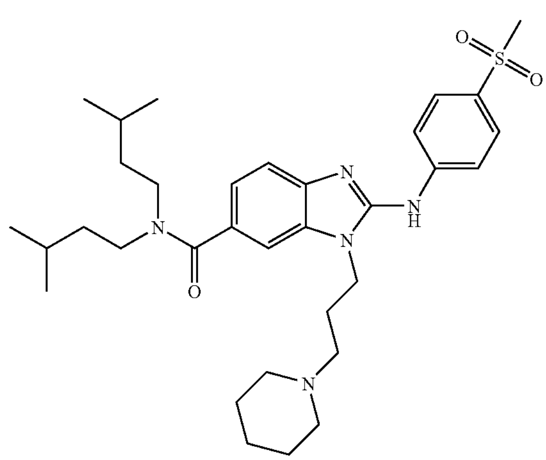 | 596.6 | 8.9 |

-continued
| Examples | Molecular structures | [M + H]+ | rt (min) |
|---|---|---|---|
| 426 | 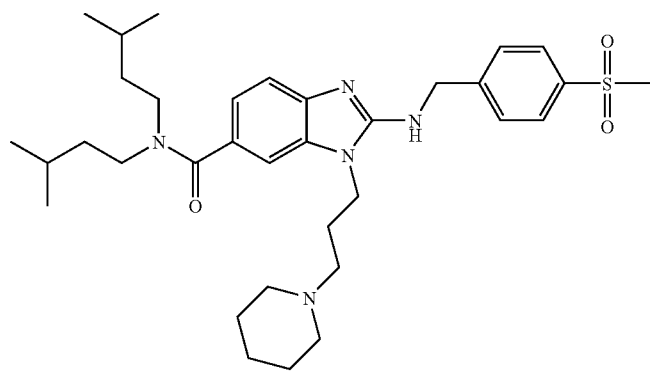 | 610.7 | 8.3 |
| 427 | 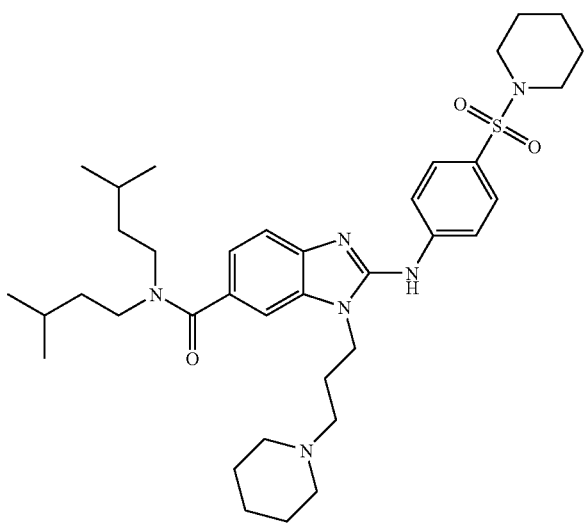 | 665.7 | 9.6 |
| 428 | 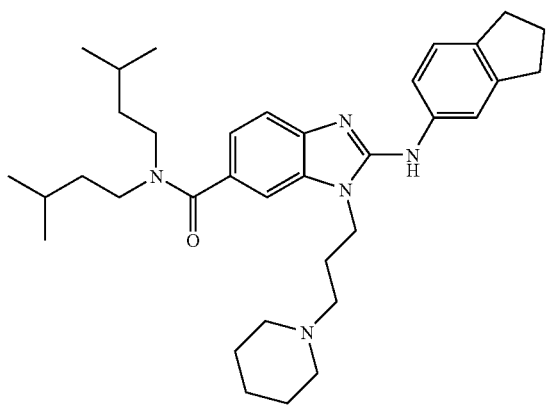 | 558.7 | 8.7 |

-continued
| Examples | Molecular structures | [M + H]+ | rt (min) |
|---|---|---|---|
| 429 | 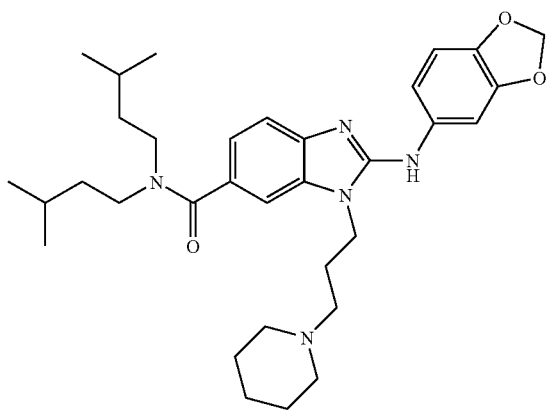 | 562.6 | 8.4 |
| 430 | 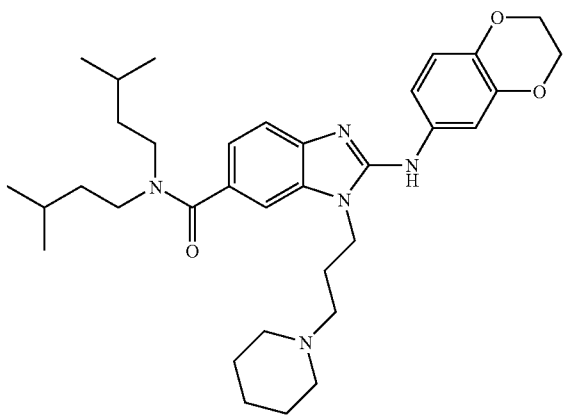 | 576.6 | 8.5 |
| 431 | 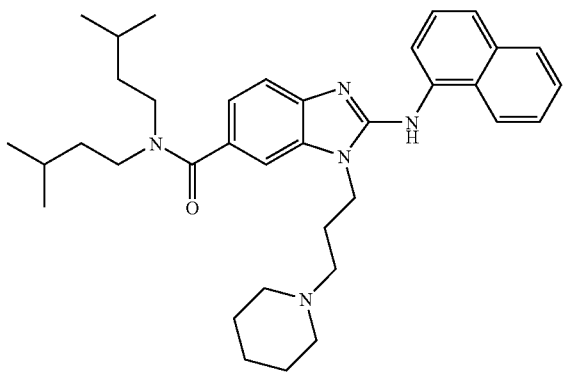 | 568.6 | 8.6 |

-continued
| Examples | Molecular structures | [M + H]+ | rt (min) |
|---|---|---|---|
| 432 | 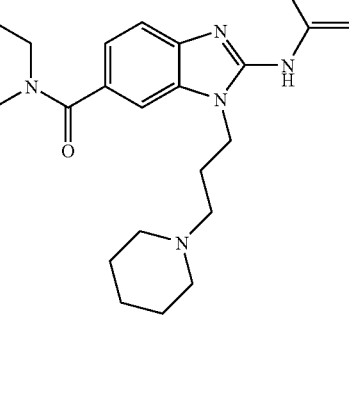 | 557.6 | 8.5 |
| 433 | 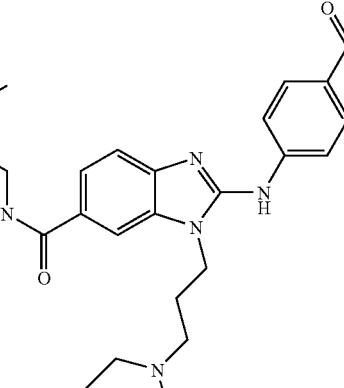 | 590.3 | 9.3 |
| 434 | 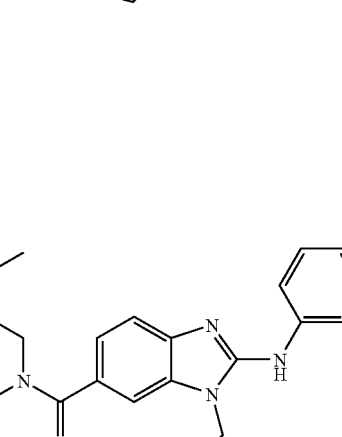 | 562.3 | 8.6 |

-continued

| Examples | Molecular structures | [M + H]+ | rt (min) |
|---|---|---|---|
| 435 | 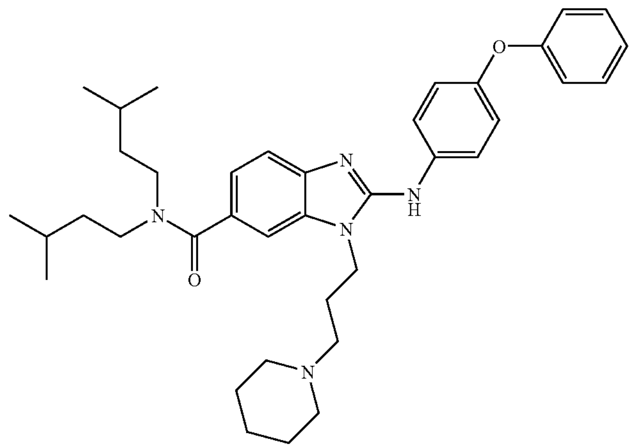 | 610.3 | 9.0 |
| 436 | 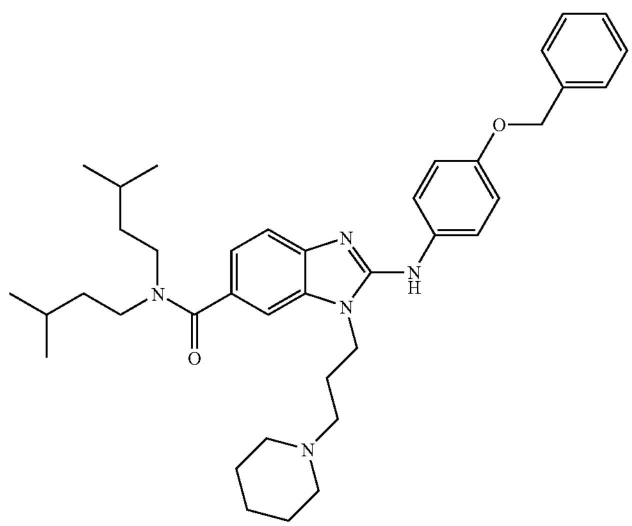 | 624.4 | 9.0 |
| 437 | 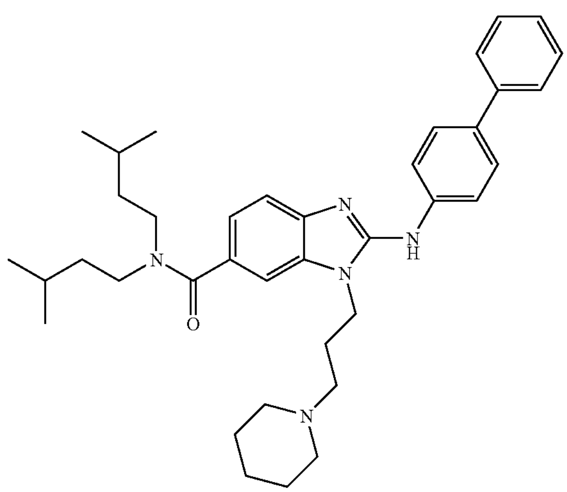 | 594.3 | 9.1 |

-continued

| Examples | Molecular structures | [M + H]+ | rt (min) |
| --- | --- | --- | --- |
| 438 | 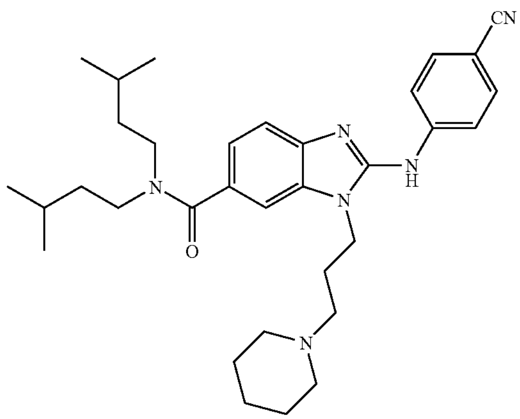 | 543.3 | 9.3 |
| 439 | 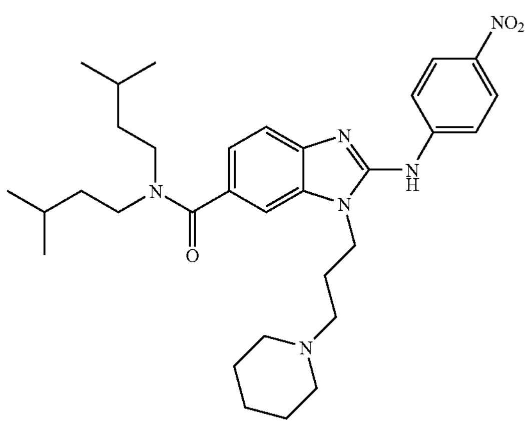 | 563.2 | 9.7 |
| 440 | 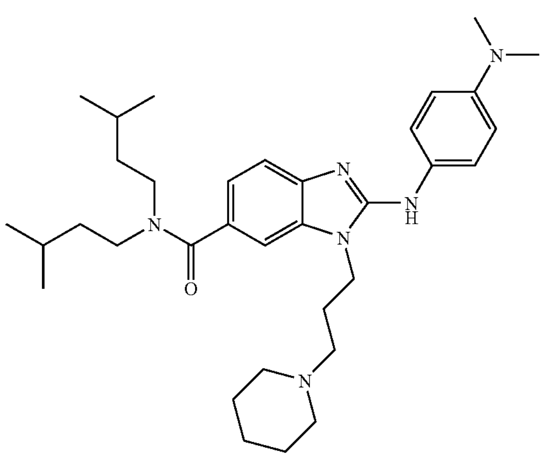 | 561.3 | 8.4 |

-continued
| Examples | Molecular structures | [M + H]+ | rt (min) |
|---|---|---|---|
| 441 | 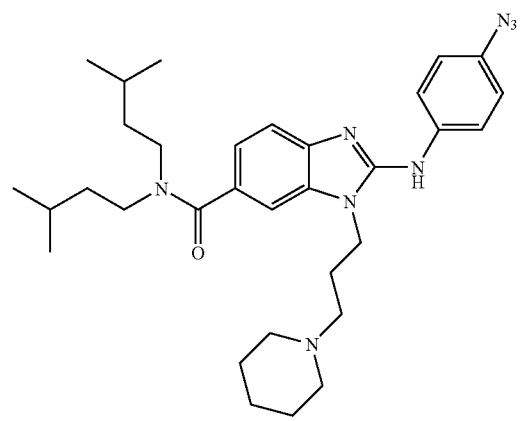 | 559.3 | 8.8 |
| 442 | 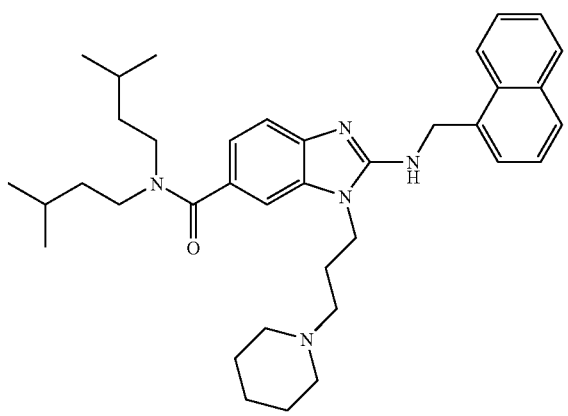 | 582.3 | 8.8 |
| 443 | 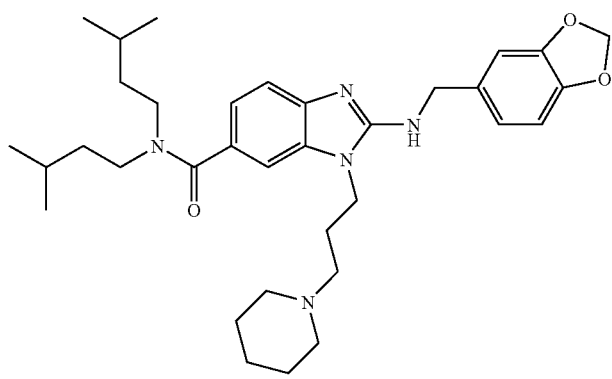 | 576.2 | 8.5 |

-continued
| Examples | Molecular structures | [M + H]+ | rt (min) |
|---|---|---|---|
| 444 | 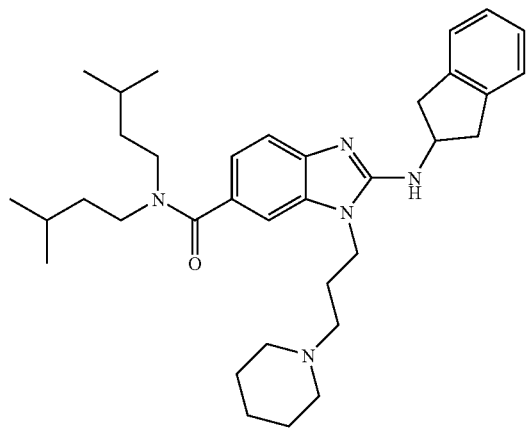 | 558.3 | 8.6 |
| 445 | 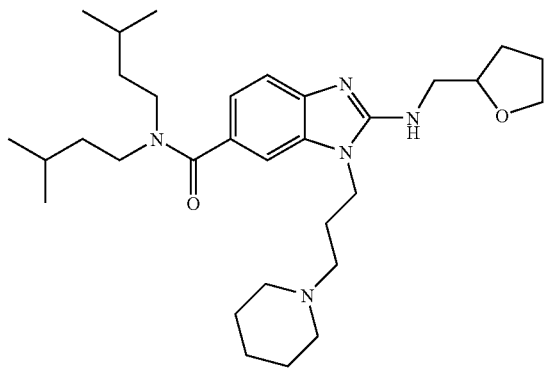 | 526.3 | 8.3 |
| 446 | 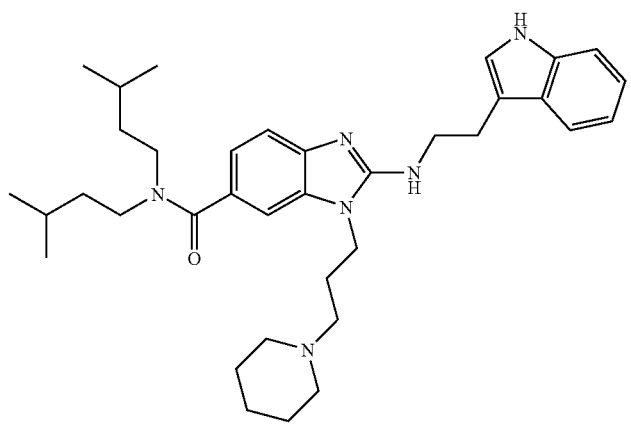 | 585.3 | 8.6 |

-continued
| Examples | Molecular structures | [M + H]+ | rt (min) |
|---|---|---|---|
| 447 | 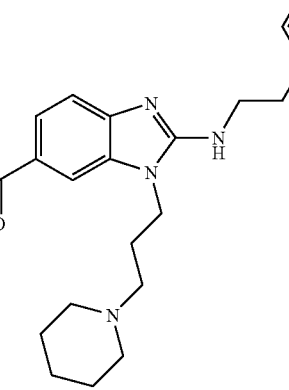 | 625.4 | 8.3 |
| 448 | 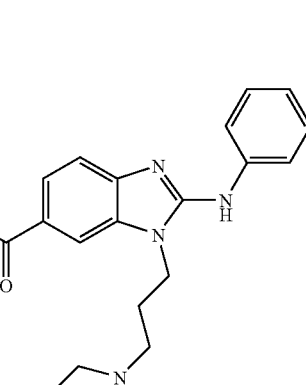 | 618.4 | 9.6 |
| 449 | 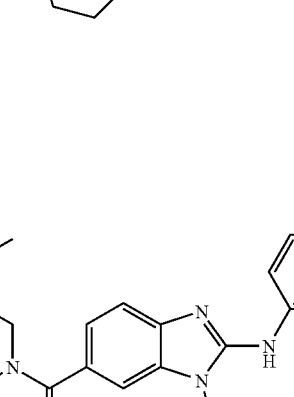 | 552.4 | 8.8 |

-continued
| Examples | Molecular structures | [M + H]+ | rt (min) |
|---|---|---|---|
| 450 | 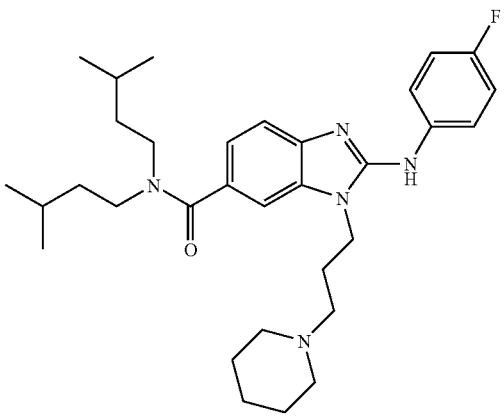 | 536.4 | 8.5 |
| 451 | 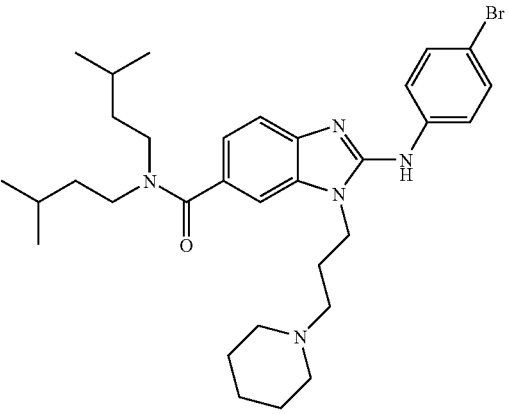 | 596.3 | 8.9 |
| 452 | 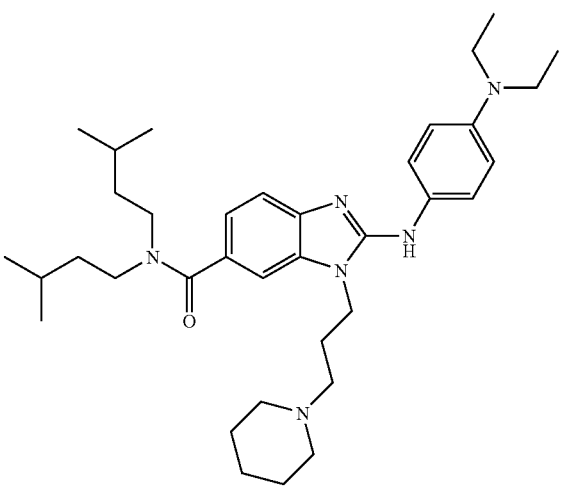 | 589.5 | 8.2 |

-continued
| Examples | Molecular structures | [M + H]+ | rt (min) |
|---|---|---|---|
| 453 | 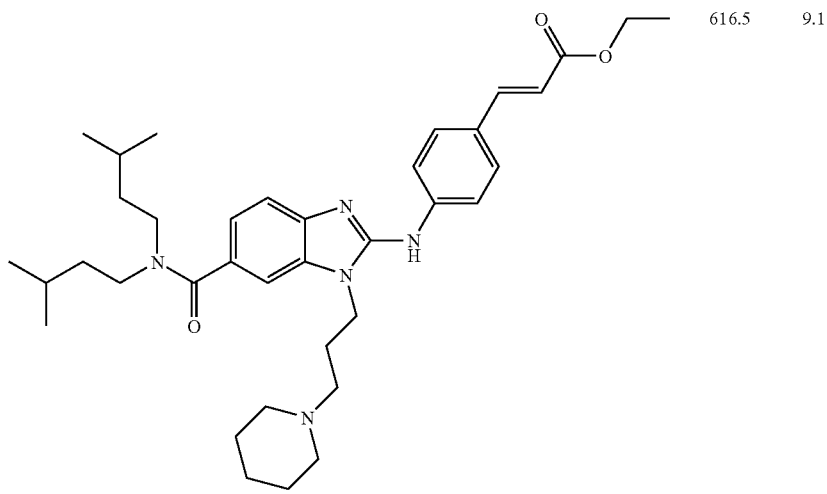 | 616.5 | 9.1 |
| 454 | 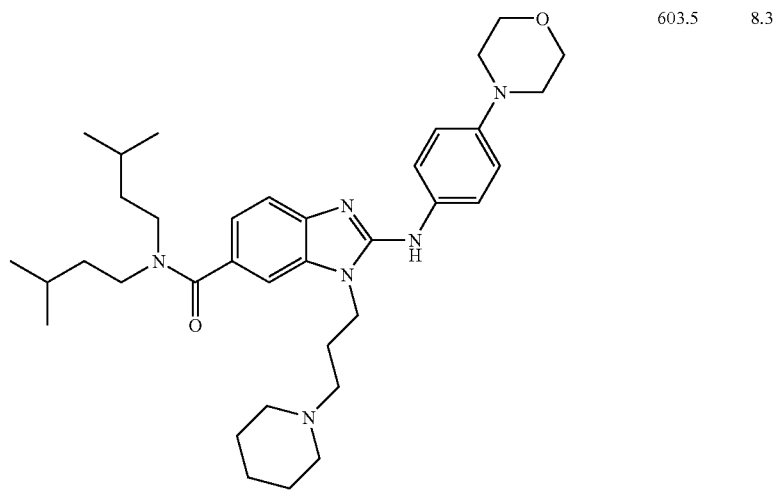 | 603.5 | 8.3 |
| 455 | 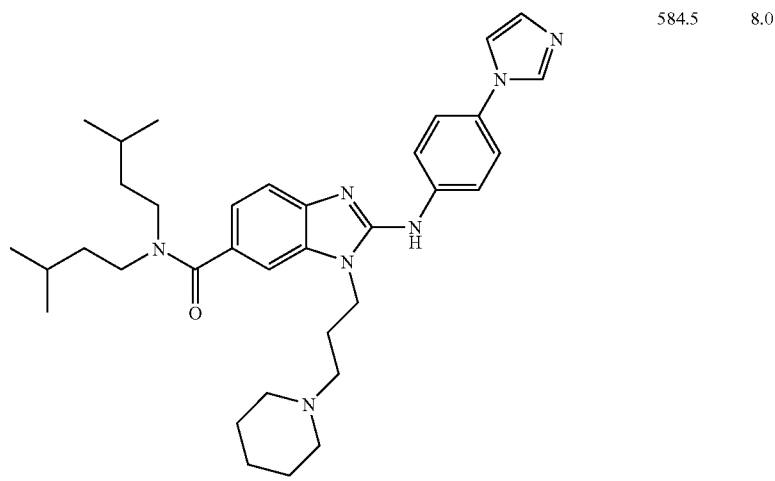 | 584.5 | 8.0 |

-continued
| Examples | Molecular structures | [M + H]+ | rt (min) |
|---|---|---|---|
| 456 | 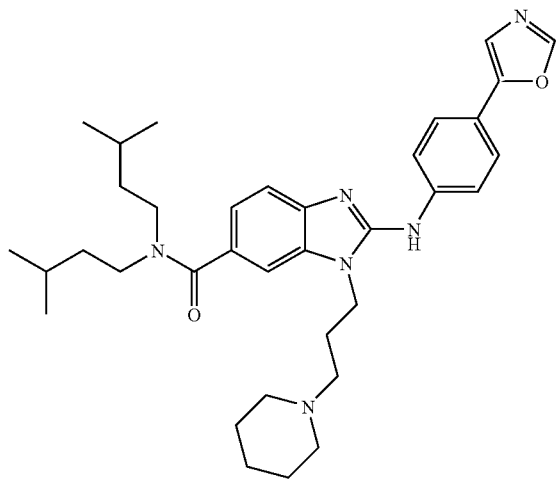 | 585.4 | 8.6 |
| 457 | 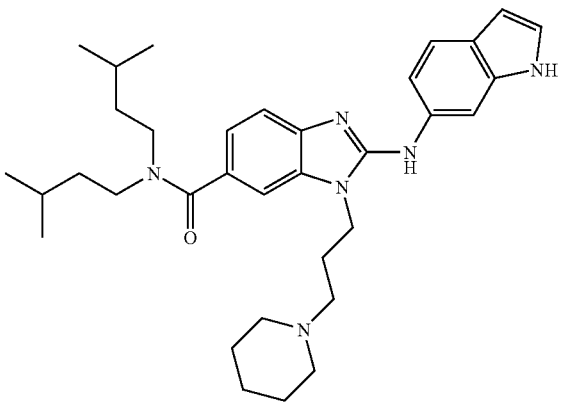 | 557.4 | 8.5 |
| 458 | 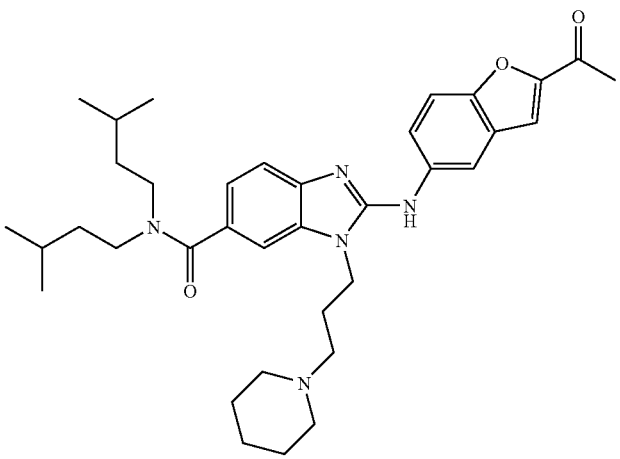 | 600.4 | 8.5 |

-continued
| Examples | Molecular structures | [M + H]+ | rt (min) |
|---|---|---|---|
| 459 | 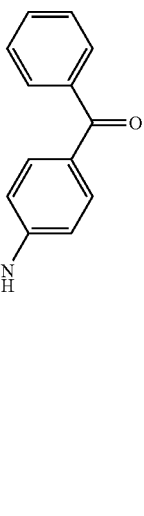 | 622.4 | 9.1 |
| 460 | 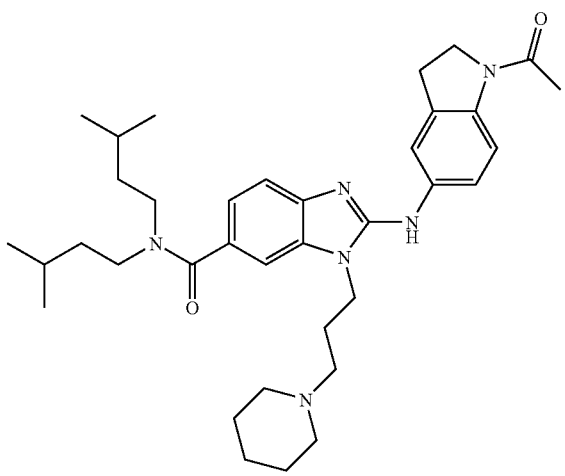 | 601.4 | 8.7 |
| 461 | 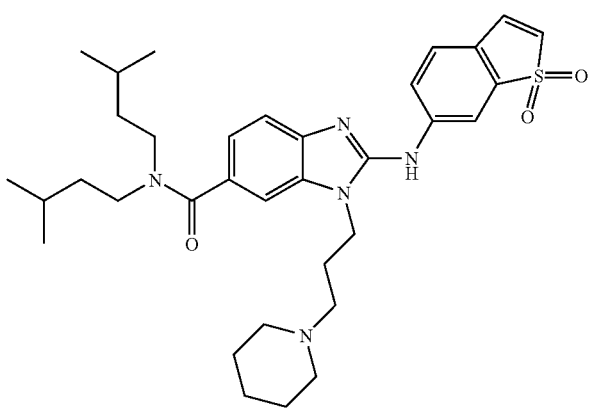 | 623.4 | 9.0 |

-continued

| Examples | Molecular structures | [M + H]+ | rt (min) |
|---|---|---|---|
| 462 | 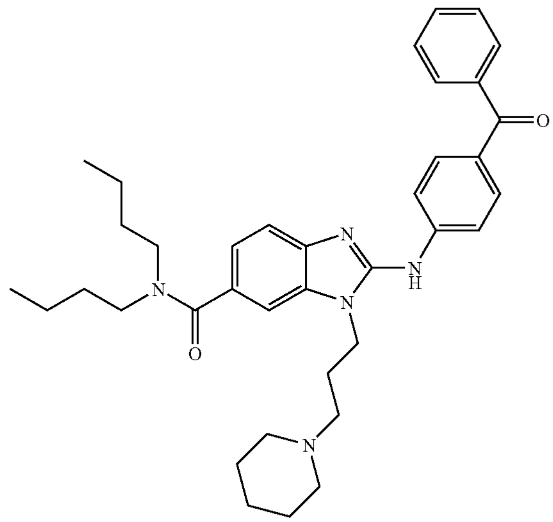 | 594.4 | 8.6 |
| 463 | 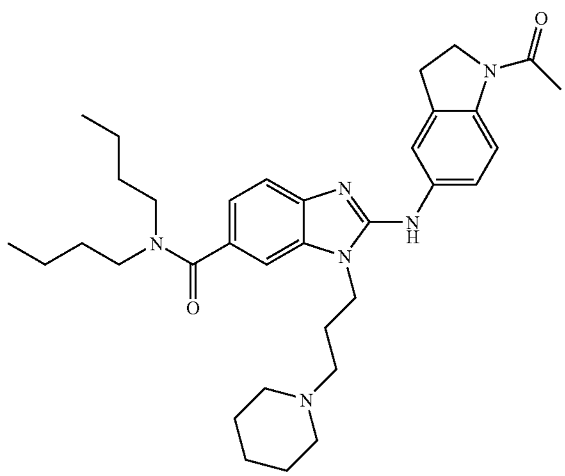 | 573.4 | 8.3 |
| 464 | 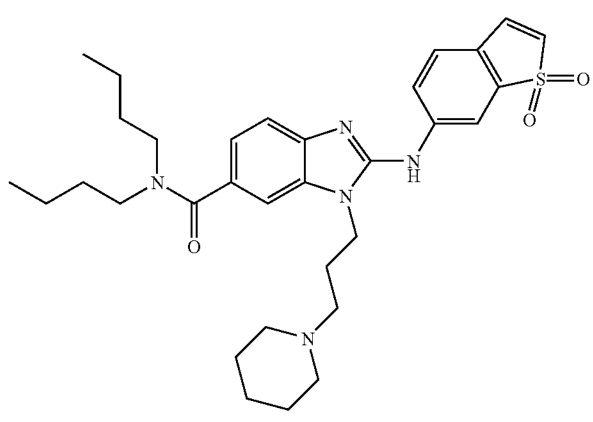 | 595.3 | 8.7 |

-continued
| Examples | Molecular structures | [M + H]+ | rt (min) |
|---|---|---|---|
| 465 | 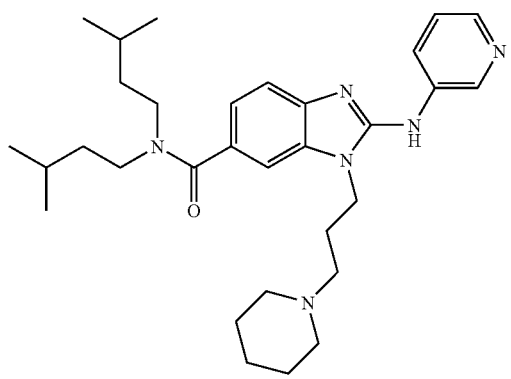 | 519.4 | 8.1 |
| 466 | 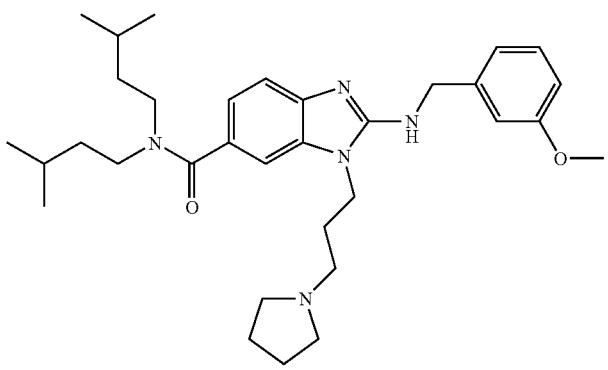 | 548.4 | 8.4 |
| 467 | 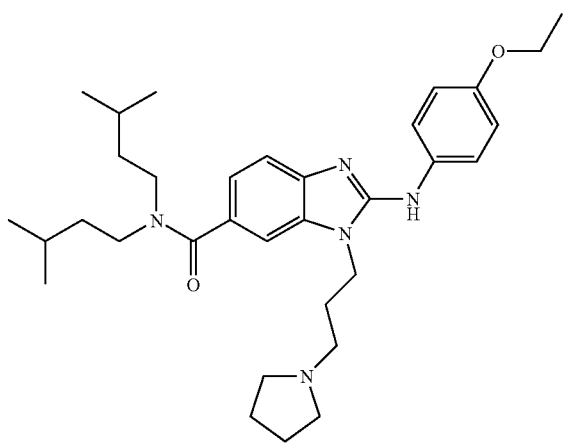 | 548.4 | 8.5 |

-continued
| Examples | Molecular structures | [M + H]+ | rt (min) |
|---|---|---|---|
| 468 | 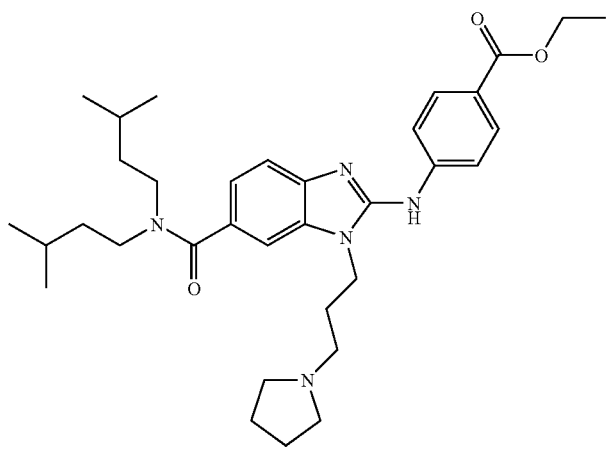 | 576.4 | 9.1 |
| 469 | 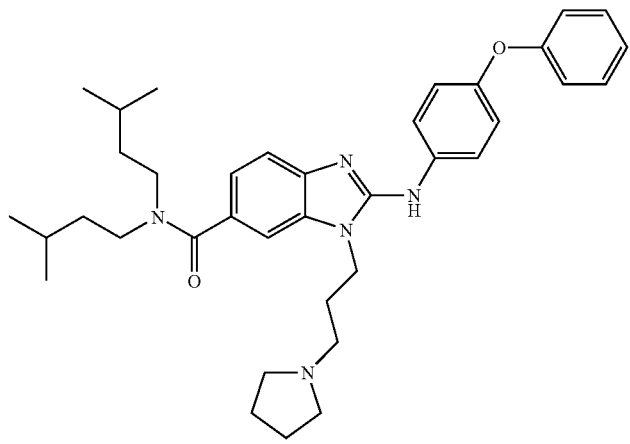 | 596.4 | 8.9 |
| 470 | 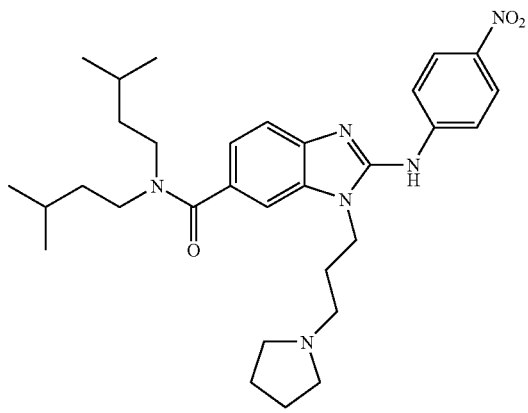 | 549.3 | 9.5 |

-continued
| Examples | Molecular structures | [M + H]+ | rt (min) |
|---|---|---|---|
| 471 | 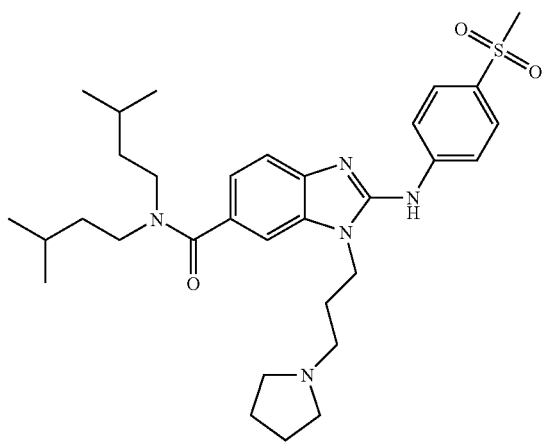 | 582.3 | 8.8 |
| 472 | 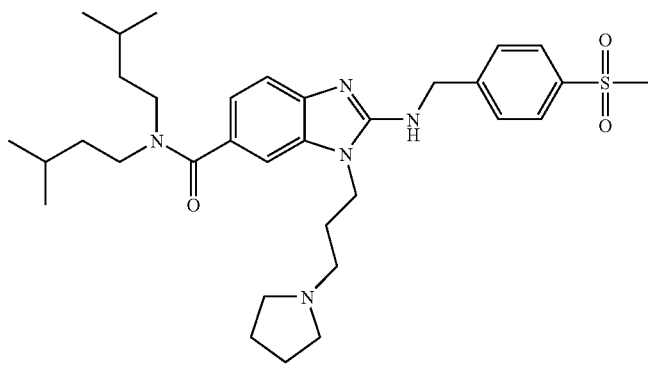 | 596.4 | 8.2 |
| 473 | 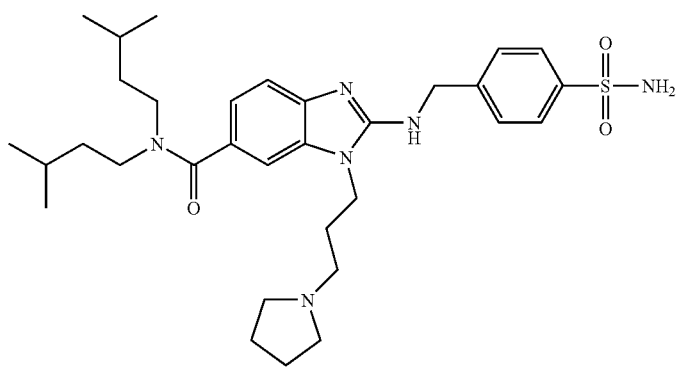 | 597.4 | 8.2 |

-continued
| Examples | Molecular structures | [M + H]+ | rt (min) |
|---|---|---|---|
| 474 | 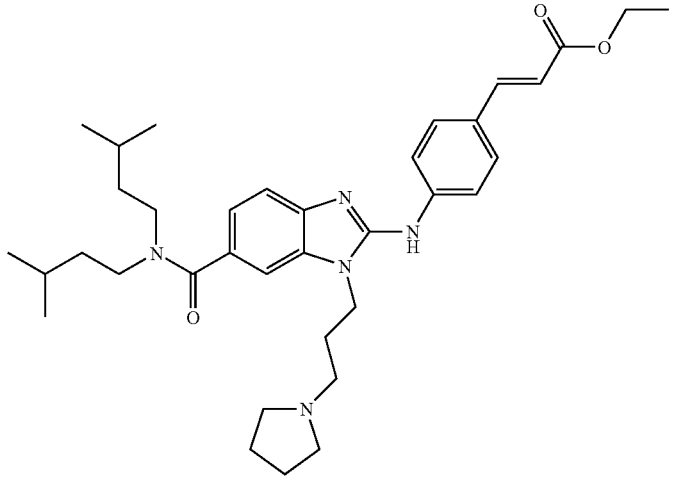 | 602.4 | 9.0 |
| 475 | 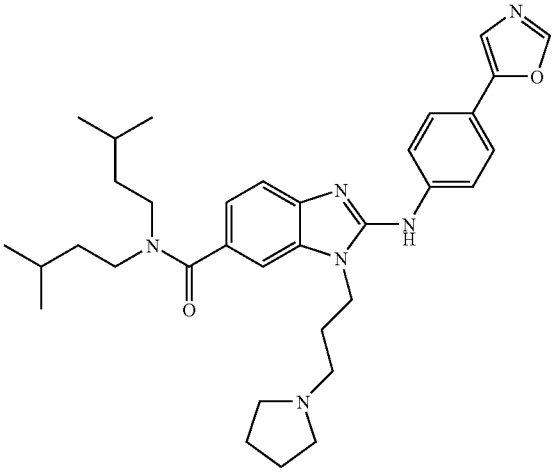 | 571.4 | 8.5 |
| 476 | 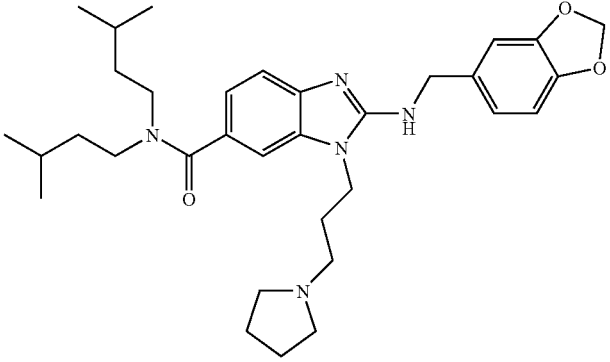 | 562.4 | 8.4 |

-continued
| Examples | Molecular structures | [M + H]+ | rt (min) |
|---|---|---|---|
| 477 | 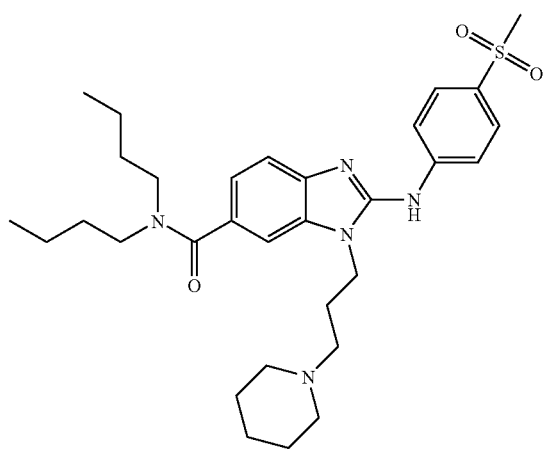 | 568.3 | 8.3 |
| 478 | 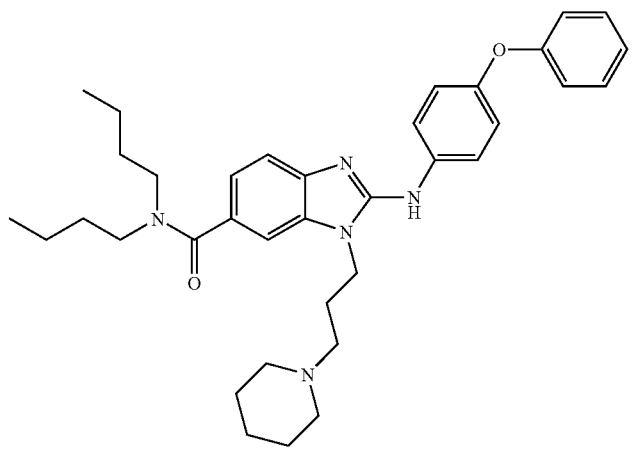 | 582.3 | 8.5 |
| 479 | 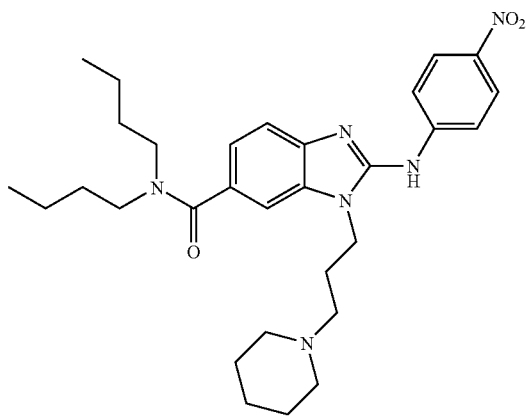 | 535.4 | 9.1 |

-continued
| Examples | Molecular structures | [M + H]+ | rt (min) |
|---|---|---|---|
| 480 | 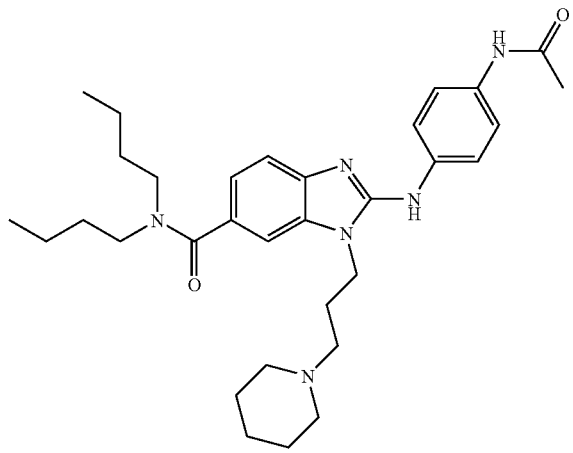 | 547.3 | 7.8 |
| 481 | 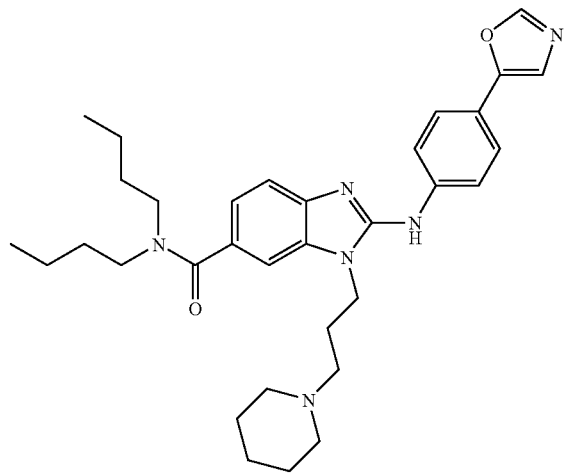 | 557.4 | 8.2 |
| 482 | 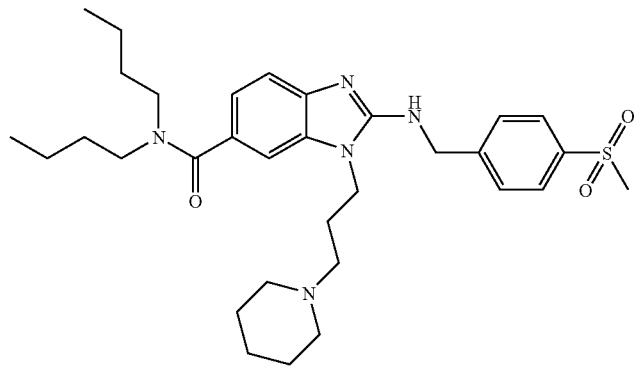 | 582.3 | 7.9 |

-continued
| Examples | Molecular structures | [M + H]+ | rt (min) |
|---|---|---|---|
| 483 | 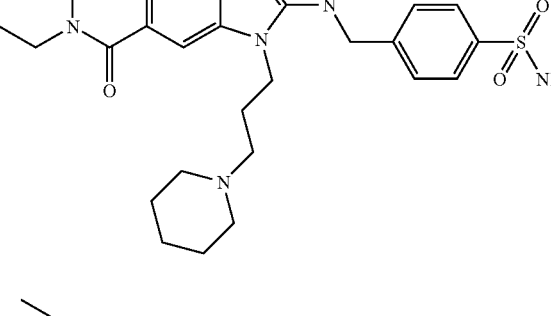 | 583.3 | 7.8 |
| 484 | 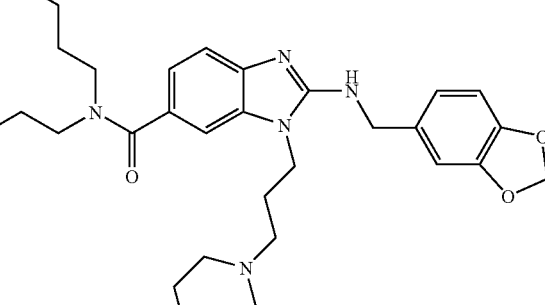 | 548.4 | 8.2 |
| 485 | 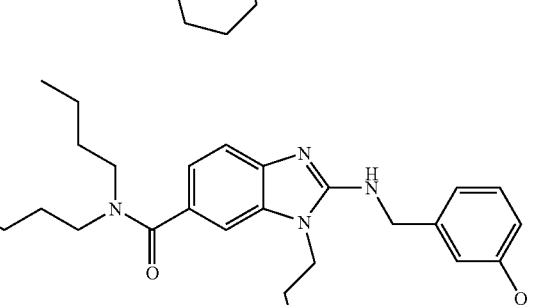 | 534.4 | 8.2 |
| 486 | 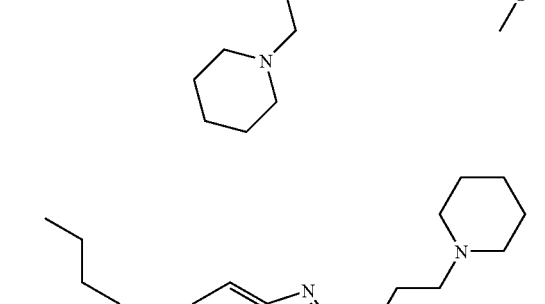 | 525.4 | 7.6 |

-continued

| Examples | Molecular structures | [M + H]+ | rt (min) |
|---|---|---|---|
| 487 | 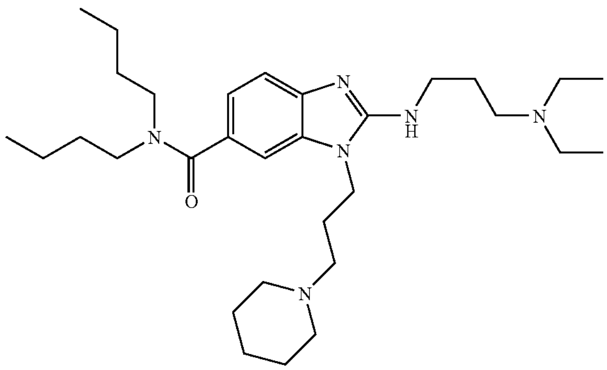 | 527.5 | 7.5 |
| 488 | 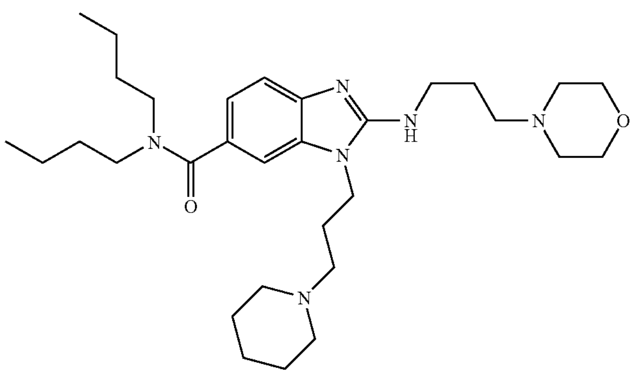 | 541.4 | 7.5 |
| 489 | 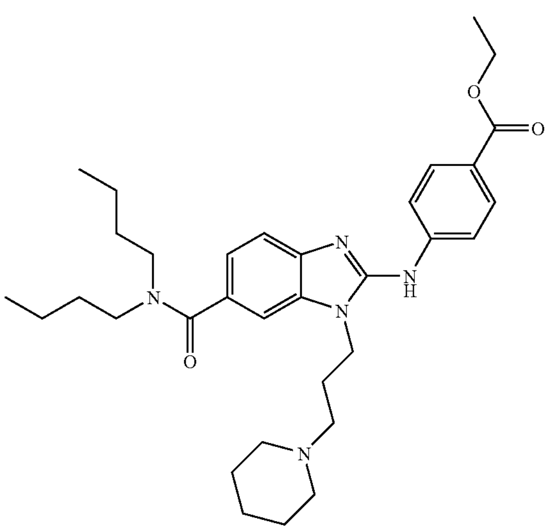 | 562.4 | 8.7 |

-continued

| Examples | Molecular structures | [M + H]+ | rt (min) |
|---|---|---|---|
| 490 | 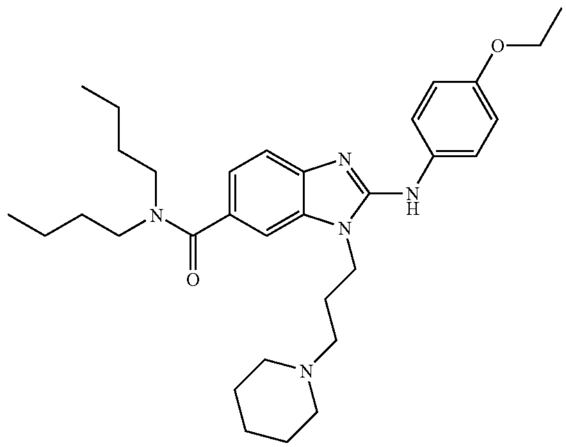 | 534.4 | 8.2 |
| 491 | 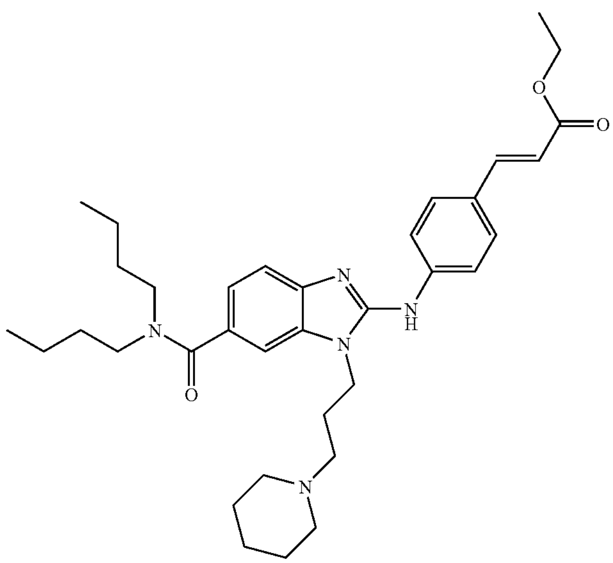 | 588.4 | 8.7 |
| 492 | 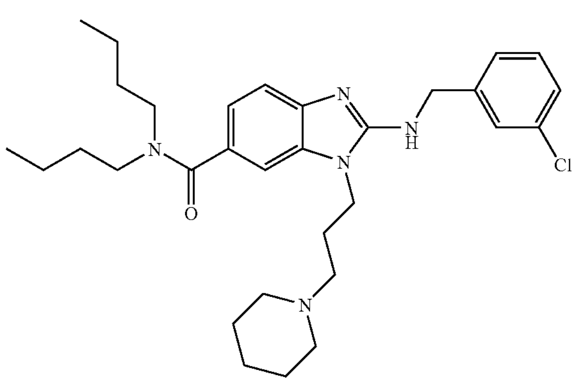 | 538.3 | 8.3 |

-continued

| Examples | Molecular structures | [M + H]+ | rt (min) |
|---|---|---|---|
| 493 | 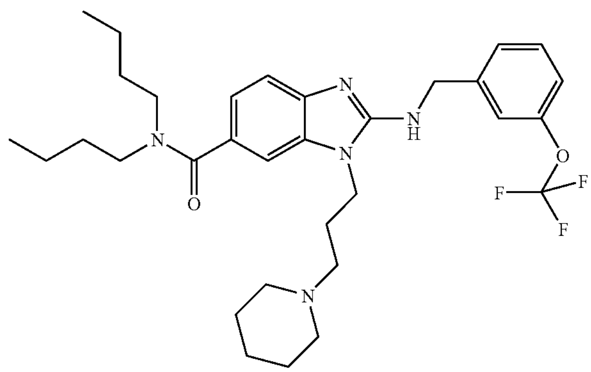 | 588.3 | 8.5 |
| 494 | 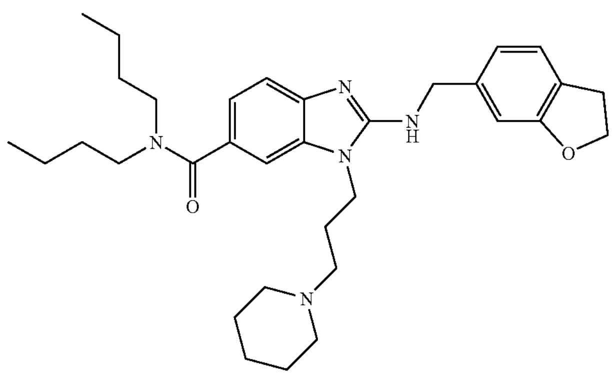 | 546.4 | 8.2 |
| 495 | 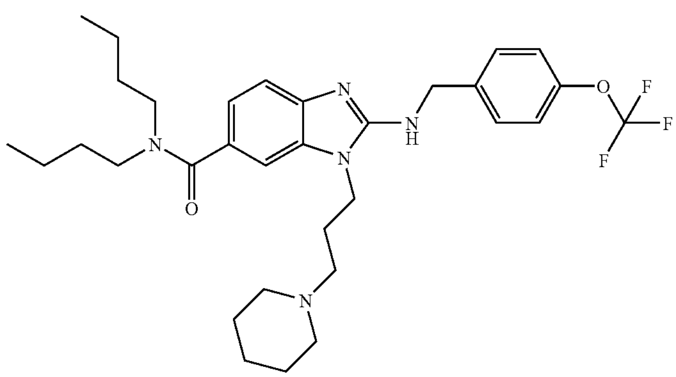 | 588.3 | 8.5 |
| 496 | 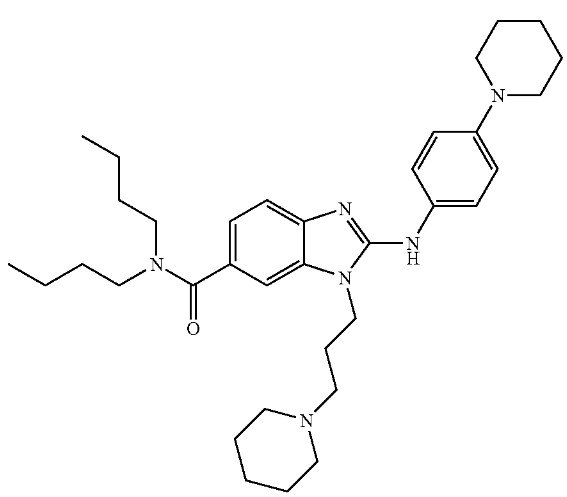 | 573.4 | 7.9 |

-continued
| Examples | Molecular structures | [M + H]+ | rt (min) |
|---|---|---|---|
| 497 | 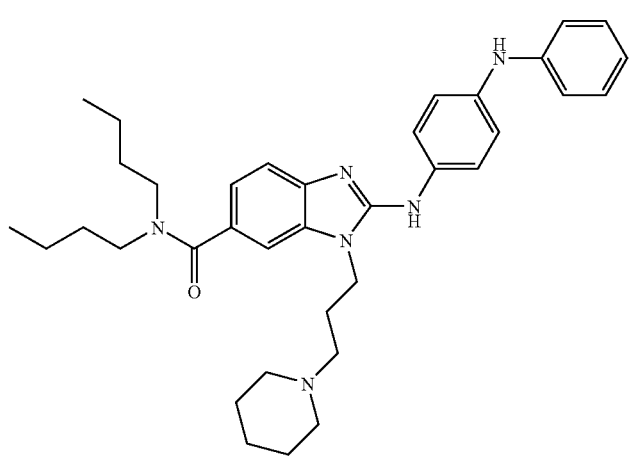 | 581.4 | 8.5 |
| 498 | 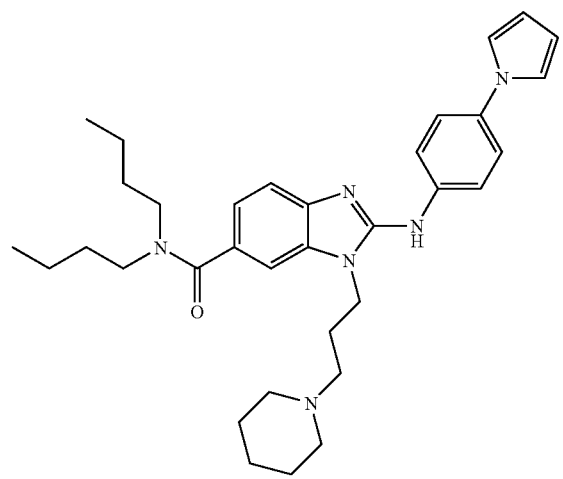 | 555.4 | 8.4 |
| 499 | 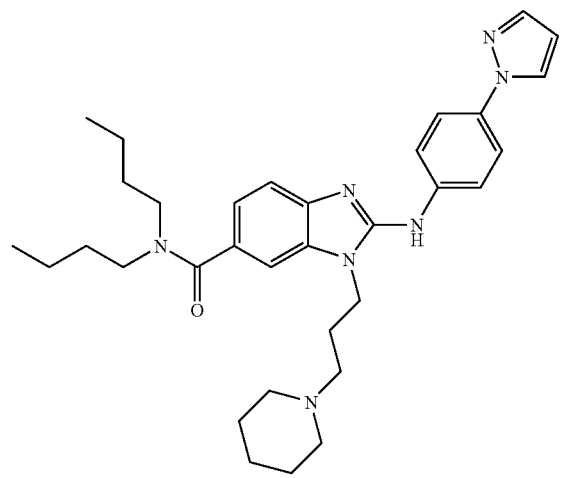 | 556.3 | 8.2 |

-continued

| Examples | Molecular structures | [M + H]+ | rt (min) |
|---|---|---|---|
| 500 | 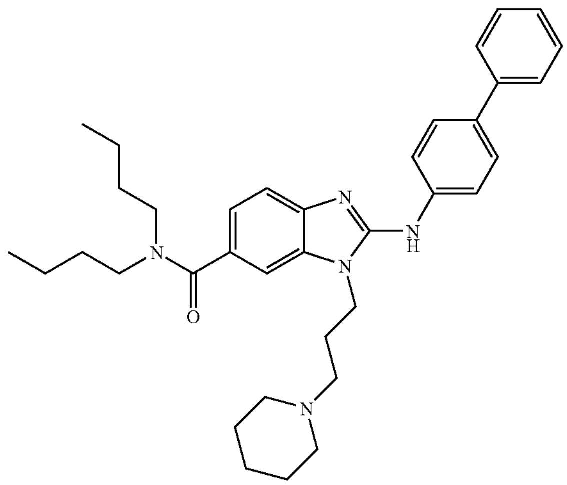 | 566.4 | 8.7 |
| 501 | 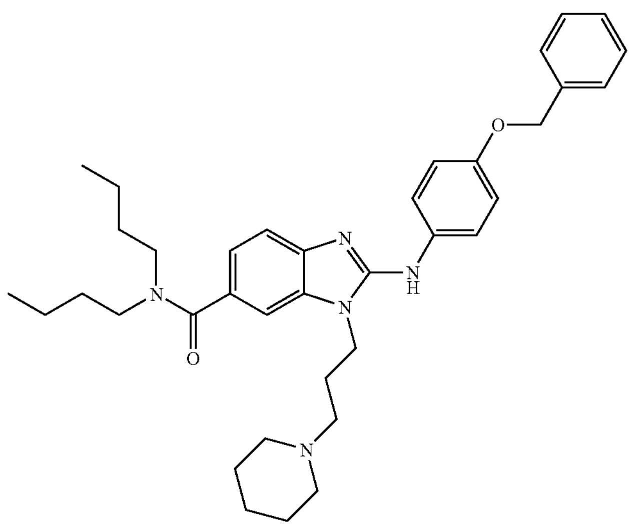 | 596.4 | 8.6 |
| 502 | 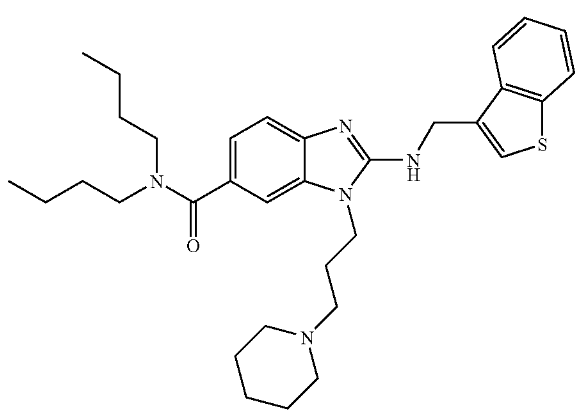 | 560.3 | 8.3 |

| Examples | Molecular structures | [M + H]+ | rt (min) |
|---|---|---|---|
| 503 | 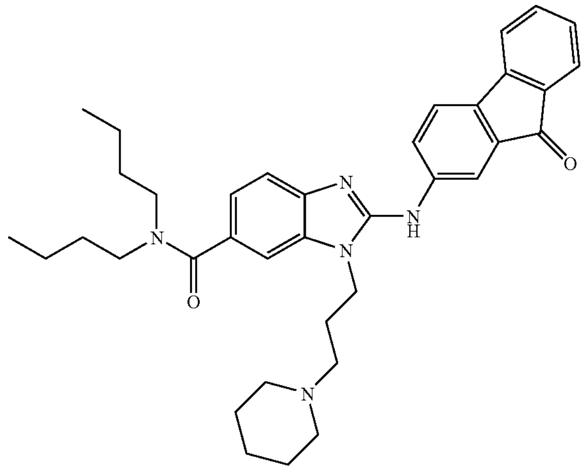 | 592.3 | 8.8 |
| 504 | 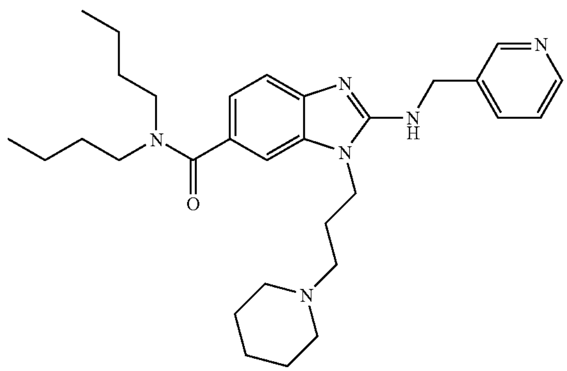 | 505.4 | 7.7 |
| 505 | 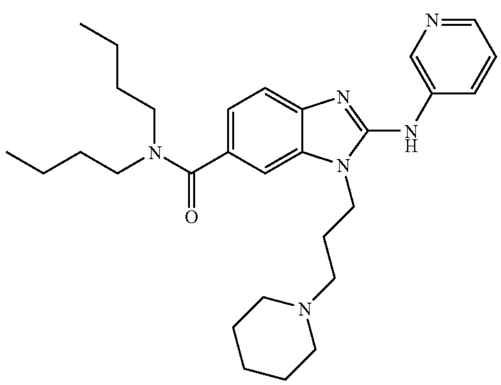 | 491.4 | 7.9 |
| 506 | 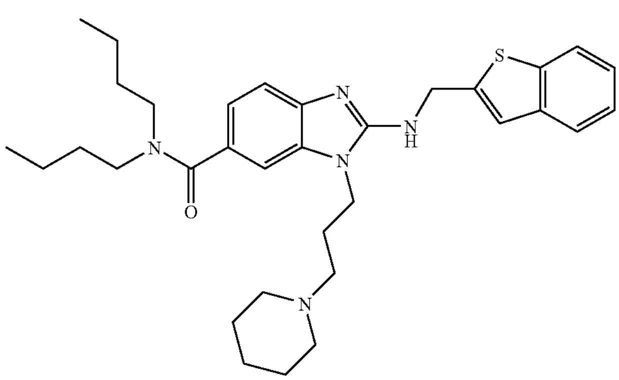 | 560.3 | 8.4 |

-continued

| Examples | Molecular structures | [M + H]+ | rt (min) |
|---|---|---|---|
| 507 | 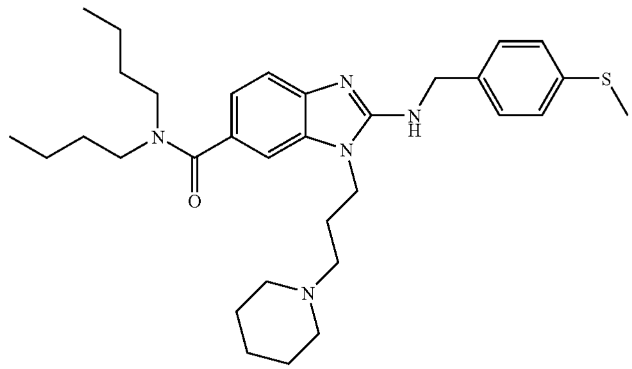 | 550.3 | 8.3 |
| 508 | 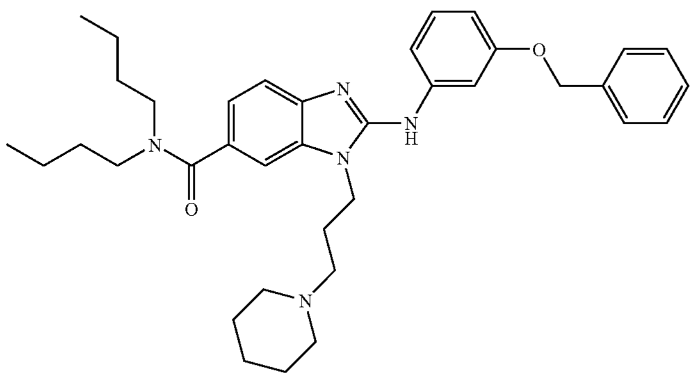 | 596.4 | 8.7 |
| 509 | 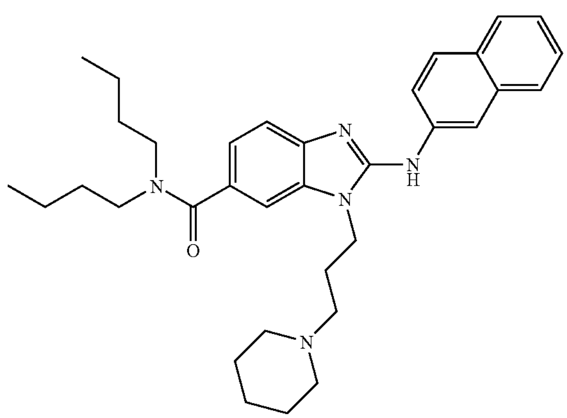 | 540.3 | 8.5 |
| 510 | 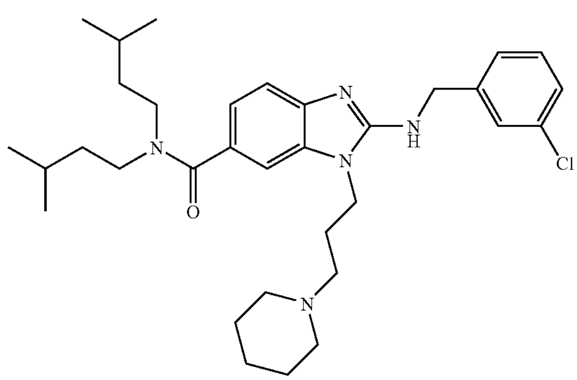 | 566.3 | 8.5 |

| Examples | Molecular structures | [M + H]+ | rt (min) |
|---|---|---|---|
| 511 | 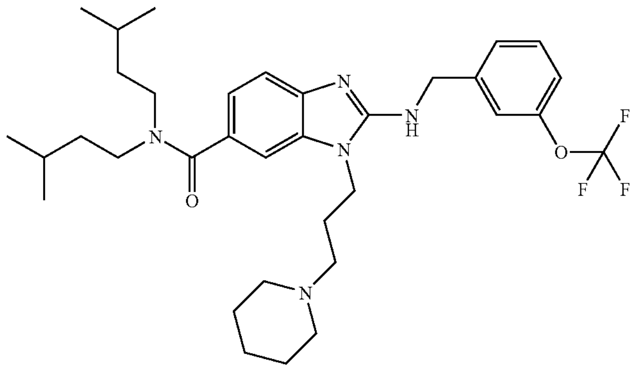 | 616.4 | 8.7 |
| 512 | 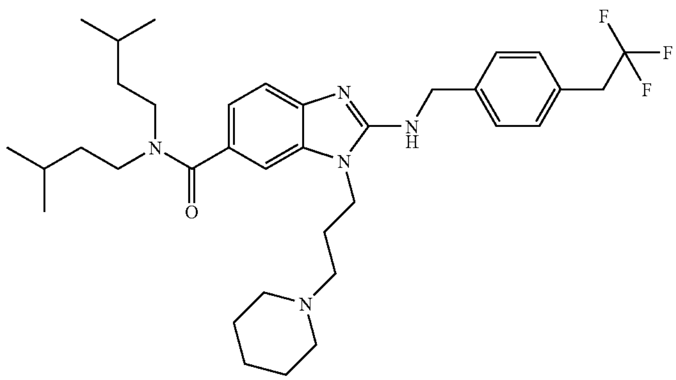 | 616.4 | 8.7 |
| 513 | 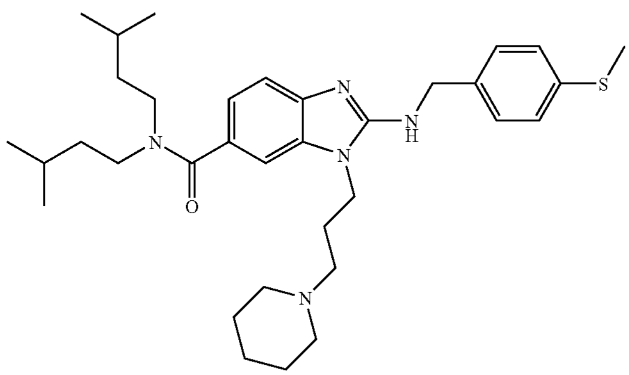 | 578.3 | 8.6 |
| 514 | 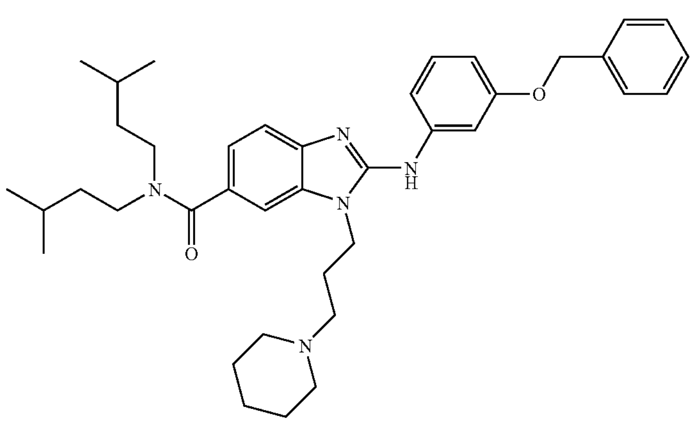 | 624.4 | 9.0 |

-continued
| Examples | Molecular structures | [M + H]+ | rt (min) |
|---|---|---|---|
| 515 | 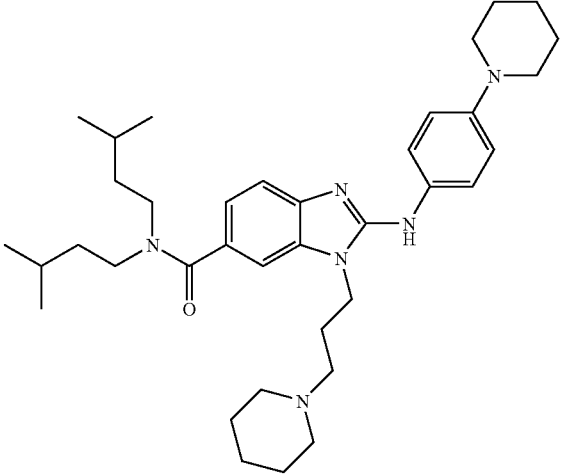 | 601.4 | 8.1 |
| 516 | 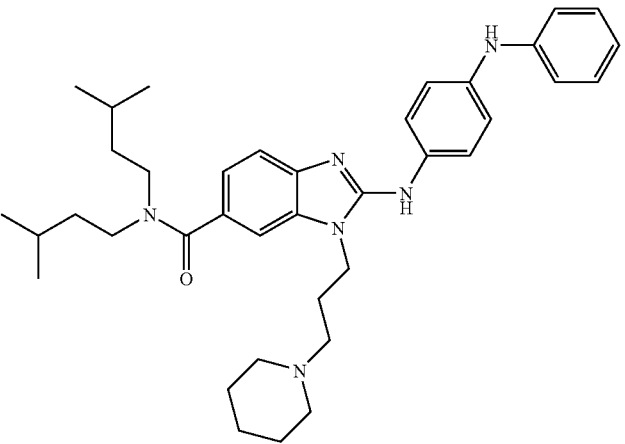 | 609.4 | 8.8 |
| 517 | 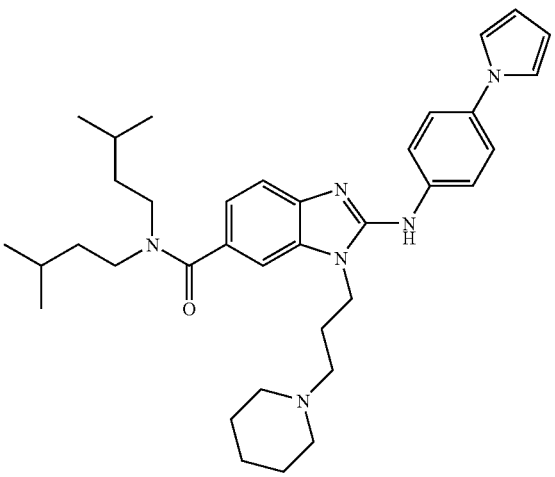 | 583.4 | 8.7 |

-continued
| Examples | Molecular structures | [M + H]+ | rt (min) |
|---|---|---|---|
| 518 | 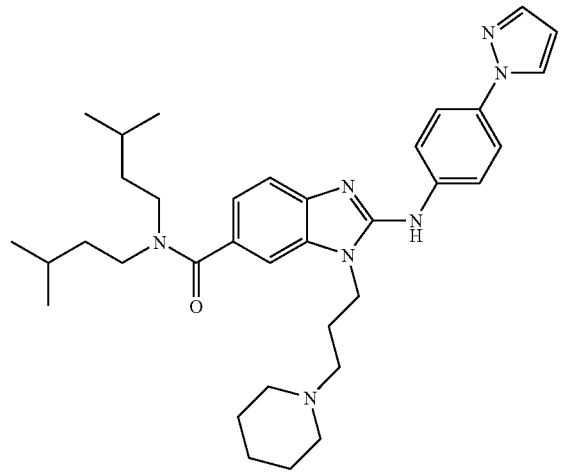 | 584.4 | 8.4 |
| 519 | 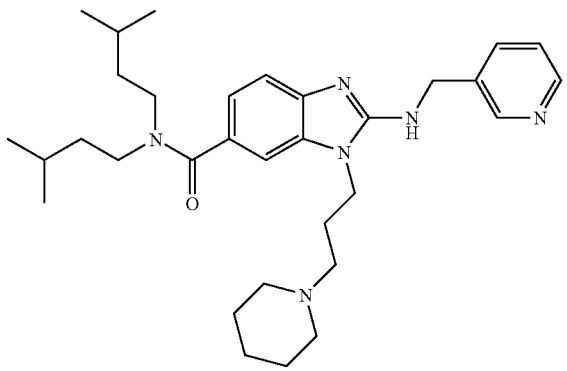 | 533.4 | 7.8 |
| 520 | 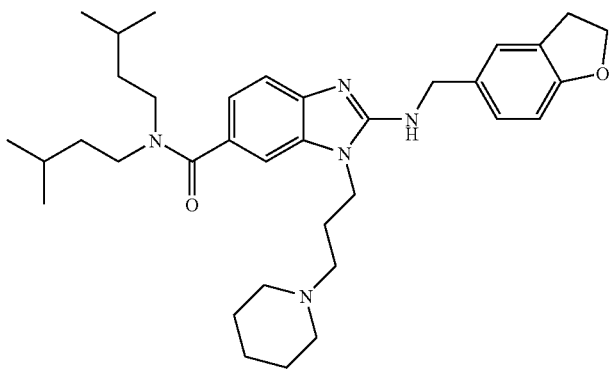 | 574.4 | 8.4 |

-continued
| Examples | Molecular structures | [M + H]+ | rt (min) |
|---|---|---|---|
| 521 | 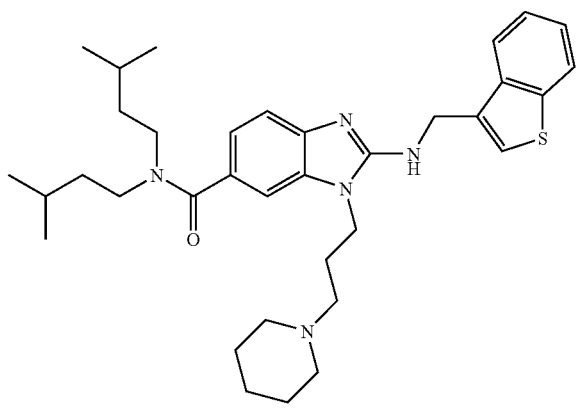 | 588.3 | 8.5 |
| 522 | 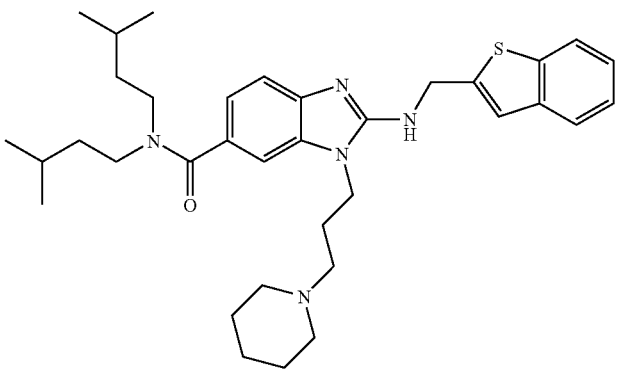 | 588.3 | 8.6 |
| 523 | 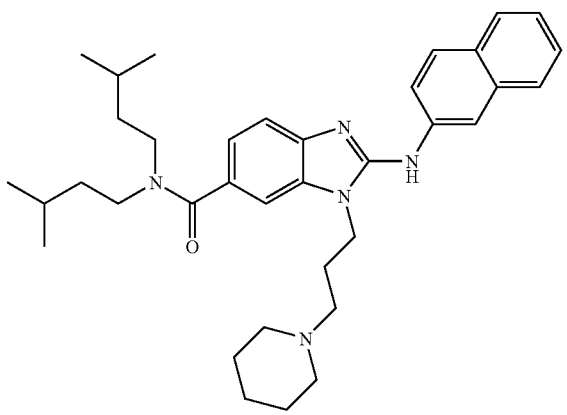 | 568.4 | 8.7 |

-continued
| Examples | Molecular structures | [M + H]+ | rt (min) |
|---|---|---|---|
| 524 | 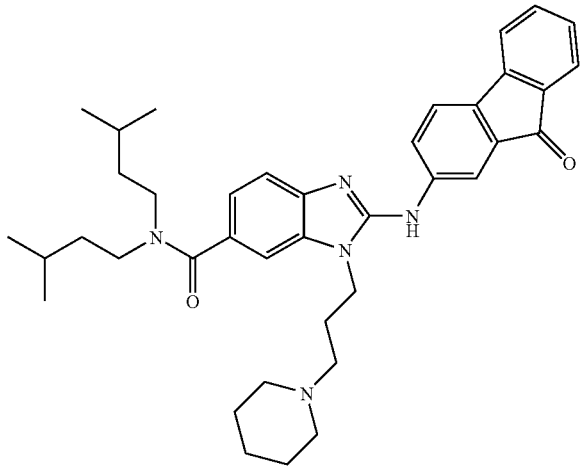 | 620.4 | 9.1 |
| 525 | 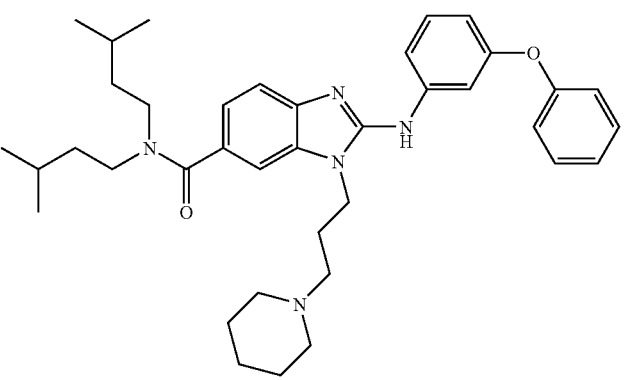 | 610.4 | 9.0 |
| 526 | 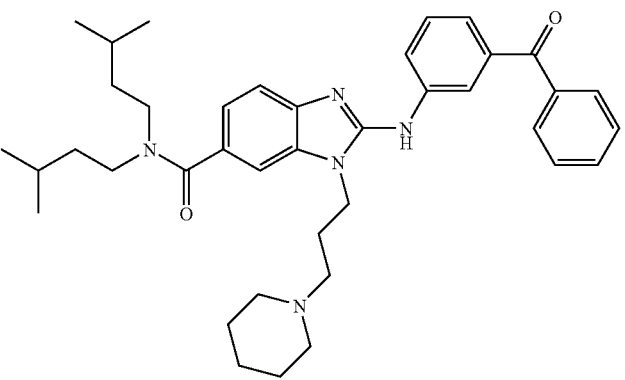 | 622.4 | 9.0 |

-continued
| Examples | Molecular structures | [M + H]+ | rt (min) |
|---|---|---|---|
| 527 | 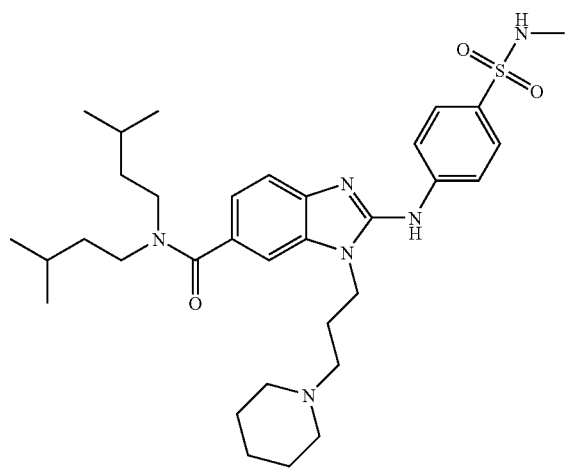 | 611.4 | 8.7 |
| 528 | 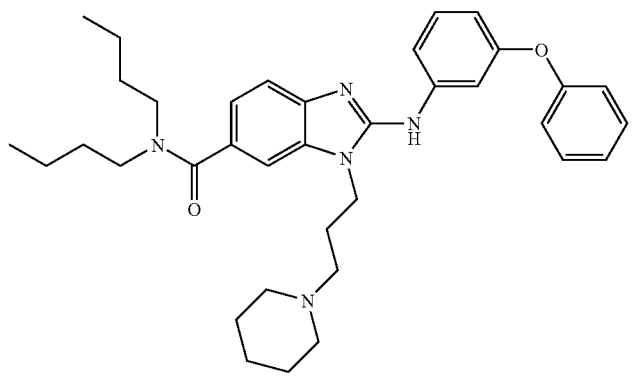 | 582.3 | 8.7 |
| 529 | 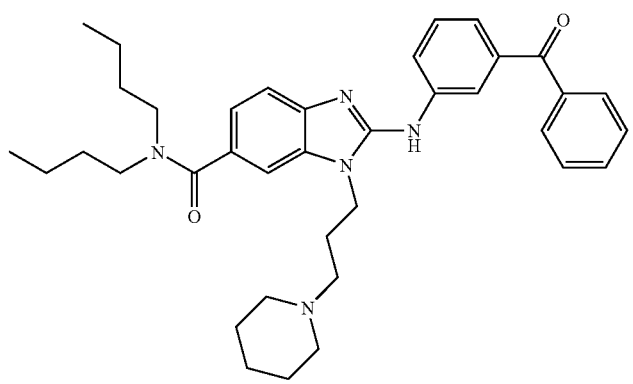 | 594.4 | 8.6 |

-continued

| Examples | Molecular structures | [M + H]+ | rt (min) |
|---|---|---|---|
| 530 | 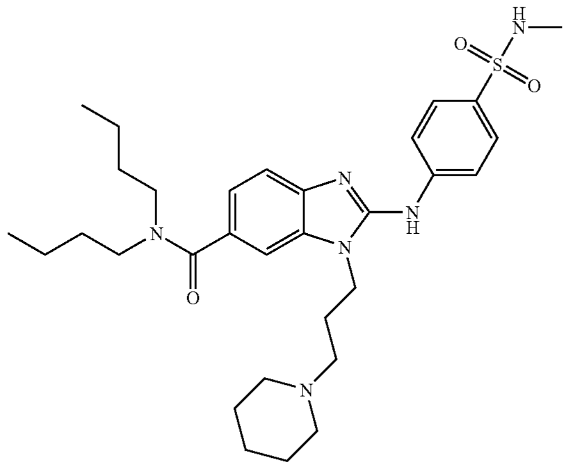 | 583.3 | 8.3 |
| 531 | 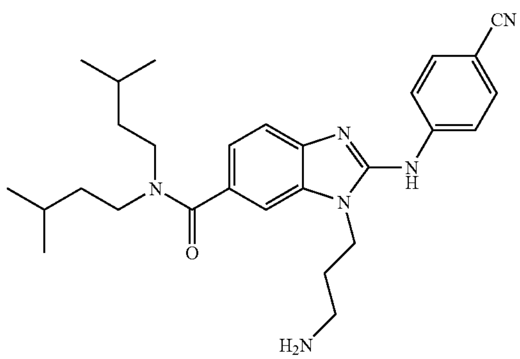 | 475.3 | 8.7 |
| 532 | 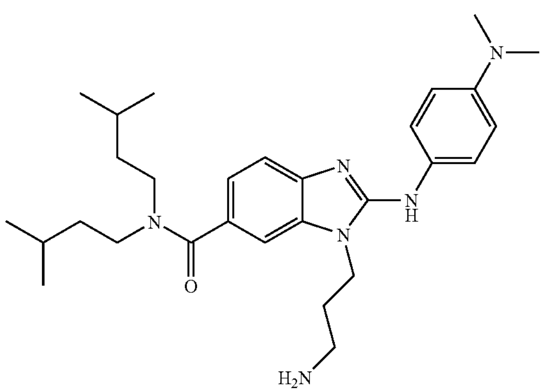 | 493.3 | 8.0 |
| 533 | 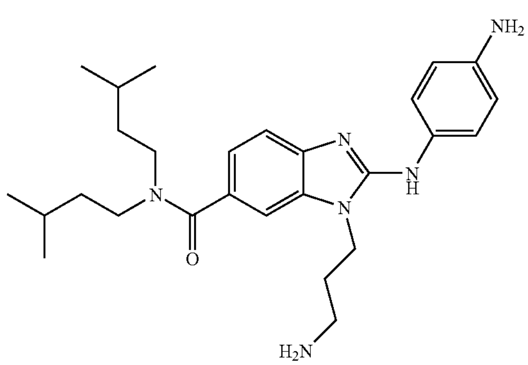 | 465.3 | 7.8 |

-continued

| Examples | Molecular structures | [M + H]+ | rt (min) |
|---|---|---|---|
| 534 | 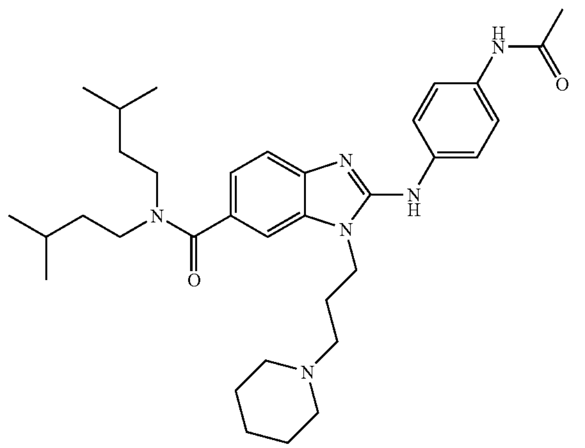 | 575.3 | 8.1 |
| 535 | 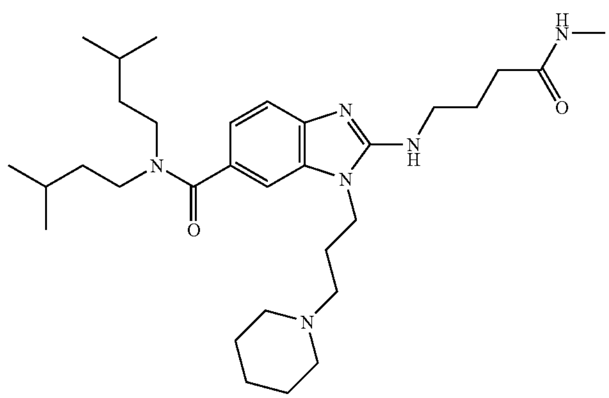 | 541.5 | 8.0 |
| 536 | 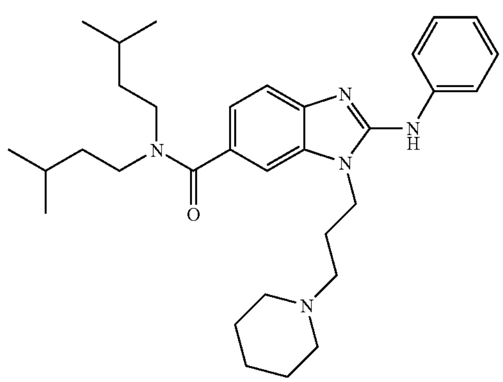 | 518.4 | 8.2 |
| 537 | 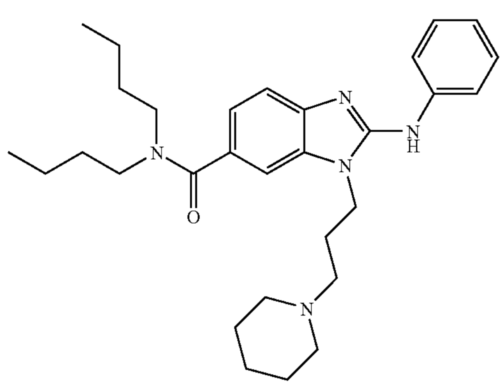 | 490.4 | 8.0 |

-continued

| Examples | Molecular structures | [M + H]+ | rt (min) |
|---|---|---|---|
| 538 | 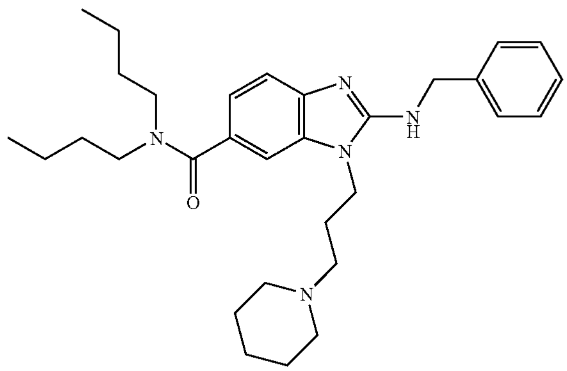 | 504.3 | 8.0 |
| 539 | 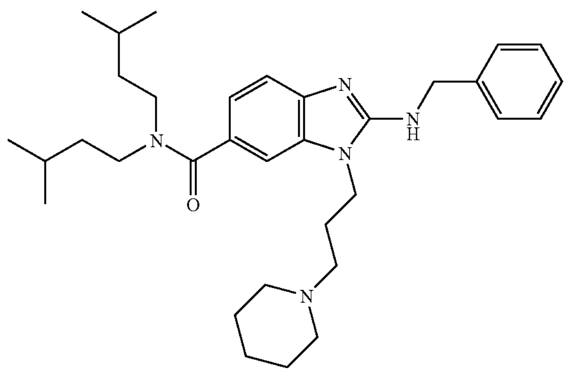 | 532.3 | 8.3 |
| 540 | 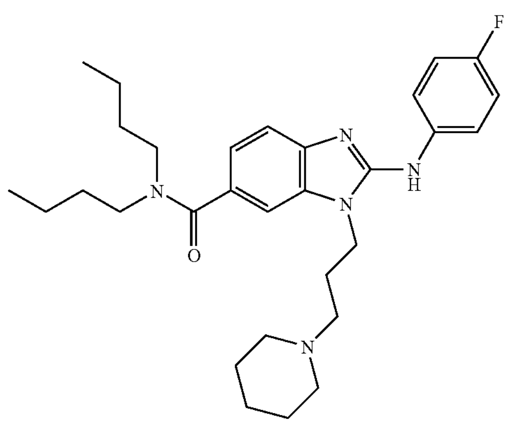 | 508.3 | 7.9 |

Pharmacological Study

The affinity of the compounds of the present invention for the different sub-types of melanocortin receptors was measured according to procedures analogous to those described below for the MC4 receptors.

Study of the Affinity of the Compounds for the MC4 Receptors of Melanocortins:

The affinity of the compounds of the invention for the MC4 receptors is determined by measuring the inhibition of the binding of [$^{125}$I]-[Nle$^4$, D-Phe$^7$]-α-MSH to membrane preparations of transfected CHO-K1 cells.

The CHO-K1 cells expressing in a stable fashion the human MC4 receptors are cultured in an RPMI 1640 medium containing 10% of fetal calf serum, 2 mM of glutamine, 100 U/ml of penicillin, 0.1 mg/ml of streptomycin and 0.5 mg/ml of G418. The cells are collected with 0.5 mM of EDTA and centrifuged at 500 g for 5 minutes at 4° C. The pellet is resuspended in a phosphate buffered saline (PBS) medium and centrifuged at 500 g for 5 minutes at 4° C. The pellet is resuspended in a Tris 50 mM buffer medium at pH 7.4 and centrifuged at 500 g for 5 minutes at 4° C. The cells are lysed by sonication and centrifuged at 39,000 g for 10 minutes at 4° C. The pellet is resuspended in the Tris 50 mM buffer medium at pH 7.4 and centrifuged at 50,000 g for 10 min at 4° C. The membranes obtained in this last pellet are stored at −80° C.

The measurement of the competitive inhibition of the binding of [$^{125}$I]-[Nle$^4$, D-Phe$^7$]-α-MSH to the MC4 receptors is carried out in duplicate using polypropylene 96-well plates. The cell membranes (50 μg of proteins/well) are incubated with [$^{125}$I]-[Nle$^4$, D-Phe$^7$]-α-MSH (0.5 nM) for 90 minutes at 37° C. in a Tris-HCl 50 mM buffer medium, pH 7.4, comprising 0.2% of bovine serum albumin (BSA), 5 mM of MgCl$_2$, and 0.1 mg/ml of bacitracin.

The bonded [$^{125}$I]-[Nle$^4$, D-Phe$^7$]-α-MSH is separated from the free [$^{125}$I]-[Nle$^4$, D-Phe$^7$]-α-MSH by filtration through GF/C glass fibre filters (Unifilter, Packard) pre-impregnated with 0.1% of polyethylenimine (P.E.I.), using a Filtermate 196 (Packard). The filters are washed with Tris-HCl 50 mM buffer, pH 7.4 at 0-4° C. and the radioactivity present is determined using a counter (Packard Top Count).

The specific binding is obtained by subtracting the non-specific binding (determined in the presence of 0.1 μM of Nle$^4$, D-Phe$^7$-α-MSH) from the total binding. The data are analyzed by computer-aided non-linear regression (MDL) and the values of the inhibition constants (Ki) are determined.

The agonist or antagonist activity of the MC4 receptors of the compounds of the present invention was determined by measuring the production of cyclic AMP by the CHO-K1 cells transfected by the MC4 receptor.

Measurement of the Production of Intracellular Cyclic AMP via the MC4 Receptors:

The CHO-K1 cells expressing the MC4 receptors of the melanocortins are cultured in 384-well plates in an RPMI 1640 medium with 10% of fetal calf serum and 0.5 mg/ml of G418. The cells are washed twice with 50 μl of RPMI medium comprising 0.2% BSA and 0.5 mM of 3-isobutyl-1-methylxanthine (IBMX).

In order to measure the agonist effect of a compound, the cells are incubated for 5 minutes at 37° C. in the presence of 0.5 mM of IBMX, then stimulation of the production of cyclic AMP is obtained by adding the compound at concentrations comprised between 1 pM and 10 μM in duplicate for 20 minutes at 37° C. The antagonist effect of a compound is measured by inhibiting stimulation of the production of cyclic AMP induced by Nle$^4$, D-Phe$^7$-α-MSH at concentrations comprised between 1 pM and 10 μm, in the presence of the compound to be tested, at concentrations comprised between 1 nM and 10 μM in duplicate for 20 minutes at 37° C. The reaction medium is eliminated and 80 μl of lysis buffer is added. The intracellular cyclic AMP level is measured by a competition test with fluorescent cyclic AMP (CatchPoint, Molecular Devices).

The invention claimed is:

1. A compound of the formula

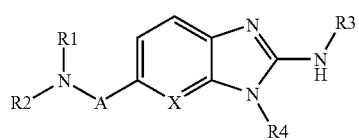

(I)

in racemic, enantiomeric form or any combinations of these forms wherein:

A is —CH$_2$—;

X is —CH—,

R$_1$ is selected from the group consisting of hydrogen, (C$_1$-C$_8$)alkyl optionally substituted by hydroxy or at least one halo; (C$_2$-C$_6$)alkenyl and —(CH$_2$)$_n$—X$_1$;

R$_2$ is selected from the group consisting of (C$_1$-C$_8$)alkyl optionally substituted by hydroxy or at least halo; (C$_2$-C$_6$) alkenyl, alkenyl and —(CH$_2$)$_n$—X$_1$;

each X$_1$ independently is selected from the group consisting of (C$_1$-C$_6$)alkoxy, (C$_3$-C$_7$)cycloalkyl, adamantyl, heterocycloalkyl, aryl and heteroaryl, the (C$_3$-C$_7$)cycloalkyl, heterocycloalkyl, aryl and heteroaryl being substituted by at least one member selected from the group consisting of:

—(CH$_2$)$_{n'}$—V$_1$—Y$_1$, halo, nitro, cyano and aryl;

V$_1$ is selected from the group consisting of —O—, —S— and covalent bond;

Y$_1$ is (C$_1$-C$_6$)alkyl optionally substituted by at least one halo;

n is an integer from 0 to 6 and n' is an integer from 0 to 2 (it being understood that when n is equal to 0, then X$_1$ is not alkoxy);

or R$_1$ and R$_2$ form together with the nitrogen atom to which they are attached, a heterobicycloalkyl or a heterocycloalkyl optionally substituted by at least one member selected from the group consisting of hydroxy, (C$_1$-C$_6$)alkyl, optionally substituted by hydroxy, (C$_1$-C$_6$)alkoxy-carbonyl, heterocycloalkyl and —C(O)NV$_1$'Y$_1$' with V$_1$' and Y$_1$' independently are hydrogen or (C$_1$-C$_6$)alkyl; or R$_1$ and R$_2$ together form a member selected from the group consisting of

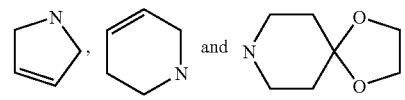

R$_3$ is selected from the group consisting of -Z$_3$, —C(R$_{Z3}$)(R'$_{Z3}$)-Z$_3$, —C(R$_{Z3}$)(R'$_{Z3}$)—(CH$_2$)$_p$-Z$_3$ and —C(O)-Z'$_3$ R$_{Z3}$ and R'$_{Z3}$ are independently hydrogen or (C$_1$-C$_6$)alkyl, Z$_3$ is selected from the group consisting of Z$_{3a}$, Z$_{3b}$, Z$_{3c}$, Z$_{3d}$, or Z$_{3e}$;

Z$_{3a}$ is (C$_1$-C$_6$)alkyl;

Z$_{3b}$ is selected from the group consisting of (C$_1$-C$_6$)alkoxy, (C$_1$-C$_6$)alkylthio, (C$_1$-C$_6$)alkylamino and di((C$_1$-C$_6$)alkyl)amino;

Z$_{3c}$ is aryl or heteroaryl;

Z$_{3d}$ is selected from the group consisting of (C$_1$-C$_6$) alkoxy-carbonyl, amino-carbonyl, (C$_1$-C$_6$)alkylamino-carbonyl, di((C$_1$-C$_6$)alkyl)amino-carbonyl, (C$_1$-C$_6$) alkyl-C(O)—NH—, (C$_3$-C$_7$)cycloalkyl and heterocycloalkyl;

(C$_3$-C$_7$)cycloalkyl and heterocycloalkyl being optionally substituted by at least one member selected from the group consisting of halo, nitro, (C$_1$-C$_6$)alkoxy optionally substituted by at least one halo, (C$_1$-C$_6$)alkyl optionally substituted by at least one halo, (C$_1$-C$_6$)alkyl-carbonyl, (C$_1$-C$_6$)alkoxy-carbonyl, amino-carbonyl, (C$_1$-C$_6$)alkylamino-carbonyl, di((C$_1$-C$_6$)alkyl)amino-carbonyl and oxy, the aryl and heteroaryl being optionally substituted by at least one member selected from the group consisting of halo, cyano, nitro, azido, oxy, (C$_1$-C$_6$)alkoxy-carbonyl-(C$_1$-C$_6$)alkenyl, (C$_1$-C$_6$)alkylamino-carbonyl-(C$_1$-C$_6$) alkenyl, —SO$_2$—NR$_{31}$R$_{32}$, heterocycloalkyl, heteroaryl and —(CH$_2$)$_p$—V$_3$Y$_3$;

R$_{31}$ and R$_{32}$ form together with the nitrogen to which they are attached, a heterocycloalkyl;

V$_3$ is selected from the group consisting of —O—, —S—, —C(O)—, —C(O)—O—, —O—C(O)—, —SO$_2$—, —SO$_2$NH—, —NR'$_3$—SO$_2$—, —NR'$_3$—, —NR'$_3$—C(O), —C(O)—NR'$_3$, —NH—C(O)—NR'$_3$— and a covalent bond;

Y$_3$ is selected from the group consisting of hydrogen; (C$_1$-C$_6$)alkyl optionally substituted by at least one halo; aryl optionally substituted by at least one member selected from the group consisting of halo, nitro, $(C_1-C_6)$alkyl $(C_1-C_6)$alkoxy; aryl-$(C_1-C_6)$alkyl optionally substituted by at least one member selected from the group consisting of halo, nitro, $(C_1-C_6)$alkyl and $(C_1-C_6)$alkoxy;

$Z_{3e}$ is

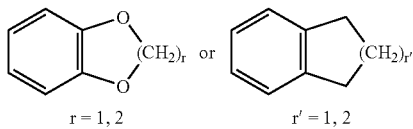

r = 1, 2    r' = 1, 2

$Z'_3$ is aryl optionally substituted by at least one member selected from the group consisting of halo, nitro and $-(CH_2)_{p''}-V'_3-Y'_3$;

$V'_3$ is selected from the group consisting of $-O-$, $-C(O)-$, $-C(O)-$, $-C(O)-O-$, $-C(O)-O-$, $-C(O)-NR'_3-$, $-NH-C(O)-NR'_3-$ and a covalent bond;

$Y'_3$ is hydrogen or $(C_1-C_6)$alkyl optionally substituted by at least one halo;

$R'_3$ is selected from the group consisting of hydrogen, $(C_1-C_6)$alkyl and $(C_1-C_6)$alkoxy;

p is an integer from 1 to 4; p' and p", are independently, an integer from 0 to 4;

$R_4$ is $-(CH_2)_s-R'_4$, $R'_4$ is selected from the group consisting of guanidine; heterocycloalkyl containing at least one nitrogen atom and optionally substituted by $(C_1-C_6)$alkyl or aralkyl; heteroaryl containing at least one nitrogen and optionally substituted by $(C_1-C_6)$alkyl; and $-NW_4W'_4$;

$W_4$ is hydrogen or $(C_1-C_8)$alkyl;

$W'_4$ is $-(CH_2)_{s'}-Z_4$;

$Z_4$ is selected from the group consisting of hydrogen, $(C_1-C_8)$alkyl optionally substituted by at least one member selected from the group consisting of $(C_1-C_6)$alkoxy, $(C_1-C_6)$alkylthio, hydroxy; $(C_2-C_6)$alkenyl; $(C_3-C_7)$cycloalkyl optionally substituted by at least one $(C_1-C_6)$alkyl; cyclohexene; heteroaryl and aryl;

the aryl and heteroaryl being optionally substituted by at least one member selected from the group consisting of $-(CH_2)_{s''}-V_4-Y_4$, hydroxy, halo, nitro and cyano;

$V_4$ is selected from the group consisting of $-O-$, $-S-$, $-NH-C(O)-$, $-NV_4'-$ and a covalent bond;

$Y_4$ is hydrogen or $(C_1-C_6)$alkyl optionally substituted by at least;

$V_4'$ is hydrogen or $(C_1-C_6)$alkyl;

s" is an integer from 0 to 4;

or $Z_4$ is

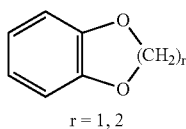

r = 1, 2 s and s' are independently, an integer from 0 to 6;

and i) when $R_3$ is $-C(O)-Z'_3$ and $R_4$ is $-(CH_2)_s-NW_4W'_4$ and $W_4$ and $W'_4$ are independently, hydrogen or $(C_1-C_6)$alkyl, then $-(CH_2)_s$ is neither ethylene nor $-(CH_2)-CH((C_1-C_4)$alkyl)- and ii) when $R_3$ is $-Z_{3c}$ and $Z_{3c}$ is phenyl or naphthyl, then phenyl and naphthyl are not substituted by cyano; and it being understood that when $R_3$ is $-Z_{3d}$ then $Z_{3d}$ only is $(C_3-C_7)$ cycloalkyl or heterocycloalkyl;

or a pharmaceutically acceptable salt thereof.

2. A compound of claim 1 wherein $R_1$ and $R_2$ are independently, $(C_1-C_8)$alkyl;

$R_3$ is selected from the group consisting of $-Z_{3c}$, $-C(R_{Z3})(R'_{Z3})-Z_{3c}$, $-C(R_{Z3})(R'_{Z3})-Z_{3d}$, and $-C(R_{Z3})(R'_{Z3})-(CH_2)_p-Z_{3d}$;

$R_4$ is $-(CH_2)_s-R'_4$;

$R'_4$ is heterocycloalkyl containing at least one nitrogen and optionally substituted by $(C_1-C_6)$alkyl; or $-NW_4W'_4$;

$W_4$ is hydrogen or $(C_1-C_8)$alkyl;

$W'_4$ is $-(CH_2)_{s'}-Z_4$;

$Z_4$ is hydrogen;

s is an integer from 2 to 4; s' is an integer from 0 to 4;

or a pharmaceutically acceptable salt thereof.

3. A compound of claim 2 wherein the heterocycloalkyl of $R'_4$ is piperidine;

$R_{Z3}$ and $R'_{Z3}$ are hydrogen;

$Z_{3c}$ is selected from the groups consisting of thienyl, furyl or phenyl unsubstituted or substituted by at least one halo or $-(CH_2)_{p'}-V_3-Y_3$;

$V_3$ is selected from the group consisting of $-O-$, $-C(O)-$, $-C(O)-O-$, $-C(O)-NR'_3-$ and a covalent bond;

$R'_3$ is hydrogen or $(C_1-C_6)$alkyl;

$Y_3$ is hydrogen or $(C_1-C_6)$alkyl optionally substituted by at least one halo;

$Z_{3d}$ is $(C_1-C_6)$alkoxy-carbonyl or imidazolidine;

or a pharmaceutically acceptable salt thereof.

4. A process for the preparation of a compound of claim 1 comprising reacting a compound of the formula

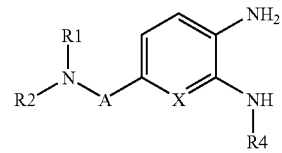

in which A, X, $R_1$, $R_2$, $R_4$ have the meaning of claim 1, with an isothiocyanate of the formula $R_3N=C=S$ in which $R_3$ has the meaning indicated in claim 1, in the presence of a coupling agent or yellow mercury (II) oxide in the presence of sulfur, for a period of 3 to 48 hours, in a protic or aprotic solvent, at a temperature of 50 to 80° C.

* * * * *